US010640752B2

(12) United States Patent
Gjessing et al.

(10) Patent No.: US 10,640,752 B2
(45) Date of Patent: May 5, 2020

(54) SALMON GILL POXVIRUS

(71) Applicant: VETERINÆRINSTITUTTET, Oslo (NO)

(72) Inventors: Mona Cecilie Gjessing, Haslum (NO); Torstein Tengs, Slependen (NO)

(73) Assignee: VETERINÆRINSTITUTTET, Oslo (NO)

( * ) Notice: Subject to any disclaimer, the term of this patent is extended or adjusted under 35 U.S.C. 154(b) by 0 days.

(21) Appl. No.: 15/539,039

(22) PCT Filed: Dec. 22, 2015

(86) PCT No.: PCT/EP2015/080982
§ 371 (c)(1),
(2) Date: Jun. 22, 2017

(87) PCT Pub. No.: WO2016/102569
PCT Pub. Date: Jun. 30, 2016

(65) Prior Publication Data

US 2018/0216080 A1 Aug. 2, 2018

(30) Foreign Application Priority Data

Dec. 22, 2014 (SE) ....................................... 1451636
Jan. 2, 2015 (NO) .................................... 20150012

(51) Int. Cl.
*C12N 7/00* (2006.01)
*C12Q 1/686* (2018.01)
*C07K 16/08* (2006.01)
*C07K 14/005* (2006.01)
*C12Q 1/70* (2006.01)
*G01N 33/569* (2006.01)

(52) U.S. Cl.
CPC .............. *C12N 7/00* (2013.01); *C07K 14/005* (2013.01); *C07K 16/081* (2013.01); *C12Q 1/701* (2013.01); *G01N 33/56983* (2013.01); *C12N 2710/24021* (2013.01); *C12N 2710/24022* (2013.01); *C12N 2710/24034* (2013.01); *C12N 2999/005* (2013.01); *G01N 2333/065* (2013.01)

(58) Field of Classification Search
CPC ...... C12N 7/00; C12N 14/005; C12N 16/081; C12N 33/56983
See application file for complete search history.

(56) References Cited

U.S. PATENT DOCUMENTS

2005/0031643 A1 2/2005 Szalay et al.

FOREIGN PATENT DOCUMENTS

WO WO9412646 * 6/1994
WO 2004/042059 5/2004
WO 2009/009039 1/2009
WO WO2010030683 A2 * 10/2010
WO 2014/052378 4/2014

OTHER PUBLICATIONS

International Search Report, International Patent Application No. PCT/EP2015/080982, dated Mar. 29, 2016.
Nylund, A. et al., Morphogenesis of salmonid gill poxvirus associated with proliferative gill disease in farmed Atlantic salmon (Salmo salar) in Norway. Archives of virology, 2008, vol. 153, side 1299-1309.
Mar. 16, 2007 (Mar. 16, 2007), "1095521080467 Global-Ocean-Sampling_GS-32-01-01-1P3-1P6K B marine metagenome genomic clone 1061005988693 3', genomic survey sequence.", XP002755217, retrieved from EBI accession No. EM_GSS:EK571604 Database accession No. EK571604 sequence.
Jan. 11, 2001 (Jan. 11, 2001), "T7 end of clone AZ0AA09F06 of library AZ0AA from strain CBS 712 of Kluyveromyces marxianus", XP002755218 retrieved from EBI accession No. EM_GSS:AL423644 Database accession No. AL423644 sequence.
Aug. 12, 2004 (Aug. 12, 2004), "Synthetic leader sequence encoding DNA SEQ ID No. 99.", XP002755219, retrieved from EBI accession No. GSN:AD026706 Database accession No. AD026706 sequence.
Jul. 5, 2004 (Jul. 5, 2004), "SubName: Full=CNPV070 putative rifampicin resistance protein, IMV assembly {ECO:0000313|EMBL:AAR83416.1};", XP002755220, retrieved from EBI accession No. UNIPROT:Q6VZS7 Database accession No. Q6VZS7 sequence.
Jan. 22, 2014 (Jan. 22, 2014), "SubName: Full=Uncharacterized protein {ECO:0000313|EMBL:CD182430.1};", XP002755221, retrieved from EBI accession No. UNIPROT:Unreviewed Database accession No. U6GQF8 sequence.
Gjessing, M. C. et al., Salmon Gill Poxvirus, the Deepest Representative of the Chordopoxvirinae, Journal of Virology., vol. 89, No. 18, Jul. 1, 2015 (Jul. 1, 2015), pp. 9348-9367.
Gjessing, M. C. et al., Erratum for Gjessing et al., Salmon Gill Poxvirus, the Deepest Representative of the Chordopoxvirinae, Journal of Virology., vo. 89, No. 21, Oct. 2, 2015 (Oct. 2, 2015), pp. 11174-11174.
Hypothetical protein, conserved [Eimeria acervulina]: CDI82430, May 22, 2018.
EST_crog_evp_901459 crog_evp Caligus rogercresseyi cDNA clone crog_evp_514_115_fwd 5-, mRNA sequence, May 23, 2018.
Office Action, NL Patent Application No. PA 2017 70543, dated May 30, 2018.
Hanson, L.A. et al., A broadly applicable method to characterize large DNA viruses and adenoviruses base don the DNA polymerase gene, Virology Journal, 2006, vol. 3, nr. 28, side 1-10.

(Continued)

*Primary Examiner* — Bao Q Li
(74) *Attorney, Agent, or Firm* — Casimir Jones, S.C.; Tanya Arenson

(57) ABSTRACT

The present document is directed to a new poxvirus infecting salmon. The present document further discloses the genomic sequence of this double-stranded DNA virus and the use of this sequence information for detection, diagnosis and/or vaccine development for the virus.

14 Claims, 13 Drawing Sheets

Specification includes a Sequence Listing.

(56) References Cited

OTHER PUBLICATIONS

Miyazaki, T. et al., Histopathological and electron microscopy studies on sleepy disease of koi Cyprinus carpio koi in japan, Diseases of aquatic organisms, 2005, vol. 65, side 197-207.
Nazarian, S.H. et al., Comparative genetic analysis of genomic DNA sequences of two human isolates of Tanapox virus, 2007, Virus Res. 129 (1), 11-25. Genebank Accessesion: EF420156.
Varga. A & James, D., Real-time RT-PCR and SYBR Green I melting curve analysis for the identification of Plum pox virus strains C, EA, and W: Effect of amplicon size, melt rate, and dye translocation, Journal of virological methods, 2006, vol. 132, side 146-153.

* cited by examiner

| | SGPV | Amsmo | Melsa | Vacco | Deevi | Psevi | Canvi | Crovi | Squvi | Molco |
|---|---|---|---|---|---|---|---|---|---|---|
| Amsmo | 4.22 | | | | | | | | | |
| Melsa | 3.66 | 2.48 | | | | | | | | |
| Vacco | 1.59 | 3.82 | 3.61 | | | | | | | |
| Deevi | 1.42 | 3.91 | 3.23 | 0.61 | | | | | | |
| Psevi | 1.40 | 3.50 | 3.31 | 0.54 | 0.34 | | | | | |
| Canvi | 1.83 | 3.78 | 4.25 | 0.91 | 0.74 | 0.65 | | | | |
| Crovi | 1.44 | 3.43 | 3.29 | 0.72 | 0.42 | 0.45 | 0.70 | | | |
| Squvi | 1.38 | 3.63 | 3.31 | 0.48 | 0.27 | 0.23 | 0.57 | 0.42 | | |
| Molco | 1.53 | 3.49 | 3.22 | 0.57 | 0.36 | 0.41 | 0.65 | 0.46 | 0.35 | |
| Yabvi | 1.49 | 3.57 | 3.11 | 0.57 | 0.18 | 0.31 | 0.69 | 0.42 | 0.25 | 0.34 |

SEQUENCE LISTING

<160> NUMBER OF SEQ ID NOS: 15

<210> SEQ ID NO 1
<211> LENGTH: 241564
<212> TYPE: DNA
<213> ORGANISM: Piscine poxvirus
<220> FEATURE:
<221> NAME/KEY: misc_feature
<222> LOCATION: (81224)..(81224)
<223> OTHER INFORMATION: n is a, c, g, or t
<220> FEATURE:
<221> NAME/KEY: misc_feature
<222> LOCATION: (82289)..(82289)
<223> OTHER INFORMATION: n is a, c, g, or t
<220> FEATURE:
<221> NAME/KEY: misc_feature
<222> LOCATION: (114612)..(114612)
<223> OTHER INFORMATION: n is a, c, g, or t
<220> FEATURE:
<221> NAME/KEY: misc_feature
<222> LOCATION: (225842)..(225842)
<223> OTHER INFORMATION: n is a, c, g, or t

<400> SEQUENCE: 1 tatgtttta gtttttcaat ggtcagacct tcagtgttaa aaatatatat tttagttttt 60
caatgtcggg acctcccggt gttaaaaaat atgtttttag tttttcaatg gtcggacctt 120
cagtgttaaa aaatatatat tttagttttt caatggtcgg gaccttcccc tgctaaaaat 180
atgttttggt ttttcaatga tcatgacctt cagtgttaaa aaaatatgtt ttggtttttg 240
gttttccaat gaccatgatc ttgtgttaaa aaacatcgga ccagaggaca agttctctca 300
gatgaattct ttgatgtaag tcttgtcggt ccagacatca caagaaaata catgtccgtg 360
taccgagtca gtcagtgaaa gagaaccaat gaccgaaagg gcaataccta acatctcagg 420
tgtacagtac tcgtgagtgt acttgttgac cgtgtgagtc ttaccatcaa ggagtcgttc 480
tctcatggtc tcgatgagat ttttcattgc cttgtcatgg ttcttttttt tcttttcgta 540
caagaccatc gggttctcct ggttgtattc ccatgccctc tcttcaaacg tacgaacgtt 600
atgtctgtgt ttgatctgat caagtaatcc tgtgtaaaca cccaggcagt acattttatg 660
atcttcctca gaagtatcat gacccctgac caaggtgtac atcacatgtt taataatgtc 720
cgggacagac tgagatgtct tgatcctgga gtaaagaccc tgggtgtcat actttccttt 780
gttgaactgt tcccctagaa ggtcatcgtg tttacgtcca cgcatgttga cccagacctt 840
ggtctggtgt ttcctttctt ctatcagagg tttgtgacac tgggtccagt caagaacact 900
taccatacaa atgatcttgg taagtcccgg acatatctct gccaatgcat tggtgaacgc 960
attgacctct acccaattga caaatgattt tattcctaca attgtcaggt ctccgttccc 1020
tactccaaga tgtttcatga ttgtcatgtc ttggccgacc atgtccggat gaatgataca 1080

-continued

```
tgcaaacatg gaactctgga ccttctgggt gatcatggta tttaccatgt cttctgtcca   1140
tacgttcctg gtactggtaa agattaatgt actggtcgag cgtaagtcat caaccccgatc   1200
tcgtaagacc ttctcggtcc agactctgaa tgaagttcta ttgtccattt tttattgttc   1260
ggataaacag aattattaat tataaagtta tttttcatta aaaacttcag aggtcatgac   1320
ccggtccagt acaaacttcc atctccaaaa atccggagtg aacaggtcgg tcatgttatc   1380
ttcgtacgac aagtaagatc cgaccactga aaataaagaa cccatttttt ccaagaactc   1440
tggatctccc gggtcaacca tttttatgaa atcattgacc tcaggaacag acttgttctt   1500
gtccaggacc gaattgtttt caggaaatat cccgggacca aaagtaaaat ctgataattt   1560
aacagggaca tctggtttgt tctggaacag tttaaactga gctccgactc cgacgtacaa   1620
tcctagtctg tacatccctt ggccggttct tacaatgttc ttggcccggt caaacaaaat   1680
tactggctcc ctggtcggac catgtataca aggtctgtgc atacaagggg tgtccgtaca   1740
atgtctgtcc atgatccaag agtccactat cccaaaatga aaatcagaaa agtctgtgaa   1800
ttctgtgatc cggtcatgta agatgaatac cctagagagt tcttttctta ccttgaccgg   1860
gttatatctt ggactgaggt tccccctatg ttgtacagac gggatcaatg acaaaatcaa   1920
ttttatattc ggtaactttg gtatcagata atttatcagt atccactgtt tatgagtcag   1980
gacatcaatg accaacattt ttattttttt ataatagttg acctccccgt gtgtttctat   2040
gaaggtatga acatgtttgt tggcacgata cagaacagac tttatcagtc cttggacaaa   2100
aatgtttttg accggtccga aaaccactat ctctgtgttg tttaaaacat tagtgttgag   2160
tccgctcctg atcaaaccag gaaattcaac gtgttctacc aacatttttc aacatgtaca   2220
aaaaacatct tttttctttt ttaaaaaaac tcttccaggg tcaacctgtt cctccagtaa   2280
tcaggagtaa aaataaaaca ggtaggtccg tccctgaaaa gatacgaccc tctgatcgac   2340
aacattgtcc cgaagatgtc acaaaagtcc atcttactgt cacgcaacac tcctcccttc   2400
cactcttgca ggacagtgta ataaaccaag aagttatttt gctcaaatgg actgtcctga   2460
acaaaattat tggcataaat tccgttgttg tgagagtaat tatcgatccc gacctgatca   2520
cgatcgtatg cttccatctt gaaattacct ccttggttgt tgtaaagtcc tagagcaaac   2580
atagggtctt gtcctagggt cttttgattc aacatttcaa atgtggtcga gaccacatgg   2640
tctactgaat cgccacttga gaaagcaata ggccaggccg cttctgttcc ctcgacgaaa   2700
cttttattat ttacaggacc gtgcatcaca caagtggcag agacatacac ctgaacaatg   2760
tctgatcggt ccaggaccgg aacacccact gtcttgtaat gatctgaaga catcatcatg   2820
acaacgtgct tgacagaagg aagttcattg acaaaccgat tgatagcagg tgatgtccag   2880
tcagcatcct tctcgacacc gacaaccagc atgttaccac ctccctttcc tagtcgtctg   2940
tagaccttgg cctccttggg atcaactccg atgtattcca cgatacacgt ggcagactct   3000
gtcacacaag aagtaatcat tgacatgata aattctcttg tgtacgtatg gtatttggaa   3060
ctgagtacaa gagtacttgt tctctccaga tctcttgtgt ttacctcgtt attgaacaga   3120
ccagggtaat cagtgtacct ggtcagatcg tgctcagtgg cagttggaaa aggccgactg   3180
tcaataggct cgtccctgac aagaatgtta ctgtacttgc acaacatttt ctttctggtt   3240
tttactggct ggttttactt tctgtaaaaa gaaccttgac acaattatgt atgtacgtat   3300
gacttttata aaaatataat aaaatttcca ttatcagaat aatggtttct caaatgatga   3360
tcagaaccag gtcttttcaa gtcctgcggt gtcgtaagcg ggcttctttg aaggaggact   3420
```

-continued

```
tcctctggct ccttcctgat cagacacaga agagtcggtc cattgatcag aagcgtcctt   3480
gaattcttcg gtctctgtct cctggcgggc ctttccacag acacagtttt caggactggc   3540
catacaaggt ccggaatctt cagaatcata cgaagaatca tcttcgtggt cggtattgtt   3600
atcctgatgc tcttggtaat catctgaccc gatacaatca agacactggc aaatgaaatc   3660
tgactctgga gtcactcggt cccgttcata aatgccatcc tcatcaaact gaccggtcat   3720
gaagtcggta gggcagtgac tttccaggac agtcagtaca catttcagtt tccagaagtc   3780
ggtcccgaac acaaacaccg ggtttttgcc tgctttgaga ttgttgtaag aatccagtga   3840
cccaagaaaa gaaccgaatc gttccatggt catgtgggtg taatccagga gcatgtgatc   3900
atgatcatag tcatcaaaat cttctccgaa cgaccgaggt cctgtggtgt ctctacagga   3960
aggatgtatc atgtcatcgg ggaacactcc ctgggaacga ctgagactcg accctctcat   4020
gaaacaagaa gccagtccgt tgtagattcc tgacacgtaa gcaggagatc tcctgacctg   4080
acccggtacg aaggaatcac ggatctgggt gtctgtctga ataccatgtt ccagatcttt   4140
caagagctcc attgtcgtgt caatcattgc tgagacgtct ggaccagctg ggttgatttt   4200
atcccagaat gtatcagagt ccctgagtcc tccgacaaag tcagggttgt tacactcttg   4260
gttgttgtga acatccacaa acaccttcat gaagtgacct cggacagaaa ctggacattg   4320
agaaccacat gttacccagt gttccatcga gatcatacaa aagacctgct tgaaattgat   4380
caggaagtca atgaacgggt caagtctgta ccagttagca ggattgtcga ttccgacgac   4440
catcagagac ttcccgtcgt atcctagtcc tttgtaaatg tcatgttgtc tggcaccgac   4500
aggcctcggc acaaagttga gcagagaagt agccgttttc ttggtgtatc ccatggactt   4560
gaccagggaa ttcgtgtaag aaccgtagac cgaagtgaaa atgaccgtgg tgacttccag   4620
gagctctgtg ttacttacag gatcatcaag aagatcccga agatatgacc cagagtcacc   4680
tccatgatcc tcctggtgat tttctgggaa aaacttcttg gtgaactctc cgacagtgta   4740
ctgagatctc agtggtggtc ttgtcagtgt ggtcttgtca gtggccatct tgtcttgtca   4800
gtggtgatct tgtcgggtct tgtatgtaag tggtaaaaac cttaataatt aacaagtatt   4860
tttctttttt aaaaaaagta tattcctttg gaggtcattc ctccgggtca ttcctccggg   4920
tcattcctcc gggtcatttg aacactctca gggtattttt tatcttccag taatcaggag   4980
tgagcacata agtaggttcc cctggtcttt ctgtcctgat agaacccatg accgataaca   5040
tccctgcagt ttctaacatg acctgaggtt ccatgatttt cttccaggag ggttttcctc   5100
ccagaggtcc tcctggacaa ccaggtcctc ctggacaaca acctgtggta tggttgaatt   5160
gtttcatcac ggtaatttct tctgtgtctc tgttgtataa atctggagat ttttgatagt   5220
ttgacatccc aaggattcct tgttcgtatg aaaagtccac gacagaactg taaggaagaa   5280
gttttgactt gattcctagt tgagccccgg ctccgttgta cattccaagg atcatgtctt   5340
ttcctttccc ctcggactct ttccttagct tttccaagat ctccaggacc gtgtcttctt   5400
tgtcaatctg aggtaccatg gtcataccaa tgaaaaaatc ttgagaaccc atgtcaccta   5460
gattctggac acttatataa gtcctggtca ggtccggcct gggatgatca cggtccttga   5520
tcttgaccca gtctggcaat gacaccatcc tggcaatcaa cttcagatta ggtagttcat   5580
ccacaagatc tttggtgtgc tcccacatcc cggccccttc cattgtcacg accaacatgt   5640
taccttttgt catacctgtg tatttgtaca cttctaattc tccgactgtc agatccggta   5700
catgaaatgt acatattgtt tctggtctga cagtagaata aaacatggac gtcgtgaact   5760
tttttgtaaa agttctgtgt tctgacgtga acacgaccgt ggtagtttgt ttcaatatgt   5820
```

-continued

```
tacatcttac gtttttcaga cgtaagttac tgaatgatat cttactgtca tcaaaaatgt   5880
ccatgatttt atgtgttctg ataaagttct ttatggtatt gtttttatg tttttataat   5940
taaatgagaa tgtatctgat gtcggttcct atgcctcatt attttatatg tgtatgtgtt   6000
accacattga taatgtttgt ctgaccttgt ctgacccaag ttatttccca tgattaaaaa   6060
aatgttctat tgatcagatg tatcttgagt aagattctga aaacttaaat tataataaaa   6120
tatctactaa taaaaaatat ctactaataa aacgttatca tgaatattat catctggact   6180
tttatttttg taagtctggt acgatcatac atcacagaag caagtgacat gtcacaagaa   6240
gatgtatcag aaaacactca cttgttaaat aataaacatg ggtgattatt tatttaatac   6300
atgatgtttt taaacataaa aaaagataat ttttttaat atcacttttc atccgacatg   6360
tcaaacaaaa tctatcaagt tacatcttaa cttccagaaa tcatgggtga acacataaat   6420
aggcatacct ttttcttttg atttaagtgt tcctagcgtg gacaacatga cagaaaactt   6480
tttttgtttg taaaaaggtc tggtttcatc caacagatgt aagtccgtca tcagagagtt   6540
ttcatatttg ataccaacag gtaaatcaaa ctcaagagtg tcaagacatt gatcagtggg   6600
taaaatcccc ggtaattgtt tgtacacgta agctctgttg actttattgc ttgacaagtg   6660
gagcatcatt tttatggaca tgcccacgta taatcctaat atgaatcctg ggcttttgtt   6720
ttttatttta tcttctaaca tggtcaaaga tttgtctatt gtctcattat aattataatc   6780
ccattctata ggccaactat ggtcgacgcc ggtaaacaaa tcaggtaaac tcagttcgtt   6840
tagttgttca acttttacat aaacaacaaa atttggaatg ttcaacttgt tcaaagactc   6900
gttccaaatt ttgttgagtt cctcgttcat gatggccacg accaacttca ctttaggtaa   6960
catgttcacg actgttttta taaatggcca atcgtctgga tcatatacaa gtacattaag   7020
aagggcccct gtatctttgc caatgttatt ataaatttct ggttgtttat gacttccttt   7080
catatttgga aaaaacttac aacatagtga cggataaaca ctgttgtaca acaatgaaag   7140
tattagatta ttagattgat ctctgtcact ggaaaaaaca acagtggtaa catcaagaaa   7200
tgatgaatat ggtttattaa aaaacttacg acattttcgt tcaaacacaa cgtcatcgcc   7260
gtcgtagtaa acgatgtcat ctgactggtc agggcacata tgtggtagat ccataataat   7320
atgtgattaa aaaaaagtta ttgattttta tgttttactt tgtcatgatc aagtgtgtcg   7380
tgtttactac agtgtcgtgt ttactacagt ggtcgtgttt actacagtgt cgtggtttta   7440
aatgtcatct atgtctatgt ctatgtctat gatggtatgt tcacgcgtga tatggtcgtg   7500
ggtgtctatg ataccggttt caagatctgg taacacaaag cagtcgtatt taacatgaga   7560
gtctgaagaa cccggaggcc aggaatcaga ggggtcgtat atgttgtcag tttcctctgt   7620
ttcatcatca ttatgttcat cacactctga atcccccaat gatgaaacag aggaaactga   7680
caatgagtca ttgtcaaact ctcgcagatc actgatgttt ttcatcagtg tcttcaagag   7740
atccaccaat aactcatttt tgtcagccat gtttttgata tctcctgtgg ttaagtctgt   7800
atctgttgtc tgttataaat gtttatattt caattaataa tatcattgat gttgaatcct   7860
actttccaaa aatccagaca tgccacgaac gtagggttcc ctggagtttt tgatttcatg   7920
gtacctatta ttgataacac agatgccata gcagatatca aaagttgtgt gttcagatga   7980
taatctcctt gaaatatttt tgtgattaat aattcagtca atgaatcgtg atcggtgaac   8040
gagttaacag agtgttttaa actttcaaaa cataacaaag aatttgaatt gaatttattt   8100
atttgcgggt ttcttgcatt cgcagattgt aataatttaa ttcccatccc attatataat   8160
```

-continued

```
cccagaatat agtctggact tttgttttcg gtcattgttt ttaatttctg tatgagagtg   8220
ccgattgagt aaattaaatt ttgattatta tccaactccc aacatgcgtt aaatccttcg   8280
gtacattcag gtgttttcaa ctgagtcatg ttttcaatta tcacgtacac attgaaagac   8340
ataggatcta tgtcactgag agcatattct tcgtacggca ttatacaaag tgcgtttgca   8400
ttaggaaatt ttgtcatgta agtttttata tttttccatt cagcaaactt gtgtatggct   8460
actcctagta gcataccacc attcgacccg atatgattat aagaacatat agagttacaa   8520
atatgacttc gtctggtgta aaaaatacat tctgatgatg atttgtttaa ttctgagtgt   8580
aaacaagatt caagaaacaa gtacggagca tattctattt ttgtgaaaaa caacactgtg   8640
gtggtgtctc tgatcacctc tggtgaaatt tgaatttttg tgaaatcgtt ttcacgagcc   8700
attattcagg tcatggttag ttaaacatat tttttatgtt ttaacaataa aaaaagacgg   8760
ggtagggggt gttatatatt agggtatata aaaaatgttt ttggtgggat acgggaacgg   8820
gagggaaggt gtgtattata tgggaaattg acacaacagg aagggctttt ttgttttttt   8880
atgacagaca acataataat atatacacca tgaacatgta gcatgtgcat gtaaaaacaa   8940
tcctaatatt taggaagtat attcgttctt tctgtattag gtacttacct attacacaga   9000
acgctcggcc ttttgacaaa aggccggtac tttctaaata tcaaaaatgt ttaacatgac   9060
atgtacatta atgaaattac taagttatac aatgaaatta ctaagttata caatgaaatt   9120
actaagttat acaatgaaat tactaagtta tacaatgaaa ttactaagtt atacaatgaa   9180
attactaagt tatacaatga aattactaag ttatacaatg aaattactaa gttatacaat   9240
gaaattacta agttatacaa tgaaattact acagatacac gaaaaatatc atcaaaatag   9300
atgtcggtac acttgtggac aatctccgaa agatacctta tcttgtttgg ctcggaattt   9360
atgaaaaaca ccgagccacc caagatcgat attcagtgat tgtcagacaa gtgaactgac   9420
attaattgga tgtatttaat ttacaaatat atgtatttac atatgtatgt atgtgtgtga   9480
gatttacaac tgagactatg tatgtgtgtg tgtgatttac aattgagact atgtgtgtga   9540
gtatcttaaa catatgaaca tatgaatacg acagggtctg ctcctccagg gtctgctcct   9600
ccagggtctt ctcctccagg gtcttctcct ccagggtctt ctcctccagg gtcttctcct   9660
ccagggtctt ctcctccagg gtcttctcct ccagggtctt ctcctccagg gtctgctcct   9720
ccagggtctg ctcctccagg gtctgctcct ccagggtctg ctcctccagg gtctgctcct   9780
ccagggtctg ctcctccagg gtctgctcct ccagggtctt ctcctccagg gtcttctcct   9840
ccagggtctg gtctatccaa atgagaacgt agcattataa gttcgttcag agatatcatt   9900
atcaaagaca ttctgaaaac agcaagtcaa taaagttgtt tatattgtca tgcgcaccaa   9960
ttatttacct ttatatttca gtaaattttt tagtgtatat tgatcaactc gtaaggtatt  10020
tcaatttttc cagtaatcgg gtgtgatgac gtacacttcg gatatactga tatgtctact  10080
gtacgtcgcc agtgtatgct gtaaatgtac actggtaatc ttaagacatg ccgacaatat  10140
catcatacat tttttcatat tataattatg gagatgtctc gatgttgtcg ttgggagtcg  10200
cagtgtatcg tcatattcct gacgtacata attggcatgc atacatcctt ttttgtacag  10260
gtctccattg atcgcccaat tcattaaata tcccaagaca ttatattttg tactgggaaa  10320
tatcttgatg tctgcttgat acgtggagtc gaaatccagt acactcaggt cactgttaaa  10380
atcttctctt gtttcagtag gcgaatatct ctggtgatat ttggaatcaa tgattccaga  10440
aatgtattta aataaataca cacagtacgt atggacttgt ggaatttcca caagatcttg  10500
aaatttcaca attgccttca gtattttcaa ggcctgacct ttattgacgt agtcaatgaa  10560
```

-continued tgtttctgaa tcatgccttg ccttacgttt ggcctgattc atctgtagca atggaatact 10620
agactttcca atgaacttat gaatctttac cttgttcttg ttatatttcg caccacattc 10680
atttaagtaa tccctgtcgg catgatcaga gtcttcgtca aacaaataaa taacaataca 10740
attatttaac ctacagaaca agaaatccca gtcgtctgtt gtcatcggag aatcaacata 10800
atgtaccatg agatatgttt tgtcggtttc gttctgatta aaaacatgta ccgaatcatt 10860
taattgtagt ctggacatgt tctccttttt attaaaggtg tgatatccac tgatgaataa 10920
aggagcatgc tttgttgtct tggtcgtgaa caacaaaaga tgtaagtcac taaggtcaag 10980
agtgttgtca ccaagagcgg tcatgagatc aaggtcgaga gtggtgtcac ttacaaggtc 11040
gagagtggtg tcacttacaa gatcaatgtc aagatctgac tctgttgtct cttctgactc 11100
tgttgtctct tctgactctg ttgtctcttc tgactctgtt gtctcttctg actctgttgt 11160
ctcttctgac tctgttgtct cttctgactc tgttgtctct tctgactctg ttgtctcttc 11220
tgactctgtt gtctcttctg actctgttgc ctcttctgac tctgtcatta taacaaactc 11280
ggtggtctct gtcattataa caaactcggt cttcttatta cactattcaa tcttatatta 11340
tattaaacaa aaattaatgt tttttctttt ttttaatcgg aatccgatga agtttcatct 11400
tggggaaata tttccgggaa cacacaaaac ggagagaaat tccaatggat gttaaaatac 11460
aatttccagt aatcaggagt cgagacaaca aaggttctat tctcttgacc tttttgtgtt 11520
cctagtattg ccaacattgt tccgaatcta ttcaaaaatt ttctcttgga caccagggtt 11580
tcgttttttt caatgcccat ttgatctttg atgattttat ccacgtcatc agaagattct 11640
tgattgtcaa aatactctcg ttcggatgtg tatatataat atttaggtaa tgtacttacg 11700
tcatgggtga atataccttc tgtgatgttg tacatggagg tcagaatacg cattttaaca 11760
cccatcgcgg tgtatattcc tcggatgtat tctttactct tgcctttgat tttcccatct 11820
attcctgaca tgacagttcg tacaatactg gtcggtttca tgtgcgtgtt tatgttccat 11880
gcgtcactga caccttcatg aaaatccaca ctggtctctg tgtctataca atcatgatgt 11940
ttaaacagca tcgtgatatg tggtttaaca ttcaaagcat cctcggcctc ttgattactt 12000
tctgtattag gcatcaaata taccccctga agttttgtac aaaagcatat aagatctttg 12060
gcatgtttcc attctccttt ggataacccg accaccagta aatttccttc atcttttccc 12120
atccctccga acaaggttcc tgtttttgtg atcacaaatt ttttagtacg taacggaaat 12180
gccacatgaa atatcatacg caaaaaagtc ggagcatgtg tgtttgtcat acttgcaaat 12240
aatatggtag tggtattatc tgttaactct gatactgata tgacattaca cattatattt 12300
ggaaacgcaa catcatcaag atctcggtca ttcggatatt ttggatccgg gatgaaaacg 12360
gccattgtac acaaatgtgt tttataatta atgacgtatg tatataaaaa ttctattttt 12420
ttattgttct gggaacaact tttctttttg ccatttgggg atcgtgtcaa aaatacaatc 12480
aaccttgaca cagtcagtca aggttgattg ttccatcact ttgatttcca tgacacatct 12540
cagtagttca gaactggtca aattagattc ctccactgat gaatccttga caacacacga 12600
tgacagatca gatttcttta ttgcacacga catcagacac gagtcacata tctctcctga 12660
tgtctcgcat gttgtcagat tacattttga cagttgtgaa gaaatcagtt tagacgtcga 12720
caccgtacac atgttcaaaa cggtctcgtc cacggtggaa tttttaagta tgctattttt 12780
tattgtctcg ataaacaaat tacaccagtt cagttctgat gactctattg ttccattttg 12840
tattttacac gtgtccaaga ccaggtcgtc acaatcagaa ttgtcaatat tagaatcatc 12900

-continued

```
aatgtcagaa ccatttattt cagaaccaga gattgttgat ttgacaacgt tactcttttt  12960
caatttacaa tgttctatga tgacgttttt aaaatcagaa tcagcgacct ctgattcttt  13020
gaccgaacac atttccatct cacaactaaa aagttcggac gtgatacatg tactttcctt  13080
tattatcacg tctgtcaatt cagagtattc cacgacactg tcttccacga cacaacttgt  13140
tgatggtttt ttctccgaag agattttaga agtatggaaa atttgacaag tgtacaactt  13200
actttttcc actttgatt ttttcacaca agagtcagag accagtgatt tctgaatcac  13260
ggaattatca cagttaattt ttgacaaggt acattgttta agttttgaat tatcaaaagt  13320
acagtctgca catttacttt gttcgaccac actctcgtag aacatggtcg agtcataagt  13380
accatcttca aaaagacagt cattggcctt cgaattatta cattcacttt ctactactgt  13440
acaacttatg aactcacaat gatttatttt acacactgac agcacacagg ttgacagaac  13500
acaatctgtc aacgtacaat tataaaatac tttattgtca aaagtaatgt ttgacagtat  13560
ttggttttca atcattcgtt ttgaatcttc ggtgttcatg gaccgcatct tatctatgat  13620
ttcatccatt atatgagata ttaaaaaaaa ataaattgtt ttttcttttt tgatacatga  13680
tcagattgtg ttcatttttt ccagcatgaa ataaaatggt tcggcccata tatcattagg  13740
taactcgatg aacatttccc ggtacgaatt aaatcttaat tctctgtcag gatcgaatct  13800
gtctgagatc agatcatcaa tgtacgtgac aggtgtgtca ccgatacatt tattcaatgg  13860
acaattgatc agtacgcaaa atatcaacgt ggaattttcc acgttgggct gtcttggtat  13920
atcttctgag ttttgtttgt tccttgatat tgagtcagat atcatacaat tttgtagata  13980
gtgatcagag atctgacaat ggtccaattt gcatgtcatc aataacacat cttctgattt  14040
atctttgtaa atgtaagaat ctttgataac tgatttaatc acgtccgaat ctatcagatc  14100
agaataatcc atgttggaca tttctatcag atcatggtcc aacatacaat ttatgacgtc  14160
acttgtgttt atgatacttc ctgtgatgat acagtctgtg gtattacaac ctgtcacgac  14220
tatactctca ccaaatgatt gagacatgga agagtcagtg acattacctt tgaaaagtgt  14280
acaatttgtc atagtacatt gaatgacatt tcccaggtca gtgtcattat taagaatcac  14340
tgattgtttc atatcagaaa gaatcaggtc tgaaaattta cagtgtgaaa gtttaatttc  14400
tgattcattg attgtactct tgtctgttct acatcgtaca atcatggaaa gggtcgtgtc  14460
actcatgatc aaaatggaat cttccaagac agaacacacg actttactgt tgataatttt  14520
agtaagtatg atctgacttt ttttaaacgt acttttttcc acgagagaag ttgttgtcct  14580
ggtataattt attacacaag agtggaccat acattccaca agagttgatt tttttgattt  14640
tgattccatg agagtacacc gtgacagttt tccctgactt gcttcacatt ttgaaattac  14700
agaaagggta atgccacaat tacacagtga tgtatttttc acacatgtac atctttcaag  14760
tgtggtcgac cagacctgac aattttctgt cttacaattt tccaatcgac aattactgat  14820
atgacagttg atcaaagtcg agttcattat tgtttgaccg tccaaggtac aatggtcaaa  14880
acatgaatat gcgactttac tgttttttat cactgatttg gtaaatattc cacgttctat  14940
taattggtct gagacggtac tgtaatcacc tgtgtagacc atcacattat tatgatcagt  15000
gacatgtcct ttttggcaat ctaaaataca atgtgaaaaa tgtgatttgt taatcacaca  15060
tttttccaac agggtgaact ttatattttt tcctgacatg ttgatttttt ttaattcata  15120
ttttttaatt catatgtttt tgtcaataat catacatact attttttaca tgtaatcaat  15180
cccccagttt cggtcatata ttaatcttac cacatgtatc ttcccttctt ttgttgtctc  15240
aaatagcacg ttgtcgtgta tcacgttagg cacaattgtc aggtctgtcc atttatttgt  15300
```

-continued

```
atctttatca aaacgttttg tggtgaaacg aaacgcctct gaaaaatatt ggacaaacac  15360
attatgatat ccatcagcat ttttgaaact aaacaagtaa ttgtctgtac ctaccaactt  15420
ggaattaaaa ttaagacagg tatgatcaat gttcttgaac caacttccaa tgtccaaaaa  15480
ctttttctt aaatccccgt aatatcttac ccgatgttct cttccttcat ttccccactt  15540
atatcccggt ggtaatccat tagatatcaa tgtatgtatg tcacatacaa cagaactctc  15600
tattctattt gaccctttag cgtacaaatg tcgagtcaat atcacttgag agtttttgat  15660
cctgatagta aactttcctg acctgacctg gttatttttt ttaacggcat attctacatt  15720
gaacggtgaa ccacttgtca gaataatcgc ctgatcattg acttctctgt tgcatttcca  15780
tgtccaatac gcgtcagaat tataaaaatg ttttctgaat acttctgaca tgtccaatag  15840
taaatcacct aatcgtgcag aaagttcaag gatctttttt ctacaggatc tgttactgac  15900
atgaaatgac atcatgtaaa cctggtcgtg atggtatgta atagttgttt ttaattatac  15960
tttttcagaa acataaaaga aattcatggg ggggaaaaaa agagattcag taaataacaa  16020
acaaacattt gtggccgtca aacattgcga ccttttcatc atcctgattt aggaaaatga  16080
aaccctccat gtgtttttct gtcatttcga ccacggtcac cagatctgtt gtttgtatgt  16140
cactgcgcaa gtttgtcagg taccacgagt tgttcaagta cgtgagtttg catcttgttg  16200
ccagaaggtt ctcgacgtga ctctcaattg tccattcatc agggcagtgt tgatcaatgg  16260
acacctgtgt atttcccagg tcatcaccga tgtaaaatcc gtacctgaaa aatgacattg  16320
ttgctcaacg aaagtatcaa atgtaatact ttttattcac ttatgacacg attacatata  16380
aaaacatact aagaaaaaac atattaattt aaaacagatc atatccaagc atctcaagat  16440
tgcttgtgaa cttgaaaatg tctggagtgg tcatcttcat gtacactgtc tgacctgtag  16500
cgtacaccag ttgtccgtct ttttgtgtgg gccttcccat gatggcgctt ccgtcaggtc  16560
gaacaacaac tcgactctcc agattggcag ccacagaaaa tgctgaactc agcaacttca  16620
acatggtcgt ctctgtctct gtgtacacgt atggagttcc atcaactggt gctggtgtag  16680
gtggctcatc gtcctctgac tcatcctcaa agtcatcatc gaactcctca tcaaagtcat  16740
cctcaaagtc atcctcgacc ccatcaaatc cggcagcatc agaagatgct cctgattgag  16800
gcgaaaccac ctttgtgtaa ttctctgtgg tgttgtcatc agaagagtca tcaatgttcc  16860
caccttgtga gtcatctgtg tcattgacct cctcgtggtt aattttatca catccgcgaa  16920
tcttcacgtc agtgtcctga ctgtctgcga taaacttctt taccattgcc tttgtgatga  16980
cctgattcag aaggaaagtc attgctgaag taccgctgaa tccatatgat gtgcgctcat  17040
gctttgcgaa gctcgcgtcc agactcatgt atcctggcca gttgacataa tcaacaagag  17100
gcatggcagt agagaacctc ttcttgttca tcttacgagc aatgtagttg gaagcggctg  17160
tcatgaaccc aaatgcgaat ccattctcct tcttctcaag tatctcattt gtcaaggaga  17220
caatcttcaa cacatctccg ttatcaatga aaggaatcaa cgtggtgaac ttgtcaacgc  17280
catcattgta tccatatagc tcccgtgatc ggcgattaat tctgtctgaa tgataataga  17340
cgtgcttact gtatgttgtt ggagcaggga acttactacc catgacaatc ctgtcatcat  17400
ctgagtcacc gatcatgtaa ataaccgttg acagaatagg aaaactctct aggaaaccgc  17460
ccatggctga aaagtctgtc ttctcgtcga tccattgagt caagagatcg cctcctcgtg  17520
ttcccaatcc cttgtacaac tttacatttc cggcttgaat cactatctct gaagtttgag  17580
tcttcttgta agcagcaaga tccttcagag aattaatgaa acatgtgttg aacatgttca  17640
```

-continued

```
actggttttt ctgaatgaac acgacaacac ttacattatc aaaacggaca ccgctagagt  17700
taccgagcaa gaagttagcg aattccattt tttctgagaa gtgttacgag ttctttctta  17760
tagttctgat cttttaaatt acaaggagct tttgttaata taaatataat atttcaatta  17820
atttaaaaaa atacatttat atcagacata aggtattaat atatataaaa aggtatgatt  17880
aatgattaaa gattaaagat taaagtttaa ctgtaagagt ttcaatcaaa gaggttattc  17940
atgcaccagt tacatatgca tagtggatga ggtcgagatc catcaaattc atctccgtca  18000
acagtgtctc caatttgttc aaagtgctcg atgtcttcta tctttttgcc tgttgccaca  18060
aatgccagcc agagctcgag tcgacgctgt ctgtctcctc tggtccttct ctgctttact  18120
tgatgtttag ccatatggac acggaatgac aggggtgctg tcaagatctc catgatgggt  18180
tttccggatc tgtcagagaa cagataactg gaccgttcaa aatcatatat gagccgggtc  18240
aagacctgat tgtcctcatc gcttcggcga attctatata tgtcggcggt caaatcgtcg  18300
acgagaacct tctctccggc ctctgggttg gtcagtgata cttggaaatt tgtaccatca  18360
tcgataataa tttcacatgt catatgaggg gacggattca tcatggtcct ggtcagggtc  18420
tgtctcagaa caggtgtgac agacattttc gctatctggg tcgctggtcg tcggtgtgtt  18480
taaagaggat aattttaaga ctttattttt gtgttttgtg aaaaacccga attgacacaa  18540
cttgttggtg tctgggtaaa ttatatcata aacgtcttgt atgatagttt ttaaagagac  18600
gtttacatca gacacataaa tcaacacatt atcttcctct actttgtatt gtaacgattt  18660
atttattgat ttccatatga ctttaaaaat accagaaggt ttagaatgct taggaagata  18720
caacccaaac tcaaaaacat taagtgagat attttcaaaa tatatcaatc ccacacaggt  18780
gtcgtacgtg ttaatgaatt gatcattttt tgatatactg tacaccatgg tcttctcgga  18840
tcctgtatcg gtaccggaat cagactccat atctgtatga taatcccttt ctctctctct  18900
ctagattctc tcgatctttt ttgtaaattt ccaattctct ggccaggagt tccttactct  18960
tttccaagaa ctgaatctcc tgttgacaat aagccgttct gcttgacaaa actcgttgtt  19020
ctctgatgag atttgccgac tgtctgttca agatctcgag tcttttgttt agtttgtcaa  19080
gattgtaaat ggtatcatcc atgtcagatt caaaatcaga gtcataaaaa gtaataatag  19140
tcgacattat taatttttaa aaaccactat gttgatttac ttaaattaat attcattttt  19200
taattcggtc aggaacaatt atctgtgctt gctctgtgtc tactatgatg accactttat  19260
caccagagta tataaggtat ctattgttgt cttggctgac ttcacaggta tattggacat  19320
tgtcgacaga gttaagtgtc tttgaataac tgtccaattc aatggtgtaa tctttatcca  19380
ggatcatcgt actgttgtta tttgacttgc ttattaccag ccaatttgtt ccgttacggt  19440
aattaccagg gacaagtcgg atgctcatgt ttgtgataag acaataaaag taaaaaactt  19500
aagtacttgt acttattttt tctatttact tacttgactt ctgtgggagg aacagggatg  19560
taaccgtaaa cgtaaacatt cacaaagtta ttgatccact cccgaaaagt tttactataa  19620
aaagaaagga cattgactac cacgatgaca ataagagtaa gcatgatcag cgagggaacc  19680
cccgcttgtg aaaagtgcac aaacttggta acaccacaca tatttaatag gtaaaaatat  19740
ttattatttt ttaagtgaac aaattatgat aattattaac cattacattt ttatagaaca  19800
cgtcagacat gtgttctttt gttcttcttt tctgggtctt tttccgttgg tggtcccttt  19860
ggtgtttttc gttggcggag aggattcttg tttcctcttc tgagtactct ggttgttcta  19920
catcaggagt attgacatgt tttacatcct ctgaacactc gtgctttgcc tcggcagcga  19980
gccttctcga ttgagccttt gatcgtctgc gatttgccac cctttcatca tgaatatgaa  20040
```

-continued

```
tcatttgcat tttatacata ttcaactttt tcttttgtag atcagtcagt actattttgc  20100
gtggtatctg ttcgtgttct ggaaagtttt tgtcaagata cttctgtact cttgacggat  20160
caacacctgt ctccagcccc aatacatcat gtggtaaata tattgtccac gggcacttgc  20220
gcaataacag tatcaatttc ctcataccca ttattggttc cttcttaaac atgttaaaaa  20280
taaacttaaa atttcactat tggattctac ccattatcgg accgaatgtt ttcatacaaa  20340
gtttgaaatg gagtttttca acttccaatg atcacccgat gaaatcatgg aaatgtccat  20400
gtttccatgg agttgtttca acatctcact tagtatgctg tcacccttgt ttctgaaaac  20460
agccacggca actttgatga ccttttcaaa aattgactga ccagactctt ctggttcgga  20520
aggtaagaaa ctcatatgat ctatctcggt ctctgtcatg atacttatca tttccaacca  20580
caagtacatt tcttgttctg tggtgtatcc cggatcagta ctttgtaacg caggtcttct  20640
atgatacggt gggagtattc caagatcttt tctatgatga tcaaagacca tttcgtacat  20700
gacttctttt ttgtcaatgt acagtatgtc aagtatcaca gacagaccat aaaataccccc  20760
ggacagatac gccggttccg cgtctttttt tgtaaattct atgaatttac agatggttgt  20820
taaaaatgat ccgatgtcat cagaagaacc tgtgtttaat ttccatgtgg taatattaaa  20880
aatcaggtcg tctattcctt tcttcagaag atgtggtgcg aacgtcacca attccttcag  20940
ggtatttcta tgtaggatta tttttaccgg atacgtgtca tgaatgcgaa attgtttttc  21000
attgttttta ttcaacatcc atgttatctg agagagatac ggaaagtatt tttccagttc  21060
attaagagag gatatgtcgt cagtgtcaga aagtttcagt atcaacatat ttttattatt  21120
aggtccgatc ccgtcgaata acctcattgt gttaggactt attctcatgg ccgtgtgttc  21180
aatttctgca ttggaataca atcttgtgat cagttcattt tcccaacaat cgtttgatgt  21240
gatcaggaga ccagacacat tttccagctg atgtaatttg tgttttgtca ggaacaccga  21300
aggaacatat ttcatcaatt catgaaacaa ctccatcata ttggttactt ggtattatta  21360
tttttcaaca atttaattat ctcaagatcc gtgtctgtca aggtagaaac tgtcaacaga  21420
gcttctgggt ttataaaatc atctagtaca attttagaat ccgtaatcac agacacaggt  21480
gtctggggat tgtattcggt agggaccagc aattcatggt ctatccccgg gaacatgttg  21540
tgttgtttta ccaaacgatc acggacaaat tgaacgtcgt cgttggtgta acagattatg  21600
atgtcatggt ctggaatgtt tttaaattca ttttctatca tgtcccagta atctctcatt  21660
agaggagaca tcggtaaaca aattttcttt attttattgg tattagaaaa aactattaat  21720
tccttgattg ccccaggggc attgttcatt aacatgtaca caatataaac atctgtcaca  21780
ggaaattgtt tcaatataag attactattt tttgattccg agagtggatc cgagtaatat  21840
tgtaaaacag acgataaaag aatttctgac ttgtttaatt tagtaggaca tatcaatgtg  21900
tacccactca tatttaacat aaaaggattg atatttaaat atctgacact catttattac  21960
actcatttaa ttgtatatca tttctgtcag gaggttttcc ctgaccatgt gtaaacatga  22020
tgtgataagg taaacacggg aatctatttc atccgattcg ttgatgattt ttgtcatcag  22080
ggtgtcggtg aattcagtca gggcttctat caacaggatg ataaagtttt tctgaacttg  22140
tcgtttgaac tcttcagact ctttttgta cgtgtcgctg aaatacgtct ggatgtaaga  22200
aaacacagaa cccagactat tctttttgat gtttatgaaa tccttgtaat cgtaggcagt  22260
gttgaaaaaa tcattcatct tttctatcca gggtctcaca cactgttgtg cgacgtcgac  22320
aaaatcaaca gctaagacgt cttcgggaaa cattctctct atgcgtgttt tgttgaaatc  22380
```

-continued

```
cagataagct atgtcatcca gttgcatgct catcgatttc atccgtgtca cgtaagtgta  22440
tttcaatctg acaatcattg cgtagcaaag tcctgctaac caagactctg atttatctgc  22500
ggaatccttg aacaagttgt ttatgatgtc acatatgaac aattcaggat cggactgact  22560
atgttccatg atatgtgttt tatcatgatc cacgtaaaat tcgaatccgt ctgtcaaatc  22620
atttgtccaa ctacctacag gaatagcatc aaaattgcac gcatggacaa tttgtttgac  22680
catacctttt tcaatcctcg ggtccaattc tggtaatatc attgtagtca ggatgaagat  22740
tttttttaaa ttctcaaagg acttgtcaaa agtgtacaga tccttcacaa aatcatcaca  22800
tgattctact cggagcatca gccaattttc accattatct tcgagatctc tgaagaccgc  22860
tatctttctt gacacgtatc cgttgtttga aatcatgtag ttgttgattt gtttcttcat  22920
cccataaaga gacaccatga tgttgaatgc tgtcgtataa ggaacgtcct catcagagac  22980
aatgatcttc gttatggtac ataacgctgt gttttctgtt aagatcccgg tgtgaatgta  23040
ttttctataa gtacaaagta cgtccatgtt tagagatata tgatatcgtg gtaagatatc  23100
acactgattg tgtgttgaaa aaaataataa aaaatcattt ttcagacttc ataagttgat  23160
ttcgtgtcag tttgtgagtt tccatgtgtc gtctgttgta aaaatactta cattcttatg  23220
tctgagtccc atggctttat tgaacagtcg gtctgacaca tacaagaaag cccccatcag  23280
caaatccact gatgtgaaca agacaaattt gttgatgtct tcttccatga aagtcatatg  23340
atttatgtca ggaaggaaat cacagatttc cttcctgaat cttaaattaa atgtggtttc  23400
gagcaagtat atattataat acaacattgt tgtaaatatg ctggagtctg tcttacttat  23460
ggtaataaca tcagagttgt tcctttgtaa acaaggactt ttcatatgct tccatacttt  23520
acactctatt tgattattca cacatggttg tttctttgtc agttcgggat agagattgtt  23580
tttgaaagat tcaatagaat atgtcagaga ttttatgaat ccagatatta taaacaaatg  23640
ttctggatcg tcagattctt tgtttttaca aaattcgtcg accacaaaac aaaatgtttc  23700
cagaagagta tcaaatgatt cactgttgta cataaattcg acccgacatc gaatctcctc  23760
gatgtttttc atgtattcct cgtacccatt ttgtatgaaa catgttgaca tgattttatt  23820
ttccacttgt cctgtttcct tcacactact ggctttgatg atgacctcgt tgaaattgac  23880
caaagtgtta aaatgatcaa tcacgtaatc catacatctg actcccatga tggttttaca  23940
agtttttaga ttgggcaaaa actgtaccat gtatccgatg tcatgaattc tactttcgtg  24000
taccgtgacg tacatggtca tattcccggt atctctattg gtaaacacat ttatcatccc  24060
accatttatg tcatcaaatg acattttgat tatgggacat ttttgatttt ctgaatgaat  24120
ctggtctttc caataactgt actcttcaat catgaataca acatcatgta tggtatgata  24180
ccagtcttct gtgaatggaa cattcatcaa ataatcattt ccgtatgttg ccacaaattg  24240
atttcttgat gtcaaataat ctgttgaatg atccaaattg tgtgtgatga cgtttctggt  24300
tgcgaccaca ctaccgtttg ctgttcgctt agacattgtg tcattactta tattattata  24360
aaaattcaat tacataaacc ctggtctaaa accatcagat gtaaaccacg tctgtccaat  24420
acaatccgat acccaatatg gatgatttcc aagagttttt aaaagagaac gccaaagttt  24480
cttcataatc cccctgattc ctatgatgca tcggaatcat tatttttgat ttttgtttga  24540
tttgtctgga ccaggtattc cagttggtca ttgccatgaa aatggttcct tcgtattttt  24600
tcaatgttct ggaaaataat tcccattctt ctggagctcc tgttttatta tataccgaga  24660
tccgtttatt acaagaactt acgttggtaa atctccagtc tgctacccaa cataacggag  24720
ttttgttttc ataccacata tgaatcatac gtgcctgtcg atccggtatt gtcaatcctg  24780
```

-continued

```
gtatatgttt gtcaggttcc aatatacaat ccacgaccca tgtctttatg taccaggatt  24840
ttttacacag acgatgggca aatatacttg tccagacttt tgatgcacac gggatcaatg  24900
tccaatacaa tcttgtcata tttttgtgta tatcaaaata tatttcgtct gtgtccgttt  24960
ctgattttat ttctacctga tttttgtcat ggtttatttt gtaccatatt atatattttt  25020
taccatcgga tattatcaag attgattttt taccatgggc tgtagtgact tttacttctc  25080
ctgtggtcag accactgact tctccggcat gtaaataaga tttagaatgt cctatgttta  25140
tgtatttttc tggactggtt cctgttatgg tcactaccgt gtcacttgaa taatataaat  25200
cactgaccgg acattttatt tccgaaggaa gggtaaaatg tctcaagagt tccatgacgg  25260
aataagattt tttttatggt gtgatttttc tgtttatatt aatttcacca catttgcttt  25320
gttattttct tgttcgataa ataatttaat agttgacctg atcacgtcag atctatgttt  25380
ctcgtttata ctagaaagat aattacaata cacgtaacat aaattaacag attttgtcat  25440
gatcactatt tcatctattt ctttctttgg tacttttcgt ttgatcacga ccggaagtaa  25500
ttcctctatt gtcatgttgt ccagcttttt ttcctcgtta taataatagt ttctgttaat  25560
tattatactc cataaaaagt catatatttc tttgaattct ccttttttct catccggact  25620
tttcaacaac atgcctacat aaaaaaaata ttcttcttct tcctcggaaa gtacattttt  25680
taatttcaat gttatgtagg cctctcgtaa taaattaaat actatacttg cgtttagaaa  25740
accgatgtga ttgtttaaga aaaaccaagc ttttattatg aaatctcgcc aattatattt  25800
tatttcgaac gtgccgttca ctgcccgtgt gaaattataa tgatgtttta tcctgttaca  25860
aaaccaatgc tcgttaagat aattcaatag ctcattttcg tttcctggat aatctatgtt  25920
attatttgtg gtcacccagg taatttgttt ttttgaaatg ttcaatggtt cggtggtaaa  25980
atccattttt attatcaatg tcaccttttt gcttttatga tttattcata atttatggtt  26040
ttatgatttt ttcatcacaa ccgcgtacca aaaagaaaac atcaaaataa ccgtacggta  26100
aatacaatgt tgttgttttg tttaattttg acctaagggt caaagttatt gtttgatcgg  26160
tgcatatcaa tccgtacgta ccgtcagatt ttaacttgtt gtacaataat atttcgtggt  26220
ctatgagaga tttatgaaat cttactttta ccagactggt gtttttatac aacaccaggg  26280
acactacgtc atccatacat gatatatcgt attcgttgtt gtctgagata tctaagttta  26340
ttataataga catcatgaag tggcatgtta tggatcatgt cataatattt aattttttac  26400
aacatttgtt ctcctgtaaa caataaaaac caaaatactg acaaagatga aaaaaatcac  26460
caaggtaaca accaagatga tgataatggt cttacgtgaa atgtttttaa aaattcctga  26520
tgactttttg gtctctgtct catgataatt aaaatcatca gacaagtcat cagagaagtc  26580
atcagagaag tcatcagaga agtcatcaga ataatcatta tgaactcgtt cgcctgacgc  26640
gtcaggaata ttgttcatga acgtttcaaa tttcaacatg gactgatcac ttaaatactc  26700
gggaacggtt ttaccatcat ctacatgatt ggtcggtgtc actttattag tagaagtatc  26760
accacctgtt ctgtcatgaa ttatggtaga atatataatt tccctgtttt tgtttttaag  26820
aataccettt ggaagttgaa ccgttgtcat ttaatatgtc caaaaaacac tgtcattggc  26880
attttttta tttatgtctt gtttactcca gttatataaa tgcaaccagg aagtaccacc  26940
cagtggtttc cagtgtgatc caaaactttg atgtttacca gaaataacat ttacctgatc  27000
atggcctctt tcccatccta tgttttttaa atggtataat acctctttta aaaaatttgt  27060
ttttatgatg tacacgtaca aaacctttgt tttacttcca cgacgattca cagtgaatgg  27120
```

-continued aatggtggcg acatgtccat ttaatgtatt gtcgtacatg attttataaa aacacacgtc 27180
tggatatccg gacgagtcag gtagatgaat atcttctact aaccaattgt ttgaaatgtc 27240
cgttgatgtt atcatgtccg tgatagaatc tacctggatc agtcgtattt ttttatgtaa 27300 atttttttc ggtaccgggg tcagacacga cgtgaaatat gatttagact gactgacgtt 27360
gtctgtacac tttttagtac ttgtgtgtaa ccccaaccat ataccgttgt ttttagcata 27420
gcgggtaatt tcttcgatca tgtatccagc cattttttta cctctatgtt caaatgccac 27480
acataaaaaa tctatattaa acccccgaaa cggtaccgag tctatccaaa tggtttttat 27540
atttccagaa atggccccga tcaattttcc atcatatgaa atcccgatga aaacggtgga 27600
atctaaatta taccaataca gtaatgcctg atcagaataa acaacaagac agcttttatt 27660
tataccgtaa ttatttttaa tgaggttttt ccaatcatca aataaaacgt gttcgaccca 27720
ggagtaacca ttatttaatt ttttcggaca agattcatca gtgacaatgt cagatataat 27780
aagtttagaa tcagggacct gttttggtgg aacaaaaaac gaacgccaaa aactcattta 27840
atcatgtcat gttattttag gaacaaatga aataccatac tcgtacggat cggtgaggaa 27900
ataaaaaagc cattctttgg cagtgcctat ttttgtaaaa aaatcggtta atattttttt 27960
acagttacta ccggagggaa cattcatttg aattatcagg gtcccacatg atttaataaa 28020
aatactatta aaatgataca accacaacaa caactcgtct tcgtcgacgg catgaatcca 28080
tatttcagtc aatgacccga acatgtggtc aggaatgtcc aggactgttt tcccggtgaa 28140
tttccagtaa tgaatcatac gtcccctttc ttcttgtaat ttccaataaa catgattgaa 28200
cccggtcatg taatttatcg gttttaacaa tctgttactt atgtttttat tacatactat 28260
ggcgttttta ctggcacata ctaacatggc tttttttgac gtgtcccatt gggataattc 28320
tttttgtatt aaagtcccac cggattctcc ttttttagac gaacatcgtt ttaacatgtc 28380
aagtagtatt ttttttaaaa cgtcaactcc catctgtaca ctaatgtcgt ttaaaaggtc 28440
agccatttat gtgttaatat attaatatag aaaaagtata taaagaagta agttacgtcc 28500
acttaaaaaa aatggatgaa atcgtgaaca cgttcaatga ttatgtgcgc aaaatcaaca 28560
aggccactga tgatcctaaa ggtatgtata ccttgagttt taaggatttt tcagatgaca 28620
tgctaaggta catctcgagt ctggaatgtg acatctgtgg gatgacagac atcaggattc 28680
attcttgtgg attctgtaaa aagatttact gtagtgattg ttcagaaatg ttcaacaagg 28740
taaataaaac ggtatgtatg tgtcctagta aagacactgt ccaatggtct gtttttttcac 28800 acatgggcaa ttacatccag aaccctgaga atccgcagat tgacatcact gacatcgatc 28860
aaattatcaa aaacaaaaac aaactggaat ttattgtgga cactgacagt cttgtggaca 28920
tctcaaaaaa cactgttgat tcactactga atcaacatat cggaggattc actcacacca 28980
gattccatga atacactgcg agaatgtctc tggagttgtt gagttgtata gagaaacgag 29040
ctgatctgaa tcgggtctac attcaacaaa agcatatcct tacatctctt gacgaacaga 29100
acattctcca actgattgac atctggcatc ccaacaacat tgagaaatat tctcaacaac 29160
cgtccgggat catatcaatg gaacactttg tgacattcta caaatccaac ttctctgtca 29220
ctgaacgtaa tgcaatttac caatactaca caggaaacaa gacagaggaa actaccgaga 29280
tcacaaaaat gtacgtccgg aaaatcattg attacatcgg accagagaac atcttggcat 29340
gtatcctgga cattgaacaa ttgttctcag agtgtatata tgaaatctcg tacctcctgg 29400
acgaatgtat caacgtcgaa gtctcagatc tgaaaacatc ctcggtcaac atcattggaa 29460
ttccatgtcc ggaaccgaac tgtgtcaagg gaatcgtgga cgtcatcaca aagaagtgtg 29520

-continued

```
tggaatgtgg atctcatttc tgtaccaagt gtaacacaaa actcttggtc aataaaccga  29580
caaaccacca cagcatgtat ggtaagatac tcgacgaact gatgtattct tacaatccag  29640
aatgtagaca catacgatca agacaagagt tttacaacat ggcaaacaca aaagaaaaaa  29700
agcaattcat tatcaaccat ggaatactga agtatttcag tgacacttca aatttccaga  29760
ccatactcaa cgaacgctct atgatcacac acaatctgat gttgtcgtct cagaccctca  29820
agaacatctc tcgagaacta caggaactag actacagagt aggaaaagac atcaaggtaa  29880
agatttctga aactgtcagt gctgtcaaga aaaacccgat ctactgcccg aatgtcttga  29940
cacggttgtt tgattttccg aaagaaaacg gaccagacaa cgacgcagaa aacgtcataa  30000
acgaacatgt gtgcattcca aagaacgtac cagaaggaaa caacatcatg ataagaaaat  30060
gtccgatgtg tgctgtgaac atatccaaag tagaaaacac atgtgacgtc atgttctgta  30120
ttaattgtaa tacaaaattc aactggctga ccggagatgt cggggtcggt ggtgaaaaca  30180
gagaactgac cgattacatg aaacaactga caaacaacaa gatcaaggta cagctgactc  30240
ttgattatgg agatttcacc atttttgatg acctgatccc cctgagcttt tttgagcaca  30300
gaatcgacac agacctcttc aagattgtac tgtttggtca gatctcagat gtgttcagtc  30360
cgaggatcaa agaagtaatg aacgattttc tcagaaaact tgaaaaaatt gcgatcgaag  30420
cctacaggca cctgaacaag tcatcgtacg aacatcattc agacatcggg tattttaaca  30480
aaatcaaata catacctgtc gacaccatcc aaagctacaa cactttcgtt caggacgaat  30540
ataaaaaaat cttgtacaaa tctcttctcc aagaagtcaa cctgatcttc ttcttcttgc  30600
acagatggat agtgtacgtg atgaataatc cagactctat cgtttgcata gagcaagtca  30660
atgaccaact tgtgaagttc atcacaccca gatttccagg atttattctg gcattgaatc  30720
acacgatctc aaaagcacaa atgttcattt aatcatcgat gtccagatcg attgtcatag  30780
gaagcttctt tgacttctta gtaggagtct tttcggtggt ggtctttgta ggagtctttg  30840
ccttcttggt caccttcttt tcagtggtct tcttcacacc ctttgccttg gcccctccgg  30900
cctcatctgt atttttatta gtcatgtcaa atgtcacagt ttttgtattt acccgtccct  30960
ttgtcgtggc agtactcttg tgtgccagga ccctggttcc tccgggactg tctgctacat  31020
tcagataaac agagtcctcg gtactcttgt taggtcgacc gatcttcttg ggcagtggct  31080
tcagtagttg cttgaccttc tttccaccca tgggatccac gacatctggc tgacttgtgg  31140
ctgccttgtt gttcttgatc tctgtggaaa gctctgaacg accctgcttg ttaccttcct  31200
tgaccccctc gttcctcaca tgtgcgagtt gatcctgaag catggccgta aaattttctg  31260
tgtacatcgc gaccatattc tggatatcat ctctgcttga attttcctta catagtaccc  31320
tggcaatttt attgacaaag gtcccggccg caacgtctgt cttcaatttt gttttacatg  31380
tgttgaacat ggaatacgcc ttcccgatat caatttccat ttataataaa aaattatctc  31440
caaatatcaa aaattttact tcgtactttt tcatcagttt ttgatatgtt ataaagggtc  31500
agtacataat atgcaaaata tgtttttgaa aaagtcaatt ccgaaagaat tgtttttttt  31560
gtcaaatcca caagacctga tccaaacacc aatttcattt ctttcatcag gattataaaa  31620
ggattgtttt tctcttcgtt ctgttgtaaa aactcattcc atatcttcat caatatttca  31680
atcgaaatat tgttccagta atataaaaaa tatctactca acaaacgatc cttgtttaat  31740
atagcatatg tttcaggaag aggtaaataa ttaaactttg atctgttcgg tcttgatata  31800
ttcaaatcta ttaacttccc agtttttgta tctgctgtgt tcacaatata aaatatttca  31860
```

-continued

```
gtgaaaagaa tatttaatat ttctgtcatg ttcggatgag ttcgtaacca acatgcgaat  31920
atcttgacat tgatattgtc agaggacatc atttcttcag taaattccaa aagataatca  31980
tattgagact ttttggtttc acaatacaca gtgaataaac tacttgttat ctgatcttgt  32040
aaagactcta aggttgacgg tatgagtggt ttatttccta cagttttcca tgcccctgta  32100
tcatgtaaaa aattagataa aaatgattta gataaaaagt gattcacggt caggaccgtg  32160
tttattttac taggtgtccc ataatataat aaatcaggat gttctgtgtt tatgtccacg  32220
acatcctcgg tagtgttctg tgttgacaac atagagtgta tactgtcgaa cacattcata  32280
aaattaatac taatatattc gtccatttac atgaactctt gaaattaaac cttccaccaa  32340
aatcctacgt ccgcacacat tatgttgtta gaatcaggat gatatttcac acttttgagc  32400
aagacaccgt gcaccaggtt catgtccgga caatcatcgt ccaagaacca atctctctgt  32460
atgtcagata ttttaatttc cggatatttt acagacatgt ctgcgagtgt ctgtttgatt  32520
ttccatttca tctcgtcagt gatgggctgt ctgtatttga gatcatacat ctcaaagaca  32580
tctatgtctg tggtcagtga cttgtctttg acaagagtca tcagtatgtt tatcaacttg  32640
ttcacttcct tatcttttgt gaagtcgtag acaaaagaac tcagatcatt tggtaagaat  32700
aatctcctga tcggtttctt gttcaggata ctattttcca acgattgtcc catggtcatg  32760
tgatcaggtg ttcggattcc gaacactgtc tcctggtctc tgatgtacac agcaggtcgg  32820
agagaatgaa gaatgatata attatcttgg atggtcttgg agaactggac tttttgtatg  32880
atagaatatg cctgagatcc agagatgtag accagttcat tgttgagatc tctggtctgt  32940
gcacacagta ttaccatctc gatggtatgc gtcatcttca taggataata cgtcgagatt  33000
atcacatgtg ccgaagatgg tctttcccct ctgtaataca cagacttctt tccatttgat  33060
gacacgtcat acactgtcat ggtcttgacc aatgtctgga taagaaaatt actcaaggcc  33120
ggatctccgg tgatgatcag aataggacaa ttcttcttga ctgttgtcat gatgtcaaga  33180
aatttcatta gacttctctt gatgtcgtag gtttcctcct gagacgtttt tcgtgtacat  33240
acgtaatggt tcgttttcca atcattgggt ttgacgactt cgatctggca ggtctcggga  33300
aaattcagtg tctctggatt ttcataaatg taaactacca ctcgtttgcc ggttatccag  33360
tggttgagat tcttgagcaa gaatagattt tctgctcttg cgtttttgac gaaaatctgt  33420
aagtgttctg ttttttgttt tctgatggaa attactgtgt tgatccaggt cctgatgtca  33480
tcactcagta tgtacgtctc cacatgtggc tccatcgatt cactgacatg taccatgtat  33540
ttctgaagag tgactgcttg tacacatgag agtttttctg tatttcctaa caacacgtac  33600
ttgatggtgc ctggttggat cgttttcatg atatattcca tatggtttct gaaattacat  33660
tcccccaatg ttttcttgag acaaatggtc gtctgatttg ccggtgtcgt tttcgggttt  33720
aatttgtcat tgatcagttc atcgcttgtc acagagaaat gcaacatgtt gaaaagagga  33780
tgagagatcg gaagttcgcg aattaaaatg tttgaaatta tcattttaaa catttctgga  33840
agatcggcta tagaggtcga gaatggaagg attatcatat tttccgtgat agatttaatt  33900
ttcccgaggt tgacattatg tgtcactgca ttgatcagtt gagaacggac tgttgcatga  33960
cttggattgt acgttgtcat gtcgtggtca tctgtcagta actcaagaaa gttgttgatg  34020
ttggtgatca aatccgaaag aataggtcgc ttacaaccca atctactaca agtgtcatgg  34080
tctttgcata aatcactctc agggatacac ggagtatact cgaatcttct ggaaaaatca  34140
gatccccacc ctagtgatgc aatagattcc attatacctt tactatttga gagatttgaa  34200
gttattttat attgttattt ttcattttaa aaaaagatga acatgacatt taaaaaatgt  34260
```

```
cattctatgt catacgtacc gaaagtacta aaatatctgt aatcactttc gtacaagttt  34320
tgatcagcca ggtcattgac aggaatgtaa tacggcaaga catcacgttt ttgatcacat  34380
ctgaatctac gaaaacatgc acatgccaaa caatagatga tggtcacaca gcacaacgga  34440
atgactatca tgaaaagtgc agacatgatt atatgttata aaaatattta tttttattc  34500
atttaattta tttccatagg ttccggttcc ggttcggttg accttatttc ctttgtgaaa  34560
aagatacatt ttgtgaaggg cccttctggt aatgtctgtt tttttggttt tttattttca  34620
ctgatcaccg gatgttcagg ctctgccaca ctaggatcag tggtcactga taccttctgt  34680
ttcttttttt taggaacatg tataaaacta gatttgttca caggtatctt attagccatg  34740
tcgtgtatcc gagacattat tccattcaac ccatttttag tgtcgtacaa atcacccgac  34800
atcctcggat attgaattat tttcttcatt atgttttttt tcttttcgtg aaacgtacca  34860
tttatgtaaa aagaacattc cccctacaga taacatgaca caacatgtac ctaccaagac  34920
catgtacatt ataaattgtg tggaaatcac atgtattttg tatttttaa aaatcacaat  34980
cttccactgc cattgccata tgacagaaag tcgagccgca cataaataat caccggtgtc  35040
tgatattttt aacttgtgta tcataagact catgtctcca ggacctcctg tttgttgatt  35100
tttaaacaca attctgtgtc tgtcgttttg atctttatca taataaaagt ttttattata  35160
agaaacaatg tcacattgat ttgtctgtaa tgacccgtta cagtcttttg tccaaaactt  35220
tacagtttct ctcacatatg tcccttcttc atcctgaaaa catggtaatt ctatatctgt  35280
gttttcaaat accgtcacat gtacgtaatc atctgatgaa accctacata gtaccacaag  35340
taatcccgtt aaaaaaaaaa tcatctatgg cgctaaacaa agggatttaa taatattatt  35400
aaataaatat ctgaagtatc tttctactat acgttctacc gtaagctgta ctatgactaa  35460
agtgattatt accaaaccca tactaaagag aatccataga aataaaagta atgtattata  35520
aaacatgatg atattttata aacaaaacag atgttttgtt tatattttta atatattttc  35580
aattacataa acgaattctt caacactcca ggatgtacct taccacactt tgaccacgga  35640
tgacgaccta ggacctcctt ttctgattta aaaatgtccc acatgtatct gagaaacgcg  35700
tcatagaacc aaaattgtac ataatgaaca gtgtccggat gatatcctga aaactggaaa  35760
ctattctttt ctacgaggtc agttatgtcc agttggtgtt tgtatgtttt ccaacaatga  35820
tcaagtaatt cttttatgtt actttcttga tcattgccga atacctcatc tttacacaat  35880
tcaaagtttt ttccacctgt caattcaatt gtttccgtag aaccacagct caataacgta  35940
ttacgcaagt aatccatcgt agatcaatat catattatta tctttatttt tttgttttca  36000
taataaaccc actggacaac atggtttatt tatatatgta ataaacatgt tccgtgataa  36060
ccatgttctg taataaacat gttctgtaat aaacgtatga tatacataaa tggaaacgac  36120
taaaaacacg gaatggatca actttgtcat gtccgaacaa aatatccttg aacctccttt  36180
tcatgatatt catcaagaat ggttcaggtt atggtattca gtgtttcttg gttatttgaa  36240
ttttagttac tgtaattctg tcataaaaat aaaaaaagaa tttattaaaa aagccatgtt  36300
ggcaattaat ggtatagaaa ccatacaata taattatcat cataagaaaa acgaaaatgc  36360
ctttcctcag ttgatacata catacaccaa acagatacta tttaaagatt ctatgatgag  36420
cgaatcatta atgaaagaat taaatattac atcagacata atagaaaaat acacaaaaga  36480
agatctgttt ctgtcaccta cgtacgttct cgtttttata ataaatagat tttttaacaa  36540
cacaggtggg ttttttaatt ttttaactca ttgtaaatgg catatgaatt agatgtcctt  36600
```

-continued aggaaaatgc ctacagaaac attattgagt tttgtggacg taattaatca agatagtttt 36660
attatattca cagatacatg tatgttaaga accatggtaa tgctatctga aaatgtaacc 36720
gacgaaactg aaataattta tttacaactt gttgcagcat ggagtgagag acctgattgg 36780
tttgtaaaaa aatacaaaga tttctttcat aatcctttgg ataaataatg gaatattcca 36840
ttctaagaag tttaggacat ggatattttg gtaaagtctt gttagtaaag gacaaggaaa 36900
ataaaaactt tgctgtaaaa atacaggcaa aaggaagtac gtacagagaa attcatagac 36960
tggaacaaga ggccaacata atgaagaatc tagatcatca ttttattata aaggggtatg 37020
atttcaagta cgtgaatgac agagcatgga tagtcatgga atatattctg ggtaaaaact 37080
tatttgagat catgcaaaaa atggtggtct gtccatttga actgtccagg ttttatttgg 37140
ctgaactagg catggccctg gattatctac atagtaataa aattatatac agagacctga 37200
agcctgataa tattttgatt aatataaacg gtcatgtgaa ggtcacggac tttggtttga 37260
gtaaatattt ggatacggaa accacgttag gattcagtat atgtggaaca cttgaatata 37320
ttgctcctga aatattaact ggtgtaggat atggattttc tgcagattgg tggtcgtatg 37380
ctgttttagc atatgaactg gtcaccggtg tcgttcccat aactgttccg gataaactca 37440
gtcttaaaca aactcttaaa caatcggtta ttaaatttcc ggaatttctt cctgtggtga 37500
taatgaattt tttgacaaaa tgtcttgtaa ggaatcctat cggacgtccg gagtttaatg 37560
aaataaaaaa aatgaagtgg atgtcagaga tagattttga caatttaagt cttgacaccc 37620
cacctccgtt gaatccgtat acgttataca gatgtggtaa gcaactaata aagttgtaaa 37680
tctaattctt tgacaatgtc ttgtctaaat tgagagtaca taaatgtatc ttgaacaagg 37740
agttcaccga acggaagttg ttccaatatg gttttcacta gtttttcctt ggtgatccct 37800
gccgttattt tatcatgggt catgaggtat ctgtcaatgt ttgccaaaaa caaataattg 37860
acatacgtcg acaaccagcc tattaataac attaatgttt ttttatttct cggagacgtg 37920
accttatgtt ccaaagatat ttttccgatg acagatctga atccgatctc aaaatctaaa 37980
tcagattcca gatcagttcc tttttttaac attttcaatt catttaaaaa catgtctaca 38040
tgtttatctt tgaacaaata aaaaatataa ttcaatacgt tatcacaggt ttccatgtat 38100
aaaaataaag atatttaaaa aagaactcac ctgtttaact ggtgatgtta attcccgtgg 38160
acccgaaacc tcctcgcttg atctctctac gatcaagttg ttcctcaacc acgctagaaa 38220
gtggaatacc ttgaatgctg atcctctcaa aagcaacgac ctgacaaaag gatgacccctc 38280
ttgggatgta taccttctta tcaccgatgt ttgtgagcat gatactcaca atattttcat 38340
aatcaggatc aatgataggg aaatttccca tgacaatgtt atgcttaaga gcatgactcc 38400
tcaggacaac tgtgaaccag tatctgttgg aatccagaat gatacttaca cccagagaaa 38460
tccatacact cttccttggt ggaatcataa ctgatgattg attgaacaca atgtccattc 38520
ctacactaaa gggtgttcct gttctgaaca tgttcattct attggacttt ggtccgatga 38580
tatgagcgtt cactgtttta acaatctcgt tccctgaata ttttttctgt aggacatttg 38640
tcaaataagt tttctctgat ttcatgtgct tctcctcttg ttgattatta taatcatatt 38700
catcagtgga atcatactct gactcttgct ctgactcaga gtcgtttgtg acaaatttat 38760
ttggggtatt ttcaatgatc tcatacggag aatcagaatc tgaatcagat tctgagtcgc 38820
tttgttcagg agtataataa ttaaggtcgg tctcttgaac aaggtctgtg agatgaacaa 38880
ggtctggtct ctcaactact gtcgtggccc aaggagtctt tgaccaaata taatctacga 38940
tgctataata catcatcatg acagtgtatg aaatcaagaa aatatttagc tgtacaacga 39000
cataaataca aaagttcgta ctacgtagaa tatccaactc tctgaagaaa atcaaaagag 39060
gttctaggaa atcagtatga attctgtcag gagtgtacat gttaagataa tccattgtat 39120
tttagttttt ttgatatgta atctattaag ttaatatctg tttttgtcag aggtcgagtt 39180
tctttataac tataagttcc gtcggatcgt actagtttta aaatagtatc acttaatcta 39240
caagacaaag aaatgttaaa agattcccca aaataagttg ttattatact ttttttaaat 39300
atattttcag ttatgtatgt cacgaataat tcgttcaaaa gttcaggagt tatcatgtca 39360
tgtcgtttga gtttcttcca tgtattttta aaaactatgg tacttatccg ttcatgagtg 39420
ggatgatcag tttttgtgat gtcaagaagg agctctgaat attcaggtat ggatctcaac 39480
atcgtgtccc aataaaatgt taacgttttt ggacatgatg tctggacatc tttcatccaa 39540
tacgtcacat aattgtccaa caatctattg accgggcacc ataaaaaatc taaattttga 39600
aaatcagtgt cttcatgatc caggacctct tgatgatttt ttaaaaataa atcagaccgt 39660
cctaataaag acatatttaa ttatttaatt atttatttga acaggtcatc caataataaa 39720
tagaatagaa attatgtcga tggtcgactg atttactcaa tgtttcataa aacgtttggt 39780
catgaaatat ttctgtgttg tttgttttct ttttgtaaac gataaaaaca ttttttaatt 39840
tgtttgttac attttgtatt tgtactggtc tggtatcatc ggttctgtaa tacactgggt 39900
agtctgaaaa aatactgatc atcaattgtg ttttattatg ttctgatata tcttctgtca 39960
attcgtgtcc gaacaagttt tttaataaat caaatttctg atcgtacacg gtgtcactta 40020
tgaaatccat tatgctaaat tttttcttta agatcatgaa cttgtctgat gtgctatcat 40080
aatttttctc gtatacttta atcagttgat tcatttctgt cactgccaac gttctaaaat 40140
atgtgttcca tacataagac atctttaagt attatttatt gtttttatat tttttaaatg 40200
aaggatcatg aggatttaaa tattatcacg gttgctttaa tgagtaaaaa tataattaaa 40260
aaacttttat tattattaat atttgtgata atttgttgga taattttcat tatttggctt 40320
atcgtatcta ctaaaaaaac attaaaacat aatggctgag tcactcaatc aagagtcgag 40380
tcaatatctc atgaatagaa tcgatgcttt caagagaatt ttcgcatcga catcaacttc 40440
tgtcattgac atgacagcaa cttctgtcaa gaacatcatg tcaacagcac acttcttcgc 40500
agatggactt gcttatgtgt acgagaacac atgtagatct attgatatca caaatggaaa 40560
ggctgaccca gcggatttcc catcatcacg tgatgagtct ccgatgcctc cgagacaggc 40620
acgtatgcaa cagtttttga gtaaatttct taatgattat agtgtaccac tcagtggact 40680
tgtcctattg tctgcgtatt atgtcctgac caccactcaa gaaaatttcc atgagcaggc 40740
ctctcttagg gccagggcct ctgctagagc agccgagtcc gatccagagg gtgatggtga 40800
ggctgaggtc ttggccgagc cagaggagta tgtccccaca gaaagcgttc agacggaaga 40860
ttgtccctgt tgtactccct gaacattttt ttacatttca ccggtgtcgt cgaacatgaa 40920
cgagaacgca tcgtacattt cactgtttat aaacaccgtg ttctcagagg aatgattttt 40980
taatctactg atcattgtca aggtcgttga cgcgtcatct gcttcgagta atgtcctggc 41040
ttgaattaat ctatctcggt ctgtttttgc cacatgagat gagaaatacg agatctggga 41100
tctcggagga aaatttcttt ccttgattct ctctgctgcg tatctaaatt tactactgtg 41160
tggttcaatg atcatggagt gatcatcact cttggtcgtt ttcatgacaa tgtcaacgtc 41220
catctctgtg tcttccatgt ccttgagatt gagcaacaag ttcggctccc tgttctctat 41280
gtaagtaaac aatccgaact tgacaagaag catggtcagg ggtatcagtt tatactccct 41340

-continued

```
tttggtcttg gacaagcaac aaagtgtgga acctaacgtg gacagaaatc tgtttttggg  41400
agatttctcc catggatgtt tgtactttac gtcgattctt gacgtaggac tcagatacac  41460
caatgaattc aattcatcga tattgtcgac aaaagagatg tcaagagtcg acccggtcct  41520
aatttctgtg tcgttgttat tataatagaa attgagaggg ggagcgtctt gatattcaaa  41580
tgtcttgacc tttgacactt tcacaaatcc gacattggac gtcatttccg ggcccatctt  41640
tttatgtaac atgtacattg tcaacgggtt gtatgtcgaa acacacaact ctttcacggc  41700
gtaacgaagc cattgtaaaa gaggatcaaa cgggtgcggg tccatgacat ggtcaagaac  41760
cggtgttttt tccaatacca gtgtagggat ctcacacatg atatttttat acggagactc  41820
gtccgaaatt tgatttaatg ccaaagactc atctgtggag tcagacgata tccaactcat  41880
gtattttgat gtctctgtct gtatggaagt tttatgcacg agtctgggta ctacggaaac  41940
gaattttgat agggacacat tgtgtatttc cgtcacgtgt gtaaacatgg ttaatacgta  42000
tgtatatcag tacggacaat tgttttttta gattattttt ctattccaag tggacacaca  42060
ttatacgggc atgtgatcat tgcgacgtca ttttctattg tcacaggaag atgacaatag  42120
tggtcctcta ctgttgaact tttcgcacag aaacgtatga acagacacag ttgcttgaga  42180
ggactttgaa taaacggttt catcggtcct gaattttctg ctcgctgggc tgccattttc  42240
atgaactctg accagtttga aatgtaaggt actgctttgt cgtacacaga caacggaaca  42300
agaggaggga gtttgtttct tgattctgaa ctaccgtatt cgacgtatct gaacaggatt  42360
gtcttggtct cctcacatgt ttttaatttt acgacaaagt gcgcttgact tttgtcgtcg  42420
ttgacggcca tgattttact ctccagtcca ctgttacacg agcttatgac acggttcaag  42480
acgtccagtt gtttttccag tgttttgtag tttatggcgt caccgagcat cgaattgaaa  42540
actgtcccgt tttctggata cagtaacttg aagtaaaacg tcaacaggtt catggaaaca  42600
tttttacccc agagaagata tttgatagaa agtttctcta tcacttcgtc tgtcaaatca  42660
tcaaaatcaa aaaatacgtt tctcgggggc accggattcc gtagactgtc tgtgtctgga  42720
tatattcctg atataaacaa ggtgtgtctg atatcattat ttattccgta ggtgtttccg  42780
ttgcctgaat aaattatcag ttggaaacat tccaactgat attttcgtag cgaaaccgga  42840
ttgtttgttg ctaccacgat aagtatcata tcatacttgt ttttactggt gtccagtaaa  42900
tacaagttgt cataaatgtc agtcacccac agaactaatg tttccatgct taactagaga  42960
agttccttcc gattttatta aatttcagtt ttttccattc aggatgttct gtgtcaaaga  43020
aatatgcagg aatggtccag gcaggaaagg cattacattt caccagatca gccggtgaaa  43080
tgtataatcc aaacaatctc atagccgggg caatgttgta attgataatc ttggaaagag  43140
ccggggccat tctactggtt ttttcttcat atgttccacc ggtcaccgga gcagtaccga  43200
gggcgtacgg aatctgatat tccctgaaaa tttgccaacc aaattcaaga cataaggcca  43260
cccagaaatc tctccaccac tgaccatttg tgtttttgtc catggtagtc agcggatcct  43320
ttgcaaaatt gtttttggcg tctgtccatg tataaggaat attccttatg taaccagaat  43380
catgcctgaa ttcaaacttc ttttctgtgt cacctctggc actgaagaac attgaataaa  43440
tattattact ttgttctgtc cccataggta agagatccca tgagcccatt tggtgattat  43500
ggcccacttc gtgataccat ccccaattac ttttattata ataaaagtcc cataaaagag  43560
ctcctccatc atgggctgat gcccatggat acccggcatg tagccaacca ttactgattg  43620
cgtaatcaga ttgagcaaat tgatgggctg gtccggtcct ctcatgtcct gacaaccatg  43680
aataatcttc gatgatgtca tccacgcgtt tttcaatatc tggtaaaacc agtttaagat  43740
```

```
ctccaggaag acccgccagg aatcttgacg gtcccacaaa gctatggtgc cttgattcta  43800
ttagcatgga aattgggtat ttggtactgt ctttccttac attttccaat agatcataca  43860
ttgcaggttt ttctgcgtcc gaacacctat gagaatagaa cgcatgagga caaacgttgg  43920
tacacgttat tttaaatgtt ccgtctgtgt taaatacctc acgtatactg aatgccaata  43980
caccggcatg agcatattta aacgtgatag atgtttgtcc ggcggctatg atgtattctc  44040
tcctatgatt tctatgatct ctacgtagat ttcttgtggt aggttccaga tatagattgt  44100
cccaagacat ggacgcgtat attctcatgt ctgtagtaaa tgttttactg atggtcacgg  44160
tatgttctgt tccagggagt agccacattc ctgttccatt aatctgacca ggacaatcat  44220
acacttttgt gggtttccaa gtgattgtcc tgggtgttac gttttcattt gtgtccagac  44280
tgatgaaccg gtcttttacg gattggtcat aataccataa attcttgtac agtacgtact  44340
gaatgacttc tgctgtcata ggaatgttaa aatctccaaa attagtgacc ttgttgacca  44400
attccacaga gttctgtgtc ttgataaaag atttccaatt gttaaaacga taacttttac  44460
aatgttcgaa tgcccattga atcaggatct cccatataaa aataacttta gacggaaaat  44520
atttatctgc gaacactttt gttccggtaa gggtataaat atccatacaa gaatttacac  44580
tgatcggatc agatgttgtg gtaatgacag gatttttcagg agccgctatg aatcctagtc  44640
tttcaaatgc tccagtagtg gatctaccga cagccggttc ccaccagttt cctgacacgt  44700
taaaaaccat cacgttcccc tcggcaatga acattgcatc gtcgtcgact tcgttttctc  44760
ctacgagata cgtgaccctt ctgtaattaa tttttttttg attcggggta cctagttcgt  44820
tcaggtcaga cagagcggtc atgacatcca aagaatacat cttggaaata ttttgtaaca  44880
acgtaaggaa aaagtcggac gtaccagaat tgtataatcc agagacagca ataaagagtc  44940
cctttccgta ccgaccgatc aatacgttac tgtttgccga attaaacccg tagacgtatt  45000
gacctaccgg aatcaacaca ggaccgaccc cgcagttaat ttcaatttga ccattaagtt  45060
tgggaagtgt caatgacatg tcctctagtt ttttaatgtc aggatttctg taagattgta  45120
gaagaggaaa ttcaaaagtg ttgctcttta ccaggagttt tcttgaattg acctccaaca  45180
tgtttaccga aaaaaatcca aggattccaa tattggaatt tataggatcc gtgatgtaat  45240
caaccttatt gtacttgttt attttatgca tcttgacctc acttgtcatt ccgtataaat  45300
tcacgttagg gtgtcttgca cttatgtcat tagaaattat caaaattact tcatctagtt  45360
tttttaccca gaaacagaat gaagtcttgg accaagagtt gatcaatgaa agaggtagta  45420
tcaaaagagt ttttttagca atggattctg tgggcttaca tgtcttgaga agtttccatg  45480
tcgttatgta tccgaccttt ccacacattt tcaacatttc ctcgtagtac acgtaagccg  45540
gccaatatcc tacaaaagta gttttattaa gaggcttgat acctccataa atatgaccat  45600
tagctgtaaa caaccatggg tctaattctc ctatgttaca cgtgacagga tttatactgt  45660
cgttcattta ttgaatgcga gtttacatcc cataccgaca aaaaacagca gtaaaaaaaa  45720
caaaaaagta gatattccgg ccacactccc gataaggaaa ttatcaaaca ttggagaatt  45780
tttaatttta tccacgttgt gaatcagttt gaaatatttt gtaaaatcag atattagttc  45840
tgttgtataa tacggattcc ccggtagcct gttcatcctg aacaaggtca taccatcttc  45900
cttgacagta gactccgttc ctgagtttga aaacactgaa atatttagat tttgtgtttt  45960
ggtcccggga tacaattttg taaaatcttg gatcatggta ttacacagag gctttaaatt  46020
tggataatta ataatatcat tgtcaaaaat caagattcct gacaagttcc agtttcctg   46080
```

-continued

```
tgtttcagat accttttca atccgttcaa tactatgttc catgggtacg tcgaaagttt  46140
aggagagacc ggcatggtag ttgatatgtc aattataata gttccacctt tgatattttc  46200
gtttaaaata tttcctagtt cccatgaaaa attgacgtct ggtattccac ttgaattata  46260
tgggaacaca gagtcttttg aaaaaaacgg gaatagtttc aagatcgtgt cactgtcagg  46320
gttatattgt aacaaatctt tctgttctgt tctaaacatt ttaactgtcc cctgggatat  46380
tacccagggt gcttttccta tcaatacata aacatttgtc atttatactt tttaataatt  46440
tgtaatacga tcaatataac aaagacaaga agcaaacatc ccagagacac tttcttgatt  46500
attggtttaa ttttttgatc tatgtatatt tttcttttaa tgatttctat ggcgtgttcc  46560
gattcctcga tggtcggcat ttataaaacc aaataaaata aatataacaa gagttttgtg  46620
taaaaattaa aaaaattatt ttgaaggaat catatgggtt ctgacagagg cctgactggt  46680
agtcacctca tcaaacaaga ccgcacctgt tgcggtaacg accttcagac gagttcctgg  46740
aatacgtgtg acccaagcag aattaccata gaccacgatt gaggccacct tgggaatagg  46800
tgtgccaaat ttaactgtga ggaattggcc tgggctgtct gtggcagagt gaaactcacg  46860
atacgcacca ccgtctgtct tcattatatg ttcgggtccg gcattatccc aaagtccctt  46920
gaactcaaat gtgtaagtag atttgttatt aagaacagca ccgttggcgt ccaacagaac  46980
gatcttcacg atctcaatga taccggtatc ctttgaaaac tcgagtcgtg aaaccatagg  47040
tccataaata agtgtgctga acttgtttga caaggccttg aactttccgt ctttgtatgc  47100
cttgtacaca agggcgattc cgacaacaag gataataaac ccgatagttg ctcctacacc  47160
tgcaacaata gttttggtct ttgcgtccat ttaataggaa taaaagatgg aaatattgtt  47220
gaaaagtttc aatatgaata ttatcatatt ataaaaaaaa ttgcattatt ttttaaccga  47280
gatcagagtt taagatatga gaaaccccat gtctttttg tacattaaac aaacgaaaat  47340
tcttgatttg tgtcgtatag ttgggtctcg tcattacctt ctaacaacat ggacaaaaaa  47400
tctttttttg tcaccagaga agaagatatt ttgaaaaagt ctatttttgg attcgaataa  47460
acggtacttc gggatcctgt gaaaataacg gtttttacga caggtgcgtt cagggattgt  47520
ttcatcagat ttttgataaa atcagaatga gtgtctatca atgtacttgt catgtcacag  47580
tacactgccc aagaatctat gttgacaagt gcgacgttct tgtccgtgag ttttcctaat  47640
acacaattca aaattctatc tttgttttta ggacttgtga tcattgttgt cataatggaa  47700
tgaaccacat gcatgaatat attgatgttg acatttgtca tttctgtgat gatgtcagtc  47760
agataatttt gatctacccc cttgcacaat tctaccatgt gtttaatttt aggagttgac  47820
atacagagct tcagattttt tttaaatgac ccagccatcc agttagggct gaccactgtc  47880
aagaagtgtg gaatcagaac atggccattt tcaacgtcta gtattgcctg aataatatta  47940
tttgaaatag aatcgtcaaa aactccaaag agagtgatgt caatgtcaac attttcccgt  48000
atgatggtcg ggagaagttc gaccatattc ttaaaattag gttcttttga caacgaggtc  48060
atgagagaat gtgctttgta aaaatacaac tctttcatga ggggtagttt tatgtaagac  48120
aatcccatta tctcattgta tgcattttcc caatcctgat gagacagtct ttctcggatt  48180
cttccgaact ttcccaattt ttgcatacca gaattctgtt gttcccacac aggttttttt  48240
ccattacttt cattaaaatg ttttctggac tcgtactgag gtgtgtccag tctaatgttc  48300
tgggatggaa taaagtgatt tcctacaact ccctctatct gacatcttcc tttgttttct  48360
accctgttga caactgctgt cccggtcagt acatattgaa gatttcctac cgtgattgtt  48420
aatgagtcca tttttcccg attctttaca agtcgttgaa taatttttat tttttttttt  48480
```

caatttacaa tcatatattg aattggaata atcatagttc catgtgaaca gacctctttg 48540
ttttctgttg tttggaatat catacgtgta ttcccccatt atttttttaa atagtccggt 48600
cactgaagga tcggtcatgg acacaagaaa aagatacagt agatttctct ctctttcttt 48660
taaccagtca aacccgaaca cgatcggtaa atgtatcaaa accaattcgt acattatgtc 48720
cgtatttaat aacacaccca tgatcacggt caccttattg gaataatacg acaatcccata 48780
aatatcaaat aatgttttcc atagatcatt tatggacccg atacgttttt tcacatgata 48840
catgcttttt attttacaaa tgtcaccagg tttaataaat ttattatata atgcgtcatt 48900
gattatcaac gtgacaataa tttttttcaaa aaaagtatca tggtacccta tgaaattatc 48960
aattttataa ccatgttttt taatagggtc atcagtaatt tggttatcaa attcaaaaat 49020
tcgtttattt tcaaaaataa attcccaaac agataaccaa ctaggttttg tagtttgttg 49080
ttgttctgat tccaatattt ttaggaagaa agccatttta ggactgagtt tcccgactgg 49140
ctggactgta tttttagaca tggtattttc tttgttttat caacgtattt aatatagttt 49200
ttttgtattc ttaaactatg atctcccaaa tgtgtgtgta atagtggtcc tccgattatt 49260
gttttattat tgtttttatc tatatattct attattagaa taacagattc tgttattcta 49320
tgtctgtatc ctgttatcac actgtccgtg tattcgatat atgattttag ttcgttgcat 49380
tttatttctt tcatgattat gttcaactga taagctgtca gttgattata ttcaatgtct 49440
tctatagaaa aaacatccag tacatagttt aaaaaaatcag actttaacat gtctacatga 49500
tgttgaggtc ctaccactcc tttgaaacaa attgtaggta caatgttatt atcaatctta 49560
cctttggtaa gagatactcc tttagatgaa taactggaaa aataatccat cccggaaaaa 49620
ttaaaatttt taaacgtgaa cggatattcc agatgaatag gactactcaa tctatctttc 49680
acaaaaatag tatcagattt acactctacg accccgaaat tttctccaca tattaattca 49740
cacaagtcaa cttggggaat gatgaaatgt ggaatgacgt cgaaagacct catgtctgtt 49800
ttcacaaatt tatctctgag cttatgtagg tccagtttga tccaatgatg acgagtttcc 49860
acgtgatcat ctttattaat cacatgttgg aatcctatga cagaactgat gtttgtttct 49920
tgagtgatca ccagatgaac gacgtacgtt aagttttctg taaagatata acgactcaat 49980
ccatgtaata ttaaaaattc gttttcgtta ctgtaaccta ccaaaaggtt accatcagaa 50040
tcattacgac ctgaaattaa ttgtttttga aagtctgtcc atggatcacc cttgagggct 50100
tttatagaac agtttaattc ttggtttggt tttataaaaa aacttgtcag gacacaatac 50160
atgattttat cacataactc tgacgatggt attaaattat tttgatcggt tatggtccac 50220
aagtcatacg ttatgtattt tttatcctgt cccatttaaa aaaattaaaa attaccagtg 50280
agcattgtat tcttagaaat agagacagat ctattttggc ttgaatctgc tggtttgggt 50340
gtgaaattca gaacgcctgt aattttcacc tctctggtga aaatattttc gatcctctcc 50400
attgtgaatt ctggaagagt aataaaatta ctgatgtttt caaaatcaga aaagtagtct 50460
ctgacgttgt cacaccactc gtacacactc ttcacatttg aaatatctac aggaatagga 50520
aacatttgtg ttgcccatcc ggaatatgtt gtcatgatag aattcacagt agagaaaata 50580
ctaccgtcaa gagaataccc gtcatttaga tatcgcagca ttatgttgta aatgtacaac 50640
aaatgaatca tgttgatagt ttcatctgcg atgttcattt caccaaatac tgagtagaac 50700
ggtgtatttg taataaaatt agcgtacaaa tttcccatgc cgtcatcgat agatctgaga 50760
tttcccgatg gtgtcttgaa aaacttgtct agttcacttg tataacttgt gaaagcagtg 50820

-continued

```
tacaaatact ccgtggtgta actggtgatc aagacatttc tacatgactt ccagaaataa  50880
tatagaattt ccatggtgga aaatttcttg atacgtagag aagacatcag tgtttccaac  50940
tgagtgagaa catgacctat cacgatgtta ggactcattt ttgtgatgat acacttgtaa  51000
aaatcagaaa tgagaatctt caattgatca gactttttttg agatatgagt agttatatgg  51060
tcgtttatgt gactaatcca ttcggacttt gatacagaat cgtccatgaa cgcattattt  51120
ccaataaact ccacacattc attccagatg tccatgatct ttggtacaga cttgattctt  51180
gtaagataaa cagtgatagt gtttagaatc ttgatttcca aactacctct ggtagttttg  51240
ttcttaatat aatcaacgat caagatatct gcgatgtaat accagtgaat ttttgtccaa  51300
ttaatatttt tcatctcgta attggtagaa tgtttagaca gataatacat gattgtatcc  51360
ggaatattat catgagaaat actgaacgtg tccgatcgta gggtaaaatt aatggtcttt  51420
ttcttctgaa tagtcttgtt atatcctgcc aatacagatg aaaacactgc cggatcgata  51480
taattataat caatttcaat attatctaga tttgtgtctg tgtattcatc tggtttgtaa  51540
ccagtttctg gttttctatc tttaatgttt gatgtcaccg aagaaagaga gacattttcc  51600
ataaaaagtt taatatctga attccctgag gtattttcgg tggaccctgt cggaacctga  51660
gggctgtcag gttggagagg attgagagag accgagttag tgaccaaagt attaagtacg  51720
ggattagcaa ctgaagtagc aactgaagta ttagcaactg aagtagcaac tgaagtatta  51780
gcaactgaag tgacaactga agttgcaact gaagtattag ggaccacagg atttagtggg  51840
accgagctgg taaccagagt gttggtgaca agagtattcg gattggtcac gacagggcca  51900
ggttggacaa tggtatttgt gatggtctca ccatttcctg agactacggt attggataaa  51960
atatccacag aaaaacgtgg tttgtccaca atcaacaaag aagttgattt aacagttgtc  52020
atttaatatg ttaaattaaa tgttaaaaag tgacattgat aacttaaact attgttttaa  52080
taaaagtaga ggaggagatt gttcatgtat gttaaaatat tataatggta attacgataa  52140
aaaaagtaaa aattttttat gtgacacaaa tgtgtgtccg tggtacagtg tcatgacaag  52200
acaaatgata aaagacaaag gtgattgtaa tattgtaaat tgtacggtga acattaattc  52260
catgaatatt aattccaatg atgtattgat cagtaacaca tgtggagcag aagcggaggt  52320
ttcaaatatg ataaccgccg attcgtggag taaagaaata ataacaacag aaacgtttcc  52380
tacaagatat aaaatatatt tactgccatt tttatttatt gctttgatat tttttggatt  52440
aggatacaat gattttattt ccggtcaatt cgtcggtgat cctgtgatca ctaaaggaac  52500
tttgtgtatt agttaaatca aatcggattg gcacgttcat caaataatta tcccatcgat  52560
tcgattcaga gcaggtagtt tcatgtggtt catcttgttc tttatgcgtc cgtctccaac  52620
attgtgcaca gacccatgta ttacatccgg gacacagtag gttcttacaa gagtctgccc  52680
aataaaggaa tctatgacat gtcccacaaa cacacattct cggatccaga ttaggatccg  52740
caagaagttc tttgacgtcc ttgtgtcttt gggttaaatt tgtttctatt tttgatttaa  52800
attcattaag atcatccagg aactgttctg gggtcattaa tgaaatggtc caattgttaa  52860
ttttgcattc tgtctctacg caatttatac atgtcaccga tccaggaaat atattaaatg  52920
atttaatgta tccggtgttg gtttttagtt ggtcaaataa cctggaagaa tttgtcatga  52980
tgtaatttct gacaggtaac aaacatctat tatctgacat gttaagaatc ttgtgcatgt  53040
ttttagcatc gggcccgtcc agggtcacga ctccaaattt tatcaaatca taacatgtcg  53100
tacattttat gtacgacgtg aaatgtaaag gacatggata tattactttt gacatgtcat  53160
tttttgtaat taccaaaacc cgtcttccgg tcgggacaat gtttttttgat tcaatacgta  53220
```

-continued

```
ataaaatgtc gtcgacagat tcgaataatt tattcattat gagaggtcta caatattatt  53280
attttcaata tagtattttc aatatattat tttcctatag tatttttcaa ttccactgtc  53340
catattagga agataaaatt ccatgatttt aaacgaactc acggcccctt cacatatttt  53400
acacggtaat tcagaaaagt gcatttttgg taattggagt tttttcactg attttgacaa  53460
aagttttttt tgttctggat ccgtcaacgg actaaatggt atgaacatac tagagctgtt  53520
cacgacgtca aaacataatg atttgatacc gtacgtgtta ggatcataat ataaaacatt  53580
atccgataat cctatcctga tgaccgaggg ccagtttgtg taaccttcgg gagggtctgg  53640
aattgtaatt gtttttctg atgttgtcac gtaaaatgaa tatttggcag ctccgttatt  53700
ataattgata tctatcctat gtaaattctc tatactttct atgtttttg tacaaaatct  53760
taacattttt gaggaaacta acatggttgg attttctttc aacacaactt tcaaggataa  53820
tatgtttccc aaatacttga cagaattttg caaatccata tttaataatc ataagttata  53880
tttttcatt tacacagggc cgtgtaaata tgataaattt tgtcacatgt tcttcctagg  53940
accggtgcat gagtagtcca tgcataattg aaaattctgg tggctatttc aaacgcataa  54000
agtttatcat gaaatatcaa atcatataat ccatttgtta tttgagatct tcttaatacc  54060
tggttgaaat aacacatttt ttcttcgtat attactcctt cttgctttgt caccacgtta  54120
gtggtcaaat ttccggtcaa gttaacgatt cttaattcgg cagaagtagg ttttgcaaat  54180
gcctggacat aaatttttcc tactggaatc tttacctctt ttgtagtagg ccaagaatcg  54240
ggaaatggac atctccactt gagcatccag gcacatggtt tgagtttttt gattattgct  54300
tcttgcaaat cataatcgtc caatagattt tgggtggtag gttcaccgtc accacttgtt  54360
ctgatatcag aaattaagac aattttcttt ccgggatatt tgtcaacgac atgctgagcc  54420
cattttacat cggcgtaatc acgagtgtac gtgtatctat ttttatgtct atgtacgtat  54480
ttttccaatg taactgacat gggagtagga tctattaatt cccatgtcaa cccaggaaaa  54540
aaataatcta tggcagggac atgaaatccc ggacaacttc cgacgtacac caccacaaat  54600
gagtttacat tttccctgtt gaacaacgga gtgtctcttg tgatttccgt gaaaaacaaa  54660
agctccccga gaagaagttt caactggcca tttgttttat gtgggaagac agttttatcc  54720
atgttctttt cccattttaa ttgtttggtt atctggtcaa acgacattat aggacatgtt  54780
tccagggtca gggatttgaa ttttttgtga ttagctgaca ttccagaagt gattcaatca  54840
atttaatatt gtcaaagtta agtcctggac aaaacgacac gctgtttatt tttggacttt  54900
tatttttata atttttcatt aatgatcttg tgaacatgtc ggcatctcta atatgtttga  54960
tgtcgggttc cggaaccaca catgtgtttt ccagaacttt tggaataatt ttatcagtga  55020
agacccatcc aatttcttct tgagtttgaa tacctggtaa attcttccct acaagattcc  55080
tacaacttat gttaagacgc tttataaaac tcaacacatt agaagtttgc agagataccc  55140
gatcataaaa atcttctttg tcctgatcag tcatgttttt tgtcatgttg ataaaagtca  55200
caggagataa aattgctgtg tttatcaata gttcatcagg agaacagtct gggtcatcgt  55260
ccactacatg tgaaacagga gttgaattac ctatggcaca tcttgtcagt tgtgccagaa  55320
catcagatgg aatacatgac gactcatctt tttcaaaacc atgaaacata cttgtattta  55380
aaattaaaat taatttgttt tcagaccgtc gacgaaatcc aaacatgttg ttctgatcgg  55440
tatattgaag tttttactga cattattcca tgtgtaaaca ggtttattat tttcacacct  55500
gatggtcagt tgtttgacgt ttgtgatgaa cttcagaatg ttaaaagttt ccaacctatt  55560
```

-continued

```
gtagtccgtg aacatgtccg aatccggaat gatgtattca aagaaagatt tcaacagact  55620
ggaatttgac acgttccctc cggtcactat ctgttgatat aataataaaa attcaggcct  55680
gtaatattta agtaataaaa taataatgac cattatttga ctgaccatta ttatacttcc  55740
tatgacgtta aaaataaagt tattggaaaa attatttttt tccaggaccg gtcctggaaa  55800
aatatgattt atctgcacgg tcatttaaaa aattaaaaaa gttaagattt cagattagca  55860
ggaacggtca gcttggtcag cttaggtgct agctccttgt ggatggcctg gagatttttc  55920
atgttgagct ccacggactc tgactttttg gtcatgagag tcttccatgt atccggaaca  55980
atcttgacca gcttattatt tttgaccaga tgatacacgt cgatcagctt ggcatttgtc  56040
atattataag tgtcaagaag ccacaacttg tttcctagat attttgacat gacggtcttt  56100
ttgtctgtga gttctgtgaa atccacttcg gtttctgtga caggtgtagg atcaatccaa  56160
tgaagtccat ctgtcttgat atccagaatg acaacaaagg tcatattttc tggctttacc  56220
aagggctttt ccgcggtgtc atccttgtga gccctgacag aaacatcact gaggtctgat  56280
acatttgtaa gaaaagaata agattgtctg gagttgacat aattaagaag atccccccatg  56340
gaagaatctt ctaggggagc cccattatta ataaacttcc aaatagaatc ccaagacaaa  56400
atagtgtatg ccacaataga agtcattttt tgtgaggtca gaccttttct ggtttttgtt  56460
cttggtctga ttctgagagt actgagaaca cttttacctg tcatggacgt attacctgct  56520
cctagattat cgtaggtcaa ctctggaatt tcaataccat gatttttaat caatttgaca  56580
ccggccaaaa aattttccat ttagtacatt aaaatatttt aatgtactaa atggaattta  56640
catctgtgga aagtaaagaa agtaaaatag gaagtttaaa taatactctt aacggaaacg  56700
aagtgcgttt ggcaaagttc gcaaacaaag atcctcaatt taaattacaa aaatgtcaca  56760
aggcaacagt ttgtaagaaa aacgtggcaa ttttatggac tgcactgagt gccgctgtca  56820
gatcaagaaa attactcaac atgccacttg tatgtggaat cgtggaaacc cctacttaca  56880
ccactctact tactgaaaaa cctactttca caaatgtgac agctgtcaat aatccaaata  56940
tattcagtga caaaaacacc ctgattcaaa tatgtatgtt gttcaaaaca tgtatggaca  57000
acagtatttt tatgacagaa cctgtgtttg acgcagtgga agtcactcct tttaatattt  57060
cgtatttcca taataacgtc ggatggtaca tgcagaatct aaaatatatt atcctcttga  57120
atccggaaac tgaattatac gtagacggga caatccagga tgatcattat cttaatataa  57180
tccaggattt gttcatcggg gtcgatctga tcggagtcga caacacacta caatatgaca  57240
gtataatgca tcttctgacc accgaatgtg tggataatct gaatgccctg acattgtcat  57300
tactcaaaac aaaaaaacgt aactcgtcca tgcagagaat ttcaatcaat caatctgctg  57360
ggaccctggt attgtacagt gctgggatca acgaagttta ttatggtatc acaataacaa  57420
aacctgacaa cgctggtatg gtacgtattg tcacaggttg ttcacccggg acaatggtcc  57480
aacacacagc actggaaatt ctagacatta acatccgaca ggtgtatttt gcaggaagtc  57540
ttctgaccac acctcccgga tacataatca acacttctgg atctaacatg atttttttaat  57600
caaatgatac caagaattct ttgtacatgt ctgataaaat aagactcttt agttgttcca  57660
acgatttggt tttttccaat tcttttttat tcttgacggt cagagcagaa ctgaacggaa  57720
ggattttaaa ataatcccat aaatgatttc gtagttcgtt gtcggacttg gttatgaacg  57780
tgaaattctt taacagatta tttacaaatt tacgcatttc gtaataccaa ttacactggt  57840
tcggatcaac atgtaaactt tcaagtggaa acttgtcatt caaatattca ccggtgatca  57900
tactaaaatc aaaatcatgt agtttaattt tacacttggt aaaattgaaa acatgggtcg  57960
```

gtaatccagg aatggtcaag gtaaaatcat tactgtttac caacaatata ttattaagtt 58020
tcatgtcata atgtaaaaat agtggatatt tcacataaac gttgtacatt aatatcaaca 58080
attgcaataa acaagatctt aacatggtag gatgtgattc catcaagtta atctgtgatt 58140
gtttttttgt gattaatccg atggtttgtg tctgaggtaa gtatgtcaga ttgtccagac 58200
ctcctattgc tttatcataa atgaaaatgg tacctgtgga aaaatctgtc gtacgtttat 58260
gttggaaaaa gtaaaacaga ctggaaagat ttttattaaa gattatgtta atttttatca 58320
ggttaaagta cacaggtccg ataagataat ggaataaatc ccattccagt agttccttat 58380
atttttgagt tatcgattga tccacatgtt ttccgtcttc tccggtgatt gtttgttttt 58440
tccaagtttt ataaattaac aaaatcatca aagccactat ttcatacatt ctatgcaagt 58500
atgaaatgtt gacgttggta accattgtct tgggtttact gattaaatca gaacaaccag 58560
aatcaaagag attacggctc aacatgttgg gaatatcata ttcgggacac ttttccattt 58620
ttgtgttttt atcttgatac acaaatttga ccacgtgatt gttgtaataa aataccatac 58680
caaatgctcc ggtttgaata aaatatagtt cgtcgaaacc ggtggtagat gaaaaaatgg 58740
gtgcgatcag tgatcctgat tttttatagt ttttttgtaa ttgtgcgata ttaacaaggt 58800
acggtaaact ccaagagctt ttaaatttat taataatttc agaatcggta ggtagttcat 58860
gtgacaggtc caatacagaa actagttgtt cataataaat ggaatcgcct tttatttcga 58920
cttgttcacc tttgggtttt atagataata attcttctaa atccgtgtaa ccagaggttt 58980
tgtttatgtc cgataagtac ttatcaagat taaacatttc catttataat tcgttaattt 59040
aaatgacgac tagcgaattt gatagaaatt tattaaaagc agagcctttc cgagcggcgt 59100
ttttgggttc ctctggtact ggtaaaacaa cttatctttt tagtttattc gacacagata 59160
taaaaaatca ttttaattat gtatactgtg tttctacaga attgaatttt attaaacaat 59220
attcgtccca tatatggcct gataaattta tagcgcatga cagactttct ctgggatcag 59280
gaaaggatat gggagtatca tctgtcttac aatctatcct ggaagagatc atgaattttg 59340
cagctgacct tgtaaaaaaa agatacattg aacgatctga aaaaaacaca aaaatttttga 59400
taatttttga tgactgtgat tctattctga caaaaaacga aggtataaaa actttttctaa 59460
caagatgtag acatgtcaac ataagtataa ttgtcctgat tcaagatctc actcagatcc 59520
cacccatgtg gagaaatcaa ctttctcatt tattttttttt cggacaagtt tccgaaaaat 59580
ccaggaaaat catcaccggt caagccggat ttaatagcgt atgtgacagt caacttcgta 59640
tgatagccac catagatcca ggacattttt ctttgaaagg atctcctctt gttttggtaa 59700
aagataattc aaaagccgtg ttcaaggaca gagcaaatca tgacacggta aaaggtaaat 59760
acaaattaga ttttttattc tacagtagat ctcaacaaaa gaaaaagttt ttggaatggt 59820
acaaaacaaa tagaaggaca aaaacattga ccttggatga tttgaagagg gcattgaaaa 59880
caaatttttt ggcctgataa atgtctcatt ctattgtcat caagtttaat aacggtgcag 59940
agatgcaagt gaccgagtgt gcttatctca gtgagattcg ggtcgtccca gataatcaac 60000
aggcatgggt agaattcaat cctattgtca gagtaaagga catggttttt gactcaccca 60060
aatctcttcc gttgccttct aattatcttc aggaagattt caattacgac acagatcctc 60120
tgatcaacac caagagctca tttcaactac cccttaccag acaggtagac gtactgaccc 60180
atcagccatc ttcttctttt actccttacg gacaaaggac aggattggga gccggagaca 60240
tgagtgtcaa gtccaagaga gctcttcaca agagtgccat gacaagcttc ctttctacca 60300

-continued

```
ttaacgcaga cgattgattt ttttattctg tcattatgaa attttctttt tttatgaatg  60360
gacaagacgg atcgtttaaa tctttcccga cgtaacaata aaatgttttt gattttaatg  60420
accaaccgga atgatgccct gatttttttg atctaggaag taaactgatg ttgtctacgt  60480
cccaatcata atcagagatt gtcagactca gacaaaatat aaataaatta ttccagcaga  60540
ctgtcctccc atgtaaaaac atgtatatac aaagactcca cagggcgacc agacaagttc  60600
tgacagtgat tttatcatct ttgacttctg tttccagtga ataatgagtt ccgtacacgt  60660
gtccgtccga tgattcaaac cacatttcat caagaatact gttgaatgtt ttactgaatt  60720
caccgttctt tttcatacat gtttccacga actgaatccc tggtccgaac atgaccgtga  60780
aagtgttgaa gcccggacat atttttgaaa tgtcaaacac gacattcccg accgtgtttt  60840
cttttatgat tcttttttgt aagacgtcca tgacttgatt tcttgtcttg tgtatatttt  60900
ttaaatcgat ggaatgtttc tggatgacat gttccagaag aaccgatccg ttgacaacga  60960
ccttttctga ttgttcatat gttttatgtc tacgatcttt cactcctgaa ctcctgaaca  61020
tgttgatcaa ggtaattacc gaatctactg ttctgaaatt accgattgac tgggtcggta  61080
tatttgctaa aaaagatgtg gtgtacacac aacaatcaaa cacacctaga ttatattgat  61140
ctttcatggt tatgtaattt ttaataaaag gcacggccaa aatattaaaa tcccccagac  61200
ctacaagata cgcaatgacc gacaaagagc tcaacaacaa cccaccgacc gggctgtaaa  61260
aatcaacgtc tccgtattta cattttttcat ttagtaaccc ggccaagaac gaaccatgtg  61320
ccacagaatg tttgtccact gccattatac ataaacttat gtctcgcatg aacacggata  61380
tccattcaaa tggttttacc tgaacatgag actcaccttg ttctgacatg aattttttta  61440
cttttgtcat tatgaaagat gtctgttcag acgggattac tttatttta atatgtagat  61500
ccggtagttt tgctgtgttg tccacgatcc attttaactg tttacataaa gtgtgtttga  61560
aatcaattat tgcaaacacg ttatttttcc gatcagtact tgggtcgggt ctaggacata  61620
tgaaaaagtt ctcgacattt tctctgacct ggtcgtcggt caaaatatga ggaggttcca  61680
tgtgtgtttt caattgagat atccatgtct gaagattatg ttttctatgt gctagttttc  61740
catgattgga atacaactct tgaaactttg gatctatagt gtcatgggga gtaatgagat  61800
attccaattc ttttgtgaac gtgtcacgta gttcttccat gctttttta ttatctttga  61860
tggtaacggc agcttttctg tatgctggta ttactctgtt gtgatgtaac gtaatgatct  61920
tttctgttat ccatccgacg ttaaaattag tcaatgtttg tattttattt gacatgaccg  61980
gagtggtctg taaatgtaaa tacgggtctg ctgctgtaat ttttttcata tttaattatt  62040
agaagtagcg atacttttaa aaataaaaaa tcaagtttta ataatagatc tgactttatt  62100
gaaactaggt ggattaaaac tatgctcaca tgaattacat acgtacttga ttgtggctgc  62160
ttcgtctatg gatctgatct gcattagtct gatgtccacg tctgtttttt tacatcgtgg  62220
acacgcagca ataatggtag gttcttctgt tccaaaatat gaagagtaat catcttccag  62280
atccagctta ttttcgtcgt actcgatgga caacagtata catttgaacg cgtacataag  62340
atattgccac tcttcttttt cttgattctt gtattctaaa atactctgac tgtatttatc  62400
cattttcata ctctgatcat aaatgggttc ggtcaggaac gcagattttg tttttacact  62460
gaggacaaga ttaagtccgg tgtctatggt gttggaaaat ttggttcttt ccaagacctg  62520
cttggtttca gaaaatttca aaacggcatt tttttccaca gaagatttaa gccaatcaga  62580
tagtttttca atatcttcgg gtttatttaa ttttgctttg atctccggaa atttattcaa  62640
tgccgaatct atcaaagcaa tgtaatccac gacagtggtg ttatattcca tttaatatat  62700
```

-continued

```
gtctaataga aaacacagtt gtttttgcac cacgagatgt gtcgaacaat tttttcagtt  62760
cgtcgtttat tttggtctgg gcactttctt gtacagggtt tagtcttttt ataaattgtt  62820
tattcttttt tatttgatca tgtagagaaa taatatcaga ttcttcttga gaaataatag  62880
gagggagagg tggtggaggt ggtggaggtg gtacaaccgt attgttacac aaagggtctt  62940
tgaccaactt accgagtctt gtcagtccgt atttttctac ggcttcggtc aagagctttt  63000
ttatggtctc tgtgttgtca tcgaaatcgt ctgtcaattc atattccaat tcataaggga  63060
tgaacgtgtt gttagaaaaa tcagtggtca catgacattc tgtcatggta tgtctggctt  63120
ctttcatgaa cgacatgaaa tcagtttcta tgttatcatc cagaatgatc agatcttgga  63180
cagagtttgt ttttttattc gggatgatcg ggtcaggaaa tatagaaggt tcaaattcta  63240
actcgtctat cctgttgata aaactctcct tgaaaacatc agtgaaagct tcctcgatgt  63300
cattgttgat caaggtgttg gtctgaagtt ttttataaaa atctgctaat tcatcaggcc  63360
agttgtgtaa agaaaaattt tttgtttttt tattttcaaa aataacatcc ctgaaatatt  63420
cacatttcgt aagataattg ttgttcattt ttttatttag tatctgacaa actattcaaa  63480
tcacatgaaa tagttaaatt aaataattta actatttaaa attgttcggt tgtagagaga  63540
tgccatcctt catacacata attatgttga tatattttat gtgtgacgta cgcttcgact  63600
tcatcaggat gtttacactt caagatttta aaagcatcac gttttttctg aatggcgtct  63660
ctgaaagacg acggaggtgg aacatattta tttacatcat gtacgtgctt gagaccggtc  63720
tctgggtcaa acgtaggttc gttgtctaca gagacacctt tgtcttctga ttcgaccaga  63780
cttattttca tacaactttt caaaacagta ggtttgaata atgggtattt tttaacagag  63840
gtggacagaa caggcatgtg gaaattacca ggaggtagag agacccgggc ccggattgca  63900
tgtggatcta gggtgacaat gtcataagga tcatcgtagt tcagatcttc atcaggttgt  63960
tcacgtctga caataccatg taaggcaagt agactacaag cacgtggaag aggtggtggt  64020
ggagactctg gtggaatagg tggggcaggg acaggtggga tatgtctgct acgaccgggt  64080
tgatactttt caggaatagg aggaacagga atcatatgac gtggaaccaa cggaggacca  64140
ggtagagaag gaagtacaat atcatagaac ggtatgtcct gtgtcttttt attcatgggt  64200
acataaatac ttgtttctga ttttttctta tttttatttg tcttggatga aaacaaacta  64260
ttaggagaat cataaacgaa atcggtatca tttgaattgt ctaatgtggt gtctctatga  64320
taacacaaag acgcatgttt agacgggcaa ttaataggct tatgttttct ggatatgtct  64380
gtaagacacc tggggtctgt gtaatatgtt tgttcgatct tcggaatatg taaggccggg  64440
tgatacataa atcttccgtt cttccatctc aacggaagag tcacaaaatc tgctccgtta  64500
taaaaccatc cgttcccgtc gttgaaatac acattattat ccctgacaat tctagacagt  64560
aaaatctctc cgtactctga cacgtctacc caatacacgt tatttacatt ttctatagtg  64620
tttctcggtc cgataatttt aacaagtctg aaccaatcta atccgtcctg atctgtcact  64680
cctgttatgt tatcattact gtcaacgaac cattcccagt taggaatttt atcacatgat  64740
ggtaatctat tatccacacg aatttgacta tattttttca caagatctct atggttagac  64800
attactttta tatatgaccg taatatttat tttttaataa tactttttct attattacta  64860
aatgaatgaa acagaatttt ttaatgaact actcatcaca aatgatttta cagatattaa  64920
catcgaacat atattaaatc ttaaaactat tctatcaaaa ataggacagg ggtttatggt  64980
cggtgacaca gcaacagaaa atcatcttat cctactttca catttttata aaaacaccga  65040
```

-continued aacattcaaa acaataatca aacatttttt gaatccggga gtaaaatttt attctgcatg 65100
gaacgagttc cctgattatc ttattaaatt tgtaagatta ttagacggta agatcaacaa 65160
catcatagag aatcataata acataatcag ggcctggcct cttgttaact ctgttttacc 65220
ggtgtacgtg gacataagcc agaatcctct gttgaatcct actgttccta catcagataa 65280
tgtcatagaa acttacattg attcgacaga gttgaagaaa tgtccagaaa gagaaacatg 65340
catgaaaatg atttggttgt acaacacaca gaaaaaatac aaaacttatt acaacaccga 65400
tgatgatttg tttgaaatat ttcatgacaa catgtctatt cctgttatat tcacacctat 65460
gtctgatatg ctacaggatt ctagtttgga tcatgtgaat ttctatcaag gtataaagaa 65520
taaaaaacta ttcaaaacaa cttacctggg aaatgttgct tcttttgatg atgcggtagt 65580
aagtatcata gatcattatg tcaataaagg agtggtcaca gacaacatgc ttaaattttt 65640
ctggagtacc acaaaaaatc ccggactgaa agattttata atgaccgcgt tgtcaggttg 65700
ggaaattggg ttgtacagta aattggaaaa attggatcct cgaattaaaa aaacagtcga 65760
agagatcata actcatttgg attttttcaa atcacaaaac gagttgaaat ttcttctgga 65820
taataacatg tatgatcaaa aggttttttg tgataatctt gcaaatgtgc ttctttctgt 65880
aaatccacaa agttttaata ccgctaataa tttaaattca aaaacacaac tcgtgacaaa 65940
ggtgatccaa ggtcaattac cattcttgag taaaaaaaac atgagtaaac tactgtcgta 66000
caatccatgg acaattgaca tttctctgat attgacacat attcagaaag aacacaaacc 66060
agaattatta gagtcctgga tcaaagaata caacgcctgg catattttcc atgaaaaaac 66120
agaaactgtc agattgattc atcatgacgg attcgttgaa ttccctaata atttggaaat 66180
cattttaaag tcgtgtccgg gtatattgat tgataaatca atgattgtct atgaaataac 66240
aaccatgttt gaaaatgtcg gagtacaact acatgatgaa accgatctga ttaaattttt 66300
atatgaatta aaatacaaca taaaacatta cacaggaacc cttaccgatg tctgtaataa 66360
taaaattaat aatattcaat cagtgatcat gttgtgtgtt cagcaaaaaa attttgtatt 66420
catgaaacaa ttcagacaat tttcatgaa taacattaaa attacaaaaa ccgtattgga 66480
taaacttaat ataaaagata aagaaagtga gacaattaaa gaaatcttaa acttgtaaat 66540
ggcagctgtg gtgaatccga tccctccacc acctccacca cctccaggag gagtaccagg 66600
agtagtacca ggaggagtac caggaggagt accaggagga gtacccggcc caggcagacc 66660
tgcactcaaa cctgttcctc aagttattac cacgaccaaa gaattgtatg atactttttt 66720
gacaccggac gcgttcaaga caatcaagaa aactccgaac ggaaagacaa aggccgacaa 66780
gtacctggct aatttccatc aattatggaa agacagtctg gtacacgtag gtgctgtcat 66840
ggctcctaaa acactagatt ttaaaagtct tagttttcct gaagccaaca tagaatatta 66900
taacagaatc agtaccttca tcaacacaaa ccctgtcatc aaagtttctg caaatagttt 66960
atatccattg accacaccta tcaaaccgac cccgtacata tcggatgaat ttcatagtaa 67020
cacattaggt atggacatct cgaccgttca ttcatacaac ttcggaatgg gatccggaat 67080
agaattaaaa ataggatctc tgggattcat ggatttcaca aacggtgaaa aaatcaccct 67140
gggtcttttg aaaaaattct tcacactgag tactttgttc ggttatgaca gacatacagc 67200
agaaggacaa tttgttctca acatgaaaat gtcagaactt ccatggaagg aatttgtcac 67260
atggattttt cttagaatgt tcccgtactg gaatgatctg gtcacccgag gaaattttaa 67320
ttttattgat ctaggccata gtccgaagtt tattcaggcc tctatggacg acaccgagtg 67380
gacaataatt caggaagaca tcatttggta cactgttatt tatccctgtt tcaggataga 67440
cgcggttcct tattcaacat ttaaaaaaat agtcacacat ttatttccgt ggaaagtaaa 67500
ttatcagatg gagtttcata aactcagtac gttaatggac attgcaaagg cgcttggtat 67560
gccgcagtct gtgtggtcat atattttta tggaaagtca gacgtcgacg atgattattc 67620
taaatggatt caatcagtta tttagaagaa tctccattgt ggaatcagac caattttcca 67680
cctgggccat gttgtataat tttgattttg ttccgaacaa cttggaagag aatcctttta 67740
tgaatgcctg atcagaatca aacgatttaa aaacccgatc gcagaccctt gataaaatga 67800
tttcataaaa tatcctcatg ttagaaggaa ttttttcttg tgaattttct agaatatatt 67860
cgtacatgcg tttattttt acatttgttt gccagtttag ttcacgatca cacacgtacg 67920
tgtaataata tctttctccg atcatgactg tcttgttcgg atttgattta ttccattctt 67980
tgataagttt actattggga ttttctccct tttctgtgtc tgctccgtat cttctggtaa 68040
agtaaaattt attattttcc acctttgttt ctttcccggt caacagagct ttgaattctg 68100
caagaagaaa ctgaacgaca tgtcttctca ggacattgac gtcagggttt tgttttatca 68160
gcgtttttat ttttatgtcg acttgtttgg acagatccag ataatagtca cacatgtctc 68220
tttttttata tccctttcct gaaatctctg gttgatcatt ttctttgtag tctgaattat 68280
atttctctcc gtagtatttt tttttagaaa acatgatgac gtttatcagt atgtattcga 68340
actcgaccac gaactgatca aacaagattt ctttgttgat ggtatcttcg aaaaactttc 68400
ctattttact tgccattgta agaacatttc ctgtggtgtc aaaaagtaat ttggtgaaaa 68460
tactgtctgt gtcaccgtaa actcttttta ttttacattg agtgagtttt gtctgactcg 68520
ggtaaaaccg tttaagtggt tcatttttcc agatttgcat tataggattg gtcagataca 68580
atccatcttc tttgaattct gatgatttga aaacatcatc cagatattgt aacatgtctc 68640
ttcctatact tgtacatgct ttggcactgt gaatggattt aagtacgaat tcattggtgc 68700
ctaataatcc ataaatacta ttcgcggaaa gtttggtgac caactgtagg ttgtcataaa 68760
ggaaataatc atccggacat gttttcattt tctttttgta atctttacgt aaggaaataa 68820
actcctttaa caacgacgga atgatcccga tctctctccg atcatagacg agtatctcac 68880
tgatgtattt accggtcaca cttccacaat tcactactat gtaatcgggc catgtgtaaa 68940
tttccttaag tttcttcata caccaaatga gtttgaccga gtcggttatg tacacatgac 69000
ataccaaagt ttccggtgac aagtttccaa atatacaact gttcggataa agactgttgt 69060
aatcaaaaac caacacaggt gcactgatga ttttttcatc tggttcgaac acagtggctc 69120
cttgatattt tgtcttttga acaacacacc tttccagata aagttttttt gatttcatgt 69180
aatattccaa tatgggacct ttcgatgttg tcgtggcata ccaaaataat actttgtctt 69240
gtgataattt atacaagaac gacgcggcgt ttattttata cttgatgttg tatttttccc 69300
agagaaacag acacagatta gaatcgtgtt gacagtacgg tgctatttct tctgctatct 69360
tcatgttata attaatataa atcttgtcaa tctcgacgtc gtcttttcca aattcgaaat 69420
attgttctgt ttccaagttt atgtgtaatg gcaaataagg agtctgaaaa gacaacacag 69480
tttcagttat taccttgtta catatcggta aacaataatt gtccaaattt atgaagccgg 69540
cactttccaa aagttttgtc aagaaataaa gacttttgtt ttttgtactt ctgaattccc 69600
atgtccaatg atcggttcct ttttttacca aggtcccgta accgttaaag ttttttttg 69660
acagggcttc aagactgtac gagttcagac cgatctcttc tttcttgaca aagttatgta 69720
ggtcaaaaaa caatgtcccg ttggcagaat atatgtcaca tctttctgta ctgaggaggt 69780

-continued

```
tagatgattt tgatttttta aaaaccaaag gagtctctgt gtctgtactc ggtatctttg  69840
tatggatcag aggtataccg tacacctcta atcttttgtt aacgtacggg atgtccatac  69900
aatgtccgtt gtacgtaagt acataatcta tctgatcact ttccagaaac cctttgatga  69960
ccaacaacaa ctgtttttct accatgtaga aatattttat gtcgggcttt tttttataca  70020
ctgaataaaa ctcggactga tcattacacc agacagagtc tgatctgagt tttattttat  70080
tactccagtc cggaatcgac ttggtgtcaa caagacaaaa ctttctactt tttgttattt  70140
tgtctaatgt gatggcacag tgtgtgatag gttgagtttg tggagaaaat tgtcctacgg  70200
tataacactc aagatcaaag ctcaggatca tcaggggtgg acagaaataa ggaatgggtt  70260
cgaacggaaa atccatcaaa tcagatttcc atacatttgg cgactcctct ctgatcctgg  70320
gatctgattt attgaacgaa tacgaacctg ccgggttgat cttgttaaat acaaaaaacc  70380
attgtagacc ggtgtaactc ttttccgtga ggcaatgaag atttatgttt ggctttgtac  70440
aaaccagtaa tgaaagttct ttgttggtat tttttttttt aaaattaaac gcacagttta  70500
ttccttttgc gtacgtgtta tctaatatgg taaattgtcc tatgtcaaat ctctgttcat  70560
acgttccttc taattcgtcg gcgtctgacg tgtacatgag ataacaacat ggtaaaaatg  70620
tcttgaacca tattatttcc ccactttgtg ttcttgactt accggccata tatgatggtt  70680
ttccccatcc gtccctgatg atattccaat ttaaaaaagt tatacaaacc ttgtcttgtt  70740
ccggtaaatt ttccggagtg gtcaatgtcg gtttcagttt tttttaaaa tgcatttttt  70800
cccataattc taattccgaa gccctggaca tttttacgtg aacagtttta attattaata  70860
tttaattcaa ttttaagttt ttcaatgtct atggtctggt ctggtcggtc tgtcttgaat  70920
gtattgtaca gggatgcata gaataataaa atcacattcc agtcttctga ggacatgatg  70980
ttattttttg ttatgtttaa tttagcatgt tccctacact cttcacatgg aagaccagac  71040
actattagcc atgtgagctt ttttaaaaca gctaaattac tcttgaaaat aaatataaca  71100
ctgaaaataa ctaaccaata accgtgtccc catacagaag tgttcattta aaataactat  71160
ggacaataca gtcaaagtta aaaaatgtta tttatggtgt gaacaaatgg atcaagacac  71220
agatgacatt gaatcagtat ggaatgatga ttctgttaaa aaaatgcaaa agttattaca  71280
gaacaaattt aaatcaattg ataaagatca tgatgtacta cctgatgcgt ttaaatatgt  71340
atgttcaggt aatccaggtg acaccacact acagatgatt gaatctctga atgattcgtt  71400
cacaggaaaa gaacctacca cacaactgtt gaaaatgtac aactctggaa tgtggatgtt  71460
catttcatgg ttgtacccac atcataattt catgtgcgtt ttcggattca gaacagcaaa  71520
tgatccgtct gtgtctgtgt gggacgaaga aacaatttac accagaccgc gagtcagacg  71580
atacatgtcc aaacgactag aacttaatta cacggaccaa ccgaatttta atagattgat  71640
aacatttatt aaattaccaa atatcaagca tgacgacgcc gaagaatttt cgtcagacga  71700
agacctggat caattcattt cagaatacaa tgacaacatg agatcattca tggaaaaagt  71760
taatcaggac actgaagata aagtttaaat ccttcattca tttttatgat atttctaccc  71820
tttggatttg tgatgattat ccctttgtat tttttcatgg ttttacatgt caggtttatg  71880
tcagagatat gttgtattac cttgtccaat gttccgaggc cgttactttc cagaatacaa  71940
ccattttgta ttttaaattt ttttacataa ttattggtgg aaatacaaat gtcaatgcat  72000
gattcgttga cgtcaataaa tccacttaaa aaagaaacga tcttggaaat aaaagacaga  72060
tccgtgttag gtttagaagt gataagtcta tctatttgtt tatcttcaga atatataaaa  72120
atattattta caacaaaagt tgtttcagac atttaaatca aaaaaaatta ctcctctaca  72180
```

gagtaactac atctgtttac aagctcatcc accttgatct tactgagctc aatagttaca 72240
aatacatctg aaagttctct ctctgtctgc tcatcaaatc tctttgtatc agggttgatc 72300
tttgagttga aagcagctgt caggagagaa tgctttgtgt acaggataga ttcaacattt 72360
acataaggaa cctgtaggta cttcagaatc ttcttgtttg caagtgcaac agggaagtac 72420
aagtcggtcg aacgcattgt cacctgagcg atgtagttgt tgaacgactc ctctgtgaca 72480
agctttcctg agaatgaagg actcttcttg aaacactcct tcagtcttgt acctagagca 72540
gtgggacaga tgttcagaga cctgtcatca aactgacttc cgttggaaat cttcttgttc 72600
ttgatcaggt tatcccaaag agactcgtcg atactgtaat caacattatc atatgagaac 72660
actgtcagag gcttgaccaa cttagtgaca agagtcttgg aatcactctt gaaaatgttc 72720
agaggatgtg tgttgtcact gagcttactc aggatcttga cctctgtgga tgagaagtta 72780
agtgcctcgt aattggaagc acttcttgtg accacgtcat ttgtgaaagc atagatctga 72840
agagtagaga taagatcctt tccggagatc tctgtcttct cgtacgatga cagatacttg 72900
tcaatgaact tgcggtgaat gttatcaagc ctgtgtacga cagcaggaag cttcttggaa 72960
gtcttgggct tgacaactgc cttgttgata ttgagaattc cactgttgat atctgagaca 73020
agctcatcga atcgtctgtg catgtcactc atgtaactct ttgtgagaac agtgacctgc 73080
ttctgaataa gtcgcctgtc gttggtagaa agcttggact gatcctttga tgcacgagac 73140
tttgaaactg atctggtagg aggaggctca acaacagtct cggtcacgac ctcctcggtc 73200
tcgacctcgt cgtcacttga atcacttgac tcaactctgg aagataccag aacctcctca 73260
tcctcatcct cactcattac tggaacacga gagaagttct tggaagacat tttggttctg 73320
tttgtatgtt ttatgatata attttatata ctttttattt tattgggctt ttattaactt 73380
aaatataatt tttctatttc ttggttgatt tggtattttc ggcttattaa tatcacaaac 73440
aatattaatt aaccttttt atgttatgtt gattttatta atgtaacaac agtttatttt 73500
ttataaaaat taagatattt tttcttttt atcagcggcc aaagtttcca ctattttatg 73560
ataacattcc atcatgaaat ctacgtcgtc ttcacctacc tggatcatca tgatgtataa 73620
agcattcaaa aatttttcgg taccggttcg atctttcatt tataaaaaaa tattttttac 73680
ttcttggtct tcttcttggt cttcttggga acagtggccc agaccgaaga aaccttagaa 73740
ggtttcttca aatcctcgtc gtcatcatcc tcgtcgtcgt agatgtcttg atcttcctct 73800
gtggaactag cctcagattc taccactatc acaggcttct ttgacttctt gacggtttta 73860
ctggccttct tagaaggctt cttcttgacc accacctcct cctcagactc ctcgtttact 73920
tcttcatccg aatcctcctt acctgaatca taagaaagaa gtttatcggc agcagtcttt 73980
ccctttacct tcggaatacc tctgatcatt ttagaagaat ctggcttcat gtcagaatca 74040
gaatcattac ttgaatcttc aagcataaga gatggggtct caactgtgat ctcctcaccg 74100
ttttcatcaa tggtttttgt ggtcacactg tcactacacc tgatccaatt aacaccgaaa 74160
tgaatcttgg aacaacttac ctcacatgcc ttcttgacgt actgaggact ggtgtctggt 74220
acctttgtct tacctatact caatagcaca ggactgatag acatctgaca agtaacgttt 74280
ttcatttccc tgaatttctt acatcttccg ttagacgtgt tcttaccttt tccacacatc 74340
agataatcct gaagaaattt aaccttcttg gaaccgactc catttcctac ataaagaaca 74400
gcgtccttca tgtaactgtc cttacaataa aataccttgt ccaaagataa ggtattgtcc 74460
cacatgacat ccgaatcaac tccgagtaca ttgagatgct tatgattatt atatttattt 74520

-continued

```
atgtatgcca ccaacaaagg gttacattca agaatcttga ttctaccttg aagttcaaac  74580
tgtgattcaa cagacccaaa ctttggcttc tcactgacag agagtttggc ctggataatg  74640
aaatcattta catttttact ggaaccgtca cttagtgtga cagtgacata attatctcgg  74700
gcccaataaa gagtcccgtt tttattactc tgggaaaaat tatgtgtcac agaataaggc  74760
atttcatttt tatcacagac aacgaccctg tgtttatgac atgacttggg ttggtcagga  74820
accttctgac atgtctcaca tcctgccgaa tgtgaattct ccttgatatg ataattatta  74880
caagaagaca aaagacattt gtacttgaga tgagcgttgt tcatgtccat tttcacaaaa  74940
tagtgtcaca gtttattatg taaggattac ctgtttcgta caagagtccg gatcgtttaa  75000
ccgtactaga tagtttagga ttgaactcgg gtacggaaat atcgtcactt tctaatttaa  75060
cggttatttt ctttttgtat aatatatttt cttttttcca aacacaagga gtgttcagaa  75120
tacgattcac gaatgaaagt tcgtttttta aaatcactgt cacagccaaa ggaccgttat  75180
taatttcttt aattaaaata caatttcctt tattttcgga tgatatgttg acattgtctg  75240
gcaagtcaaa aatactcatc cagacaacat gtttccataa agaagttttt tccacttttt  75300
cttttattaa catgtacatc tcggcgttgc ctaatttact tccgtttatg atatttcctg  75360
atccctcgta tgttgtcttg ttaaaattta ccggacctaa tttgacggtc atgtgatgtt  75420
tactcaatgt tttaattttt gattcgttgt tgccattttt acaaagtata ctgtaaccta  75480
ctcctgtgaa gtttttactt gattgtctgg atccgtaaaa caaatgagtt attgtatgtg  75540
aaggattaaa tggccatggg tatgaaatgg aatcggtagg aacagttccg tttgattgcc  75600
cgtacactac ttggtttgtt tttgacatga tgtttttgtt tattacaaat ccgagtgatt  75660
cgaatatttt tgaaatttct tcaggtacat tttcagtggt acattttaaa acaaatccgt  75720
taggatacat cgggggctgt aatggttttt ccaacaacca ttcggtccac ggtgtccata  75780
aatcatgtaa cacaaatcct ttagaaatta atttgtctac caagatatga aatctggacg  75840
tgaaccaata ctcactttcc aggattgtca gatcccgttc aaggactttc catatcttgt  75900
cggtttccga ctcaaatatg gtgttgtgaa aaacaggtct gataatatca gagaaaaaaa  75960
aagtacatgc agaaatagga gattctgata tttttgaaaa agaaacacca ggttctactt  76020
tgtgtatttt agaaataaaa taatccattt atggtaaaaa gtcaattgaa aaacaacctg  76080
aattaaattt caaaacatta tcagacactg taaatccagt aaccggaatg tcttctgatg  76140
tttgagcaaa acccaatata taagaatcag tggtttcgta gtgtttgaga aaatttcttt  76200
tcccgacatg ttgtaaccac agatcaaact tctctggtgg gtcttgttca ttgaacagtt  76260
ctgtgatgtg atctgtggga accccggggt cttctgattt cttacaaatt acttttatgt  76320
tgctccactc tgcgaccgat gaatcatttg tcatcattgc cacacattgt ctttttatga  76380
cgtcgtcatg gacctgacgt cttttcctga ctttcctgat cttgtcacat attatgattt  76440
tgtcataggt cggtggacag accattatca ttttatcaat ggcacaacac ttggcttttt  76500
tcagttcatg aaaccatatt cttaaattat tgaaatactc ccgattccat gttcgatgtg  76560
attcgtacca atcgtcattt tctaggtcaa caaaagaagg caacaatgtt gaatacatga  76620
gtttccacac tgttttgtga tttttggtac acatacgtaa aggtatctga cagtctccac  76680
gagattcggg tcctagtgtc aaggtcttgt ccttgatttc ctggaaagaa cttcttatga  76740
gtctttcttt gattatcatg ttatacgcag tgttcccgaa tgtatccgat gttttgatga  76800
acatcggata ctcccctagg acaaacacct tgattccttt tgataacaag atgaccccta  76860
ccagagacac attttcatct tcgtaggtct gttctatcag gtctgctatt ttagatattt  76920
```

```
tatggttttc attttttgcc ctttgtatga attctggtaa gtcgtctctg gtcaggacaa  76980
caggaaatgt ccatgttgcg tatttcaaat attcaaaaat acaagaccag aacatctgaa  77040
atcttatgtt tccgtacatg tacggaaacg gtgtcagtcg tttcatggta ctggctatgt  77100
catccacgta agaccattct atcaatgcct tggtgacctc gttgacaaag tcaaattttg  77160
aaatgtaata ttcatccatc gcccaaacct attgtgaatt attagttttt tttcttttct  77220
gaaaaataaa gactaattat gtgggcgcta ttgttatcat aacagagggt caaaaaagag  77280
ttaatatatt aatcatggct tcaggtggag agtacacagt ggtaacgaag aagaggcgtg  77340
ttgatcctgt tgcaaaatac gtacctccgt ttcgtgctag aaatgtggct ccttacatac  77400
aaacacacaa atgtaaggag ctcaatttca agcgtcatcc tattctgggg gaggacggaa  77460
tcatcagggt tcctgctaaa acagggaaga tgatgtctgt ctggatgatg gaacagttgg  77520
agtactttgt caggggggacc aacgatgatt tcagtagacc gaataaaacg ttgttgatgg  77580
acatggacat cgaagacccg atatacaagg caatggactt tgagtactta ccagacattg  77640
agtttgagac attggacaaa gagaacacaa aaatcaaaga ggattgtgtg gctatcatcg  77700
ataacgtaga cactgccacc ttgatctgtg gagtcacaac acctgttcct ctgatggtaa  77760
aacacatggg taagttagga ggcctttctg gaacaggggt cctgggaccc ggagggattt  77820
ctgattgtaa cttaccagac aacattctac ctggcacttt ccatccatgt tacaatgaga  77880
tgtacatgca cacactcgtt ccttgtctgg tacaagcagt gaatctcatg gtgtctccga  77940
agccgaagcc tctgctttgt gtgatctgga cctttgacat gaaaaagaaa aaggtgatca  78000
gtgtgtgtca caagaacatc atcggacaca tcagacgttc ttacgtgatc acagagggag  78060
gaatggatca tatgaatctt ctactggaca tgctcaggga gaacgttctt gcgattcatg  78120
gagtgaaatt gaacgaggga aattggtcta tgatgaacaa agacattgcc cagatggcat  78180
ctcttttgtc attcaccaag ttggagtgga caaagcttct gataaaatct ccggacgtag  78240
gtaggctcat gatcaagacc ccaaggaagg ctctgacaga tttcaacgca tggataaaga  78300
aaatcggcga ctgcactgtg gctcacaaac acatgagcat gttgtcggga tggtgttcca  78360
gggatgcaga catggacgat ccgataagac agaggaagat aattggacac aacaatgaaa  78420
tggaagttac ctgcactgtc aacaaaccat tcacagatct ctctaacctg ggaaaccaaa  78480
tagattatct gggtgcaagg aagctcatga ttcaccttca ggaaaacgga ttcgaacact  78540
acgcgagtct cgggaacgga tttggaaagg cagcgagtgt tgtcgggagg gctctcccga  78600
gaaaacatca caataagccg atcaccatgg acgtgttgat gttgatagac agtcatcaca  78660
agtgcgtttc atgggctcct gattatccag agaagacaat gaccggagat ttcatgtccc  78720
tcaggaccga gatgacaagt gagaacccag gtttctgtcc atacccgtat cttgccaggt  78780
atctccatca tacctcgtac gtgaacggag ccataatggt gttcaaggcg accatcacac  78840
ttccaagggt ttgtcactgg gatctgtttg agaatgtctg ctcggacatc agggtcagga  78900
aaatcatcaa ggtcattcct atgtaatcag taaattctat gtaatcagta aattctatgt  78960
aatcagtaaa ttctatgtaa tcagtaaatt ctatgtaatc agtaaattct atgtaatcag  79020
taaattctat gcaatcagta aattctatgt aatcagtaaa ttctatgtaa tcagtaaatt  79080
ctatgcaatc agtaaattct atgtaatcag taaattctat gtaatcagta aattctatgt  79140
aatcagtaaa ttctatgtaa tcagtaaatt ctatgtaatc agtaaattct atgtaatcag  79200
taaattctat gtaatcagta aattcagtag taatagtagt aatcagtaaa ttctatgtaa  79260
```

-continued

```
tcagtaaatt ctatgtaatc agtaaattct atgtaatcag taaattctat gtaatcagta  79320
aattctatgt aatcagtaaa ttctatgtaa tcagtaaatt ctatgtaatc agtaaattca  79380
gtagtaatag tagtaatcag taaattcagt agtaatagta gtaatcagta aattcagtag  79440
taatagtagt aatcagtaaa ttcagtagta atagtagtaa tcagtaaatt cagtagtaat  79500
agtagtaata gtaatagtag taatagtaat agtagtaata gtagtaatag tagtaatagt  79560
agtaatagta atagtagtaa tagtagtaat agtaatagta gtaaaaataa atttttataa  79620
aaacacaaaa aattagatag tcgtcatggt actgtatcat ggggtttgtt tattttggtc  79680
ggtcaccggc gtcgtggatg taaacacaaa agccgtatgt gttgtatttt gtagagggtc  79740
tccgttgtcc gggggaggtg ggcctgtcgg actcaccgga tcatgtacga ccttattgtt  79800
aaaggtgaat atactggatt gattattgtt cttggatttc tttgtctttt tcagtgtgaa  79860
taaactttta cttggaacac ttgtgaatgt aaatccacta ccgacaccag tatgagtatt  79920
atgtttatga tcatgttggc cctgatcatg ttgattatgt ttatgatcat gttgattatg  79980
tttatgatca tgatgacctt gttgagttgt ttggtgacct tgttgagttg tttgatgaac  80040
atgttgagtt gtatcattag caccatgagt cttatcgtga gcatgttgaa ctggtttaga  80100
agcatcatga ttttggacag gaacatgttg agttgcttta tgaacctgtt gtgtatggtc  80160
attaacatgt tgagttgctt tatgaacctg ttgtgtatgg tcgtgatttt gaacaacagt  80220
aataactggt ttatgtgtga cagtaacttg ttgagttgtg gtattaactt gttgagttgt  80280
ggtattaaca ggagtatgct taggaacctg ttgagttgtg gtattaacag gagtatgctt  80340
aacattttgg gttgttttag gaccttgttg agttgtttgt tgaccttgtt gagttgttgt  80400
attatcacga ttatgattgt taccttgttg atttgtggta ttaccaggag tatgcttaga  80460
tgtttgttgg tttggatcgt gcattgtttt atgaccttgt tggtttgtac taggacctgg  80520
gtggcttgtg ttaggaacaa caacgttctt attatcattt ttgtttgtat gattagcacg  80580
ttgatttgta ttaggaacga aaacaccttt acgacctgtt ttttttgtat ttgggacatt  80640
gttcttcttc tctttcctat tgattctata catagaatgt tgtttattat aatttgccat  80700
atctttatta tattgtccaa acaaattatt ataatctata atttccccta gaacaatagt  80760
gaaacttgcc aaatatgcat tattagtatt gagagcactg gtgaattcct tgatatattc  80820
aggctgttga cgttgattag gatgagtttc cttatatgtt tcgagtctgg ttttgaactt  80880
gatacgattt ttcatggctt ttaaaatttt attcaactcg gcatctgtca tctgtttttg  80940
tgtcacagga tttattatgt taaatacagg ctttactggt ttatccaagg aaaatgacgc  81000
ggttgatgct gatgaggtgg tgtcactgtc actatcatct gattgagaac ttgtactact  81060
tccggaagac tgaccttgtg cattgttagg attagcattg ttaggattag cattgttagg  81120
attagcattg ttaggattag cattgttagg attagcattg ttaggattag cattgttagg  81180
attagcattg ttaggattag cattgttagg attagcattg ttanggatta gcattgttag  81240
gattagcatt gttaggatta gcattgttag gattagcatt gttaggatta gcattgttag  81300
gattagcatt gttaggatta gcattgttag gattagcatt gttaggatta gcattgttag  81360
gattagcatt gttaggatta gcattgttag gatgagcatt tccttgtaca gtgttaggat  81420
gaccatttcc ttgtacagtg ttaggatgag catttccttg tacagtgtta ggatgagcat  81480
ttccttgtac agtgttagga tgagtatttc cctgatgagt atttccctga tgagtatttc  81540
cctgatgagt atttccctga tgagtatttc cctgatgagt atttccctga tgagtatttc  81600
cctgatgagt atttccctga tgagtatttc cctgatgagt atttccctga tgagtatttc  81660
```

-continued

```
cctgatgagt atttccctga tgagtatttc cctgatgagt atttccctga tgagtatttc  81720
cctgatgagt atttccctga tgagcaacgt tattaggtga ttgtggtctt ctgattggat  81780
ttggacggat aagtgtcata tctccaggtc gtggagtagg agacatactt gtacgtctat  81840
gattagaatc atgttttggt tttaccggag acatactctg tcgtcttgta attgtcgtac  81900
cgggattaaa catgtttctc tttaatgaag tagttccggt aggactagtt ttccttgaag  81960
tagttccggt aggactagtt ttccttgaag tagttccggt aggactagtt ttccttgaag  82020
tagttccggt aggactagtt ttccttgaag tagttccggt aggactagtt ttccttgaag  82080
tagttccggt aggactagtt ttccttgaag tagttccggt aggactagtt ttccttgaag  82140
tagttccggt aggactagtt ttccttgaag tagttccagt aggactagtt ttccttgaag  82200
tagttccagt aggactagtt ttccttgaag tagttccagt aggactagtt ttccttgaag  82260
tagttccagt aggactagtt ttccttgana gtagttccag taggactagt tttccttgaa  82320
gtagttccag taggactagt tttccttgaa gtagttccag taggactagt tttccttgaa  82380
gtcattccag taggactagt tttccttgaa gtcattccgg taggactagt tttccttgaa  82440
gtcattccgg taggactagt tttccttgaa gtcattccgg taggactagt tttccttgaa  82500
gtcattccag taggactagt tttccttgaa gtcgttcctc tccttgatgt aggacttctt  82560
cctcttggtg gtgttcctcc tcttgatgta ggacttcttc ctcttggtgg tgttcctcct  82620
cttgatgtag gtcttcttcc tcttggtgat gttcctctat cgggacctcc atcgggacct  82680
ccatcgggac ctccatcggg acctccatcg ggacctccat cgggacctcc atcgggacct  82740
ccatcgggac cttcgtcatg atcatgatca ttaataagat tatcatcatc aaaccacaat  82800
ttgataatct tattggaaaa atattttta atcacgttga tgtcaagaag attatatctg  82860
aaccaccaat ataaatcatc tatgttataa ttagaaggag taggaagaga cgatctgaat  82920
atttccaatc catttttatt atcattaatc gagtacggca tgttgatatt tttagtatca  82980
tcaattttat caagagggca ataaacagag tgaagttcat tattgattat ccaaaactct  83040
ctaggatggt tcttgatata gaacggacct gaaatctgag catgattgtt cttctccaga  83100
tccatttcca ataaagtctc tggattgata ttttttccac tcgacgtgat attgacataa  83160
ttccacaatg aagtattaag ttgtcgttcc attgccatgt catatgccat cattgccttg  83220
tatcttttta cactggccgg attcaatgat gtgtaaatgt tattgaaata attggtttcg  83280
actgtcatgt atttttcgga aaacacaaca ggtgcatttc ttggaatgta ttgagatcca  83340
gatccgttag tgaaacctac atctttaaca agtccgataa tttcatcaaa tgaattatac  83400
accgtgaaac taggtactat gtcatgtttg gaaaacccgt caatcttgat agactcgtac  83460
gtatcttctg tttctctgtt gtacgaaacc acgtcattgt tttccatat attcatgaat  83520
accaaaacac agtacaggaa ttgtcggacg ttcaccataa ttttatcaca aaaatattca  83580
atgtcgggaa ctgtcatgta tcccagatat tccatgtatt gtttgtttgt ggccagcatg  83640
tccttgatag agcgttcggc atcttctttg atcatgatgg cattactaca tatgacgtcc  83700
caattagaat aatgagaata attacaaatg tttctacaac tttccgtaat gaattggatc  83760
aacttgttca agtttaccaa gttgataact gtgaaatcgt tattagatcc tctgaaatca  83820
atgggaacga atttccctag gttcttattt gcaagaatac gtatgattga gtattcgtct  83880
ggagtaaaat tattccacga atccagatcg accttggtat cgaaatcgaa gatttccaga  83940
caattttcca gacgttgtgc tgctgaatca acaaaatctt tactgtacgt gttattgatg  84000
```

-continued gcaaacgtaa gagcggtcat actctggaag tgtagtgaat taacattaca catttcatac 84060
agactagtga gtctaggacg ggaaataatt gaatagtttg gaacaataac agaggcgtcc 84120
acgatattag tcatggtgat aggattcaga agtatcctat taatttcatg tagacccagg 84180
acatcagtga cctcttctac aaatcccaga ttccagtttt tatcatccac cacgaccttg 84240
ttatgacgga ccagatcata acagacattg tcctttctca cacaaatagg gggcatttgt 84300
tccatggctt tatctattga aagactgagg tcacctacag gagatttact gttgtcgtac 84360
atgatcatat taatcttgga caggacctgg ttgacctgag aaacctgtat actacaacac 84420
tttttgattg tttcatgaag aagataaatt tgattgaccg caggattgtc aatattttgg 84480
tttttcagta gtgttctatg aaatgccccc ttgataagtt gttgttgtga ttcattcaga 84540
tcatacaaag aatccctacc tttcacagaa gaaaaattca tgtcttgttc gattcctgtg 84600
accagaatgt tgtctccgat ctgaacccat tcacagcaca tgttccaata atctgtcgat 84660
gacatattaa gaggtgatgg tatactactt ctcaatccgg tgtccatctt gatcaattcc 84720
acacacatca attcccaact cttgtacacc ttcccccaga attccaattc cttaccagaa 84780
ccaaaagttt gattggttct gatattatca ataattttaa caagtactat tccgtaccac 84840
atcagttctc cgaacaacgt acgttgttcc ttgacactaa gagagttagc ctgaatatca 84900
gattgggaat actttgtcca catattcata aattccatgt tcagagcgtt tgtttttgaa 84960
attttattct tatctaccat cattgttttg accacatttt ctgattgagc cagtagttga 85020
tttggaatga tagataaata attgacagct ttgccataat caaacttctc tgtgtacaac 85080
atgttaaaca aatcattatt caaactgttt ttatacgtga tgatcgaatc gtgtctgacg 85140
accagggcca aagaattaag aattgccaga tcaattttag caagtagaat tgttttaatt 85200
ctgacccact ctgtcccggg gtcaccactt attggggtat gaccttgtac aggaagactt 85260
ctgggcccga tatcaaacgt actagggtga gggtgagttc tgggcccgat atcaaacgta 85320
ctagggtgag ggtgaataga atgaggactt ggttgatgtc ctggagccgg ttgatgtcct 85380
ggagccggtt gatgtcctgg agccggttga tgagcaagag gagccggttg taccactgtc 85440
gtggtcggac gggtatgagt atatgttgac gagatcgtgg tgtcccagaa ttcatcaacc 85500
aatgaaacgg gtcgtggtac cgggttaaga ctgacaggct ggtgcggtac cggattactc 85560
gtggtaacgg tggtgtacga agacaattta tgaaacgtgt acagaccaga gtctgataca 85620
agttgagtga ttacatcatt gatgttttta ccggtatgaa ctctacaaag atgttttacc 85680
ctatcagtgt aagatgattt accagagttt ttaatattat aataagtttc caagtggacc 85740
accgggtacg aattaatttt ttccagagac aacatattat aatgcaccca gaggagttcc 85800
tccaatttgt tatgaaattt aaatagggac tgagacgtca cagattttttt tctgaaaata 85860 gtatgaagtg actcgaacca gtcagtgtat tcttttgaaa atgtcattgt tttggtgtaa 85920
ggataaatgt catccagttt tgtataaccg ggatgataca atgacatgtt gaccggacaa 85980
ttataatcca catttttaag accaaacaaa ccacatacgg aattcaaaag tcttctgtat 86040
gctccgtcag gagtcgtggt attttccaca tttccaatag tcaaattgtc atagttaatt 86100
ccgttgattt tggatttacc ggtcggacct agtacacaaa tggtgttata ataatcatct 86160
atatgtttca tttattaata aaaataagaa tcgtttttta tttatattct atgtatttta 86220
gatgaggatt tttagtttgt aattcggtga gtttggcttc tattaaattc aacgtgttct 86280
tttttgtatg tttagccggt aaagttattt taagtttttc acaaatgatg agcaaagcat 86340
ttttggaaat gttaactgtg ttcaccacaa tgttttttcc atcaagtgaa tattttaaca 86400

-continued

```
tttttcctgt tgatttggac accaggagcg aaacctctat tcctgtggaa tcacgtgtga  86460
gcacgatatt ttcttccttt gtgagaggga tacttataca atgcttaggt aatgttagtt  86520
gtatgggtac cgtgataatc tcatcgttcc cccatggata atacaaaaga caacttccga  86580
aaatgtcatt taaaatttgt acgtgtgcgt ccaacaattc tgtgattatc ttatttaatg  86640
tttctaggtc cggtcccggg aaggtcatga acgtcatgaa tttactatct gtacgtttga  86700
ctctcggatg agatttgaaa tatatacgaa gtaattcaac taccattgtt ctccaaagat  86760
ttttatgaac gggatccttg tactgctttg atattccctg gaagatcgag taaattttac  86820
tcgactcatt tgactttgat tcgagataat attgcttctt gatatcaaat ggtaacttgt  86880
caatttcttc atctgtcatg tcaggtttca attgtttatg tttatatttt tttggtacac  86940
aagagagaat acgtatcttg acttcttcgt tgggattttc ataactgaac ttacgaatgg  87000
ccctaccaat gatttgagtg tattgactgt acgtgtcagg aatagtaaga aaccataggt  87060
tttttacttc tttcagtgtg taagactgac ccagagcata actggcaaat aataaactga  87120
tgaaatgacc atgtttgttt tttctggtgt tgaacacttc cagggtcgga gtgatacttt  87180
cgttgaccct ggaagtcaaa attgtaaatg ttatgaataa acattccacg cacgtttttt  87240
tatgtttaca cacgaaacaa ataggatctt tggcgttggc tcctttgtac tcatttattc  87300
catttgccaa cattatactc cggataatca acgtgccata agttgcgtta ctgaaatata  87360
taagatgttt ttctggcttt tctattcctt cggtcaggat gtatttcata aaatacttaa  87420
atttggaact gatgtccaaa gtaacaaggt cctgacctgt caacagtcca tcgttacttt  87480
tcagattggg aagtaatgac gtaaacgcca aattattgat gaaattatct actttataca  87540
agaaaatctg tcctagggca cacattgaaa cgtttactac cattgtctca aacatctcat  87600
ttgaagacat ttcacgggtc ttgtcataat ctacctcttg tatattttcc ataggacatt  87660
gaatcatagg aatattaaga acaggttgac ctatgtattt cggagtaggg atactttctc  87720
cgttgttttt ataataactg atctgaccct ttagtagaga ttccaataat tctttccctg  87780
tctcgttcag ggatatatgg atgattttag tttttttgatt gatcaactta ggaggactga  87840
tgtcacttcc tgtcatgagc ctgattatat gaaccagggc cttgggtgtg ttactgatag  87900
gacttcctgt gaggagcatg aaaagcacat ttgttttttg tttgattgtc aatagaaact  87960
ttcctgtggc atttccaaaa atgatatgag cctcgtccac tatgaaaaca ctgtcttgac  88020
aatccatgat tttgttcgtg tcaatttcgt cattggtcga cttcaataaa ataaacgtgg  88080
aaatactgta catttttatt ttgtccatgt cacacggaca ccctatcaaa ctttgtacct  88140
gatatatttt actttgccaa atttccaaaa tgttattgtt cggtaaaatg atcacgacat  88200
ttttttctgt tgatatcaat aaagcaaata taagagccac gaatgtctta ccacttccca  88260
tgtcatgaaa tatcatggct gacattttat tatcaatgat ggttttcagg gcaaaatcca  88320
cagtggccat ctgatgaggt aaaatagtca gtcgactatg gttgttcttt tgggcatttt  88380
ccaaaatttt caagacagtg gaattcatca gggaaaaata tgtcagaaac cttttgattt  88440
aattataaaa aattactctt cagagtacgt gatcaagtgt tttttgacaa tgtacttgac  88500
ccagatatgt ccagacgtat cagtatgtga gtgtgtgttg atcatatttt ggatttcatt  88560
accaaatagt ttgatcgaaa agtgtttata tatatatgat ttgaaatcac tttcttccat  88620
gtaaacggtg tctccgaacg tgtcgtactt tgcagagtat tttggtaaaa tgtcctcgat  88680
ggtttctgta cttgattgaa ctatcaacgt aggaattttc cggataagag tgaaatcctt  88740
```

-continued

```
gaatttttcc ggagtggttt tgaacggtaa gaaaatggtg ttctctggtg tcaggaaatg  88800
ttttctgaag aaacgtttca ggataagaaa gcacgcttgt ctgtaagcct gtgtttccaa  88860
cctactggaa atttccattc ttatgggaaa gatgtttttt ctgacaccga caagaatcct  88920
acttttctcg tcgatgaaag cagatttgaa atttatcatc aggcatcttc ttactatggc  88980
tccgtccact atgtcaaaga acggctcatg atttgtgtcc actatgaaag tggcaaagtt  89040
ttgttgctct atggcgttac tgtaacagag tctactgatg attttatgat cggtaagttt  89100
cttgacgttg acacctttga tcttgaattt cgaatccgcg gtgttaggga gctcactggc  89160
aaacagtgct cttttatggt ttatctgagc aaggaacgga ttcggacgtt ttgcgtctat  89220
gacctctgtg agtaaattac tgtttgtttc cagcatgaaa tttccgatgg ccgcgttaac  89280
aatttttttt gatgtactct tcccactcat ggtgtcgccg tgaaagaacg tcatgtattc  89340
tttatgagaa ccgtacagac atgaaccgag gatgatctcg tacaattctc tttcttcttt  89400
atttcctctt gtagggggtt gaatctgatc tatgatcaga tctatgtctt tcatggcatt  89460
ttggatatct tcgtctatgt cccatgcact cttgtacatg taaccggtgt tgacactacc  89520
tatgtattcc ttggcactgg gaccttcata aaattcatcc ttcaagatat tataacatcc  89580
gttttgaaaa tacaaaacgt acgggataga atctaccctg atgggatttt ctgctccgat  89640
cagatcgatc aaattatttt ctaccatctt tctttttctg taatcttgca gttccttttt  89700
tatcgcactg tcttcgatcg acgaacttat tctaagaatg taacttgtta tactgtacgt  89760
ggccttgtca aaactccaat tgactccgtt ccagataatg aaatgatcct cttgatattt  89820
cttgatgtca tttctactgt aaatgtcaac ggctattgta aggtataaat cctctttcag  89880
gttcagggta tgaacctgtc tcttacattt tttaggattt ccatgtttac tgattataag  89940
tttctttcct tgtcttttac aaaagtgatt atttttatga agactgacga aacatatcgg  90000
acatggatta cacgaataat ccacgtcgag ttgatacgtc tggccttcca tgtaaatatc  90060
ataataatgt tccaactgag ttccgaaaac ttctgttaaa attctgttga cttcttgatt  90120
atacagagag ttgcttttta attccaaggt aatttctgga tcatctaata cagaatcagc  90180
tgcctcttca gaatgagtag gtatcaacca atattgtgcc ttggtcgttt ctggaatcca  90240
tgatattaat gagtcttcga acgttcctat tatgacagtg tgaacacttg tgtcttcaca  90300
tgatttaata gagtacgcac atctcaatgt aggaaattct ttccatacca caaaatctat  90360
ggctttcaat aaattctttt tgagagatgt cgaatgtttg ttattgatct gagaattgac  90420
cagtccttcc agagactttg tcaacataca ccaatcattc ggagccacta aaaagttggg  90480
ataaatgaca tggtaagaaa ttttatcaca gttgttggat tttgtcacga cagctgcgtt  90540
tgtcatttcc agaacggctt cgttatattc tttcagatct gtcaatttgg tcacggcacc  90600
gttttttttc atgtagaaga ttttttttt acttcctaac tctatggcca gtgaagccaa  90660
aatcttcacc atgtacggaa cgtttgattc taatgtttcc tgatctgatt tagtgagatc  90720
atctcgtgaa atgtcaatat cccaaaaaag tttaacggca aaagtgtcag acacaatatg  90780
ttcgtatgtc tcattagaac cattggccca cttgtacact tcatccggag atgaaaaaat  90840
tttagtatgt tcaaatttat tatctaacgg gtcgattttt gaagttttga gtggttttat  90900
ataaatttca ttttgataat taaacatgtt taccagttgt aatgaggcca ttgtcaatca  90960
gtccaaacgc tattttatgt tctttgtcaa aatattttgc ttcttttgct atgtgtaata  91020
ctttaaattt tttaaatatt ttttcacttg atacaggatc atatactaca tttgttctgt  91080
agttgtcaat ttttaaattt ttactgttta aatacattaa tataccggca aatatcccga  91140
```

-continued

```
atcccagaac tcccaatact aatgtgtaaa taataaagtt ctttcttgat gtgtccacag  91200
aaaaaaaatc agaaggttgt ccggtcttgt tgaacaaggt cgcgtattga agatatttac  91260
agtcggtatt agcagatcct gtgttgacaa tttttaaagg ttctgtgtaa ctgtttctgt  91320
tactgtcaca atgtatgtca acagaatcta acaagacatt ggaatcgacc agttcagtgg  91380
tcaactttcc tgaacacagt ttgtttatgt tatcagggga aattatctta tcgaattgtt  91440
tttgtaaata caaaggtaag taattttttc ttttggccat ttctgatcta aacactttgt  91500
caaacaattc tgcatttgcc gtacatacat ttatcaaaga caccctacaa ttgttaccgg  91560
taagatttaa attgttaatt gttatgttac aattaacatt gtaacccgag taatttctta  91620
aatcatacaa cacgtcagtg actatttcat tgtaccattt cttccaatga aattccaatg  91680
tcatttaatg ttttcattaa tacattttta atagtggaca ccctgaatgt ttttccatta  91740
gaatgtaaat gagcaagtct gttgagtatt gatgtttcat aaaataaaac ctcctctgtc  91800
acgtcttctg atcgattcat aattttatac ggctgttcat taaacatctc tgctatccac  91860
catatttcac ttatactagg aattaatatt cgttgagttt tttctgcctt tgtgaccagg  91920
acaaagagag gcaatattgt cctgatgtct ctgactgcca tggaatgtcg tttctccagt  91980
aacacaaaag aatccggttt ctccagtaaa ttagagtaga ccagttcatc acgtaataca  92040
taatcttcca aggtgaaaat tttctttgtt gttatttcat tgtttgttgt atgtgtcaga  92100
gtatggggaa tggtttgtat gttcgtgtaa agaatattgg tcgtacaaaa atcattatat  92160
cccttgaatg ttttcttgtt cttctgaatg tcaatggttt ttcccatgat taatgaaata  92220
ttaatacttt ttaataatat taattaatat ttcattaaac tatgaatctt cgtgatcctg  92280
aaaaattgga gttgatacga gacatgttct taaaaatagt ggaagataaa aaccattata  92340
aatatgtagg attctgtgga aataccggaa gtggtaagac cacggccatt gaatgtctca  92400
aagatatttt tggtgaaaca tcaattggtg aatacaatgc agaaacaaaa ttgagagaag  92460
gttgtaaagt tatttttgga atgaccgacg cacaagtgta tgataattcc gatgacatca  92520
ttccaagatt aaacgtgtca tcaaatgaaa ttcttagatg gatcgaatct gtttcaagat  92580
ctctggtccc agacgtgttc atttcagatg ctattgatac gatgaagaac gggagacatc  92640
ctatcaattg tttaggtgac ttgaaatacc ctgacgaaat aagacaattc aaacaactag  92700
acgattctgt ggtcatcaag ataaccagag acacggaaaa tagcggatat tcttcatcag  92760
agtacgatca tctggttcaa aacaatggtt caatgaccga cctcacaaga aaaatattga  92820
aaatcatttt gaaaaactgt ccggagaaaa acgctattct ttttttgaa aattaagtgt  92880
ataaaacaca tacaggttag tatttatcac attatacaaa cactcttttt tgtgtgtgtg  92940
tgtgtatcat tgaaaaaata tgatctttat acactctgaa caacatgtgg tattcagtga  93000
tatagattgg ttattaggag acaatgggtc tactacggga acggtagacc tacaataagg  93060
tcacttttat atatttggaa aatgacacaa ggtcttcgat ccagaggtcg acatgaatat  93120
tttcctgggt cgtgagtctt ttgtattcaa tcattatctt agtaagttgc tcggtcaact  93180
tactcacttt cttctcggta caatcaacta ccttgagaga atgtagtcct gtcatgatct  93240
gtttcctgga ccaattattt tccgatacaa agttttcggt ttcgtgttcg gtccaggaca  93300
accaacaatc cgaaaccaat tcctcttgtt cgtcttctgt tttgggcaat tcgacataac  93360
ttttttctat gaggtatttt aaattccata ccctggcata ttctttcact aggtctgtta  93420
tcaacactcc taccctttgt ttataaaacc aaagtctttt tgtgtaaaac atttcaaaaa  93480
```

-continued

```
ttgttttcag ttcacaatct gtgtggagcc aattttcatc aaagaaattg gcattgatgg  93540
tcttgacact taccaatttt ttttttactt tgtcgacgtc attgtttatg acgtacacac  93600
aactgtctga ggtcgactct gaattatcaa attctatttc gttgaccact aaccattttg  93660
taaaattctc tatgttgatg ttgaacggaa tttctgaaat cacacttttg tttatgacac  93720
cttttatcaa caatctttct tttcgttgaa cgatctcttt ttcttttgat ggttcatctt  93780
catcttggtc tgtctcaaat atcaaagatt ctgtgtcggt gtcagaatac gtttcacgac  93840
agacatctac gaaactttca tctgaactag agtcatctac cagtaaaaaa tcttgctttg  93900
tgtcgcattc tgggaaaata actttagcgg tcttttttaa taaccgtatg gtaccttcaa  93960
accctcgtac agatggtaat ggtacgtctg tctctattcc ctttagctta ttataatacc  94020
agtgaaacac ctcggtaatg tcatgaggtg gaatgtacgt gttgaatcct gtcccgatac  94080
cttccgaacc gtttatgagt aagacaggta atatcggaag aagatacggg ggttcaattt  94140
cttgattttc atccactgcc ggagtacaga ccttgaagtc tattttttta tacaattgca  94200
tggcgacctt gttcggagaa aatttaatgt acctggacgg agggatgtct tttccaaact  94260
ttgaacgaga accggcttca ccgtcgatgt caacgaaaat ttgatttagt ccacaggacc  94320
atctagaccc tagttttgca gcggatttat aaagactctg gtcaccatga tgatacaatg  94380
tctgacatac cagatgacca cagaaagcgt ctgctctcaa acttttctga cccatgtgta  94440
acagagtcca ttttattttt cttgttacca ttgtgtcacc gtctatcaat tggggtatgg  94500
cccgtctgtt tgaatacgca agaaactcct tgtacctttc catcaagaaa caactcagtg  94560
atatctcatt atattcgact tcgtcaaaca cggtaggaat tatggtgttt atcatttcag  94620
gagtattgtc gtacatggtc accagttttt tagacacgtc agaaagggac gtccagaaat  94680
ctccttcttg tgttttaaac attaattttc ttgcttgact gtttctaccg aataaaccat  94740
caagtaattc tatgtctgtt tttgtgatga caaaacgttt tttgtacaat cccatgttgt  94800
tgacaatact gacaaaatca gactctttca gagaacccag tccctttgca taaattgtgt  94860
catgtttatt tttcttgtcg gtcacaagat gtgactcgta tttggacgtg gtgaaaaaca  94920
tcttcccaca acacgtgaac ctaggaagtt caagtatatg aatcttgtct atgaaggaag  94980
gaaatatttc acggaacaaa gccaaggcca aacatgcaat atgtgcaccg tccacgtccg  95040
gatccggcac aataataatt tctgaaaaac gactttccaa ttgtttgttg tcgaatccca  95100
gtcctaaaat tttagcaatg gacaacacta ttttattgag tttactttta ctgggatctc  95160
tgatacaatt aaagatcttt ccggtcatgg cataaattcc tattttcttc ctgttcttgt  95220
atttgtcaaa agccctactc agacttgttt ttgcggcgag tccctctacc agacacagga  95280
caagattttt tttatcatat ggttttctgt aattgacaag atcaagagcg ttcttttgta  95340
cgtttgcctt tctgtttatg ttgtctctac tgatgtcttt catgatgtct ttgaaaataa  95400
tcatgggaaa aacaatcttc ggatcaaaat caaaaataat cttcccgtct atttttaatt  95460
tgtcttgtcc ggtaaaagct atcccaggac aattggctat acaaaacgtg ttgaaataat  95520
tcttgacatc tatttcgttt ttcagaatgg tttgtttgat cagtttgaaa acattatttg  95580
acataagacc gtcgtctacg ttcaatccat tcaggataca atagttcata ctttttatac  95640
gtttggtttt ttgttggagg acaaaaagac atttcccacc atgtgtcttt tttttatgat  95700
cctgatacgt gaacgtgaat ctgttcacca catgttgggt ctgttctgtc aggacaagtt  95760
tccatggatc atgtgtgtgt ggtgtactga actctaagcc attaaataat atctcgacag  95820
actggtttaa aaatgagaaa tataaaaaaa actccattat acgtcctttt atgaagaatt  95880
```

-continued

```
caatgttgtt gttatttatt tcatcatctg tcagaccgaa cacggtatta tccggaacaa  95940
aagtcacact gaaaaatggt ccgataatat ctaaattttt tacaggagtc tcttgtatct  96000
gttcgtccga gactccatct gtttttgtgt acatgtacga atgagtcttg tcagaaaccg  96060
aaagtgaaaa atgtttcgat aacatccata ctagtttcaa tccgtaacca tgtctcccgg  96120
ccacatcttt tttttccacg taattagaag atgttttcat gttggtaagg acaactctag  96180
gaattatatt atcttttgtt ccggtgacct gacctatgac aggcatgacc gaagaatttg  96240
tgatggtgat ggattgattt tctttggaat aatatatact tattatggga tccgttattt  96300
ttgttttgtt agatctgaca tggtcgaagg cattggtgat aatttcatca tacaatttac  96360
aaacaccttt atgatatgtt cctacagaaa gttttttttt catgagaaga cccttttcga  96420
caaaagtaca ttcacccacg taaaacgata aattagattt gacatgatca cggtcattta  96480
gtttgacata ttccatcacg gtaatttttt caacagagcc ctggtttcac tttttacttg  96540
gtccgtaact ttatttaaaa aattaacatg ttttttttctt tttgttatca atgtgtttat  96600
ttcctggtct tcttctgtgg aacataattc acctacgaca cttctcaatt ctcctcctac  96660
catgtatgtc tgtatcatca acatgtaaat gttaaacatg aatttaaaca tgtcataaaa  96720
aataaacttt gcatgttgta gcttagacgt acttatcttg tacggaatat aatttgtgaa  96780
attttctatg acagctcccc actctcttgc gtattgatca ttcataatta caagaattta  96840
gaatacaaac tccagtgaag gggttcgttg tttagtgatt taaatgccaa ctctttgatg  96900
aacggggatt cgaaaataac tgcagagttg ttatcaccga tggccggctt attttttttta  96960
aacaacttca ctatcaaata aataatagga gtaaataaca aaatagcaat gaatccaatg  97020
ataaatttag catattgtcc taatagatta ccaaatgcag tgaggatact tccaaaccct  97080
gagaacacac tgtcttgaac acccgtgttt gaattatttg actgcaattg taaatcagaa  97140
actagtttca ttgcacagtt tcctctggcc tgacctgtgt tgatgaaatt aatggtcgtg  97200
gttccgaaat aatttttaca agacccgaag gacaacgttc ctagattaaa ctctgaattt  97260
gcaacagcag acgcagaaca tgactggttg attgtgtttg tcatgttctg aataaatgtc  97320
tgagccgtac ttgacacccc tacattgatc ccacctgtaa aacctgcaat agatgttttt  97380
tgtgtggaac tcatagaatt aaacgcatca gataatgcgt ttattaccgc actgacagag  97440
acatctgcag aggccacaca gttattagtt atgttaacac tacagttcac gttagactga  97500
aaaataatgg atccgatgtt taccttacaa tttgccacgg cctgtgatga tcccgattgt  97560
gataaattat tagataaatt agattcaaat ttttgcataa attctttaac gtcgacattc  97620
acacccattt aataaaaaaa aataaaaaag tattcgactt ttactcttca tcgataatag  97680
ttctactatt taaaatactt gtgatgttcc gcttattaac agaagaaact ttacttacga  97740
ctccgtattg gatgataagt tttttactga tatgataatg aggagtactt ttatcttgat  97800
tagcccatac tgccttgata ccaatttgac atctacctct tatatgatca gatggtaggt  97860
aattaggaca aactgctgta tctgtatgat gacagaaaga tatgttaccg tatcctttgg  97920
tcatgaacgg gaaagatatt ctagaaaaat tatcaggata ataataacat gcgttcaaat  97980
gagattgata caatgtctca ttaccatgtt tgacagttgc gatttcaata ggacgttgtt  98040
tattgagaaa atctactcca cggaaaaatg gatcattgat gatgacgtca gagttcttac  98100
atagaacaga cctgttgtct ccctcatcgg actttgtgtt tacgttccag atttcaatag  98160
gaacacttat gtctccaatg gtaatttgat gatctatttc ataaaacaca aagttgtttt  98220
```

-continued

```
ggagaatgtt ccatgaacaa tgtacaaagt tgatcttctc aacaatatta taagtcgact  98280
gagttttgtt ttctctgaat accagaggat tagtatggaa ccaagcagaa taattcttag  98340
gaactcgttc gatcaccaag tcaatggtct tgatatttcc caattcgatt ttattgttct  98400
tcatgatctg atattttgcc ttcggagaca ggttcccgtc attgacgtcg ggtgactctc  98460
cgttaggaag gatgattata cactcagtaa gaagcttttt cagatacatg tttgtccaat  98520
tggattctga ttgatcatgt ccggcccata ccatgaacct ctttccagac agatcatttc  98580
ctacgtcaaa attaatatga gacacgttgt caataccatg tacataatgt tcatcgtctt  98640
cataatttcc cactgattcg tagttgttga taatatattg ttcatcattg gtagattccc  98700
tgttctggac agaataaacc acaattccca gaacaggctt cttgatagaa agagtattca  98760
ccagaggttt ttcatacgcc agaaaaatag tggcttcagg attatacacc atcacatttg  98820
tgagttctgt catcaccgtg acctcgatac gaagaaaaga gtttggaaaa tttttaatag  98880
tggaaaaggt atcttgatta ggatagaaaa tattaagagg gacattgatt tgggtactgg  98940
gtagaaaata tgttttctca ttgttgagat tttcggtgta gttgatatta aagttattca  99000
gttccttgga ataaccactt gttgagatat tatccttttt ggaaagagcc ctagagaaaa  99060
gagttgcccc gtcaatttca ataactttat tattctcatc gtatatggct accttcttga  99120
taagcttgaa tccaaaatac ggaacataag caataggatg attactatgc aactcagaaa  99180
cttcaaagga cagaataaat ttattgaaag cgttgatctc cttgtcgttg atattgaaag  99240
aataaacagt tgtcgggtgc tcggattgtt tcgtggcctt catgtattcg actccgtttg  99300
actccacatg aatcaaacat ggcatgtacg aggtccctgt gataatagga catccgaaca  99360
tgtcagttga ttcatattcg ttgttttgtt ccaactgttt agctgattgg ataagaacag  99420
aattcatttt tctttttttaa tataattttc atggtttaat ctaaattcaa tttttaatc  99480
aggaccctga ccattccatt accgactcgt tgttgggtac cataacattt ttccatctcc  99540
tttgtaacag tttccacgag tcttgttgaa tttttgtaca tacacaaagg aggaagcttc  99600
attctagacg gagattttaa tgaaattgca tgggacacac aacctgccat tatgtcagaa  99660
catgccggag aacaaaacgc accaattttt ccttcgaaca aagtttctaa tttgtaaacc  99720
aaaggcccta tgtcatttcc acaggtaaga catgtctttg aatcattgtt gtattctaaa  99780
atatcagaat gaatatattt gattatgtcg tgatggttag gcaagatgag cttgtccgtt  99840
tccattgttt atttatacat taagactaca ttcaaaatca taattaaaag taatttcaga  99900
tcgttctggt atgataataa tagtcctgtc ttcttttttt ttaagctgtt cttcgttatt  99960
atattttatg aacatgtccc atattaattg attctcatta ttcctgtaag ggttcttgac 100020
catctgggga tgtaaataag atatggcatt gacactcatg aaaattttat tcagaaaaaa 100080
attataattt atggacttcc ctgaacgaat ggtctggacg aacaaaacca atgaatgaaa 100140
aatagaagtt atctgttcga acatttcctc actcatgtcc tctatgtgat ggttgttcag 100200
atcacttaaa atttcaaaaa ccttttttata atctttactg gtgtatattt ttttattctt 100260
cagacgctta cttatgaaat tagaatccac gtcttttatg tcaatgtcca tttctttcaa 100320
ttctaccttg agctcttcta ccagatcaga attatcagat ctggtcagga gtcgtttgat 100380
gacattttta aaatgaatga atttgttccc gacgtaacat gacgaatttg ttttggtttc 100440
tttcccgtcc acgaacgtgt acttttcaca tgatatacaa aaaagtttac cgtcacaatt 100500
aagaacggaa tttatattac attcatcaca atacttgtaa tctaataatt tactcatttt 100560
aagtttacga tcttctatga cacgaagtaa atgaggagga acaaacgtgg aagtctcttt 100620
```

-continued ttcatgatct agtaatttac cgtccagcat aaaagaattt tccatttttt aatattaatt 100680
taaaattaca atcctttatt atttattgcg ttgttccatg acattattca ttctgtcgaa 100740
acccaaactt cgcttaatgg tttcgggaaa atttatcttt gtaaaatcta aaggtgtatc 100800
taatattgca ccggcttcat aaatataatt tatattttta ttactgatta gccatgctat 100860
aaacaaaccg aaatctccca atatggctgt ggtgacgtct acgtcacatg atttacattt 100920
gtcaacttct tcaaaaacaa aatccattta aaagtaaaaa cttattttaa gcaagacaac 100980
aacctgtcag gtttttgata acaagaccgg atgtcatgtt gtcattctta taagaatcaa 101040
catcttgaga gtacatcaag atacaacaat aagatccgat aagatcatga gcaagctcat 101100
cagagatgag tccgtccacg aaagatttct taccgtttgc gatgtcagac ttcttggcgg 101160
cgatcatagg agccagaggg tcaagtgcca accatgtgtc gtagtcattc actccctttc 101220
cgtcggccgt gtcacgcgtc cacatggaca tcaatgcacg cgtcatggtc tggtctcttc 101280
ctgttcctga tactgaatca tatgggtcat agatccaagg tcccttcttt gtgaacagaa 101340
tagtaaagca aggagatccc tccacgatgg gctgaccgaa tccagaaaac tccttgggtc 101400
tgtaacatac agcagacttg atgtaatacg ttgtcccgta ctctgtagtg atcttcttgt 101460
cgtacataag aggcataccg aaagagttac gtccgtacga gaagcaggcc ttgtccatac 101520
tcctgacagt cttttgtctc tcgatgaaaa acaccattgt tcctgttccg gtgatacttg 101580
atcttccgtt actggtgttg tacgcgaatg aaccaggcat ctggtgacct tgattagcaa 101640
gagggttctg aagaagatgg ttgaagtgtg gggccatatg gttgaactga ttaccgatct 101700
caaattcatt aggaaatcgt accgggaaaa gaccaggatt ggaagtgacc ggagtcttgt 101760
gaagaggctt catttcaaac ctctttgtga aattattata atcaatcata ctcaggacgt 101820
cattaccgat accgatgtta tcatttgcta gatcaatggc ttcatgaact ggaatggtca 101880
cgaacggaca tgatgtcata ccaccacctg attgcttgat gataaaactc ttgtgaccga 101940
ggactctcag acacatgtca agagtcttgt cctccttaca tctgatgttg tatccgttca 102000
tgtttgtcat cttgtgaatc caatcaaatg ccttcattga ccctaccctc ttgaagtccc 102060
cggatctgac ccgaagaaga atctttcgca gagacatgtg aaggatgatc ctctgaatct 102120
ctgtactgat ttcatctgtt gtcccgttga gataaaccct gtcgtctggt gtgtcaataa 102180
atctggaatt caacaaagca atgttggttt cgtccacggt tccaccatga tacaactgct 102240
ttaccagact gtacgaatcc cctctgaccg aacaattttc aaacccggcc atcttcaccc 102300
cgaacatggc caccaaaata ggattgatgg aatccatagg tcctccgtac acaagaagtc 102360
cattttcaaa atcactgatg tcactgaact ctgatgattg ataaatactg agttctgtga 102420
tttgattata atcattgttc tctgcgatca cgtccaaatt cttgagctct gtcttgatga 102480
catttgaatc cttccccttg taccggatga tgttcaatac atggttccat ggtgtcccgg 102540
tagactgctc cttgaacatc ttgacaacca tattcaccat tctcttgaaa ctctcctcgg 102600
acagtctgat gtcttgaccg acgtaaagat ctgaaatttg ttggagagtc agtttaccag 102660
aactgaccac accctttagc ttggtaaaaa tataacttgc caacctcttc actgacacgt 102720
ccacgttttc aatactagac gcaaggtcct gaatagaagc aaacttttct ggcttcttgg 102780
acgtgtctga ccctgccttt tttgtcacct tcttcttgac aggggctgcc cctccacatg 102840
tgtcagaact cagataaagc ttgcatgagt taaccagggc acatgtcgga caatttgccc 102900
cacatgtcat accatgaatg gtatgaccga caggggcaaa gtctgttgat gattgagtca 102960
ttgacatacc atgatctacc aaaacatcag agtccagtgt gctattaagt gatgcagtgt 103020
ccatgtcaag tagattactt tctgttgtca tcccacctga catgtcattg acaaggtcat 103080
gatcgtcatt tttagaactg attgcaaaat aattacaatc aggaagacct agcttgttga 103140
gactaatagg atggaattta tgctttccac aaaagcattt agatgtactc atttattaat 103200
taaaaagatt gttaaaaaat aatataaatc caactgttaa tttatcacaa aaattaaaaa 103260
aaaatcacct gatgaatctt ttgtggaaat accacgattc atgaatttca caggatttat 103320
gaatttattc acaggatgat actcgtgtaa atattttta tcccatggta attctatgtg 103380
tcgagtaaat ccgtctatgt aatcattatg acttatgttg attaatttaa aaacatttcc 103440
tgtttcatga tctattttac aatttttcaa tttaaaatta taatcgatca tgacgtttat 103500
ttgattgtgt ttattattga ttgttaatat aataggtaac atgtttatgt tacccggagt 103560
aattttatgt tgtaatgttc tgaggacgtt tcctttctga tcacatttac atgtcgggtt 103620
catggtcatg tatttatttt tatcataaac ataaacgtct gtacattcat cacattgaag 103680
tagaaacgaa gtttcaataa ttttattttt tcgtttggtc gagtacatgt cagactcgga 103740
cagttctatg gtccatctac ataattttg tggagaaatt aaattgttgt atttaattct 103800
gtacttgttc atgtattcat cgtttttaa aaatgaaaat gcattgttta taaacataaa 103860
atcatttgaa ttaccacctt tatccgggtg aagagttaaa agattttttt tataatttaa 103920
aacagcaagt tgatctaaac tacaaagcat ttattatgga tgactatagt gcaaatgatg 103980
tgttttcatc agatgatgat atgtacgaag atgaaaatga tctttccatt tcatcagaag 104040
aagaagtgga tgattcgtct gatgtggtag acggtataat tcctacagat ccagacatgt 104100
ctatcataga tgaagtatca gaaactaatc atgtggaagt agaggccatg tctaaatacg 104160
acattatcat gaaaaactac attattaaca gattgggtat ttttgaatta acaggaatct 104220
tggcccacag acataatcaa ctggaaaaag gaagtatacc attatttccg atcaccgaag 104280
aatattataa acataactct acatgggacg ctgtcgtgga agaaatcatt ttggaaaaat 104340
gtccgattgt aatttccaaa atgaattaca atctgaaatt gtctgattat cctagggaac 104400
aggtattgta tagattggag gaatgtgtga acatgtggaa tgtccagaac aaacccatta 104460
aaactttttc atatttcaaa caaaaacata atatttaaaa aattaggtcg ggacaataaa 104520
atcaaaaacg cctgtgtctg aacatgatct ggtccagtca tcaaacacag agtcatcaga 104580
atcattgaca acaagtggga acgcttcctc gatcaaaggc tgaatctttt cagtcgtgat 104640
gttcatgttg acaaaggttc cgatattgag atatttttcc aaagttttcc aaatagacaa 104700
cactgtctcg atcaaaatat ttttatttga ttccctgatc tcggtcttga tatgtttggc 104760
aatctcgatg acactaagag cgaccctttt gtaatcatct gagtttttca tttttctggg 104820
aatattatat ttctccgaac acacttccac aaatgtctcg aacattttta caaatgtaga 104880
aagattagaa tttgtgtaat tgatgattcc ggtcgtgaga atagaaatgg tcttgatacg 104940
ttgaccgatt tcctcttgag acttgtcatg cttccacttc ctcagtacac tagatcgctt 105000
gaacaatgtc ttgataatgt cagtgacctt tgattttgtc ttgatattag aaggatactt 105060
ccatgtgact atggtgtcta ggaaaatttg aattgtttcc ggagtcatgt aaaatgactc 105120
agtgatactt tggagcttgg cctggttttc aggcgtttca atggcagatg gatacatcac 105180
attaactatt ttcatgatgt aaaatttatc tgtccagatc ttgtccatga tcttgataat 105240
gttgtttgta cacgtggtga tttctgctgc ggtcagggaa ctttgttttg tgacaatgga 105300
aaacacactc atacaaattt caatatcttc ttcgattttc tttgtttcct tgttcatgtc 105360

-continued agtgatgaca tttttaagct ttctcttcac aagtagaaat tgtacaattt ccattattga 105420
gtcagagtac agatctcctg tttcctgtga tgttttcacg atgtgattgt acacactttt 105480
caatgttccg aacagacatg attggacaaa tgacaattcc ttacattcga caagtttcat 105540
catgtcaaac aattgtttct tggactgaca aaagtctttg taattaatag aaatgacatc 105600
aatgttcctg ttcaggatca ccatgtccat gtcaaaattc acggactcga cagaaacttc 105660
attcttacta ttggaaccaa gaaccgcgtc tattgtcaat ttgacaaaag tttcgtaaca 105720
tgacttgacc ttttccattt aatatctttg tcaaatatta aaactagaaa agtatttttc 105780
tagaatattt tttgtttctg aaatatgttc tatcgaattt ggaattttga aaagctgaaa 105840
tatattggtt aaaaacgtgg tcatgaatac ttctggttgt aatgtttcca cacatgagaa 105900
aaaatgtctg aagaattttt ttgctgtttt cacgtttgtg ttttttcttt caatgtttat 105960
tttgacgacc ttgatcggat aatcagaact tattgaatga gaaaataata ccccgtctac 106020
gtaaaacttt ccgaacttca gttccatccc atgactttta ataattggct catcagaaat 106080
tttaaaagga ttattgtccg cgataatctt ccttttgttt atagattcat aaacttcaat 106140
ttcatcagaa tcatttgatt ttttaatttc acgaatgttg tggagtagac tttttatcag 106200
gaccttgtat gaatagtcag tgtacggaag actatgataa ttttcaggat atatcaattt 106260
acttttgtac atgaggacga ccttgttgtc tgtgatgtac ttttgaattt cttcatcttt 106320
gttgatcatg tgatgatttc cggtactgtc cttaccggtc acgatcacag agtaatcatt 106380
ggcttctttg attctcctgg tttcctcttc gattaccaat ttggatttgg tgttcatcaa 106440
cgtgtccatt ctggatttta gaaatccaat tttatccgga agaatgtact ttccatattg 106500
aagaatgtaa aggtcgtatc cggccttttt ggtgtcgacc ttgtcaatac attttttata 106560
aataggagta ctggactgat cttgaataaa acaacatgga atacattttc cgtttatact 106620
tgcaaatatt tttaaaaatc ccaggtacct gtacgcgtcg ttgtctggac cacatttgta 106680
aacgttggtg tattcgtcga cgtaaaaatc agatgacttg tttttgaaga atcctgtacc 106740
ttgttctatc aggtcaatct gatcttgttc agaaatctct gatgaaatca aaggctttct 106800
atttttacca attgtgttct gacagatcct actccaataa tatggtttca atccgagaaa 106860
cggatttgat ttgaaattgg gtgaatgaat atgattgtaa gacactatca tcatggtaaa 106920
gtatttctcc agggacttgt aaaagttttt catttttatc gtgatcagat tttttgcaat 106980
gatgatgttg gtttttttat caggggtcaa tatgatgttg ttggtacttg ttttttcaaa 107040
caaaaaatta acatcggtcc cgagaggtaa tgaagagtta ataggtgatc cgagtgatac 107100
tttgaatacg acttctgacg tgacccttct gtaatcatac tctctcatta tgaaataaat 107160
ttcttgaaaa agagatttat tttttatgta tatcatggac tctactatga caattcctaa 107220
tatcccgtcc tcgaatacct gtatggtaag atgctctttt tgacaatcta atctattgcc 107280
tgttatgtaa atattttctt tgtctgtcac gaagaaattt actgatatcc tcggagtagg 107340
taatgattct gcatattttt ggatttttga cgtgatcaat ctgagtttat tttcagtgat 107400
ttctgtcctg aattgattat ttacaaaact tgtgatggta aaatcaggaa ttaccttttt 107460
aacacattca aacagactat gttcgtgttc catgttccaa gatatcccgg tctgtccgag 107520
gtcattgtcg tttatgtcac ttgacctgac cacccataaa attaaattat cataacagtc 107580
aggatataac ttgtacaaca acgagtcatt tttttgtaat cctgtttttg ttatgttgta 107640
aggattaaat acctgccggt caacgtaact gtaatctatg ttatacctgt tattataaac 107700

-continued tatgataggg gtgtctatct ttaggagatt catcaaataa taacgtattt gagcgttgtt 107760
taacgttaga aaaacatgat tattcacatg ttctggctca ggaataccag ggactttatt 107820
tttaagaatt tgataaaata aaaatacatt tgaagtttta ttaattgatt tgaaatggct 107880
aaggtataag attttttcta taactttatc gggtcctgta agtataacta attgtgggtg 107940
aataatggat tcactatcag acatttttga cactgaagat gatgtattta tagacgacaa 108000
taatcatttc gtttttgaaa aagaggatat agacatagaa cagacaatag gaatcaatga 108060
acacagagat cgattaaaat tttgtccaat gaaagagtca catggtagat attatgtggt 108120
catatcaaaa agtgaagaac gtagtcaatc attggggttt ttcaatcata gaaaacgatt 108180
tgtgtctttg gatgaagagt tcaaactgat cacgttactt tataaacttc agaacgttaa 108240
cataattaaa aaaaataaca tcataagtag tatttatctt gtcctattat atctgttgtc 108300
tcataatatt gtcctggctg ataatatatt gttactgtat ttcatagaaa tttgtaaaat 108360
tgtgtacaga cctaccaaac tcaaattgtc tttgatgaat ttatacagtg tcataaaaac 108420
tcatgagaac atagaaatag aaattgacga gaacacgttc tcaaattatc caaatggttc 108480
aatctcggga ttggtcagag gattcgtgtg ggacatcaga cataaattat gggaggtcga 108540
atcccctctt gtgaccgcga aagacaactt gttcttgtcc gacactgact cgtttcttgg 108600
taggttcgaa tccgggttgt gtaatataat aaaaaggtta tattctgcaa acacaaaact 108660
ggatttattc ggatccaaca taaaaaaaca tgacatggtc ggacgtctga tatggagaac 108720
gtatcagacc ataataaatt acattgaaaa atattcaaca tttgaaaaaa cacattctta 108780
tccgttgtcc gacatacaca agatcaaaac cgatatcttt aacatgactc cgaagtggga 108840
ttatttttgg tcagactata aaattttacc agagacatca gacatgatca gagaactcga 108900
atcattaaaa agaaagaacg taaatcacaa aataatccaa caagaactta aaaatataaa 108960
aattgaatct tataaaaaat ggttcgagaa taatccagag tattcgacca tgttgaagaa 109020
taaacgtcaa cggatcattt tgacagatga catagatttc ttgatcaaaa cggaaatact 109080
tttcggagac gactttgtca cgttgatcaa aacagaaaat cagatagtcc aagacatgat 109140
atccaaatcc atagaaaacg tttttgggac aatggagaaa aaacatgcgt cgacattttt 109200
tggttttaag aaaaaggttt ttggttcgat ggacattgcc ctggtcaatt gatttttta 109260 tcctggattt ttacttctgt agtcacttat tcttgtgaaa ataacggaaa tgatcaaggc 109320
aaaagtaagg aatattatta tattcattag tggtttgata atggtattat atttcaggac 109380
gtatctgttt atgtttgcat ttctggaaac aatgtcctga cataaaaaaa caatattagt 109440
ggatatatta taaaaagcac tggaaagcat gacacgtaat atagtttcag aagcattcag 109500
acaagacatc cctgccattt aaaaattaaa aaaattaatc ctgaggagga aaatcttcga 109560
actggacggt tctgtcattg tcagtgactt gtctacatgc cccgataatc ttcctgtcga 109620
aatccaccaa gactttttgt gccagaggtc tgaccttggt ataaatatta gtgaacagat 109680
ccgctgacaa tgaagtgtca tcaattgtgt gtccacctgc tctcagaacc tccactagct 109740
tgatcatgaa atcaagttga agagcgaact tgtaaagatc tctgttcatc acaaacaatt 109800
gtctgaactt gttcatcacc tctgtcttga tttctggctc gacctccaga tccgactggg 109860
cctcgagctg tctgatcttt gccatggtct gttgcatgaa gtcggctccg tgaagagcat 109920
gtcccaagaa ctttgtccta ctggaatgag taggatcgaa cggagccata ttaggattac 109980
taggaccaga tgaaccaggt ctactaccta cacttctgtc aacaagtgac ataagacgct 110040
ttatctccaa tgacattctg gcttctctgt cctctgtcgt gtctgtcccg atgagatcat 110100
caatgtaagc tcctccgtac gcgtcgaact ttctggcaat ttcattgaac atgtccttgt 110160
cgaagcttgt accgaacgca gtgttcatgt tacacatctg agccctgata cttgtaggaa 110220
tcaaattact gatcttgtgt agactctcct caaggttgat aggatcacac ctgattccac 110280
tgacctcttc atagaatctg tcatgttccg gctgaagaaa ctttacgttc ttgagatctg 110340
agctagactg acactctgca aatcctacga cgtctacctc atggaaaaga ggagggtcgt 110400
tcttgatcac aatactactg agaacacctg aaccggcagc gtctctggca gtctccagtg 110460
tctggagctt ggtcagctta gtgggatatg ccaaaaactc tagaagctcc ttggattgaa 110520
gaacaagaga tttcacgatc ttttcataag gagtgtcacg actctctctg ctcaactttg 110580
cctggagatg aacaggggtg attgctggtc tgatgatgag atgtccactg tcatctgtcg 110640
ttgtgtctcg aaaacttact tgatatccta gctttgtaag aatcaaccag attgtctgaa 110700
tataatgagt cagatcacta aactttacaa attctccatg tcctgttcct ccctccttca 110760
tactgacaca atatgcggcc aggacctgga taggagaagc cgcgtccttg atcattgaca 110820
tgaacatgtc aaactggagc tttgtcattt caagcttagg attggacttc agtatcatct 110880
tcttcctgta ctcggacgaa gacaaattat tcactgtggc gttttctgcc atgatgtcat 110940
ctgcaatgac cttcagtgac ttgtacaatg tcatgcttcc tgtcatgtac ggaaggaaac 111000
agaccctctt cagattaaca ttaagaggga gctgattaag aggaccacag aaagtgattg 111060
ctctcatgtt accatcgatc atgacgtcct tgtcgtacaa tcccattacc agactcagct 111120
tggaaatgat accctttgtg taaatacaca tgacagtcca ctcttcagca gaaattccag 111180
accagaacat actcaattgc tttccgtttc cgttctgagt cagttccttc tccagataat 111240
tgattggttc gtatccggga tacaacatgg gagtgtatgc gacagagaaa tgagcagcgt 111300
acttgcacaa gaacttgatg ttattaggtg tgagttggag gagcttcttg tgagaaagaa 111360
tcttgataag aggaccagga agtggagccg ctgctcccgg ggcccccggg gctaccggtg 111420
ggttgatgac cgtaggtatc aacacaggtg ccgcattctg atcaagctcc cacatcttgg 111480
ctctcatgat ctcaggataa tttgagacgg tcaggacatc aatgatatca acttcagggt 111540
caacggcagc gacagctgcc ggacctccga ccgccggaac acctctggtc acttgttgga 111600
cgtacgtgac gttgttggaa aagttaccgt tgtcgtcggc acctggatct gctccgagag 111660
acatggaaac atgcctgtag atgtcgactc cgtgtccgat aagataatcc aacttcatca 111720
gatacaaggt gtatccggga gacaagacaa tcttctttgg aggtccggca gcaggagcat 111780
gtgtgtgata ataacctaca tgtggaagac cacttttcct acaaggggca ccacaatcaa 111840
tggtcgcagt agaaaagaaa tctccgaaat aatacaggaa caccatgtga gccatggaag 111900
cctccctccg atcatgtgtg gccacgatac caggaatgaa aatatcagca gtgttgtaag 111960
aaaccatgtt gttgtttggg accgtcgttt cccatctggc ctcgtctggg ataacatttg 112020
ccggtccatt ggcctgagca acataaggag ccgcgactcg ggccgcgtca tctcttgtgt 112080
ccattacttg attgtcccag gtaatacgta gataatcaac acctgaattt gccactgcag 112140
tggcattggt ctcgtacatg atgagacctt gacttttggg aaagagcata ccagggatgg 112200
cagcgtactt tgcccagacc tcggtcaatc cataagtggt cagaatataa ttgaagctcg 112260
gtcctggtag gacagtctgt acataattca aaatagtaag agaaatgtca gacttgagaa 112320
ttgagtcatt ggcataataa gccccgacgt tttcgggaac catgaactga gacgaaagag 112380
aactcatgat cttgtccacc ttgagacggt tgaacatgcc caggttattt ccgatatttt 112440

-continued catcggcgaa cattcctaca ggcaatgcct cgttcactgt tcccagtccc ctcttttcct 112500
tgaaagaaac atgaggcatg gagtctgcat gagtgacata atcaccgtta caatatccac 112560
cggcaaatct actgatgacc tcaggatgcc tgaatctgaa ctgtagaaat tgtagggtct 112620
ctggtgaaat agttcctacg tcggggacca cgaaaatatc agaatttaca atttgatccg 112680
tggtcggatc atgagtgatt ttcccgtcct taattttata aggaaacgac gatgctgttt 112740
ccgcgaaaca tttatgattg accagggccg tcgaaaaact ttttagtgac gacaatgtgg 112800
taagtttctg aacagggtct gtggtagcat gagaactaat tatatcaata ggatgagtat 112860
acgtggtatt catccattcc aaatttttat catttgccag atacggaaga gtttctataa 112920
cgtgctcgag cagtttattt tttacagaag tttcggtaaa caccgaagac atctttttgt 112980
taaaacattg ttgctgatgt ttttcatcaa tagcttttgg aaatcttgtt tttgtattaa 113040
accggaacat catttatctc acagaataaa tacaaaaata agtatgtctt cggaaatagt 113100
tacaagtgat tttttcgata aatatataga taataattat actgattcta gtattttagt 113160
agacaattca cctgctttac ctcaactcag tgttaatgat ataaatccta caacattaga 113220
tgctcttgta aaatatatga atcaagaaac agaggaagac aatgataata attctgaaaa 113280
gttttctgtt tttgatgaca cagaaaacct ggaggaggac aatgacatag acaatgttga 113340
tgattttgac aatgaagatc atatcgtgga cgatgaaata gcagatgata acatgagtaa 113400
aatagtttgg gatgaaattc aaactacatc tactttgatc aaacctgtcc agaatacaat 113460
tgaaaaaaag aaagacatgt acgacgagta tgcatttcct caatttattc ctaaaggata 113520
cactaaacaa gatgctgtta ttaataaaca acgtcatgtc attgttccgg aaactgtact 113580
agaaaatttg ctagagactc cagatgatac ttttgatact tcagataatt acttgttgaa 113640
cgaatcagac accatgtcca tttcagacac tcatcaagat acttttgaca tggtgaattt 113700
aagtcatcag acagttgaca tgaccgaacc atttactgat catgatcgtc tgaagaagct 113760
cgaggaagaa aataaaaaac tacgccagga aagcaaactc gaactgagtg cgaatctagg 113820
agagtttctt gcacagatgc agtttctact actgaatagg aaccaacaca aaaacagaaa 113880
aagtcggttt cataatcaag tgttccaaga cctactctgg taaaaatata gtcttgcgac 113940
agagtgactt tgacgggtgt gacatgacaa caatagattt gatttataag aagctgaaaa 114000
aaattcagac cgatcatcaa aataaatttt acattttgat ggttttgaaa atgattttca 114060
taggaatagg tagagttata tcaatgttcg ggtttgtaaa aatgggtgaa ataattaaaa 114120
atttggaata tgaaagtcta tttttgggaa tagacgaaga atgtgatgaa ttacaagagt 114180
atgtatgtaa taatatgatt cctacatcat tcaagggata cactcctgtg aaactcagct 114240
ttaaaatcat gctacatttt gccatgacca tttttaaatt gtcgatgtcg atgtaaaaaa 114300
atgccttata aataagaaat aaaaaatgag tactgatttg actcttgtga tgggagagcc 114360
tgcttctgag gtttctactg aggtttccac tactgaggct tctactgagg tttctactga 114420
ggtttctact gaggtttcta ctactgaggt ttctattact gaggtttcta ctactgaggt 114480
ttctactact gaggtttcta ctgaggtttc tactgaggct tctactactg aggtttctac 114540
tactgaggtt tctactactg aggcttctac tactgaggct tctactactg aggcttctac 114600
tactgaggct tnctactact gaggtttcta ctactgaggt ttctactact gaggtttcta 114660
ctactgaggt ttctactact gaggtttcta ctgaggattc tactgaggat tctactactg 114720
aggtttctac tactgaggtt tctactactg aggtttctac tactgaggtt tctactactg 114780
aggtttctga cgattctgac gattctgacg agaccactac agaagagtct gacgattctg 114840

-continued acgagaccgt aagtgtactg gtacctgatc ttgatgatga cgcagctggt ccaggaagtg 114900
attacacgag gtctgtcatg ttttctattg gacatgaaga catgatcaca gagcagctac 114960
ttgttgccaa tacaatttcc aagatgtcaa aggatcatag caggctcaag acagagcttt 115020
ttgctgccat gctatcatat aactcactcg tgaagtttta cagatcactg cctatgacca 115080
ttcgtcatga caagtctgtg gtggctcagg cattggtggt caagaagttt ggtcatataa 115140
tgacagagat caggaccctg atgcagtaat ttttttatat tttttaaatg tttttgattg 115200
gccttttatt catggtcgtg accggtgtca tgtacctgtt acaacaaatg accctgttga 115260
gaactacgtc gagacaaaaa aatacagaac cacccccgat ggtcagtaga gaatggaatt 115320
atcttaccga gacatatgat catacggcta acacaacggg tctggtaaat tcgacaagta 115380
ctttttctga cacggaagtg tcagattcta tgttgtatca attacaactc acgttagaaa 115440
atattaaaaa aattgttgaa tcaaaaaaat caacccgtga ttattattgg agacaatgta 115500
cacacatcgt acaaagatat atttcccaaa ttcaagaagt ttccgcggct gtctaaaacg 115560
ttccaaaaat ctttttgatg atttccaact tttcctttga accgatttct gtctccatga 115620
tggtatcggc ctgtttcggc caaatattgg aagacttttt cttatataaa actcgttcca 115680
gatcagaata ttttacgtat agtaaaacaa cgacaccgat gacaatagca cagacaacaa 115740
caagtttaac aatgagaatg ttgttcattt aagaataaaa aaaatgtacg gaaagttgac 115800
ttctgtaata cacagggcgt ctcggacaaa atctgtacgt aaatctatat ttattttctc 115860
gggctttttt ccatattttt ttggtgacgt actctttgtt ttttatgtta tgtaatttat 115920
gtgtgttgtt gtacggaagt tgtagatgca tgatcattcc tgaaatgtca ggaccgtatc 115980
cgtacggata cacgaccggg aatgttttag gtttcataaa ataatgagtc agtgtccagt 116040
tgagcatgtc aatccaagat tcatacaaat cctgtgagtg taattgtacg tctgtggatt 116100
cttcacagaa cagacaaaag tcagtacata tctcgtcgga tgaaaatgtg ttttcaaaat 116160
ttgattctgt gatcatcccg tcgtcgtcta cgacattgac aaaattcctt tccatgtaat 116220
tctgtacagt gtcaaaagcc tcaatgttcg cgatcagcca ttttctgaga gtgtctctgt 116280
ttatgtttat tcggtcagga aagatttcca accagatgtt ctcgttatca agtctgtcaa 116340
acagatgttt gaacattctg taatttccta taccaggata ataatccgaa cctaggatca 116400
tcacagactg aagccacttt atcggacatg ttatttgttt aggatcgtac aaaccagcag 116460
gacacgagta caagatgtct gcctttttgt ttcgtaaaca gaaacacaca cctctgacaa 116520
acaaatccca atcattagat acaataatcg tcggagagtc ttcgtcaatg gtaaggtact 116580
gatatatttt atgatctgcc tctccgtcta tggacggagt caagacaatg taatcatctt 116640
tggataatct cttactgagt ttcgaaagaa agatccggta cttgtcatcg aaaaaatcaa 116700
atttaggaat cgccgttccg aatcttttgt tttttttatc gttgtacagg cggcgttgta 116760
attgttcctt tactttttgt accggggccc gtccgtcaaa aacgcaaata atttcagaat 116820
atacagattt caaatcattt aatttattga gcaggtcagt aggatcaaga tcttctttta 116880
cgtaagccca tatgaaaatt gacatgtcca aaataatctt agaatacttt ccattattta 116940
cgtattcagg atcaagaata cccggaccga ttcttgcatg atccagcacg cctcgtaatt 117000
tactgatacc catttaaagt tttcaaagat aaaaaatcat ttttttactc gttgggaaca 117060
ctctcataat aattcccgac ctcctctttc ttgataggga tcaaagaggc cagaccaaaa 117120
cacattgtca gaataaatcc tgcgacacaa atgacagcgt tgacataata cactgtcttt 117180

-continued gatgtcttgt tagaaccggt acggtccgtg gagaacacaa gatttgcgac catggcaatc 117240
agcagaataa acgcgatacc catgaagatc ttcccggcat gttcatgaac ccatgcatgg 117300
aaaaccacgg gcttgaccgg gggaggtaga ttaggtctcc cggatttacc agcagcgaaa 117360
tcagatacct gaccagaatt catttattaa gtttattttt ttaacaaaca cacaataatt 117420
caacatttag ttttgtcaca ttattccacc atttaaccca tttcaaagat ggttgatata 117480
acataacatg ttttacatca tacggctcga tcagttttaa acatatttga tcgagatcac 117540
aggtttttaa aaagtcaaaa taaattatat gaatattaga atccggtatg taaagcggta 117600
gattcaacca gttcaaaaaa cccttgacaa cttgtccggt gattgattta tacgccaaag 117660
agtcaaagtt tttaaaatcc gtggaaacac agatcagtga attattaggt aataaaatca 117720
tttagttgaa aatattcaac gaaagaacaa acatattaat gtaagtaaaa taagtatcag 117780
aatagcagaa gttatgtatc ctggaataaa ccgtgaagga ataaacgttt taggtgctat 117840
tgttttaaca gtatttttac cacttaaaca attatttatt aaaatcaatt caccatccat 117900
gttacctgtt aattttttga tgtttatctc acaatttact gatttacaag aatttagaat 117960
ttctctcccg tattttccta aaaaccgggg atgtgtggat ttacattcta ctgccataca 118020
ttctatcgga gccggtaaag tagcaagatt tttggaaatt gttccgaaac ctttttttatt 118080 tttacagaca cactcaggtc tctcctctga acaatgttgt tccagaatca agtcatgtaa 118140
taaataaaaa tgaggatcgt agattcctaa atcccatatg aatcgtcccc atattccagt 118200
aaaatcagat ttggccttgg ccaaaaccgc atcataaaat gctttattag gacgtctgac 118260
ctgttgttcc atccaatctt tacaatttga gtcattccat atgtcattgt taacaatgca 118320
tttgtttaac atggtatgat cacatgtaga actttgataa ttatttacca ggttcgacct 118380
acaatacgaa ctgttgcgag tacaacattt ataaatatta tcgggagtag gtatgtgatc 118440
tatacgtttc cataaacatt cttgtccttg tctgatgtac tcatttccgt aatcgggaat 118500
ggttttaaaa ttaaaggctt tccaaccagg aaacaatttt atttcattgg cccaccatcc 118560
tgaattatca aattcataaa gatcgtattt actttttgtca tgatcaccta aaccattttc 118620
ataacagaga gcttcgtttg ttataccagg aatgaacact ccactgttgg ttatgtaatc 118680
aggtaagaat tcataattga gaaatttcct acggccgttt cccctgtcta ttgtacaaaa 118740
ttgtttttca tttgtaccgt tttctaaaaa agaaaggttg acattgtcgg tgaagttttc 118800 ggttttttttc aaagttaccg tgacacccat atttataaaa ataaaaatta cttttggaac 118860
atttgactga aatcaaatac gttattgtag tcggtttcct cgaccagttt ctctgctgta 118920
tttgtctgaa cctctggttc gaccccagaa taaaactgga cagcatcgac tcggtccgta 118980
ctgtaatcaa caacgtcctt tgcccgagtt cctacgaacc ctgtgtcagt aaacaacaag 119040
tcgacgtcga cgtcgattcc attagttgcc tcggcggtat tacgagtatg atgcttcttg 119100
gtggtctttg actttctctt ggttttcacc agagcctttc tccctcctga catgtcagac 119160
ttaccacatg catgagactc ggaaataaat ttcgcggcga agcccactcc caataccaca 119220
ccgaacagtc caaacatctt gtcgactctg gaatagaacg tgaggatttg gcttaggaac 119280
gacatactga taatggcagt gatttcaata ataatatgtt gggcaattgt cgtggtagga 119340
taatacgcgt tgatccatct ttgtgagatc cagagcaaca gaagactccc cttgttagga 119400
acgtccagaa gatacaacat gaggagcacg atcacgaacc cgatagtggc actgaaaaac 119460
caagagatag cagacgccac aacatatccg taaatcatgg tcggggtctt cacatgatac 119520
gtcctgatga tattatccaa cgtggacaaa acatcgttga tgtcgatctg cttggtctca 119580
tgacctggat ccttcttggg atttactgta gggaggacat taggctgggc cgtggtaccc 119640
ggcgaatttc cgaacagtac cacacctccg gaaggatcat tacttgccga aacaacaggg 119700
acaccaccga cagcactctc gttttccaga ccattaaaaa tattggtctg ggtcgttctg 119760
ggagattcct gtacattggt tttatcagat tcagtcaggt gctccgaggc atgaatttcg 119820
ggatctgaca atccgatagg tacactactt tttccattaa caggtgaaat atcaacactg 119880
attacatttt tacctgctga tgaattatta cgaatcaatc gagacttatg tttcatcatt 119940
taattaaaag aaaaaatata taatatatga aaattgttta tgtaataatg gcatcgggta 120000
aaaaaaatat gcgaacatgt ggtaaattag ccaagaacta tatcgattta atttcaaaaa 120060
acaccttcga aaaaggcata ttaacatggg acgcagaaca ttccaatgaa caagaaaacc 120120
ccattatatt aacaaaagta cgaccagata tatccattgt tattcctttg ggtattggt 120180 cgaatcctat attgaaaaac tacccgaaaa tcgattataa tatgacaaca ttgattccag 120240
acttaaaata taaagaaatc gaattgagag actaccaggt cacaccttat tccataatca 120300
gttccaccat agataaaaaa atagaagaat ccagaccatg ttttttgcgt cttataatgc 120360
cttgtggatt cggcaaaaca atgatggcag taaaactgat tcaggaatta aaaataaaaa 120420
ctgctgttat tttatggtgt actagtctga tgacacaatg gatggagagt ttaaaatttg 120480
ggggaatcac tgacgtggta ggtagtcaag ggtctattcc tgacacccta gaacttatta 120540
atttaaaata tcctgatatt attattatca cggcagctca tctggtaaga cgggattgta 120600
gaaaacttat ccaatcaaaa tacgacatga ttttcataga tgaaagtcat aaatataatc 120660
tgaataacgt gaatggattg aaaaaatttt tacattttta cccttgtccg ttcacgttct 120720
tcctgacagc tactccaaga gtcataaact ctttttattg taatgacatt ttatcatttt 120780
gtaaagacaa taagattttg aaaaagtaca gagtgttatc tagtacgtcc tcggtcatgt 120840
ctgaacagac caaaaaaata tacgaagggt acgactctgt aaaagacaga tataaaatga 120900
tgaggggtat ggtcttggaa aaagacactt acagactcga atacattctt gaaacggtca 120960
aagattattt tgcagatgac atgtttgact gtgggatcgt tcttacaaaa tcaagaaatg 121020
tcatgaagat tttatttaat agtttattgg aagagtttcc ggaacatgtg tacgtcgcag 121080
acgcagaaaa aacaaaagaa acacaggtgc ttttacagta tctcaaaaag aaaaaatgtt 121140
ttattttggt ttctacattt caatatgccg ggacaggatt ggaccttcca aatttagacg 121200
ctgtgttctt cagttctccc atgatcagta gaacagacgt cattcaaagt gcaggaagag 121260
taagtaggtt caatcctaaa aaacctatac gattagctgt tgtgttcaat gtgtctagta 121320
tacttaattg gataaacata atgagaaaag gatctaaact cgtgacagaa actttgagta 121380
gtctggattg ggtagaagac atatcagttc ctaaataaat gaaatttcaa aatattaaat 121440
ataaacgtgt tgtaaagatg tatattactt atgggtgtgt taatattaat ggtatcgggg 121500
catcggttaa aaaaggactc atgtccataa tcaaaggtac aaattttgat gtatatttct 121560
tacaagaaac aaagtcagat ccgactcaag aattcattaa tgacattaac gagttaggtt 121620
accgtctatt tattaattca tctacacaat ccggtagggc cggggtatgt atattgatta 121680
aagaaatata taaagatcgg acaatgtttt ataattatca acatttacct ggattcaaag 121740
gacgagtttc aatggtaaag attgacacaa tgtgtttttt caatgtgtat ttaccattta 121800
gttcgagtta tgacagtgtg gaatgggaaa gtaaaattac cattgtcaag aaacttcatg 121860
acgaagtcga attgatttta aacaaaggac ataacgcttt catatgtggt gattttaatt 121920
taatttacac aggccaaaac atgactatca ctgacagtac agggtttttc catgacgtgt 121980
tgtcacatgc agtgaccttg aaaattcata ccactcctgc tttcatgatg tttctggacc 122040
ctctcatttc tgagcttaaa tttaaatgtg ctgataacat ggaatgggat tatgtaaaaa 122100
atgatgatgt tgtcacgttg tcatctacca cagacgaaag taacttgact aatgtattaa 122160
acaatgttga tcttatcaaa catatgtgta atatttatga cgtgaagatg aaacatgact 122220
tttcatataa ttcatctact cttgctacca ttcctaataa tattaggcgt ttaaatggaa 122280
agtcgacgta tttacaacaa gttgtgttag aatgtcttag aaatgtaatt ccaatgattc 122340
cgctaggatt tgaaacaaaa tccaattcta gaatagacca tgtttattct acgactccta 122400
ctgtggcatt tgtcgatgcc aatataaaaa tcagtgatca tcagttcata tacggagccg 122460
tgtttcacaa gtaagaaacc aaaatatgct tcagtgcttt tccacattcc ccattaggta 122520
atgcgaagcc atctgttgac aaacaagatg tcatcgtaaa atttttatta ctaggatctg 122580
catcacaatt gacattggca ccatttgttg tttttataaa taatacatct atatctaaag 122640
aatcaaatgt cacggttgcc catttgttat ttatgcatat gtaattacta ggtaactttg 122700
ttgataaatc attgaatatt ctgttgtttc tcttcttctt caacatcaca ccaggaataa 122760
caaaattgta taaaaatata tgaaaaaaca aaatcagcgc aaatagtatc atttataatt 122820
gttattttta ccgagtaaaa catgcctttt tcaaattgta aagaatctaa tctgaagaaa 122880
ataaaagaag tggaacgatt atataatgaa ataaaaaaac tttcagagat catagaaaat 122940
gaagtacatc aaaacaaagc agagatccga gacaagttat ttgaagagta taatgtattg 123000
attaaggagt tgacgtatga atacggagga tttcctttgg gaatcctcac tgattcacat 123060
atgacaaagt tcagaacagt aaaaaacagt aaactgaaaa tggctcatat gatgaaacta 123120
tcaaacttta aaaaaataca atatgattta tctttaccga tcggatctta tattataatt 123180
cctaaaatgg acggtatcag tcttgtctgc tggaactctc cgaccggctt gatgtttctg 123240
acacgaggag ataatgaatt tggaaaaaac aaaattgatc tgatggagta tttttacca 123300
gaaagtgtga tcggagcaca aaagtacttt aaggaaaatc ccgatcataa aggaatcaga 123360
ggagaactga ttcttgattc aggaataaag tcctattcca aatacatgag agtttataat 123420
cctgaaatta ttgaaggaaa tgtgtcagag acggatcctg attttcctga atcattggac 123480
accacacatc cagaatcata taaagacggc catgaaccta ttactccata ctctgataac 123540
atttctgtgt ccactgacac aagtataaag atacctgaac tttccattgt ccctgtatgc 123600
cagtcgtgta tgaaatgcga agaccgtaaa ttagataatt ttcacacggt gaaaatgttt 123660
agtattttca cgatccctgc atgggtagaa gtatgggttc ctaaacggtc catcaaaaag 123720
tccgcatgtg cctcacagat atgtgaggtc ccggaagatt ttgaggaacg gatcaaagga 123780
aaaggtgtca aagacgacag tggatacagt aggacaaaag atcaagaaga aggtagttac 123840
atgattaaag gttacatgtt gtacagaaga aatttattga gtagtacaaa cagaataaac 123900
gttccttctc attgtccggg agacttcaaa attagattta tatctgtaca gtatcaggtc 123960
gaactcatat caataaaaga agacttctta cctcatttta aaatagagat caacatggat 124020
tcttgtatga gaagagaatt aataagtggg ttggcaaaca gaaaagaaat cacttgtcat 124080
cataacgtgt ataaaaatca tattcactgg gtatgttatc aggtttatgg ttcagatcgg 124140
gtcctgacag aatcattaca acaattaaaa aatcataaaa tagaaatagc acctgttttt 124200
gagaagaacg tgagaaaacc gaccactatg tccactgact acgtccaaaa gtttttagat 124260
aaatacacgg ataaaacttt tgattgtgac gggatcacgg tacgtaagaa cacaaatgat 124320
tttgataaga tagtgggtct gaagaaaaca cgttttgaac cggccatgat aaaagccatc 124380
ttgtggaaaa aacaatcttc cggaaaaata attcccagat gtgagataga acccatttct 124440
cataatggta gagttttcaa aaccctgaac atgttttctt ttgaaaacct ttgtggtgaa 124500
atgtatcagg tcaatgacat gatagaggta aagtttgtcg cagacagtcc ggtcatacat 124560
aagaatttgt cccttaagaa aaaactgacc aacgaacaat ttaaaaattt aatgttgtct 124620
ttgttcgtgg aaaatgtatg ggtagaaggt gctcatctgt acacgacaat gaacaaggta 124680
atctggtggg taaaaaaact taatatacaa aacatacaag gacaaggtct gactcgattt 124740
ctgacagcct atgacatcat ggaatacgat gtccagacat tcgtgaaatt catttacaaa 124800
gcaagtcgac aaatagaaaa aattagattg aagagtcatg tcaatctcat tcaacatatt 124860
ataaaggcaa tagatgacaa tgaagagttt gccttgagta tgtgggcctt acaaattccc 124920
ggtattcaac ttgtcacatt aaaagacaaa gtaaataaag gaatagaact caaacttgat 124980
cctgtgacaa ataaaatact ttcacataaa attgtaaata aagaattgtt tgaatcaaac 125040
cctacaataa taaagttcag agacagcatc tctgaatttt tctcgttgta caatttcttt 125100
ttcgatgtca aaacaaaaat caaaagtgat taggtacatg acaatagatc caggaaaaat 125160
aaatcctgca ttctgtgtaa tggacctgaa catatcaaca aaaacaatca ctcttgtgtc 125220
tctgtctaaa gattgctggg caaaaaacta cgacaaacaa attggttatg tcttgacagt 125280
gtttgctcct gattatgttt atgtagaaca acaaccaaag tatgccaatt cacaggtacg 125340
taaatatggt tttttattc aaggggtttg ttgggccaga gacattaagt ataaacaatg 125400
taaaccatat ttttggggaa agggtgtgaa agactataaa gagcgaaagc gtcgtagtat 125460
atcagaattt ctagaaagcc tgaaaatcct aaaacttaat tttaattatg aaaaatatat 125520
aaataaactt gacgatattg ccgacgcgtt taatatgaac ctgagaaacg taatagaatc 125580
aaaagagttt gccaaattat gaataccatt ttaaacttgt tacatgagct atccgaaagt 125640
ggatacaccc gaagcatttt taatttttac ataaagaatg agtctgataa aatactggga 125700
actttgttgg aagaactcaa aagtaaaata gaattaaccg acgactggga ttcgttatgg 125760
aacaatccta aacttcctca agatttgtta ttcaagttca agaacagtat tcaaggcatt 125820
catttatgtc ttcaggataa aacacatata ttcagaaacc catcatgtct tacaaagtct 125880
ccggacataa aggtcaaatg tttggaatct gggcggttac aatttgaact gcccaataaa 125940
aaacctgtcg atgacatgat aaaaatatat caaacgggta aaataaataa tccaaatgat 126000
ctggtgtatt gggttctccg tgacaagaat ccggtcataa gttatttgaa aaccataaac 126060
agaaagaaac ggactcgctt caccgaatta tacaaggagg tattaaacaa acctcatcgt 126120
tcaaactttt ccggaatcat gtcaaatgaa ttccaggacg atcacataac aaaactggac 126180
aacacaagtc cgtggatcaa agaatactct acacgcctac gattacaaat gtcaggtgac 126240
aagatcatat caggcggaag aaccggtctg tcacaaagta tagacataac attgaaaaat 126300
aaaacgtgcc tgatcctgtt taaaaatgga acatttcatg ctctgctttc taaaaaagac 126360
aatgaaactt ttttagaatt tataaatcta atcctggacg tcctagagtt tgtttgtctg 126420
ttccagatta tatttgtccg ggcagattct gatcttttta aatttggagc atgcctacaa 126480
tctgtggatc ggacttcggt cactgatact ttgaaaatac ttgatcctaa agtaaatatg 126540
ttttatccga taagaaacct ttcattggga attttaaaca ttattaatac aaccatgaaa 126600
atgtcaaaag actttttcat aatactaaag gaattaaata aaagtaaaca gattaaatta 126660

-continued tacaaaccca attacattaa tttcgtggtc attaaaaacc caaaagaatt gatcacacta 126720
attaacgatt ttcatgatac tttaaaaaga gtaaaaaaag tatataaaca aaaaagaacc 126780
aacccgttat ttaattctgt tcctgacata gactaaatgg ataaaaagat agggtacttg 126840
tttttgaaac ctgaccctaa atgtggtgtt ttttatagac cgttggattt ccaatacaaa 126900
agttatcgta actttcttga atttcgtatc aatgagatac ttgaaattga ccgagagtta 126960
cactctgaca aaaccggtga cgtcaaaatg tttttaaaaa tatacaacat tgaaaaaacg 127020
tttccgacaa acaccatgac attacacgct ctcaaaaata aaggctacac ttgtagtgtg 127080
aaatttaata tcatgttgta ctcaaaaaca agaacagatt ccggtatcaa agaagccatt 127140
atattaaatt ataccggatt caacgacaac atgatcaacg ttcctctgat ggtagggtac 127200
ggactaggtg acgtgtttgg ttccggagcc atattgtacc ctaatgaaat cggaggaact 127260
tttctaaatt acagatccat cgagaaaatt ggaattaatc ttcttgagaa aacaactgcc 127320
tggccaaaat ttaaaaaagt aaaagccgga cagtacgctt tcagttttag ttccataagt 127380
cctcctcata tcacacctcc ggtatacaga tattttaaaa tcgttttaga ttttaacaac 127440
ccagaggcat ttgtcataag ttcacaaaaa atgttcatca ctgtcaacat attgatcctt 127500
atcaaatatc ttctcaagtg taacatggag ttcatcagag atgaacttct caatggtctg 127560
gatccggtca atgactattt cttacacaac gtggtcaaca tgttcgtgac cggggcagaa 127620
aataaaatcc aaaacatagt gaccacaagt agtgtggtca gaagtgtggt caaggaattt 127680
atcaacttcc ttgtggaaaa agagtacaac gactccagga gtaaattgac cctgaaagaa 127740
ttcaagaaca acatgttcac aaatttctta ccacatattc acaacaacga tgatgtatca 127800
aagggattgt atctgttatt ggttgtcaag atgtttctgt ttgcaatcat caaaccacat 127860
gaatatcccg acagagacag tcatgcgacc agacgtatct tcacttacgg aagttacttt 127920
gaacaggtga caattgatga actggaaaac tttgtcacaa aaatcaaaaa tgccggatct 127980
actgtgaacc atatgtcaat gactaccatg ggtttcaact cggctttcaa taatttactc 128040
agtggtcgat tcagaaaaac aatcagtcct cacatccgta cacacgtaca ttatagttgg 128100
atgcagaacg tggtaattcc cagatctatt ggcttttatc cggatcaagt taaaattgct 128160
aaaatcttca actgtcgtca atttcacccg agtcaatatg gattcttttg tccgactgac 128220
attcccgatc acggagaaag tgtcggtctc gtgattcaac tggcccttca ttcgtacatc 128280
acaagtatta aactacaaga atataaacag atcagaaatg aaattatccg agaaattaaa 128340
aatatattgg gagtcaaatc tgatgatcct gccacatctg ctcagatgat gagattcaaa 128400
accggagtcc caatcatgat agaaaataaa atcatttgtt cagtggctcc tgatctcgct 128460
atcaagatag tcgaagtcat ccggaacata aaacgatcag gaatgttctg tgtcaatgat 128520
ttcggagtca cttatattca aggatacatc agacaaatta aatttaacat cggagccggt 128580
agggtagtaa gacctttact tgtcattgac aacggagaac tggtcatgga aaaataccgt 128640
gatgagatcg aagcgtttga cgggacctgg tcagagctac tagagacgtt tcctggagta 128700
atagaaatca ttgacattga acaattcatt tatagtaaca tcatcgagaa tcaaaaagtg 128760
tacgaaggaa tgtctctgga acaacgtaaa ctatatcagt attgtgactt cccagaagag 128820
ttcagaaatg gatacagtgc cagttgtctg ttgggaatta atcataacgc cggacctcgt 128880
gccatcttcg gatgtgccca ggtaaaacaa agtatcagtt gtctgacatc tgatatcctg 128940
aataaaattg acaacggtct tcatatgatt tatccagaaa aaccattggt ggtgagtatg 129000
ggaattatca catctctgat ttccgacaac acgttcggac aacatatcaa cgtggctctg 129060
acatcgtgcg aaggaatgaa ccaagaagat gctatagtat gtagacaagg atttttagac 129120
aatcatggaa tgaacatcct gagtactaaa aaaactcagc ttgacattcc caatgaaaac 129180
ttcagggctt ctcaacccga ttacactgta cataattatg ggaaactgaa tcatcttggt 129240
gtacctgtga tcaatagtat actagaagcc ggtgacgcaa tgtgtaaaaa tgtttctatc 129300
agggtaattg ataacctggc cggagaagtt tccaaggaag ccatcaagtc tgacatcagt 129360
gaaggataca ctgacatata tccgggaaga acggtccggg tacaaattga aaacagtgac 129420
aaggtaaagg ttcgactgtt gacagtcagt gaacgtcaac ctataatggg agataaattc 129480
acaagtcgta caagtcaaaa aggaaccatc gcaaaaattc taccagatca tgaaatgcct 129540
tacatggaag acggtacaaa accagatttc atcataaact cgaccagtat ttacagtcgt 129600
aaaactctgg ccatgttgtt ggaaatgatc ctgacaaacg tgttcacaca taaaccgatc 129660
aacgaacaag gaaaagtacg ttacgtcaac ttcccgtcat ttaataacgt ggccctggaa 129720
tcatatttcg atttcggttc gacctgtata aaaacggcac atcctgattg gacacctgaa 129780
caagtaaatg atgaactctt ctgtgagcag accttgtata atccagacac acatgagcca 129840
tataaatcca agttcatggt agggatgttg tattatcttc gtctcagaca tatgattttg 129900
gacaaggcag ccatcagatc aagaggtaag aaaacaaagc ttactaaaca acctaatgaa 129960
ggtaggaaaa gaggtggtgg tattcgtttc ggagaaatgg aaagagattg tcttatcgga 130020
cacggggctg cttttaccct gagagagatc ctccacgatt cagaggaaga ccgacaaaag 130080
gcaaaaatgt gtaacgagtg tggtgatttc cttatgttgt caaaaacaga aagttatcaa 130140
tactggacat gttcaagatg tgacattgca aaattacatc ctacgtacac agaagcagat 130200
ctgtcacatg tagtcaaggt attcaaaaca caactgggtg cccaaggaat taaaatgtta 130260
ttgaaagaat cagagacccc cagtgtatat tatacaaaac cataaaaaat taattgagat 130320
atattacctg tgaacaaaga tctccgtgac taagacatgg atcaatgtaa atacgaacac 130380
ccttgtacaa aaataaattt cgtttacatt ccgacatggt cgaaaaaact tttaatgtcc 130440
ctgatggatt tgacactgcc ccgtgattat ttatctgata ccataaagag ttactgacca 130500
cacatctcca tttttctttt ttttctaatg agacatcatt tggatcgtat atggcgaaat 130560
cagaatattc atgtttactg tcctggacgt actcgttttg tttttgagca tgaacaaatt 130620
ccaaaatctt tggccagtca gaccacatca accatgcctg ttgtaaaaaa aagcaaacac 130680
atatgacact tattattaaa aaaatatctg aaaatctcat ttaattattc gtttttttacc 130740
tgattatcaa gggccacagt aattgctttc aaaagtttat ctgattcttt tttgtaattt 130800
ttcatgaatc ctgctgtgtc taattttgta aaaggtatgg tgttcacggt attattaata 130860
caacttacgt tttgattacg gagaatagca tacaagatca cgttagagaa cgaaggagtc 130920
ttgattaatg aaacatggcc atcagaaata gccgtgggca tttcaaggac tcgtccttgg 130980
acatattcgt acaaatcttc caagatccac ttcatcaatt ttttccattc attttcttgt 131040
ccggaaagaa tatcaaaccg tacatttaca tgcgtgtccg gaaaagcgcc ggtgctccaa 131100
gaagacaaga ccggacatgt cacgttcttg aaaaaaggtt ttacatgaac gtattctttg 131160
gaagccatgg gtttttcatc gtctgagaat aaatctaaat atgaacttcc tatgaaagta 131220
ggtgtcagct ctgtccaatt acttgcgacg aaaaaacaca aatctatttt tgtgtttttc 131280
tggacagtga ccggatccag gacatggaaa aatgtttctt ccagatcagt ttccggaacg 131340
tacttggtca tctttccttg agatatgtaa aagtaagtga aatcctggag agtaatcaca 131400

-continued cgtcgtgccg tggcatcatg agacaattta caaaacactg cgacgtcatc cgtggaatta 131460
tgttcctgat cggtctgatc aaaggtcccg atcaagtttt taaacttact aagaaatatt 131520
ctgtacagtg ggatagattg aagaactcca aggagctcct cgtgtgtggc atttgttgtg 131580
ttggacacaa taataccttt tgtgagtctg ggaagacgat acctgtttgt caaaaaggtt 131640
gaaaacagag cattgtacgg actagtgatt tttgttttta catgaaatgt ctgattcata 131700
tttatgtttg gcgtttatga tctcagtatc taacttttct attatttttt tcatcgtaat 131760
gtactctgtt ttgtacatgg tctctggtaa aatatcaaga aactgatcta aaaaaataca 131820
tacctgatca aaagattttt tttccacatt ggagttttgt tccatttaaa tggaattact 131880
tttatacaag ggactggaag aattgaagtt tttaaatatg tttcggttca agttacaaca 131940
aactcatgat cttacatcca ctgaaagtaa gcaagtcgta tgtgattggg taaatgtact 132000
aggtgcttat aataatacca atgatttttc catgctacca cacatacatg ttaaaaatct 132060
caacacacag ttttttaaat acggaaaatt cagtaaccag gaaattgtga aatttttaga 132120
aactggattt aaaatatcag aagaccttct ttataaaaaa atgccatctt acaaactaga 132180
cattactttg ttcaagaatg tcaggacaga catatggaca cattttgaaa atttaaatat 132240
taaatatttt gaaaatgaca ttgtcaaaca tcggttacaa aatgaaagcg acgacatcgt 132300
attatatgat tacgtggttt ctctactgac agaacaaggt agtaatttca ccctgacata 132360
tgataaaatg tcacaactat ataattttgc gaacgtaaaa tatcaggcgt tcggatcacc 132420
ctttgcttcc tggttatatt ttaaacctga cactataatt gccggggcgt attcactcga 132480
aggaccaaaa gtcaatcaag atttttaccg actaaactta aacatatgga caggaggtga 132540
ttggttgatt tacatgccta ccacaaaaaa agaatttgaa aaggtcatta aaaaaatcga 132600
aggacagtgt atgaattctc atatcggatt ttatattgtg tttcctaatc atcaggattt 132660
tgtggtaccg cctaaatatc ttcaggcaaa aattaaaaca aaaaatttag aatggatttc 132720
catgactgat tcaagaagat gtataaatag aaaaattgag tgggtaatct gtttttttgtc 132780
cagtagaacc actcataata tagaaatttt tcattgataa atgagtgtca tcaatttggc 132840
cagtgtcatc aattattgga ctcctgctgt ttttaaaaac atcaaggaaa acggagtctt 132900
ccgaaatgat attttcacag agaagcttac tactgtcttc actgtattca atgatctgat 132960
ccaggaatct attatggaaa atggactttt tttcatccct accaaaccta tgaaaaccct 133020
tcttaacatg ggtggatttt caattgaaaa tatgaagtgg aagtctctcc agaacagtcc 133080
tcttactaat ggaattttca gatccacatg tcagtctgtc agtaccagta ccaaaagcgt 133140
caagcttttt gtcaacgacg tcgagctcag tatccctcca aagtctgaca cttcttgtac 133200
catgaccatc acaaaaaacg tcaacaccat taatttggaa gtttcttcta agattgattt 133260
tgatggtttc gtaggaaaga tcgtgtatct ccagatggcg gattttaata ttccaaagac 133320
catgggtctc cctacttctg tactgtatgg attcggttac gtcacagagt ccactggacc 133380
caatgcaagg atcgttccgt gtaccctgga ggtttctgga ggaaatgcta atatgaaaat 133440
taatctaaca gaaattaagg aaaatacaat tgatctgtac atgtacagca gtacgttcgt 133500
gacaagtacc gtcacccctt tttaagtttt ttaccatgga caaggcaata agttcgattt 133560
tatgtaacgt cagtaattgt ttggaaaaat acggagaaga attctggaaa tgtccttgtg 133620
ttgtcggaac ggacttgtta gtcgactgtg aaacaatcaa ggaattactg gacactgtca 133680
tgcattataa tctgttgtat aatccttacg ggactaccaa cacattttca tcgcagataa 133740
ttttggacag gtacgtacat ccgtcagaac agaaaataac attctgccaa gaaaaagaca 133800

-continued aaagcctggt cgagtggtta ttgaatgaaa atgcgtacgg attcgtcgac aacacttttg 133860
cagatgaatt ggaaagttat tctactttac gatggacaat agatgaagtc atgaaacgac 133920
atcatctgga tcatccatca gacgttgaca tgagtgatct ggtgtcatgt ggaaaacatc 133980
aaaaacaaaa aatatcaaat caaaacattt tagaacttgt cctgaacaag ttgttttatg 134040
tttcaaaaat acttcacttg ccagtttttg atgatgtcat atttcatgga ttcagatttg 134100
acataagtaa ttatataaat caccagtcca gacgtgggac tgtctcatgg aatccaggta 134160
aaacatcaga ctctgttgtt ttacctgtac cattcaaacg cagatcatgt aatatcatag 134220
aatgtctgag agtagactat ttaacatgtt ttaatgccgt gaccatgagt agagaacccg 134280
accgggtatg gacagggtct atgttgtctt tgtgtacggt ggagaaaaat gattttgatt 134340
ttgatgtccc gaccttgttg tccacgttac attatgtctg tttgaataat gtatggccag 134400
agtcattgac ttctcccgat tggaaaataa cttacgtgat caacatgttg ttgagttggt 134460
tgaatttatc cagggaattc ctcgttaata taatttggcc aaatcataaa ttgataaaat 134520
gtaccatgga agaaagtgga ttcaagatag agtacacaga ttcaaaactg acctgttttg 134580
acgtcggtga aacaaatgac ttacctacat ctgtcgtctg tacactttct gatcttacct 134640
acgtgaaacg ttttttggta aaatggcaca gactcacacc ttcaaaagca aacaaccctg 134700
tcattgatca aaaacacgta aaggtaaaaa tgtcattgga catgtttaag atgatgattc 134760
cggattcatc tattatattt gaaccacata gttttgtcat gaatgattta tgtaattcgt 134820
actctgtgtt ggtacccttt aaaaaaaaag acacaaagag atcatattct ttgtgggatg 134880
aactggaaat gatggtagaa tataaattta ttctcgaaac aacagactgt gatatttact 134940
gcacaatggt aaaaaacaaa tataacacta aatcatatta catttccaaa gataacatgc 135000
tttggaaaat ttatggagtg gagccagttg tatgagaagt ctgttcccgg aacacacaag 135060
ttattgaccg actcttattt tggttggcgg ttgggatttc tggatggaag ttctattgta 135120
ccttataaaa acagattatt ttcattagat cccggtggtc gagtcaccgg gaatgtacac 135180
cgatcacatg tcaaaggtgt caatgaaatg tactggactt tgaaattgat atgtttaaaa 135240
aacaagtctc tcatgatcgt tcatgatgaa aaaataacag atgaaaaaat atacgtgtat 135300
tctaattacg tggtcgtaaa aactgtaaat tgtaaacaga ccattttaga catggactgg 135360
aggttgtttc atgtgggaaa aatatatttt tttgacaagg acaagatgta cagtgataat 135420
ttatataccg acacaaaaac ttatttttat ttttacaata ataaaaaaat tatactccag 135480
actcttcaag aataaaaaca tattccaggt cggtcagggt agtcgccggg tctgtaaaac 135540
ttttccagct gatgacaatg gcgtcttctg tttcattcca aatcttctta ttaagttgaa 135600
ataccgtacc gatagaattg acacccttac gtagagaata cacgtttgaa acacctgtgg 135660
tgatgttcca tacctggttc agacagaatc gtacctctgg atgttctgca ggactgacaa 135720
tcttatccag ggtgatcttg aaagtcttct catccttact acatggaagc ttgacattat 135780
cggcctttgt cacaatatta taataagtag gagtctttga atacttgtaa taaagcttgg 135840
tttccgccag ggtcatgtca catgaatatt ttattgtttt ccatatattg gcaatcaagc 135900
cagacgtgat attttccatt tatataagta tattttaata ctaagataaa gatttgtccc 135960
atgataccat ttggaaattt tcaaatttta acctaagtag tgtatctata atttcaaaag 136020
ttttgttatc gttactttcc cattctgaga ttttgtcata accattaaac atggacgggg 136080
cctggacaac acatgttttt ttaagagtta aatcttgagt acggtttatt ccggtgtttc 136140

-continued tcagaaaaca aaatacactt atgtatagtt gaacgtgatt caacattata caggtgaaat 136200
ccttccactt ttctttattg tctgaaccaa aagcacaatt ccacacaaac acatctggac 136260
tttcaaacgc gtcaatttta ttcaccatgg gaactttcag gtacgtgcaa agttttttca 136320
cgaacatctc caaatacttg tcagaactga tattatcaga acaaagtggt aaatacccac 136380
gttgtgtttt actaggttcc ggtaccacaa acaacacttt tttatttttg taaggtttgg 136440
taaagatttt aaattctgat tctattgatt cggagattgc tggattttca gataatatcc 136500
attccatttg gaccgagtat tcctgcatca tttttggtaa tatttctgcc caatcatcat 136560
ggtatttgaa tttgtaagga ggtactgaaa tggtaaatgt tttcattttg tttttataat 136620
ggcaagtgtt ttatttattt acagttttat tcaaattcta tagattaaat atggatatta 136680
atttcaattt acaaatagct caggatattt tagacagagg gaacaccggt aaacttacta 136740
ctttactatt acaagacgtc aattttcaga cacaaagtat tttcaatgac tctttttcaa 136800
tgggtctcat aggatcaaat ataacagatc ctatcaaaag aacacacatg gaaccactgt 136860
acggacctcc cccgtcacaa gatttaattt cttacgtgga ccccatgtta aatatcatac 136920
ctaacaaaat caataaggaa ttcatatttc aaccattagt gaatctggtc ccgaaaacaa 136980
tgcaagactt caaaaaaaac aacgaggatt ttatttttga agaactggat ttttacaccg 137040
gtccggacag tatgtttgac aacataaaaa attatgtcaa taccaagtac gactcttccg 137100
aaataacaaa ttatttcggt aagcaataca agactcatgg tggtaaaata tcaacagaaa 137160
gtgaatccca gaccaccaca aaaaatgtga catttgacgt gtacgacgaa atgatctctt 137220
gtcctgataa taaaaataat tctctttcgt tttctatgat agacatggaa gacgtatgcc 137280
gggaccctac caaatctatc gatttatttt ctgacattct gagaaacgta gaagaggtct 137340
ctgtcaaggc ggacgagtca tttgagaata tggaagaact ttctgacaag gtggaagaac 137400
tttctgacaa ggtggacgag tcatttgaga atactgaaga actgtctgag aatactgaag 137460
aactgtctga gaatactgaa gaactttctg agaatactga agaactttct gagaatactg 137520
aagaactttc tgagaatact gaagaacttt ctgaaaaggt ggacgagtca tttgagaata 137580
ctgaaaaact ttctgagaat actgaaaagg tctgtcatat accagatcaa aagatgtcat 137640
tatgtgatga actggctgat aaaatgatgg agctagattc ttttaaattt tccaacggat 137700
acacctgtga aaaatcatat ctggaatacg tgtcggtctg tgtcttgtat cttgcttaca 137760
acgatcaaga aaaatacagt gattttatca atgtcgcaag aatgaccttt ttgaaatggc 137820
tcaggacagt ctacattaaa ttagtaggag agtggaagat ggtttttgat gaattggttt 137880
tgtgtaaata catcaatttc ataaataccc tgaaaaccga catggaagaa ttcaaatttt 137940
ttattctgag ggtcatttat caaaaaagtg gtaacatttt cccgtgtttg tttggactat 138000
tttaccagga taaaatagtc ggggattcat ttatattttc agatctaggt attgacacag 138060
cagggtctac acaaaacata attgaacata taaatacaaa atataatatt acggttcaaa 138120
gtaaatattt gaaaaacatc aaattattca atacatttgt gttcctttca tgggtttatg 138180
tgaacacatt aacaaaaata actgataaca tttgggtaga atccgaactg agtcggttca 138240
gacaaaaatt taaatcaatt cctgacaact atattcctga cgtgtatttc ttgaaagacc 138300
tagaccaacc taatttactt aaactacagg aagaaaataa aaaaataaat aacacaataa 138360
tcaatttgag atatggataa actctgggaa gaacttagta aagtaaacaa gtctgacaaa 138420
tctgacattg aacatttttt agaacaacca gcagtagaac ttgtaaaagc agatgatttc 138480
atagtagatg aaataggagg ttataaacag acaagaaaac gaggtagacc caagaaactc 138540
tcacacaaat cagatgctgc tttgaagcta gcagataatt acagagaaaa tccagtagaa 138600
gaatccgatg aacccctggt agatccggac cagaaaaatg ttaaaccggt ttatggtaaa 138660
aatataccca tagaaactct tatcaaaaca aacatagtta atcaagaagg acccaattct 138720
ttctcgtgtc cttacgtgta cgacatagat ctcaaattac acgaattagg accggaccta 138780
ttcgcgacaa taaaaaataa cattgccact actttttttga atcaagaaat tcagggtaaa 138840
atgttggtag attttactct ggatcctaat atcaaatttt acctaggtaa taacgtggac 138900
gacattgtct ctgtaagagt acctatcata ggtaaattta aaatttacag aataggtgac 138960
atcatccaag gtaaacttaa aatcacaaat caacaacttg tccttgaggg aattgatatt 139020
ttatgtgaaa tatacaagga aaatggtatt ataactatta aaaataacaa aaattgtttt 139080
actaaaaacg ctattgatta ttatgaagat tcggtcgtaa atgtgaaaat tgttaatata 139140
acaacaacaa ctaaatcatt tgcatttatt tcccatggaa tacttcacga aaattcaaca 139200
gcttcacatt aaatcgcgta aaataacgca tataatgaag catagaaaat tcaattatga 139260
aaataatgaa atcaaaaaga acaggatcaa aacggattcg gaaatttgga atatcatcac 139320
attgtcaatg tttgataatc ttactaagtt tatcttgttc aataacaggg tcatcagtat 139380
caatctaatt ctgctcacgt cagataataa aattgtatta tgtgaacgta gtttgtcttt 139440
tggcgacaca gaaattgatc cagataaaaa acatctccat gtgaaaaaat caaaagaata 139500
catattacca ggtggtcatc tagataaaag agtcgatgac acgatgatag attgtatcct 139560
gagagaaaca aaagaagaat gtaaaataaa caaagaattt atttatatat ttgaaaaata 139620
tttggcatat tctagtgtgt acgacattaa aataaaagca tattttcata atttcacttt 139680
tttgggaata agtgatttat catcagatca gatttcacag aacttcaatc ctacaaaaga 139740
aataaaagcc ctacatttca tagatgcgga taaaaatatc ccagggagac taggagtttt 139800
tcttcttatc aagaagaaca tcatcgaaaa tataactggc atgtcagaag tgttacaata 139860
tgacgactct gattcttaat ttttttctaa caaccggcca cgacataaat taattttttta 139920
ttcttgattc tgattatggt gtcctttgtg acgtcaccta tgatatgtcc gtcttctgaa 139980
taaattatat tatctccgat gtatccgaca tgaatatttt tcaaaatgag gtcaaatgaa 140040
taatacactg tttttacgtt tacgaatccc attttgtacg tttttgtctt gaactcgata 140100
ggttcacaca ggtacgcctt taatttatct tcgttatcag gaagagcatt ttcttcgttt 140160
acccgttcaa ataaagtttc tatactacat tgtctgaata cttcaaatag ttgttttatc 140220
tgtcttgatt tacctttgac aacttccagc aattcctggt ctacacttgt accttttgat 140280
tttttacaaa ttatgaaatt cacgttggtg taccatctac tggaatccaa catttgatga 140340
cttcccatcc tgatggctct tcccatgatc tgttgaagac ttgcttcgtt ccatgtaagg 140400
tccaatatgt aaatgtcatt aataccggtg taactgacac cttcacttcc ggacagtgaa 140460
aacacacaca ccttcaaggt cttcccgtca atatttgata tgttattgaa ttgatcaatt 140520
gcctggtctc ttgtggattt tgttcttcca ctgaattcaa tgtatgatat cttgaacact 140580
ttaaggtact ctatcaaaat accgatacct gacgctttca caaaaggctc aaacaacaga 140640
cacttcccag gggatttgat aatgtcaaca catgtcactg tgtatttagc agaataatta 140700
aacaatgaat tataaacatt ttggtcagct gatgaaagat cagtcggttc tcctgttttt 140760
agcaattcca atccttcccg ggtgaaccct ctgtttggta tggtgtcatt aaattccatg 140820
ttaaaactaa ttctgatccg gtccagatat ttatcataat cttccacggt catgtcttgt 140880
ttggccggaa gttcattata acaaaaagca ctgaccaatc tccggacaga tttaaaactt 140940
gacagaccct tttctttctc gtagtattct gcctgaacat aaagtttttc ttgttgagga 141000
ctcatggtca cttctttaaa cttgatctta cgagcagcga acccatctgt tgccactatg 141060
tcatcaaata tactgaatgc caggtttcgt ttgtacgaac aaattccttg taaccccccgc 141120
acaagttcgt ccttgtatat gagcatgttg tctttgaaca atgtgatgtc aggagtaagt 141180
actttcggcc tgagtaattc tatcattaag aaaaattcat taacactgtt cacaagagga 141240
ctagccgaca acaacaaaat cttatttttt gatttaggat tatgaacaag agaaataagt 141300
tcattataca ctcgtttcat cttcctttcg gccccgtctt ttgtgagatt tctggatatg 141360
aaattatgac actcgtcgat gatcacaaaa actctttctt tcggagtaat acaattgacg 141420
tacgtgaaaa acttattact gaacgtcgga tcatcgtaag caatgatatg aaaattagac 141480
aaatctttac aatagtccat cagggtactt gcccaaggtc gtgtgataag agaagcctta 141540
cataaaatta gaattttcca atgcggataa aataatgttt ttaacatggt gagaatataa 141600
acagacgtca gggttttacc gaaccctgta tcctggaata aaagcatacc tctattctct 141660
tcgagaccta agaaaaatcg ggctgccaac aattgaaaat cccttaaatg cttatctttg 141720
aagtctggta aaaaatgagt tgttctggct aatgccagag gcaaatatgt ccccatcacg 141780
ttcatattta aaaaagaaaa atatcataca tacatatgat attttttat tggggtccta 141840
ccttcataat tgatttaaat aaacacctat gtccgtggtc gggaaatggt gatttatgaa 141900
aatagaaata taaattaata cattaacttc ttcatctctg tataaaaaat ggacatggac 141960
ctggaatttg ctgttactgg ccctaccttt tacaatgcaa gaggtaacat tctctttgtg 142020
tccggacaca taaccacact gaaaatggac cctgacaaat cacagtacct ggacatggta 142080
aagttttata ttaaaatggt aaacctaaaa gatatttgtg gtagtgattc agactggaca 142140
tggaggtttt ctgtatctga tttcaagtcg gttgaaatca gtgactggga ttggaatgag 142200
gtatcggatg ccgaatacat cactgtcccg gtacctgaat ctatgagatt tgccggtctg 142260
gtatcgtggg ttttgatagg tatcagaaat caagaagaca gaacattgta tgattctatc 142320
ttcaatttct tcacctttcc atacgagatg atcccgttct cactgaactc tcccaaccac 142380
aaagacatca tcatcatggt atggaaaaac tcaaacgaac caggattcag atggtggata 142440
aaggctcaaa tctccggatg tgagtttctc gcaataaaat tgaatcccaa ttctgactac 142500
gtcagaatgg tactggcgta catccacact caaatgacaa tggaaaactc ggacgtgaaa 142560
atggttttgt cggaaaccga tgaagtcaca ggaaagccgg agattgtcga gaaacgctca 142620
catctcccag gagctgtcat gatcgaagaa gattgttgta tttgtatgac aaacaaaaac 142680
accatgtctt ttccacacat gtgtggacat gtacaggtcc cactgtgtct gatctgtctg 142740
attgaattat caaagaagga catggcttgt ccgttctgta gggaagagat gaaaatcatg 142800
gatgatgtcc cagagagcat cgagttccat atttcgtctg atccgaaaat aatgactgca 142860
gaaaaaatat cagtggcctg gagtaacatc ctgtttgagt gaccatcatg taataatatc 142920
atgtaataat atcatgtact tgtgctctaa ttaattcagt ttcagaaact cgggtaggtc 142980
ttcttctaga atttttttat ttgtcccgtc agctagtctg ttcaaaaaca tgttgtattt 143040
gttgtcgacg gaatttccca tggacaacac aaggagacta tgacatacgt aaattgcatg 143100
ctggacagcg ttgacaaatt taaaccagac cgtagaaaat cctacgtctg tgacaagagt 143160
gtcccacaaa gtaaatttga gaccgtccaa ttttttgaca tcggtctttc ctatgaactc 143220
tctgagtttc ccctttactt ccttgatgtt gtcttttttt attccgtgac agaccgctat 143280

-continued gaaactgtcc ttcaaccagc tgtctttata atgtttcagg accgtgacct tttcagaaca 143340
atacgccagt aaccaaagga tgttaagagt tgtttcactt gtcatggtag gaaatttaat 143400
gacagcgata gagtcctttc ctactatgtc aaagaaagga aacaacatgt caaatgttat 143460
cagatcatac gagttcacgt aaaaattgtt tgtcacaata aaattagaag actttttaga 143520
atcggtttcc tttctgtaaa attctccagg atatgattta tcaaaagaat acatgttgaa 143580
ctcctgacct ttcatgttga aatttttctc aatttcatgt cggataatgg tcacgtcatc 143640
ttctgtccat ttatgatttt tgatatgtaa gtcgatttct ctcgtggaat tctgtgaaag 143700
atcattcaat ttactggcac ctacaaacca catccctcct gttttcagag taattttttt 143760
ttcggtcttg aatcttaaat taatttccgg acatttgacc tgattaaaca ccggcagctc 143820
tattcgtatc cccgatttta tttgacctat gacacccaac aacgtatctt gtgatagatc 143880
gttattcatt atttaaactc tggatttctt acaaataacc gttctatttt acttcggtaa 143940
acctctggta attgagcggt aaaaaagtaa aaacataaac aaaatacagt taaaatcatt 144000
aaatatttta tcattttatt tcttgtgtct ggtaaaaaat tcaatttact ttttatgtcg 144060
gccaatgtat caaacttcgg ttttgactgg tccggatttc cggtcaatat agtaatgtcc 144120
gggaccactt tctgccctgt agggatgttc acgtttattt catttgttga catttttacat 144180
ttacgtaatc ctatccactc tgcattggtg atttccatgg aagttttgga cgccagaacc 144240
ggatcattac agggattgac ataggtcgta ggtgttttta ttaatcccaa tacctgttcc 144300
aattcgtaca ataatgacat cgaatccgaa tttcccacac tgagctgaat gtctgaggtg 144360
tcccctctta ttttaaaaac ttgttgacgt atttcctcga gagcaaagtt acacaagctt 144420
cctttgtttt tacaatcatt ggtcactaca tgccataact tacgcaattc atacggatta 144480
cttatgtttt gtgatatggc tatcctacaa ctcggcgaac caggtgattc cacacacatt 144540
gttatacgtt cattatgaca atttatgttg ggattacaag tgtataacgt ggaattactg 144600
agatattggg tacttactat gttgttactc atgaaataat atggttggtt tattctacaa 144660
caataatacg gggcaccata ataacttttt cttcgtattt cccagaacga ttcacttttt 144720
ttgtacacgt caaattcagg tgttgaaata ggaggaggtg acattcctat acttacatga 144780
tcacctggat ttaaagagta caaccccagg acgacgtcat tgaatttacg tgtaaattca 144840
gggccgtaat attcatgata ctgaggtaga ggaaaatcaa atactaatcc catttaatac 144900
tctacagata tttcatcgaa cctgatcatg acttttattt ttcccagttg atgtttcacg 144960
tttaactttg gttcgaatac caacccaata ggttcgttgt tcttttggtc gattgccaaa 145020
ataattttaa gaaaatcaac cttcttcttg aatcccttca gtttcataag attctctttt 145080
tgaatcttga atgaaatttt tttgaactcg aaatctggtg gttcttggcc ttgggtgttt 145140
acatttttat taattgtatg aaccacctgt gtttgttctc cgattgtctc cagtgtaaac 145200
tgaaactttg ttatggttcc ccttatgtcc tttgatgctt cgatagattt caaaagaccg 145260
atcaatatat ctaaattctc acttacgtca aatccacgtt ctggacaata atctgatata 145320
ctagtgtagt aatttgagtt agtttccaga ccgaatttga tggatgtggt gatctggctt 145380
ttgtgcttga attcattaac ggcactggat atgtaaaatt tattattaga ataaaatcgt 145440
aggaggagag cagtggattt cagacaggcg tttaattttt taatcatggt acctacatta 145500
atggtatatt gaatcacctc aaactcagtg acatgatttg taccaattat ttctttatcg 145560
tcaaagacca cctggtttgc aatgatagaa ttatatttaa aatcattgac agcaatggtt 145620

-continued tgattcaatg agctaaaaat tttaaattgt ctcggtgata tacaaaaagt tgtcatcgga 145680
ttgtattcat aaaaaattcc taggacagaa tgaaaatttt taaaattaac agtgaccata 145740
acttcggtaa tagtttcttt tgaatccatt taatcataca tgtcaaatta aaaaaaacgt 145800
atattatcaa acacataaat ggataaggaa ataggaaaat tgtttattac gggagctaag 145860
caattgttga tatttatgtc aaatggacat atatcatttg tatcagaagg aatatcgtac 145920
ataaaaaatc atataaaatc atttgagaat gaacaggcca tcaatacatt ttttttattc 145980
ctacaaaaaa atttatacac gacattggaa cgatcagaaa atttaaaaaa ttacgaagat 146040
catgtcaaat atttgctgga taattttggg aatgatctgg catttaaaaa atttgtaacg 146100
tacaattgtc tcaaggaaga taataaactt tcaccattgt ctaccaaaac tttattatgt 146160
atgcttttgg aaattacaat gataatgttc accccgaagt tcagacaatg tatcaataat 146220
tttatatatt tatacaaaac aatgtcggac gacctcaggg agaattcatc agacaaacta 146280
ggaaagctca taagactaaa aaaacaaata atgtcattca tttcttctaa gattttccct 146340
aatatgttgg tcattattgc ccaggcattg ataaccaatt atgataccat tcaaacaaaa 146400
gactccatga tctgtgagtt ttatgacgac agtgaaaatt acttcataag aaagaatcgt 146460
gaaatgaaca gactatggac ccctgttgac atgagtgaaa ttctctgtaa ggaaattgac 146520
ctttctgaca ttaattatct tgtcaagaaa tacaggggac tcgtggtcaa actggatgaa 146580
atgaaaaaaa acaaaacaga cactgccgga tcaggtgtgg tcagtgcaat tgcagggttt 146640
tttggtaaac tgggatccag ggtagtcagt agtgcagtgg caagacaagc cgctgtcgaa 146700
actgccaagt tggtaggaag ggcatccagg gacattacag aaagtgctgt tactgggctg 146760
tctcttaaac tacaaaatcc tgacacttac aagagctcac gtaagaagcg ccgtggtaaa 146820
aaaaaggatc atgacgtcaa ggatcctgcg ggatccggag tgacaggtga ttcgtcatca 146880
gacagtgaga cagagtacat cggtaagatt aacctgtctc caggcgattt catcggagac 146940
attgtcagtg acatggccca gttgaaacaa gagaacgacg atctgaaaca cagactcgat 147000
gagcaaatga aaagggcgat catggacccg tcaccaggat tcaccaatta taaaaacttt 147060
cctgattttg cagaccagga taagatcatc gaaaaagaac tttccaagac catgacaaaa 147120
ttggacgtgg aagagacaaa gggaaaggtc caagtgtctc attacaagga catcatgaaa 147180
caaccaaaaa atttatctaa cccggtcaat tacggtccgg ttcagatgga caatctttac 147240
actcttgaat tactacatct gttgaaaatg atggctgtca aaaaaagtta gttttttca 147300 aaaacaatgt cgaactctga caagaacgtc gtcgacagat acaatggcat tcccatgaaa 147360
taagaataat tattgaccag gtccactcct aattctttat ggattctttc gtggatctga 147420
aaccctgact tgaaacagta cgtgtaatta tgagagagaa tcacgtcagg taatacaaaa 147480
taacttttga atatgtcgtc caatatatga gtttttattt ttttattgaa aacggccttc 147540
cgttccggtg tgtccagata cggggtacgt aacacaaggt atcgctctct ctctagtatt 147600
tctgtcagag gtacaaacac cgcacctctt ctgaaataat tcatcgtgta caggtcggtg 147660
ttattatgac tgttgatgta ttgagccact gatccgaatc tgtcatacaa cccagaattg 147720
taaaatttgg tcacgttctt cggagataaa aaataatttc taatatgggt ttttagattt 147780
tttccaaaaa aaatacaaca gtgtgtcaac tttcctggga caattgtccc ggaaaaataa 147840
ttcccacatg tcgtcaaaat tatgtcaccg gtttccatac tcatttaaat caaaaacatt 147900
tttataaaaa tcaagatatt gtttcgttgg gtttggtaat gtcaagtagt ggtaaaatag 147960
ggtaattctt aacagggata gtacatgaaa aaagttgtgt tatacaacat tttagaagat 148020

-continued ttggtcttgt tgtcaaggtc ccggacacat gtttcttgaa attaaaatgt gtcagatcgg 148080
ttccacagtg tttacagatc gggtacaaca tatttcatac actgatttta tgtcacttcc 148140
ggaaactgta aataattcta tggcaccaga acagaattcg atccagatat ttccgaaccg 148200
ttttaataat ctaaaatcag gagtaatata caaactatct ttatcagtta ttacatgttt 148260
tttcggtttt gtccaggtca tcaggacatt cacagtttta agtaatttgt ccaagagaac 148320
caaggccttg gtagggtcat caatgtgcat gtaaaatccc ctatccagta ctatcgagac 148380
cccgagaagt ttacaaatga tttttgcgaa cttgatcacg ttcacctttt gttcttttct 148440
gtattcaggt acggtacatt ccggggtctg agccccaaga atgttcaaaa gtatattttt 148500
ccagaccaat tctatgttta ttatgtttcc gtagtcgtac gagcttatgt cacatctact 148560
gtatttattt atgaaatcta tggaatactc cagatctgct aattcagaca tgtcaggttc 148620
ggtaccacag gtgtatgttt ttaacatgtt gtcggaaata aaatacgtga catgttctat 148680
ttttacttct gtgtaataat caatggtcaa taaactcgaa ggaattgatt ctcccatggt 148740
tatttttttc cctcttattc cagaattgta atcacctccg ttgaataaca atactattct 148800
cgagatgaat cctgtaagat acgaaggtct gaatttaaaa tcgtccttac ccatactgac 148860
atttattttt tttgcttcta tgatgtcaga acaaaataat aaaacatcct gatcagagct 148920
gatgatgagt ttggatcctg atagaatact caggttcttt tttaaaaaag aacccaagaa 148980
aaactcggcg tctattccgt cagattcaaa acaataataa tctggatatt tgtttgttat 149040
gatatctttc atggtaagct ctagatattt tacaaatttt ggatccctga ctttttgttt 149100
gaaacataag atttttttct ctaggaaaac tttgtccagg gcattggaaa agtaatgatt 149160
cactgccgga acatatcttt ccagattatc ggtgaattct gtaaagaata aaacagtgtt 149220
cagaggatca gaaaagactt cgattcctcc gtagaacgtg tcttgtttgt ccacgtttat 149280
ttttttcaat attttattga catgttcccg actggcagaa gaaactttct ttctttgtgt 149340
ttgattggtc tctttctcat catgttccga gttatcatcg acatcgtaca atgttttcac 149400
gatcttgtct tcgtacggta cgtacatgta atctgacgga tcaaatgacg gatcattttt 149460
tatttgtccg acacacgatc ctacatttgt tttcagaaca ctcttgtcat gttccgatag 149520
tttttttgttt accaggaaat catcccagac gtctttgaca tgttgtaatt caccatgaac 149580
attctcgtat attttgatgt ctgattctat acttgccttc ttgacgttac cggctttact 149640
acgtttgatc ctgagttctt tttttagatc aatacatcct tcatcataaa atacgtatac 149700
ctttttttgt ctgaactgat ttagaaaaac aattatgtta tcaattatgg attcttcatt 149760
atcaaaacta tataaatatc tataaaatat agttgagaag tcgatcaata tgacatcaaa 149820
attggaagat ctattacaca ctctcaataa accaatatct cctaaaacat ttttaagttt 149880
tgaaataccc attatgagtt tgtttactta gagatttttt cacttattaa atggccactg 149940
actcaggcgt tgtatcaacc gtggacacag aaacagtcaa tgatatttat tctaataatg 150000
tttcattaag tgtcggtatc gatgattttc tccaggatca aaattcagtg gaattgagta 150060
agttggccga aggtgtcgtg gtcgatgaca cgggttttga tcagttcaaa ctagatcatg 150120
atcttatcat aatctattct aaaagttgta tggtatgtac catgttgaat aaactaattg 150180
attcagaaat cggctctcat atgaagacca ttgtaaataa tatcatgtgg attaattcag 150240
agaagctttt tacaaacgac attctcagac gtttccaaga actccctgac accgaccttt 150300
ccaaaatctg gaatttttca tctatcggag ttcctatgtt gttcatgatc agaagtggtc 150360

-continued gacctatcag atcagaggat cttatagttt tggatacaaa gcaatttatc ggcactctta 150420
atattaatcc ttctcgtaaa actttataca aatttctaaa gggtattgtc agtggctctg 150480
gataaaaaac acaagtaatt aaatacatga tttttttat taagcttgcc tacgtggtcg 150540
tagggttatt ttttgtggtc attttttccg ttgtcatgat caacgggtta gaattaaatt 150600
atgacacgtc agtgtattca gacggtgatt atcatactgt cctgaaccct cttgaatata 150660
atatagtgtt tgacaaaaca ggtcacaagt tcaaagactt tttctttaat aaggtcacgt 150720
ccataaaaaa tttacctatt gagtacatga tagaaagcta taatgttgat tgggcatctg 150780
acacaattca tgtggttgat aaaaataaaa acaagcgatc ttattcattg aatgacggag 150840
acaacataca atttttattt gaactatttt tatcttttaa atgatttatc ttgataatgg 150900
tatacgtgtc atcaaagaca aagtgtttga acacatctgg gtttctataa gtaattttgg 150960
attggaatca gattattctt ccataagtgg gttgtcacat ttattagaac atatcatgat 151020
cagaccagat caagagaatt atgtgtttaa cgggtatacc acaagaacag gaatggtatt 151080
ttggtgcaag gcccgtaaac atcttagtat ttacgacgca atgtacgagt taatttcgtg 151140
gttttttcac cccgacggaa gaatgaaagt ggacatgatc tcggactcgt tggatggtta 151200
ttacaacgaa ttggaacatg aatggtatta cagggtcaat aattataaca tggcagaccc 151260
tgtttacccg atacaaggtc tggatcttgt aatgtgtgga agaagaaatg acttcatggg 151320
gaacactgat tacatcagga aaatgatcag gaaacgattt ctggaattac gggccgaaca 151380
aataactata atgaccaatg aaatcaatga agacatagtg tacatgttaa acgaaacatt 151440
tggaaagatt tcagaatctc atcaaaaata caattatccg atcatgaaca tacccgaaca 151500
gacagaccct tctcagaata ttttttacgt aggaggtaaa acatcatttt accaagttca 151560
tatcaaactc cctgacgacc ctgtgtgtct tgacataatg attctactaa attcttacaa 151620
gtcaaacgtg gaattgagat ttttatcagg tcagggttgg tgtgtgttac actataaaac 151680
agaagcagaa gcagtaggtc ttctgaagaa tctttataat ggtctgatga aacctcttta 151740
tgtcacagag gaattgagac atacaaatgt agcagacacg gtgtcattgt tatacaccct 151800
gagtcatacc attcatcggg acagttacac cttttgtgtc cggaacaaca tgaacataga 151860
tcatttacaa tacatgttgt ctgccagtat caagatttac ggaaacgtgt tcattcaatt 151920
acctaacatg ttgaatcttg gaatgacaaa aaataacaat tacaatgcat ggcccggtta 151980
catcgacata aattccagag actcacagat gacaatagac acctggaaag tctcgggttt 152040
ttcagaaaca gattctgtcc tgggaacccg tgaggaattc aagtgtaatt tatgtagtac 152100
gaccctccat ggtaaggacg acctggtaag tgaaatcaaa aaatacaaca ttgtttttca 152160
tcagaccact gatcaacatc tggcatgtgc acttcaatac ataagcatgt tttcagtaag 152220
atataaaata cacaagggtc atgtgttact aacagaaaga ggtctgacct cgaccgaaaa 152280
tcaaatcatg aatcaaaaca ttgtgacgac ctccctgttt aaaattctaa tggaatacta 152340
tttacggacc gggaccgaca taagtaaaat tatcaaactt attccctgta ctgataaaat 152400
agaatattgt gacattgact ctgtcaatga tcttcaagaa attaaaaatt atcacccggt 152460
caagaaaaat gattgttctg tgattgtcac accattttca tttgtatgtg gattattcga 152520
cgtgttcccc gaaggtcatg atctggatga tatcctatgg acattgaaga aacaaggtgg 152580
actttatgaa atgtattgtt cactggaaac cgaaggactg tatctctttt gtcataccac 152640
acaacaattc accacagaac tgaaactacg aaacgtgatc agagacaagt tcaatgacgt 152700
gaccggtaaa acaattatct ctgtggtgtc tgacggatta gatctgtcac aaattacttc 152760
taaacgaaaa tagaattatg aattttatgt agggtctgtt ctgtttttaa ttcggtttgt 152820
gaataaatgg tttcgtttat atttttttcg ggaccaaatt tcaatctcat tgttatcctg 152880
ttcatttcaa gtgtagggtt ccatgtacac gaaatcacac tgaccctgag attcagtttt 152940
ttcagtagtt ttttaaactt tggtgatatc gtaagaatgt caggtttggt gtcccagtta 153000
ccaaattcaa gtttttcatc gttgtccagg tctctgtata ttttaataaa ttcaatcatg 153060
ttacattgaa atttgtcata aatgttcagg gtgatcctgt caatgggaaa caacgactcc 153120
agataattct ttgttaactc ccacctcccc tgatcagtca acttaatata aagatcatcg 153180
acttccagtt tgtaagggta cgtcaataaa atatacgggt acaaaaactc cccgtcaatt 153240
tttttccaat gttcgtattt attgtacaac ttgacgtaca tacctggaat gactcttcct 153300
actcttcctt ttctttgatc ggccattccc ttgttcacag gtgattcaga tccgccagaa 153360
agtaacgttc tccaataacg tccggtgtcg tacaccacag tggcatttgg aatagtgata 153420
ctagattcta gataaggtgt acttatcaaa atctgtggtt tgtgatgagg tccgacatta 153480
ctgattttat ttattaaccc gtttacgtca gggactcttc cgtgtactac aataaattca 153540
atacctggaa acataggttc cagtagttct ttgtacatgt tacattgtgc taccctggcc 153600
atgaataaaa tgccacaatg tccctgggcc ggaggaaaca tttttatggt ttccatgatg 153660
ttcttttcct cgttcttgaa atatttattt tttgattcca gatctcctgt ggtaggtctg 153720
tgtatttcct cgactttatg aagagacttt ccttctatgt ggacaaactg gggattcaaa 153780
aattcattca gacgctcacg atcatcatca atggtagcag acatcaaagt ttgtagacta 153840
ttttttgaat actttttaa gaccgctatg agaatatcgg cgtactgatc atgttcatga 153900
atttcatcta ctatcatgga ctcgtatctt ctgatatttt taatagcgat tctatgagta 153960
catatttcga ttccgtaatt acattttgtt gtgttgttgt aaaccggatc atcttgtact 154020
cctccaaatt taggaatgat aggactacct tcaaaaatac tcaaccccaa tcctttcaat 154080
aaagtactgg aaacttgttt taccaattct accctgggca gggccagaca caatggtcta 154140
ctttgtctta gtaaagcagg actccatcta ggaatacaaa tattatcacg aggtccgaat 154200
aaataattga accaaaatag aatttttgga atctgacttg ttttacctac tccggttcct 154260
ccggtcagaa ccataaattt ctttgtttc catgattcaa aaataagttt ttgaataggt 154320
tctgtcagac ctttcagagg gacctttgga atgccggtcg tagatcccaa gattttcaca 154380
agggaagttt tcttactttt tggagaagtc aagataccaa gatcactggc ggctctgaca 154440
acaccaaacc aatgctccat accgacatct tcccaattta cttcattttt aaaatacaag 154500
gccgaggcca cttcgggagg gaaaattatt ccgtccttgt ctacccagtg tctttttgtc 154560
tgtgaccaca acatgttagg aacagatgtc aatgcgtcat cagacaatga cacacatgca 154620
gtttttttct taaccgagta acctttgaca ccagaccaaa aaagtcgcca tacagaaatt 154680
aaaaggattt tatgttctgg tttccaaagg ctcttgaaaa cttcccaggt cacgtcggtc 154740
tgaaatatag ttatttgatt tggaaacata gaccattcta cttccgaaca agacatttaa 154800
ctgtgaaata tttctttgct aaatggcatc cggtaaaaaa gtaggaagtt tcagaacaac 154860
aaataatcct gaaaccacag taggtctggc tctattgaaa attgacagtg tcgtccaaga 154920
cattcccgtt ttaaatcata gtttgtattc taccaattgt aacaatattt ttattaacag 154980
agcaaaacag gtgaaatcac acagcacatg tttacccgaa tcggaactat tcggtatatg 155040
gtcacaacta tattatggaa aagagagacc acctaatttt gtggaactcc tcgaccataa 155100

-continued aattaaggac atgaccacac ttgcattact taaacatact caaggttatc cattagatta 155160
ttattacaag cctcctatcc tgacccaacc atcgtatcca tttgattacc gtaagggagt 155220
aagttctaaa ttcggttttg aactattagg aaacagttct aggtcaccag aactttcggg 155280
agacccccaa gtttttgcat ggatgaaaat gagtgagttg gaaagaataa tgatcactac 155340
atgtctgaac actccgttca cgtacatagg ctattttatt accaaccaag agttcaccgc 155400
agattgcaat gccagggtat tgatcacaga acagttcggg gtaagctgga aacgagaatt 155460
tcagaatccc aagactcaat tcatttcctg gatatgtgga aacaacggac attggacaac 155520
aggaatctat tccaaggttc acaaaatttt attttacttc gacagccaga ttaacgacac 155580
cgataaaata gcaagaaaac ccaagattgc cgtgtacagt tatgacacct gttcacttga 155640
taaattaccc ggaggcacgt tatctgaaat tcataatccc gatacccttt ccatagaaat 155700
atcttatctt gtcactgagg catttgatcc ttccatgaag ataatgatct gtaacaaaga 155760
aaccgctcaa ctttattctg cagagtgcgg gatgtactcg ttggtttttc aacatctgat 155820
gatgacacat gtcctgtcag acgggaacga ggtactttcg cgatcaccca aggagatgtg 155880
taaggtatat cactttttca aatattgtgg agacatggga atcagagaat acaggaaaat 155940
gttttataat accgaccctt tttctattat tgaaaatcca tcttcttcca tagaagattt 156000
taacaccact gagaaactga cattggaaac cctggagaac atagtgacag cagtaaaaaa 156060
taaaatgagt aaatgaactt ccgggtccct aacataaaaa acgaaaaaac cctgataaaa 156120
tttttcaatg attctgataa aaaatacgtt tctgtatttt gttggttggc agaatttcaa 156180
gaatcataca aacacacatt aaaagaatac atactggata atgacttcaa agaaatatgt 156240
gaccatttta attttatgtt ggacatggta atttttggta atcatgattt gagatcatta 156300
agaaagttaa atcctacatc tgactctttg aaaaaaaata taaaatttgt cactgatctg 156360
atcaacaaaa gaaaatggaa aaaatttatt ttgtacaaaa aaacatcaga ggtcttggat 156420
tttaaaattc cgatcatgag tatcatgttc gagaacaaca taacaggtta tgatttcact 156480
ccgtgtaaac ttgctttgct ggaacaggaa caggacctga ctaaaaaatt cttgacagga 156540
gttttattat ggaccatgtt cgaataaaaa tagaattttt aacttaataa catatgatta 156600
actcacatgc tcgtgacaaa aaatggctcc acttcgtaca atattgtttt ttggtttttt 156660
gacacaggta tgttcggaga agatttggct tatcggtgcc aacagtacca taatgtcatg 156720
tgaatggtac ggaagtgcag attctattcc tatcatgaca gaccaagata gaaagactct 156780
gtctaatctg gaagtcgaga gtaaacaagc cctgggaaaa agcaattcat gtcctaatga 156840
gaacatacca aaataccttg tgtgtgacac aggtctgacc cagacaggta ttttggtcac 156900
gtctctggga tatccatttc ttatgttaag tgagtctgaa ttcacttctg aatacagtac 156960
aggtgattat gtctcgtacc catgtctgga accaggaaca ttcaaagata agcttgataa 157020
ttgggcgacc gactccacca aggttttcca attgttgttc agttccgatt ttgaaaaaca 157080
agtaaagttt tcaaacctcg ccgttatttg tttgatcata ctgttcttgg cattgatcat 157140
ttgttctatt gtctggggat tattgttgtt cagaagaatc tgtggattca aaacagattg 157200
tttcaaaccg gtcaggacac catatcctcc ggtcagacaa caacatcacc atgcccctat 157260
ggtccctatg taccctatcc ctcgcaatga cattatcagg ccatttcctg actctgatga 157320
agagacgata tacgcgcttc cgactgacgt gtaacctttt attatttttt tattatcatg 157380
tttaaattcc agagtataca aaagttaaaa aaaactctaa actagcatcc gggaccaaaa 157440
gaggaaaaag atacttttg aaaatgttga gttattacat tttcgtggta gttgttttct 157500

-continued ctacagtaaa ttctttcact ccgttcttca gaaatgatga aaccacaaac ggcgacggtg 157560
taaaatgtta cctgaatgga ggcttcggac ataatccgga tactcttaac aaccaagacc 157620
tacagacttt gaagatgaac ttgtccggtg gagaaaatgt cgacttgatc ggggcagaat 157680
ggagagaacc tctttctgaa gatgatcatt tcaagcacat ggtcagtgtg tttgacgacg 157740
tgaccaatcc tgacatgatc tacaaagcca catctggaaa aaaatgtgaa gaggctctca 157800
tggcaaagtt tgcttcaaaa caaggcgacg tgtatctcgg tcctcggttc acatggttct 157860
ctgccaatgt ctctggaatc agagacatcc agatcaccac aggatatcgt tcacctatgt 157920
ttctgatccc gacttctgtc tccaagttcg acgaagagat cgcaaagata tttgaactga 157980
cccgtttgta cccgacagag ttcattctga ttcttcccag ggacatggat ctgaacacga 158040
ccacaggttg taaaatgacc ggagcgtttt tcatgtgctc caatgttttc ccagagagca 158100
agttcaaaca atacgggaaa gacttcaatc tttccatggt catctttcac gagtaccgta 158160
tgagtctgaa ctttcacgag tacattgatt catgggatgc ccaggaccgt ttgatcacaa 158220
aactgatcaa cctgacaatc aatcatgaaa ccgaacacca tggagtacaa cgtatcacgt 158280
acacgtttgt caagtaccag tccttttaca gaaagcactt gttccccctg atcagaaaag 158340
cagtcaacaa aatgtgtcag tacaaaaaaa gtcggctgat tcaatttgtc cggaaagcac 158400
ctgcgagacc atacgcaaca gatctctgtc tggctccttc caaaatttct aataatctct 158460
gggaaaggct caaggacaaa actggcaagt atccgtggac acctgttcag atggccgacg 158520
ccctgaagct gttcaaaaac aagggtctga tctacttcaa tgtaacatct tctgtaggca 158580
ccgaagaaga cgacaggact ttcatcacga ccggctcagc aggagttcca gattatccag 158640
gattgtgtct gtacgaacct gtggttgaaa cgagggggaa ctatcctccg gaggacttct 158700
ccactactca ggtacatgga tcctggggag gatcttctaa cggaagtcca ttgatcacag 158760
gattgtctgt ccaagaactg ttcggattca attggaaaga agcgtacgga ctccaagact 158820
acgtgttcat caagaggaat ctgaattgcg gacagatgac agacaacata ttgtcactgc 158880
atgcttacat gtacggtgtc acaattgtag gaggagactt cttcagactt aattgtactc 158940
aagacaagga cactggcttg tacgacgttt gtacgtacta ctaccatacc ttaggattga 159000
agacatctga tgaaatcttc aaacaggaat ttgacaagct ctggaccacg cactttaggt 159060
tttacaggat gacacacctg ccccgggaac ggtctggcaa ctatgacaga acgtctctga 159120
tgggaagaat catgcgtgtg gtatgtcctg tttccagatc tcatatcatc caaatcaaat 159180
cagatttggc ttcagaagga aatcatggat ccaagtcatc caggaccaga cgttctatcg 159240
aagaagatga tcctacaatt gccggatata gtttctcaga tgatgacatg ttcaccaagg 159300
taacaggtca gatcagtcca aatgacaagg ccccgatgaa gacacgaaag aagagaggtc 159360
tcggagatga actcaagaaa atgttcacag gagcagacaa gttagcgaaa tcaactaaac 159420
ccatgacaga ggttcagaat gtggctgctg acatagctga caggcttgca ccggccctac 159480
aagatcctag aatgaccacg gacgatcttc tcagattgaa ccaagaggcc aagaaacagt 159540
tcagaacacg ggtggcgaaa gtagaccttg gtaacccatc ctttgttcca tcacaacctc 159600
ctcctaattc tgttgttccc cctccgagaa ttcctcctcc gattgtcaat aggagactaa 159660
aacctggaca caagtcagga acaagtactc ttgactccgg atacggaact cctgatctta 159720
acaagttcgg atcaggctct ccctttgaca ccagtggaat gtatgctcgt gtgaacaaac 159780
cacaggtccg ggatgtacag agaggcgtgt acgacctagc cggacatgcc ggtggctcta 159840

-continued tcggagatct actcgagaga ggtccatccc tgaaacaaaa cccgttgtac ggctctgccg 159900
gaaatattgc tgtcaaatca ggaacaatcg gtggtggtaa aaatgatctt cccttgttca 159960
atgataaccc gatctacggg ggtagtggtc ctagtgtgaa tctgcctcca gttgacccac 160020
tgtactcact tcagggtggt caacaagtcg gtgttcatgt agaagctccc ggaccggtat 160080
atccaggagg ccgattcaca cgaccaggat ctgtaaaaca tgagagatat ccttacgagt 160140
tcaacccaag aggagggcct cctattccag cacaggacac aaaggaagat gcaaagagga 160200
gaatggtcga acacgagaag gcagccatgg acggaaaagt tactcttcca ggatgtaaag 160260
gaggagccgg taggatgaag agatccgctg tatgtagtcc tgttccgaaa tcatacgcgt 160320
atgatccggc aaaaactcca ttggaatccc caaagtctca accgaaaacc aagtggcaac 160380
gattcaagga taccgtgaat aagaaatgga agtcattcaa gggaaccaag ggtgtcatgg 160440
gtaccggact cgatgttcaa cagatgagcc aagaaggtgg agtcataagt ggtagggctg 160500
ttgtcagttc aggtcctggt attgacacaa gtggaatgtt catgggagca atggtatcac 160560
aacaaatgtc tcagaacaac gaaagattgc tcgatgatta cgtccgtgga aagtacgata 160620
atttatcacc tgaaaaatcc actgccgtgg cagtgctgaa actgacagac cagaccggaa 160680
gtgccctgat gacaggaggg atggtaactg gtaatcctat tgccatggcc ggaggtatga 160740
cactcatgtt cgccacagga ttggccacga cggtcatgac aatctacgac atcatgacac 160800
gtacacaaaa acatgatctc ttgatcgaga agtattcttc gtacagtaag gacatgaaca 160860
cagaacttgc cgggaacaga tggtgtcttc caccacagac acacaagcaa ctgacagtga 160920
tcctgggatc tcaacgtgac ggtgtcaaca acgacaaggt aacagacgag aagaggaaca 160980
atatcaatct gatgtgggga tcatctggtg agaccagaat tgaggttctc atgaacaaca 161040
tcattgaatc tgacacgacc atcattgtca agtgtgccgg aggtggttgg ttgagattca 161100
aggaggtttc gtcagtccct tacgtaagga aaatcaggtc caatcaggtc actggttcgt 161160
cgacgtttga gatctattct gttcatgctt tgatgtccat gtatcctagc atctccggag 161220
gatgtagtga tctggttgat ttgtacatca ctgccaagca agtcccgaat aatcaaattt 161280
ctgtcctgac cctgagcaac ccgtatgaac cacaggaaat ggcagatctt ccatctgatg 161340
tctgtgatca gtacccgttc aaaaagttgt acgtgagcat cccaggatgt tcatatgaca 161400
ccaatgacgt ctccatcgga tggacaacat gtgaccagct atttagaaat gcctactggt 161460
ctagtgcaaa tgagacatgg atgatcttga accctttcgc caaggaagga gacaacatca 161520
aagtgtggac gttcaagaaa agagacttca gagattacta tcctttggtt cctaacagca 161580
acccgagtca tagagaactg ggaaagatcg aagacaatct taacgtgttc aagtggccgg 161640
tcatgtacct gagtgacgtg tctggttgta ctaacaaaat cagggtgttc ggaattacca 161700
tctcaacagt gaatgcgtca tttgacggat ctagtctggt aaatcagctt caggtcacct 161760
gtcctgtcca ggccactcca ctaggacttg tcaaaagagg actccagtct tctctacaag 161820
agttttctct ggacaagttt tacacgtcca agagattcat gagcacagac cctgacctga 161880
tcgtatggat ttactgtcaa gacaggagca gtcccaacat caagagtgac atgatcgaac 161940
tcaaattcga tgccatggaa accagtcctc cggaacatag ttccaaacaa aattgggctg 162000
tcatcggaaa cgacagacta ttgtgtcaat cacgtagagg acttgtgtcg tccatgacct 162060
ggggtaccac ctgtggccta catgatttca ctcctaataa catcaaggag gaggttcatg 162120
aaattaacgt accaggaata acatgtccgg cttctggatt cttttctaac acagacaagg 162180
aatcaatgga aaccatccaa cttggaatgt tcaacggatt cggaaaagtt gtcattcctg 162240
tccagacact tgagagacta aaccctgctt tctggaccct gattgaaaga aaatgcaaaa 162300
cattcagtgg catgcaactt acactgggag catgtgacac aggtgtggct cctttgtacg 162360
tggaacctgt tgtatcatgg acatggcatt ggatcgatca agaagcagag gacgccttca 162420
gtatcaagga cgccggtatt gttttcaaaa acggacaata tgcgtcatcg gcactgaaga 162480
gacacaacca cagactggac cactgtcatg cttatatttc tgcaaacacc agagaactcg 162540
catttgattg tcctaacgca attcctatcg ctcctttcag gaacaagaaa atgtgtcttg 162600
tgatcgtgac aagtgccgac caatgtagaa cacctgacat tgcatgtact atcagatacg 162660
tcgaaacata cagaggtctg gtgcgtgagc agatgcgcac atgtcagggt tacacccaaa 162720
ccagaagaca aggtgccctg ggtctggaaa gagtgatcag tccaggatct ttctgtgaac 162780
gaccttgggt atatgactct gacagggatc tcttcaacgg atcacagacc atcatttaca 162840
aggtcggtct cgacatgtac cttcctggtc agatgggaaa gcctacaatt gactctatcg 162900
tggatcccag taaccctgat gatctttaca tcaagtggga cgtcatgaag ttgtactttg 162960
acctgatcac ggatctgaag aatcttcaag agatgaaaaa ctctgctctg acaaaaggaa 163020
tcaatcaact ggcagaccgt ctgacaaagg gtggaaagga aattagcagg gtgaatattc 163080
ctgtggacta tttggtgagt aagcaagtgg aaagagagaa agaaatcacg gaacttcagg 163140
ccaagattct acagagactc gagcagatgt acaccgacaa cgtgattcct tcgacagatc 163200
tttacagaaa gctgatgtct catcaagatc gaagatgttg tattctgaag taccaggaca 163260
ctattcttac agtggatgaa ttctaccctg actacgtgga ctggcaatgc cctgacccca 163320
gtgcgttcta caagaatggt gacatggaca gtggggaaat cttcggacct gaacatgact 163380
ggatgagcaa cgtgagtctg tcaagatact ttaatgaaag acccgagtat gaaaatacat 163440
gggtggtatg tatgaacaag cgtgaggtgt atttcggaga cgaggacgaa tacaaaaagt 163500
acacagagaa agtagaacat gaaatgttaa tggatgtgta tgaggatgga atgatggaaa 163560
ttgactgtgt cttggcaaat catcacatta acaagtggat acaaggcacc atcgataatg 163620
gaaaaacggt ccatcctctg gaaatgagtg ggtttgtgtg gatgacagaa atcgtggcaa 163680
tggattgtaa aaacatcaca gagcagaaaa tgatggacat tgtgtttacg tatttcggta 163740
agtacgacga ctatcttgat ttctatggtc aaggaagtaa tgacggagtc atgtacatgt 163800
caaacgtaac agaatcaacg tacattgctc cgatctttga gagatttgtt ggtgaagagg 163860
caagtaggga aagacacgcc ggaacagaca gggaaacaac taagaccgag acaggcttcg 163920
gaaactcact gacaatgaat cttgttgtca ttgtgtgttc aatggtcgga tctcttgtgt 163980
tgtacatgct cttgacaaaa atggtcaagt caagaaggcg tcggaacaga atgaaggcat 164040
tgaaaaagag tggtatggaa cagttggaaa tggtggagag ttaccctttg atgagtaatt 164100
atggaagaat tgtcaaaaga aatgtccctg tgacaagagt gtagaattcg ttaaatataa 164160
cctttttaat ttttttaatt tttagtagta tataatctgt atataattaa tgaaattaaa 164220
cttttaaaaa aaaaccatca ctgtactatt ggcagaatgg tatgtatggg aaaagtcatg 164280
gtaactctga taaatgtcat tgtcattatg acatctgtcg tcaaaatctc tcaggccatg 164340
gattgttctg gaatagacac tggtagatac aacacctatg cttgttctgg agaatccaat 164400
tcatattggg tcttcccggt acatgaatcc cccgataaaa ttggtaataa agcccacgac 164460
agatctgatg gaaattcttg gattcctatg tacacatctg acgcaagaga tgtcacactt 164520
attgccccaa aagctcattc aacagcagaa acattgtgga aaccattcga tgattccatg 164580
tcagaaaagg agtgtattta tgtcaggaaa aatccgtatt ctcaggataa aaatcagtca 164640
tgtctgatat tcttacagaa gatatctgag tacgtatcaa aaaacccagt gataaacaga 164700
cctgtgtatt tactaggtga atcggcaaag aatctgactg tcagtatgac tcagacatct 164760
gtgttcggga caccatatcg tgtggaccct catcttttgg ccttggattt acccgtttcc 164820
attagatgga caaccaacgc gttcatcaat tcaaggaaaa aacccaaatg tattatcaag 164880
gcgttttaca aaactaaggt cggtggagat ctcccccaga tatatttcag atgtacgtat 164940
ccgtctggtc tgggcacggc tgttagttac agaattgaca tggccgggat aagaaatgta 165000
gaagcaaaga gtaaacttac ttatcccgat cccaaggcca agttgtctga tcaatattat 165060
gaacccagtg aaggtgacac tgtatggttt tctaaaaaaa gaaactttga caaagaatca 165120
accggagaca tgaaagtcac cactctcgga tacgaatcgt atgtgttcat gacttctccg 165180
gtgttagaag gtttcattgt cacagacaaa tttaaggaca tgatcaggga caatgcattc 165240
ggttggatga caagtctaag tattgaagtc tgggatgtca aggtagaaca cacacacacg 165300
acaataccta tgtattcaga ccgaatgaat ttgttctggc atcataggaa catcgaaggg 165360
aagtttactt tcttgtccga tcctatgtat attttggaaa tacatgaagc aggaccagga 165420
aagttattag atatgggaga cttcgaatct catgctgttg ttcatgacgt gaacggtatg 165480
atgacaaata gtaaattcat taactaccaa cagaaaaaaa atgaattgga ttcaaacaca 165540
ttgtacaccg gaacaagctg cgtgacctgg ttcaccatca gtgaaaaact aaaccatctg 165600
acacttgtct tgacaatgta catgggtaaa acacacccag aaactaaatc ctggctgatg 165660
agagatatgg tgttcgaggg aaaccaacta ggaaccgaaa caaattataa aacagaccag 165720
gtcaggttta agcttttgaa aacagacccc aagaccaatg caaaaactta cgtggtcacg 165780
atcacagatt gtacaatggt taataaactc caggtgtttt ctgagtctat ttctgaacac 165840
acaaaaaaaa atcatcttga cattgtgtac agacgaaata aaaaaacttc ttcatggacc 165900
ggacaacgtg atattgactt tcaaacaaca agaaacatga aacagtcact cattgatgta 165960
gaatggagaa taagcacgta tcccaggaca ctctttgact ctcagtggta tcgcgacaat 166020
gttgtgtatc cagacataaa attggtagga gatgccggtg gttactacaa gaccgtgttc 166080
atggcagcgg acccagggtt ttatacaagt gataagatac agccgtttta cgtgtttgag 166140
aggtcacatg atgtcattga agaagccagg ggacatggta caagacatct ggtagtaggc 166200
aagtaccatt attctaatca aagtcgtgat gagatccctg tgatttcatt tccactactt 166260
gattcatcac agatgcttct gaagaggacc gtggtcttga tagacatgac cgacaacacc 166320
gtagagacgt ttactgatct aggaacgaca ggatatcatg attttgaaaa ataccctgtc 166380
aaatacacat ggacaaacaa aatggaatat ggaaacatag aaaccgctta ctcaaagaat 166440
catggaaatt tcaagatgtt gtctcacacg ttgtttctgt cgggtcaatc acagatcgtc 166500
cagtttgatt ttgagaatgt aaggtacgag ctaggaacga atagaaaata catgtatggt 166560
cctgacatca agaacacatg gaactcaaat ggcttggctt gttccacaga ttttttacca 166620
tctagttcac gtagtgcgaa gggacctaca gtttctattg tgtgtggaac tcctattctt 166680
tgggctgttc ccgctcttgg tgaaaacata acatgtgaag tacatgggtt accctggtac 166740
aaatacgaca ttgacgtcaa gacaaaagga tatgcagtta ccctggtgaa gacagagaat 166800
cctcatgtgt ctttacaaat cactgtcagt gaatcacaac ttcccgctaa agaaaatgta 166860
ctgacgttct ctattgcttc ggggttaaat gtttacacgg aacactctat gaccatacat 166920
cttgagtaca gtccatggat cggaccagat ggaaaactgg tggatttgac aacagagtgg 166980
aaaacaacag gtgtcatttc tgtgacagaa atgaaaaact tttatgatac taaccatgga 167040
aactatgaca tgaagacacg cacagatgga gaatattgga ggtttgaact tggaactctg 167100
aaagatctac ataataaggt actcgacgtg atcactgtca atggtgaaaa atatcttgat 167160
tggtacgacg aaagtgcaaa ggaggcagcg aaacggaaca aggacaaacc cgccagccag 167220
ctaggatcac ttggggtcga tttcagtaaa gaatatgtac tagacattga ctacggtgta 167280
caaaacacaa tggtatcggt acaaacttgt cgggttgcca cagacgcctt gaccacaact 167340
tcgacaatta ttaaatgtga aggatttgtg tccgagttaa aacagaaga gaaaaagaga 167400
ccggccatct ggacaagggt tgacgatacc aaaaaggtaa gatcactcag ttgtactcgt 167460
aactggttca atggtggaaa ttggatcttt aacatcacat gcactatacc tagtcaggta 167520
ctttctgtga caacatgggt caatgataaa aaaacccaga gtacgttcac ccaacataac 167580
aacaatgggc ctgtgacaac cgtgttgaac aatgtcaaca acaacatact acaaagacca 167640
ttgacgtctt ctgacgttat ctggttgaga atggaaggac aagactggaa aactctcaga 167700
gaaatccaac ttgacatgac cacagactgt aaatccgtgg cagaacaaaa tccatggaat 167760
gacagaaagc ccaaaggatg tctttttcca gacacagcag ggaatcccca ttgtctggta 167820
atagaaccac ccacaaacat tgatccagga gagtattata accagacaat cgtggtttgg 167880
aattctaaat tcacagagtc tgttcttgag aacaataaaa aattcaattg gaaacaacaa 167940
tatataggac tacatgtacc tattgttctg ttcacaggct ttatcataat tatcacatcc 168000
gtaggaatat gtcttttata tcataattaa atggagtttt ctggcattgt cttattggat 168060
gaacttgttt ctgtaggaaa tgctttagaa gccacaaaga agaaaatgcc aaaaacaaaa 168120
tatcttaata atagatctac cataacggtt atacccaatg attgtcacta tactgtaaaa 168180
acatggatga tggaacataa agtttctagg tatcttgaat tcataggacg ggtctgtacc 168240
aatattgatt acgaggaatt ttgggattct ttaaattatt taaatttttg tgaatctgtt 168300
tatttttcta aacatcataa aactcatgtc agtagaaagt ttaccccgat cggtgagtct 168360
tctgattatt ttaaaaactt acaagatctg ggatgagaa agacagcagt ggagacaaca 168420
cgtatgtcgg aaacatgtgc ctattgtctt caacgttata tcagacggta caagtcatca 168480
tccgagcggg agaacataaa gacaggaaag ttcttggttt ggaaaaatag acatgtggac 168540
gacccgaaag tgttctgggc agaagaagag gacaagccga cgaccttgta taaaatcaat 168600
ctaggtgaag aactttctat cataccggta ccttacgact ttcctactta tcatactttc 168660
ctacgttcgt acctacctgt catgaacact gtcacagttg atctggatga gatcatagaa 168720
ctcatgataa acacccgaaa ggaaatatgg aacatgacca aacttctcat gctttattat 168780
aataaaatat gtttgatctt ccctgggatg atctggatta tttgtcctgg gaaaaagggt 168840
ttcagaaaac ttgagctagg atatctattg tcaaaaacag atggaccaca cagattttat 168900
tatgatcggc aatataaaat gaaaaaatat acaggcgaaa aagaaattgt gttaggaaaa 168960
cgtttgtctg aattgaacca ttcactgatt gattatgtca ctgtctgatg atctggtcac 169020
gttcattaat tcatttaaaa aatatgacaa ggaaacctct gtgaaaattt tcacagaggt 169080
catatctgat ctggatcttc atactgatgt tttaaatgat atgatatcag tgattcagac 169140
atcagatgac gcccgtcaaa agattgttaa tatttcatct gtcaatgaaa ttctgtcaaa 169200
tagatcaaga gaagtttttg gtgatatggc agcgaattct aaacaagtta ttttctgtaa 169260
aggctttcat tcctggcata gaaatccaga gattctagcg aatttatccc ttaattatct 169320

-continued

```
ggcttgtctt gacaagagac gtctcactga catagtagag tctccgttga aggtgactaa 169380
aaaaattagt gtcgcaagtt ccacattgaa aaatgatatt ggtattccta caatgtacaa 169440
tatcaccaag gtaaagcatt gtattttaat cgtgcattgt ttaatagtgg cattgtacga 169500
acgtagtctt tctgatttta acagtgtcga ggtcctggta gacactgtca taaacaaacg 169560
taaatgtaca gaatatatta ataagttacc agagggaaac tttgatgacc tcaaagaaat 169620
tgcgattcgg ttctttcatg aaacatcttc catggccatg aaacaagcag tgaattttat 169680
agtccaggaa aaaaccataa agtgtgtcca gtcaggaaag caggtgaagc gattatttga 169740
tcaggaaaaa tcatgtcgta ttcttttgtt ctctgtgatc agatgtgaat ccctggaaga 169800
attgaataaa ataacgttac ctatttttaa tgtttcagca gaattttaca atgacatcat 169860
ggaagaagta cagaagataa tgtacaacta cggtgattaa aaatcacaca tgtatttttt 169920
atattccaat gtattttttt acattctaca tattctgtta ggtctcagga aatgagtttc 169980
ggtcatacaa tatctgtcta cctcagcaga cgatgtcaga gccattttta tttttatatt 170040
tcttgcctcg gcttctagtg tggtagcagt atttttcact gtactccaga taccctgaca 170100
tgatgtcata ctcacaggca aacaagttcc gacacattgt agttttgtaa gattctcccg 170160
caagatattg atcatcatgt aatcggtttc ttctactttg aatgttttaa tctgagtggc 170220
cttgatatca gggtcgaata acatctgaca caatctgaca attacacgaa gttcgaacaa 170280
ccctgaaatg tttctggtgt gtttattcaa gagcttttc atatggaaaa gagaggcctt 170340
tccctcaccg aaattaatag aataactcgt gaccgatgtc ttggccttgg gtacgtcact 170400
tagcttcaac aacaatcttt catccatctc gaacgcccta cgtaccatct ccttgtccat 170460
gggattaccg gtcaactcgt aaccgtacag tcgtatttca gcgggaacca cgtcataact 170520
tatatgggat tctccagagt tttcaagact aggtagttta ctttccagta gccactcaat 170580
catatttaaa acgtaaaaat aataaattaa tattatcgta cacacacaaa gtttatcatg 170640
ctgactctta tctttctcct gattgtccct gccaatgcct ggtctaacat ctcaggcaag 170700
cctgaattca gtttggaaaa aacagtggaa tcacctgacc ttaaaaaagg agttgtgaaa 170760
ttacaagtac cttggtcagt cgatgtcttg gatgtgctga acaaatacga ctttgactct 170820
gtccgaccta atgtaacaga tcaaattgac ttgtatcacg ggatcttgga ccaatgtaca 170880
gatgagacaa cggaacatga tagacttttg ttgttctggt cgaccctgca gacaagtaca 170940
aaaactattc agcaactggt aaatcaattg cctgtgagtc tgttgaaaaa atgtttcacc 171000
aaagatataa cgtacaagac aaacaaaaac accaccgaga tcaccactat caaaacagaa 171060
gagtattctg gaacgttcac gaaggcaaat cttcaaacca gtatggacga tcccgatgac 171120
ttttacaagt tcgaacaaat gaaaatcatc ggaggagatc ctgggaaaac aacgacatgg 171180
gaaactctca acaagaaaga agacttcatg ttcaacatca aactgatccc tgtctacact 171240
cctatgaact actcagatcc catgttttat cacaacagaa gctctcctat cctggagaac 171300
gtatacgata tctggagaga gtataagaaa ttgtaccctg catttgtcat ggacgcaatt 171360
gagaagattg acaaagccca atcagctcac gacgagaact ctcacgacga gaactattac 171420
gactcagaca ctgacctgta ctctatcgac caagtttcca tcgattcaaa actggaaaag 171480
tcactgagta ccaacaacag accagaacta ctgtctctgt ttttcgaagg actacagaca 171540
acaggaatga ccggaatggc agtgtcaaga agtgcagtag gaagtatcat gtctggagca 171600
gtaggcatgg ccggatatct tggacaagca attttgttgt tgacccagat caatcaaatt 171660
ccaccggcac cagaaactcc gtatcaacat caggttttcc tcagtaagac cggacaaaga 171720
```

```
cattgtaaca atccagctgt tccactgact gtctacgcag gaagttccct ttacaactca 171780
aacagttcca tgttgaccga cacactccag accattgtaa cagtcacgac aggttctggt 171840
atcataaacg acaagatccg agtaggttgt tggaattcca tgttgaaatc tctgacggtc 171900
tcctctaata aaattctaaa gtttgacaag acagaaggag ccatccacca ctggcacatc 171960
ttgaatcttg accatcatct tcggacacat aatattttgg aattcacatg tggagccgag 172020
cccaccctca agttcattgg agaaccttat caagaagtca agatctggag gccgaccgac 172080
accacaggag actccatgcg tgcatgtacc gaacaccccc tgaaacaaat tggctggaac 172140
acactggccg gttgtagtct caatccagtg gacactcttc aaggacatta cacctgtgga 172200
cagttacttg ctggttcatc aaagtctgat gaaaagttca ttctcatgac agacatcgtg 172260
gctgactcca tggtcaagat atttgagttc gatcaaaatc aagagttcga catggacttt 172320
gttcattcaa aggcggcacg ctcttactgt aaaggtggac tcgttaacgg atgtgtctgg 172380
ccagagaacc tgtggaagta caatgacaag aagaagcaga gaacattcaa ggtaggactg 172440
agtgctgact tttccagatt tcaatttgtc tgtcccagtg gaacaaacct gcgagtaatc 172500
aacgataccg cgggacatat tgagtggacc gtgtcagaga ccggacaggt tgatatcttc 172560
gtggacggaa tattttccac aatttccatg gaatgtcatg atcctgattt cgtcaccgac 172620
aggttcacct ttcacaaagt atccggagac gaagatgtat caacagaagt cgaggtcacc 172680
gactacaggg ttgattggtt caagacccat tacgatccac tttactctga tgacaagagc 172740
aaggtctcct cactgaaagt aggcggcata tacttcacac tgaaatccgg atcatggaga 172800
agtaactctg gagaatctgt gtgcgtgata gacgatgaac agttggaatg ttcaggagtc 172860
gcgactaata tcccactcac gtttcaattc aagacagacg ctcccaaggt gatttcagaa 172920
accacgtttc ttttcaggga catgactttt gaaaagtcta aaaattccca tatcatgatt 172980
ccggtcgaaa tcatttccca aatgaaaaaa ctggaaactc ttctgacatt gggaacaagt 173040
aaattttctg agattctgaa caaggcagag tttaaacaat ggccaggaca ggtgtacgtg 173100
accgcccaag caatcataga tgatttcacc caggcagaag aagccgaggc ttacttcaag 173160
caagaagtaa gagatgaact tgtaaaacta cagaaggagg tttctcactc tctcggatca 173220
gaccctgaca tgtattgttg ttacgacaac aaaacaacta ccctggagtt ttggaaagat 173280
gactggtctt gtcagggact gcatggatgt tttgaaaaag caagtgtcat gtggccggtg 173340
gatttgtttg atgtgtttga caccattgtc aacgtaaaag agatcattct gaaaatgata 173400
catgtcatgg tagaattgaa cagtgcagat gaaatcatga ctcatgacgt cgtgacccttt 173460
acagaaattg agacaataca acaaatcata gacagactgg acgaaccacg tatggtagaa 173520
catagtgttg ttccgtacct gtgtgccata ttcgttggag gattctttgg gattgtcatc 173580
ggatcactga tcagagtcaa gaccagtgat gatcataaac gaggaatcgt gatcactgac 173640
ccttcctcct gaactttttc cctatatttt tttattacag tgtaagtttc ccaagtgtaa 173700
gtttcccaca tgaacctttt taccagattg acttttacca gattgacttt taccagattg 173760
acttttacca gattgacttt taccagattg acttttacca gaaatgaaat aaaaatacct 173820
gacaggtatc ggacacattc ctttacatat tgtaaaaaaa agtgacaaca tgtcaatgct 173880
actactttta ctatttgtaa cgggtgtcat tcatattgat cttgtcagga cacaacctgc 173940
gaaagataat ccagccggaa gacctcttcc acctatcccg ccccccatgg atgacaatct 174000
tcctcctcct cctcctccgg aaaactttgc accattgcct gctgatgaca gacctctacc 174060
```

```
tccaccacca cctcctgtgt tattggatga taaccatgga gcagtaggtg gtgaaccaca 174120
gggagcagta ggtggtgaac ctattgaatc tatcgacgaa cacgatcacc atcgtaaagc 174180
attagatccg ttctctaaac aagatctgga aatggaacta ctgaaggaac gactggatga 174240
tctgaccaaa cctcctcttt ccagagaaga aatcaaacac caactagacg tcctccgatt 174300
aaaattgaag gccatttcaa aagtcgtggc aggaacaacc aaggaactcg aaacaaatct 174360
aaggaaagac ctggccgacc aaaaacgcca acaaaataaa gacctggaca aagcccaaga 174420
acgatatgat ctggcaaaag ccctgtctga gtcgttcatg tcactcaaga ccacaaaaac 174480
agagaaggaa attcaggacc atgaaaaaga ccttcaaggt cttttggaaa agcacacctc 174540
tgacgtgaaa actatcatga aacagaacag tgacgaagag atgaaaatgt tggaagtaca 174600
caagttgaag ttagacatca tgttgagccg attcaaggaa gtacaactca gacactctga 174660
catggacgaa cggtatcaaa agaaacttga tgaagacgct gccccttttc ctgatctgac 174720
aacaccacgc gatcagatcg ttttgaatga agccgatatc gtcgagaccg tccccatgga 174780
tcatatgaca atagatgatc aacaggtcag atacgtggtg aatactctac taggtctgag 174840
gaaaggtacc ctgtcaacgt tgataccttt tcagattcat gatagacgcg tctcgttggg 174900
ttccactttc ggaaacatca ggtgtaaaat tgacgtcact gacgacggat acacgaacaa 174960
tgacaaagca ttctacgact tgcccagtgt tcactcacct gtcaaactgg attctgccac 175020
ggtatcgatc acaagaaaga tatatgggtc agggtctctg ttactggata ctctcatggg 175080
acctgtttat ctgggagaac ttcccagatc aagatcatcg ggatcaagga caacggaata 175140
cgacacggga ctggcagaga caaatgtcag agacagtata acagattatg tccaaaaaac 175200
tgtcatggta ctttctgcgg aggtcaccgc tctcatgaaa atcaagaaac atgccgggac 175260
agagatcacc agacttggta acgcagttgt cttggtaggg aagttaactc acaaaccaat 175320
tgaagagcgt cttgacatgg caacactgaa agctgatttt gaaaaggcca agaatctatg 175380
ggaaatctca tcacacagac tggacaaact acacggttcc ataaaaggta ttgtgactga 175440
cttttccacg ggtctgatga gtatttaccc aggccatcca ttggccgtca tgatggatcc 175500
tacaatcacc caaactatga aaatggaaga tctcataaag accgtgttca ccatcgaagc 175560
agacatgcgt ggaggatttg aaaaatcccc tattgttcac cgtgatcaac ataccactct 175620
ggcacgtgaa tacagtgaac taggagagga attacaacta ctgaaacaca tgaaactgag 175680
aaacggaaag gacaagcagg tcatcattga caccggtaaa ctgtcaaagt ttacattatt 175740
gaagcgacca tctcactcac tgaaatctca tctgtcttct gggaatcatc aaggtatcat 175800
cctgacatat gagatgaacg acgacaccac tgacatgcta aaactagaga agaagaccag 175860
gaaatctttg gacagacaca ggaacatgca caagtcatca catcctaagc aaggtcttgt 175920
cagtaggata atcgataaga gaaaatcaga cagaggtaaa attcttgaac atgccaaaca 175980
aacaaaggat tactctacgt tccgtcatac atttgaaaaa ctgacagcgg ccaagaaata 176040
cagacaacaa caaaagcggg acaaaaaaga aaggcgcttc cgacccttca ccactgctta 176100
cgaaagagta accagaggta tttcaggatt gttctccagt ccattgaacc cacacgacca 176160
ctcacttgct gacaacagat tcggttcttc tgatgactgg ggacaagaac atactcttgc 176220
tatcaaagaa caggaagaaa gtagaagaca cgagagggcc agggctgaac gtagaacatc 176280
cgaagtagag agcgttcccg aagacgtgta cgaaagagac tttcaggaag gagtgtatga 176340
tgaactgaaa ttcgccgagg aagagttgag agagtacgag gagatgaaag agagagaatt 176400
acacgacgag gaagaacatc acagagaaca gcccgatgac gatgaccaat caagaaagag 176460
```

agacagtgct gattctgatg aatatgatca tcctagaaaa aatgttggag agtacgacta 176520
cccaagacct ggtgccccaa gacctgtaga atttgggcct gatgggagaa aacctgatga 176580
cccgaagcct gacgacccaa agcctgatga ccaaaaacca gccgacaccg tgtacagttc 176640
attgaatctg aggattcctc ctcttcgtga ctcttttagg agaatcaaag aagcatatga 176700
acgttccacc accacgctga aaactcaact tctgaaggga ttacatgagg atgccttgtt 176760
tgacgagaac ggtgatgatt acaaggaaat cgcagatttc atcaaagaag gtggagtatt 176820
cgatttcact aaattaccgg ataatttcga caaggacaga ctcgtaggtc ctgacagtcc 176880
tcctactaca cggacagtac gatttgctcc tgtgacacac tcgaccattt tcgagaagac 176940
catccctggt ccattatcac gaaaatatgg tctactagaa ggctcagacc gtcccatccc 177000
tcctctggtc agaagaaagg aaggtgaata catttactgg ccagatgtag gagatgatgg 177060
attacccact gacgcagtac gtaatgacct ggacctgtta agttatgaca gacttctcca 177120
atcgacacga gacagagtct ttctcgagag gaaagctacc atatacacag acaaaagagg 177180
taatgaggct gttaatccat ggggatggca atcaatgacc accaagagaa acaccatcct 177240
gaacgagggt atacgtggaa gacaacctac ttcaaccgag caattgaagg aagaacagga 177300
tgagattcta aaagccatcg agaggaaccc aaatgtagga tattctgagg acactatcaa 177360
gtacattaga gaaggagcca gacccagaca actacaacga cataattgga atcgtttatc 177420
tggactgaaa aagtcagcta ccaaaacaga ggtcaagcca gaggtcaagc cagaggtcaa 177480
gccagaggtc aagccagagg tcaagccaga ggtcaagcca gaggtcaagc cagaggtcaa 177540
gccagaggtc aagccagagg tcaaaccaga ggtcaaacca gaggtcaaac cagaggtcaa 177600
accagaggtc aaaccagagg tcaaaccaga ggtcaagcca gaggtcaagc cagaggtcaa 177660
ggtcggacct aagaccttgc caaagcccaa gaaatctgct gaccaaggac ctgaccaagg 177720
actaaatttg ggtcaggtag aaacattttc actctctttc aatgaggaac ccgaacaaga 177780
aaacgaagcc aaatcattcc gcctcgtgga tttcgtggtt gtccggttag aaaaaactct 177840
tggtagaaga cccacaagtg aggaaattca taattttgtg gaaaatactt acagcagagg 177900
ttgggatcat agactgacat cagacgagat caaggaaatt gaacaagctg aggaatggga 177960
caaggaaaat agtaaaaaaa atccagatct cgtgagcgaa atgagcgaca tgtttaaaca 178020
aatcgacgtg tctgataagg ttgaaaatct tgaaatgtac atcccacctc ctaagccaag 178080
tatctttgcc aagtttgcta aattaggtaa gaagaagaag tcttccaggg cagaagctgc 178140
gacagcagac gccgacagtg agtcagacag tgaagagaag agaagcattg acagtgatga 178200
tgacacagag aagccacctc cccttcccaa gaaaaagaag ctgtccgtag aacaagagaa 178260
aaaactccag ctgatgttga agagatcaga cagtagaaaa agtctagaca gtattgccag 178320
cacaaaaagt agggtcagta tgggtagtac cagaagtatg gcaagtatgg gtagtcagag 178380
tagtattgat agcaccaaga gtaccagaag tctaggagaa cgtctcagga caagtacctt 178440
gcgtaggaaa aattctgtaa gagactggtt ttcacaggcc atgatcgctg ataaagacat 178500
tgcaggtagg gtaaagatca gagatcacaa gaacagacac tctgaggatt acaaaagata 178560
ttggacacga gactccgata caggaagaaa actcaacaaa ggattggtgc aactggactc 178620
aagaaaggta ttggcattat tggaagagca tttcgaagaa aacagagccc tgtcttctca 178680
tgtcagtaaa caaaattggg tagacacaaa acgagtcata accgaagaag tggaatcaat 178740
ggtacgatcg gccaatgact acagaaccaa atcttccatg gcatttggaa aggcaaaaac 178800

-continued gtcatcattt gtgtcatctg tgttgaacat gttggaccat ccggatcctc ctagtcagga 178860
ggcagctgtc gtgtaccaaa aacttgtcat agacgcagca gtatattggt ctttcgtcag 178920
gggaggacaa ctgaccttac tgaacagcat gaaggataaa atggcgcgtg aacatatcga 178980
ccatatcgag gtaagattag gtatcaaaga tacggtcccc atcagtagta acagaagggt 179040
caatccacta ggattagaca tgacaaaaat caaacagatc acgtacgtgt acaagtttca 179100
tgacggaggt atacccagaa gaactgattt cttagacttt gtctctgacg tagacaccat 179160
gacacatagc aatatgaaaa aatacccggg tgagttcaag gaatatgttc ctacaatgga 179220
gcttagttca atgtacaatc tggctgtgga tcccgaaaca ggaagactgt ctcctgatca 179280
gagaggtaaa ttgatacaat ctgtagacat ccaatatctc catcacaaga aggggaagca 179340
gatcaggtta ggtattgcaa gtgctggagt agctgctgcg gacgaagcca aagaaatgag 179400
agcaggagca agtgacgcga tgggggcatt ggcatctgca atgcaaaagg gtctgaagaa 179460
gctcaagaag aagaagtctg aaaaagatct gactcaagga gaggacgggc agaatccaga 179520
tggtttgaca gaagaacaaa ggattgctaa agccgctcat gaaggtgcca aacccaaaaa 179580
gagtatgaga agtttcctta agaagaagga caagggtgat catgaagatg atcaaaaccg 179640
caagtgtaag agaagtctgg gagggagttg tgtaagtaga ccaaggtcct cgatagaaga 179700
cgtgacagaa cagctcgaga caataacaac caccaaaaca aaggtcagta agttcaagcc 179760
catgagtgaa ttgggtgctg aaataatggc cacggttgtt caattgaatc agagaacgat 179820
ggaacgagga cagtgtgtac gtgaaaagtg ttgggaagtt tcagacattc cgaggtacga 179880
catggaagtg tacagaggca ttttggaaga tttcagtgaa ttgggaattg acacggcagg 179940
tatgatgaca ggcaaaggag caatcgcatt aagatctgtc ggtgtgttcg gacagagaat 180000
tgtcgccaat gtgttcctga gatacttttc tctgagcatt ccagattatc tgacgtcaat 180060
gtacggaaag aatcatgaca gaataaacac ctgtgtccct gtgtctgatg tagtcgatgt 180120
cgtattgaca ccaggaatct catcggtaat gtacggaata ttggacattg attattcaaa 180180
gacaaacctg tactttacat gccctgtgaa tcagacactc agacaattga ccggaaacct 180240
ggtccaggtc gacatgattt ctctttcaag attcagagtc aatctgaaaa attgggacgg 180300
taatctgaca ttcggttgca cagacaagac agacatgacc ctgatcatga atcaacggac 180360
agaagactgg aaagtagtag tggaaaagga cggtggaaaa tggacaaaca tgaaaacatt 180420
ctgtacagaa aatccttgga atacgttgat gatccaagaa agttgtgagg tggatacttt 180480
tgtcagacct atgccttgtc agattcttct ggctaccagt tctgaagggc agcatcttga 180540
agacacagat ggcaatgact acatcttgga cgttacacca atcgaccatg tgacattgac 180600
aaagatccct gaagcatgtg attccatttc tggaaacgag tgctacaaaa acttcttggg 180660
aattccgaca actgtcatga tcaagatccc catgaagatg tacggatttt gtgttcagaa 180720
ttgggaaggt acaaactcca cagtggtctt gttcacagga acacacacgt gtaaggagac 180780
caaggtcact tattacaaga ccaagggaga actcgagtac gatcacaaag ggcctgacca 180840
acgagatgtc ctgatcaaca caacaacata ttcgatcatg taccaactga gcatggacaa 180900
taaaccagag tacggacgcg tccatagaaa tctggccctg aaactaggag aacattcatg 180960
gaactggtat tgtggtgggt ttgagacacc gatggtttca aatggactga cagctgtctt 181020
acatgaagat tacaccgtga ccatcaacgg gaccacgacc actcatgaag acttcattca 181080
agggacatgg accctttctg agaaatacgc agaagacctg gaatgggcac gagtaggaat 181140
taatccatgg tgtactatgg atggtcatat caagacgaca ggagaggtca ctgaatcatt 181200
cgtgagcaaa gtaaggactt ctcagtactg gaacaggaat tcacctgacc ggtccaggat 181260
gtactcttat ccgaaaactc gagagactct caggatgcca tggtcagaca tcccagataa 181320
ctttgtggtg gttcatgatc gggtcagata gacatttagg tgacgggata attttatagg 181380
gaaaatataa tcattttttta ttcatatgtt taatataatt atggtaataa taaacagtat 181440
cattttttat aaaaaagtaa aattaagtta tagagattat tctccagact tctagcacgg 181500
cacgattact ttaccatata aaaaacaatg ggaaagtcag tgttcttcac ggtatgtctg 181560
ttcatgtctt taggacatgt tcagtccctt gacagactag acccttctgt cttacaagaa 181620
tatgtcgatg acatagactc tgtaaagatc agtcaaggat acaccaccct tttgggaatc 181680
acaaaaagat gggttgacac agttgtctgt acaaaccctc cagggccact gttcgaatca 181740
gagttcagag attctctgtt ggaccacatg ttggaattca tgacggtctc gatcactcaa 181800
gaagccgtgg aaaaatacat ctcccccaag aactctgacg atcctgagaa aataaacggt 181860
ctgatcagat ctgagaaatt caccaacatc ggaatggaac ttctgggaaa ggtcgtggca 181920
ctactggata gttataattg tacccatgga aacatgcaca ctaccaaaca aatccaattt 181980
tccacttaca ccttggcgaa ttcacaaaaa tacccacggg ttcctaatat gacagtcgac 182040
gacagacttt ccatgactca attgaagaga aaaagtatca acctttgtct tgtcaaaaat 182100
aatggaattc cagagtctcc gataacggac aacagtcgaa ctcttaaggt agcacaccca 182160
gatttgacaa ggaactttgc cagtattctt ttctacttca acgggacaat catagaggac 182220
gtcagcgaat tcgaggaaac aggaaaagag ctgatcagga acatcaccag agaacttctt 182280
gattacgtca ccgagtccag aaacaaggac gccatggaga acatgacagc cactgaggaa 182340
cttgtactta gacagctgcg atatgttctc aagcagaaga ttgacaagga cgtcatgcaa 182400
ataggactgg agccacttga tcacggaggt tacgtcagtc tcaaagaatt cttccaggcc 182460
agtgaaactt cttggaggaa agatgtctgg acacatctga aagacaacac cggagcagac 182520
agaaacttga aaattgcaag cgttgtattc ggagcattgt caagtgtagg tagtacaatg 182580
gtcatcggag gagccacaat gggtccagtg gttcaaggaa tcggtggagg aatcttggga 182640
gtcggacaac taggaagcac agccatcact ctctttgaaa tgttcaaggc cagaccagac 182700
gtcagagaca tcaacactga attctgggta aactacaaac agttcattga ttcaccggct 182760
gccggagtca gaaaatgtat gggtggtgtc gacgacaaca ctcatattca aatggcatat 182820
cgttcagaga tgaatgacaa agcttggatg gacgccccta agtcaattgt ggtcattcag 182880
aagaatgtca tttctcatga catgagtaac ttgtttgtgg aatgtttctc aggaaagctc 182940
aggatgaccg agggaaacat tgacgcgttc agtaaccttg tcatgtccaa ggacggaaga 183000
caattgtaca gagtcgatta cagtggactc agtaaatggt gggaccgagt aagtctgaca 183060
tgtggaaagg agatcactct cgagattgaa ttcacagaag cacatgatca tatgatgttc 183120
ttacctggat cacgtaccgg agacagtcaa ggttcttgga cctcaatgtc tgatgtgtgt 183180
atgacagacc ctctcaagag aatcggttac accaccctag gatgtaagta cgatcctttg 183240
tccacgatca gacacgagac ttcttgttct ctcatgtacg acatgtcagt gtatgataac 183300
atcaaacaca gattcatcac tgtttctgga atatttgata ataaccagac aagtgtgaaa 183360
gtgttcgagt tcttcccagg acaacagaat tataccctgg acacgacaac ggtcgacggt 183420
caaagcaagt gtttgaaagt cttgaatgac ccagacacct gtcattggcc agagatggtc 183480
actgtccgga acacgtatcc taacaaggtc aggatcttca atgtcaagct gggcccggac 183540

-continued acaaagtttg gactgacatg cacaccagga tctcagattg attataacgg aacatattgt 183600
cacctgaaac agatcgggaa ggaaacatgg gaagtagaag caggagattg tcaagttcaa 183660
tgtttcgcga aggggaagga aagtgacata ttcagagtga caaaaaccac caaggccgcg 183720
acaggatttg aattgacatc tagattcggt accaatgtca gacaacatgt gacagacaca 183780
gactttgatg ccaggacaga agttgccatg gtcaagatga acaagttcac tgtgtctaca 183840
gtggtggact ttggagagaa catgatttca cttcgttctg gaaacaacac ctggaaggac 183900
atggtactct ctgtttacgg atgtcctgga aaatcagaag aggacggaaa gtgtactcat 183960
ctcatgaacg gaacatggac cagaaagaat gtgaagtacg gcttcggaga agtatctgac 184020
tcactgacgt tcgaatttga aaatgtcaaa ctggtcagtt cttgttctgc tactgtcaga 184080
ttgtcggatc aactactgac actggcttgc acgatcaaag actttgatca ttcacatgtc 184140
atggtcacac tggaaaccgg tgtgttcttc tgtgatcagg acaaccagga cagaacatgt 184200
gaaatgtaca acaacggcga cgtcatatca tccaaggtaa gtcagtacgt gtcgactctt 184260
acaacaggaa aactatacgg gatcatctct gatgtcatct cagggactca gttactggga 184320
aatggtatgg agtgtatggc aggtattaaa tcaatggtca acaccctgtc aggtatcaag 184380
gcagacaatg tggaaactat gatcagaaat caaatcaaga caaagtgtgg acataccttg 184440
acaatggaag gagcactccc cacaggatca tggtgttgta actcacaaca ggcaagtaac 184500
aaccggccga tctcatggaa gcctgtcagg atcagtaagt tctttgacgt gatcgacctg 184560
aataagatca gttacactgt agatcctgtc aagatcgacc aggacgtgta tcagcagatc 184620
ctgtcactga agcaacatgt acgtgatatc gagaatggaa tgtctgatct gaaaacaatg 184680
gtatctgaat actcttccaa tggaatcgtg actcttgtga caatggatca gatctccgac 184740
gactacgaga atcatgaaat gtacaagaac gagatggtca acaaaggtct taccaagatc 184800
tggcacggat ggttaaacat cacttcaaca cttactggtc agacctggac tgattacgtc 184860
atggaaagag attatgtttg ttgtggatgg aacggaacga ctcaggaggt cattaacatc 184920
tacggagaca aatgtgagga cactgtgttt gtttatcaga cacgagtttg tggaagcgag 184980
gtatgttgtc ctctgaccac gacaacgttc ttgggttgtc agaagcgtag ttaccaagct 185040
ctttcgggtc aggagcaaat ggcactgaag caactttttg aaaagaccga caagatcgtc 185100
agactcaatg ctgtcatcaa aaagaatcct ttggtacgtc gaacaattac caccagtggg 185160
ttggacaccg caatcacaag agtacttagg tctgaagatc aggaagtcga ttatgatctg 185220
ctaatggctt acaacgtgac agtggccaca tgtgtggtac ttttgactct tgtgttcctg 185280
gttgtcttgg tagtaagtat ttgcaaatcc aagaagaaga ataccctggt aaaccattct 185340
gaaagtcaag taaaactatt gaccaaatca acagcatctt ctatgtcttc tgaatcttct 185400
atctcaggta acaaaagtat ggtaactgta tgatatgtaa ctttctgttt atcgatttta 185460
tctaaataat aaatgcgcct ttctaaattt ttcttttcta attctattga atttaattat 185520
agtggtaaac ctggtattga gtacgttgaa ttagaccatg tccttgcaat aagcaagttt 185580
acaacacgta atggtaagcc agatcatata gtcacagatt ttattccgga gaaggtcata 185640
aaagaaagta ccgaatttga gacacgtatc tgggtaaaac actcagaaaa aggatgggga 185700
tatttcgttg ctctttcaga tacagagtgg aaacgaccag atttatcagg ggtttgtata 185760
acatgtgatc ctagatttac caaggtcaaa gggtgggacg tgttcttcaa atcccccata 185820
ggttgtaaac acaacacgtc acgattattg tattctaata ttcccacgag tccgagcaat 185880
catggaaaga ttgattataa gatacctggt aatatcaaac ttagtaatga taaagcagtc 185940
attgaagcca ttaaattgat taaattcacc aagggaaata ccgattttag tgaattcaca 186000
catcctaata tatttgtggc tgttgttttg ttcagattgg tcaagaccga ccgaaaagaa 186060
gaaaagctat ttttgaaatc tgtggccccg accactttcc tggaagccgc tcactacaca 186120
agtaagtgta tcgaagaagt aaagaaacat ccagaaccta attttgccaa aatcatcgac 186180
cattggatcc aggctaaaat attttacgga gtaagtttca accgtgacaa caacaaacat 186240
ctgtttgaag aaacaaaaac agattggacc ggagggcatc ttcctattga cacatcatgg 186300
gccaaacgtg tacagtactc ttggtccagt tgggcgtctg atctaccaga actttatgtc 186360
cctgtgacac atccagactc tgacagtctc aactcaataa gtcatgaaca tgtgaccgtg 186420
caattctggg atcttaatga catggatcac acaagaagtg gacattttcc acttctccaa 186480
ccgaccgaat ataccaatct taaaaaagcc gaacaatctg tcctggtcaa attccaacaa 186540
tcatggttga agaactgagt tggatcttct gtgtaaggga aatcaagatt tgaaaactga 186600
ttttttattc tttttatgta ttgttcatct ggctatttca tcatctggga ttctccgtca 186660
gggtattctc cgtcagggta ttctccataa aaatgtggtt ttttaccttt ttgattttca 186720
ccgtggtcac agaacatggt cagagtgtgg tacccagtgc accccctttg atcagagata 186780
atctggatgc tgtcctggca aacttgggta tcagaatgcc cagggaggcc atgaccaggt 186840
cagggtctgg taggattctg accggaccag aactccccag aattaaaaag tctcgtaaaa 186900
ctttgttctc ggcctctcaa ttggctaata aaatgatctt gtttctggac gacaacaaca 186960
gaagaaccag ggactttatc gccggtaagt attctgatga ttctgtcgag atcattgact 187020
atctagcaga cgtatcaact acatggaccc ggttcagttt ggacttttca ttggcatctg 187080
gttcacgttg gggattaggg gccgcaatga tacttgacat gacagtgaat ccattgttca 187140
aaatccaggc tctgttcaag gaagttcata aacaagatgt taagaaagtc attgaaacaa 187200
attacagagc atggatctct tctgttcata acggagataa atcgtgtccg gtcgggtcta 187260
atccgacaat catgaaactg agctacagaa gtaccatgta taatttcaca gacaccaccc 187320
cgaacaagtt cactgctcac atacatcctg gtgttgtaag taagcctgcc atcctcgtca 187380
aatgtttcga tggtattgtc agatctgagc aattgagtgg tagacatttt gaacgactgt 187440
ccggagacac ctgggtattg gagaatttca tagacgtgtc acatgacaaa atcgacatca 187500
tgtgtggatc ggaaccgacg ggaattatca cggtagaata cacaggatcg actccttcga 187560
tcaggccgac gatcaggttc gggatcagac aagactcttc aacattgtgt ctggacgatc 187620
ctggtcgggt gtctgtggtc gacatgacac catgtccttg gaatcctaat gtcatgtccg 187680
agaccacatt tgtctgttct gatttacacg agatagattg gacatatcag aatctgacaa 187740
tccagacaat gtttggactt tctctgtcta atgacacaaa aggcgatcat gtcttggacc 187800
tgagtaaacc agaatcagtc ataagaaatt gtgtcaagac cctgggacaa gtgtgtgagt 187860
tgggaatgtt cagtaaattt ccaggaaaat tgtcagtgat cggtcgtggt aaaataacca 187920
ctctcagact caagtgtcag gagtgcaccg gatgttctct tcaagaaagt aaacgtggat 187980
ggatcatcaa tatggacagt gaaggaaacg caacatgtga tcaggtaact atcaaatggg 188040
acaagatcaa gtcagacttg tctgacggat acgtcgagta ttctatgtac cctataaatt 188100
attttatcaa gacactgtca ctcccgatct cgtattactc tgccctacac acacaactgg 188160
tttcaaaagt atttgaagga ttcaaactga aactggaggt agacggaaaa acatcaacag 188220
ggacctggaa acatcatgga cacactgaat tacctgaaca tgttttcacg ttcaacatga 188280
cagattcgac cattgtgatc tatgatctga ccactgacat gatcacaata aacagaaagg 188340
ccgcagaatc agacaaactg atgactctca gtttggaaag tttcgggaag gtatgcgatg 188400
aaaatttcgt tcagatgaaa cacatgaaat ggtgtgacgg caacggacaa gacactgatg 188460
ttactttcaa acatgttatg aatgcctgga taagtaacga ttgtcatgat tgtcataaat 188520
cagtcccttc tcctaatatg actgacatga taaatacctg gagggacatt gtccgggatt 188580
ctcataatcc agatattatt acatacatga aagaaatacc tggtttgaga cttgttggtt 188640
ttacataaga ctaattatgt aggttgccac aattattttt tataatatga atattcgtag 188700 tatttttta ttggtaaatt gtaaaaaata taatataaaa gtaaagcaat gagacctatc 188760
acttccatag aatttggtct ttacacaaac gatgaaattg aacgatctga gatttcaatt 188820
aaaaattcta aatcggcaaa cgatcatgaa accgtgaaag acaagcgtct cgggaccgtg 188880
gataataacc tatgtaaaac atgtcgttgt ataagcactc tttgtctcgg tcattggggg 188940
aaggtaggaa tcaagaatgt ttacatcaga cccagtcatg tcaatcaaat catccaaata 189000
tcaaattatc tatgtttaca ctgtggagtt tttaaattaa agtcggcgta cgagacatcc 189060
acaaaaattg cactgaaaca tcatgatgat aaaaacaaca agatcaagat caaggaactg 189120
gccaagtcta tccttgataa aaaaagtgga atctgttgga acgaatcatg tcaacaaaag 189180
tacgttaaaa tttcattcaa caagaaaaag aaaatttgtt tcacatggaa aagtaaggag 189240
aataaactta cggtcgaaca agagtatccg ttacaaaaac tttttgaaat gttcaagagt 189300
attccggctt tgtattatcc gatgatcgga gtcaaggtaa gtcctgagaa tctcttttat 189360
gaaaagaata ttcctattcc tcctatgttg atcagacccc ctaatagttt ttggttagac 189420
gacgtgaaga aagaaactca tgaattgaca attttgatga cgaccttgat taatcagatc 189480
aagtcaaatt ctgacagtat gataattcag aaagccttga tagagtacga caacagtaat 189540
attttgtcgg cggtcaaaca aaacaacaac agtctggtaa gtattctagt agggaaaaac 189600
aacatgttga gatggcatat tttgagtggg agaaaagatc agacatgtag gaccgtggta 189660
ggaccggaca gtcaactact tttgtgggag atcggagttc ctgacatggt cttgtcaaag 189720
ttgtcgtcaa agatatttgt caatcctttt tcaatcgaga aaattgtgaa cctgttcagg 189780
gccggacagg tcaagattta ttttaacaaa cagacaaacc gtctgatgac cctgaagaaa 189840
gacaaaaagc tcaagggaca agtgactttc aaaccaggtg attgggttga gatcgacctc 189900
caggaaggtg atcatatgat attcggacgt caacccagtc ttcacagaca taatgtcatt 189960
tccagttgta tcaagcgagt ggaaggatgt ggtcttaaaa tcccacaggt aatttgtaat 190020
tcacagaacg ctgattttga cggagatgaa atctggggat gtctggaaca acatcccaag 190080
gccaccatag aacaaagtat tctgatgttc cccgtgacca tcatcctaca tgatcttctg 190140
ggcattccac tttatggtaa tatccaagac gaaattatca gtgctcatct cctagggaca 190200
gagacagaac ttaccctgac agaagtaaat tacctgttca aacaatgtcc acatctcaga 190260
caacttgcat tgcctaaagg tcagaaatat ttcactggaa aaaatgtcct gagtattgtg 190320
tttaatcaaa acaagaaaaa ccttacgtta ccgggaatac tgaaagacgg acaaatcatc 190380
atagacaaca ttggatcaga tctcattgtc ggacaaaaga ccaagtcact ttccaagttg 190440
atcatcgaaa catcatccag gttagaagga tgtaaattca tcaatgacat cggaagactt 190500
ctcagacagt atttgagatt cagacaatac ggtgtgatat tcaccgatct gttgcctgat 190560
tacgcttatg tcagaaccct gaacaacaac aatctcgaca aactttttaa aatcaaatct 190620
aattttgcaa gatacattcg tgattgtgag gatggtaaaa ttatcagact ggacgaacag 190680
accgaaaata aatacataga cactgtcttg atgtctctgg tcaaaagtaa catctgtagt 190740
atcacaaagt tcatagaaac tcagttggaa atcaatccga gaaacagtct ttatgtcatg 190800
agtaaggccg ggtataaaat gaatccgaca gaaatgatgt atattttcgg aacgttcgga 190860
caacaaaaaa tcggagggaa aaaaatgagc accggggtca acagtagaat tctaccatat 190920
catttaccag ggagtcttga tccagaatgt agaggattcg ttcttaatcc tctcttggta 190980
ggtttgaccg gtatagaata ttatttcacc atggcaactg ccagaagtca gatcgtcgac 191040
attgtttgtg aaacgtcaag aaccggaagt ctggccagga aaattttgaa aaagatggaa 191100
gacgtggtgg tcaatgaatt ggggtacgtc atatgtaata aaaatatttt gaaattcgct 191160
tgtaacgaca tcaagatgag taaacaagac acgacaaaaa ttcctattat tacaccgaag 191220
ccttctcaga aatggtattc tgaaattaaa cacatctgga ataccttggc cccgtatctg 191280
accacagaca acaaacgtaa caaaatcact caatgcagtt tcatgttgaa tcttgacatg 191340
tttttacaaa ctaataaaag tagggtagga aaacctgttg aatcaaatac gttgttcaag 191400
caggtcaatg aatgggtcga catgataaca caaaaatatt tcttcaactt gtctgacacc 191460
acaatgatac gatacacaat gttgacatat cttgatccca gtagatatcc tattgattct 191520
gtggtattga acgatctgtt tgaaaatata gaaaacagat tcatttacag tttaagctct 191580
ggatatcctg tcggtgtcat atttgcccag accctttctg aaaagttcac acaacaggcc 191640
ctgagtaatt tccacaccac cgcaaaaagc ggaggagtcg ccgccactct tggttttgat 191700
aaattcttga agctggtaag tctgacaaaa aataccaagg cagaggtaat cacgttcact 191760
tccaagacaa aggctccgtt ggaaatccta caaaataatt tccaatttgt atgtcttgat 191820
caattatgtc cggtcataaa gacacgggta gaaaacacaa aaatgtacat tgaaatgacc 191880
ttcgaccgta aacatcttaa atcagaaaac atccagattc cacaacttga aatcatgata 191940
gaaacgttct tcaataaaat tcaaatcaca gggcaatgga gttattggac agagatcttg 192000
gacaaacgta aattcataat tcgaataatc accgaactgg aagaaccggt ttctgtgaat 192060
caatacattc ttccgatgat gcttccgggt ggaatataca aaggtaaaat atgcgacgtg 192120
aaatttccta ttgataaaat tcaacaatgg gaatattctg aagaacacga cgaacataag 192180
caagtcgacg cgtacaaact tatcatgata ttggattcta ctgctatgtt gaccaaattt 192240
gatttgtcgg gtattgacgt gaatcctggt atttggactt catatttcgg attcggaata 192300
gagtctgtca ggaacaagct cattaatgaa atgttggaaa cgtacggtaa cgggtttgat 192360
tacttgtatc aatgttgtaa tttactggcc gacgtcatgt gccattatta ttatccggaa 192420
acagcaaata atttcaaaat gacaaaaatc agtatcatga aaaaaatggc aagtggagat 192480
tataaatctg tggcacaggc tgcagtgtct ggtgcagtag acgtggtcca agataacagt 192540
acttgtcatt tcctgtgtca acctattaaa gtaggaacag gcttctttga ctattacaca 192600
gacatcaacg acttcttacc acttgttgcc aagaagagca ccatcgaaga catcaaggaa 192660
acaaccctgg atctcatagg attttaaaaa actttattta gtccggccac tatcacagga 192720
atatctagtt ttatggttct cgagtcccat gtgatgtaac tattatttgt caggtacaac 192780
gccacttttt tattatcaaa taccacgtaa cctatcacgt ttacatgatc caccacgaca 192840
acgcagaccc atattctaca cccaccgaat ccgtttattg taattgtgtt gtttgtcagg 192900
tcccaaccac ccttgccttg taagataata ttaaaatctt ttatttcgtt catgggaagg 192960
gaaaacttat tatctatgat gttcacgaat tctgtcgaga ccacagggtc aagaccatca 193020

-continued ataattagat gccgggtgaa agacttggaa actggttcta tttctgaatc aacagacttg 193080
ggataaaaca aattgaactt ccattttttt tctttcatta taatcatcat aaatttactc 193140
agaaacatca atcccaggat aggattagaa actgaaagaa tagaatgtag acaaacattt 193200
aaacttgtcg aacaacgtat ttcgaatttt tgttgacgga caaaattcgt taatttagat 193260
gtggcttgca tttataaagg agttaaatga tctggttttt tctttcgata tttgtatccg 193320
cacacatttc atatgtcatt tcaacaggcc aaagggttga cacatccata ttattattat 193380
caggtcaatc acaacagacc gtgtcaccca tacaaagtgg taattcaaca ggtgtacaaa 193440
gtatcatttc ttacatacaa acattagcac aacctttggg atttttagga gttgcattag 193500
ggagtatagt gacgtatgtc gtgactccat ttaaaaaagc cataggttcc ataataagcg 193560
tattagcatc aattaaaact ttaggaatta aaggatacat catgaaatta caaaaaacac 193620
atttgggtat agatcaaaat gacatactga attccatgaa atctattgtt cctggaaaaa 193680
aagaacctcc tgattctgac ccacctcctg agtctgaccc gaccgaaaat gatcaattaa 193740
atgtaaaaaa aatagacata aatacacgat ccatggacga taccaaagta aacatgggag 193800
ataccaaagt aaacatggga gataccaaag taaacatgga cgataccacg ggtcttccga 193860
ggctctctct gaatagaatc atgagtaatc cttcttatag ggctcttgaa aaagactcga 193920
attatataag cctaggtaac gacagatttt acagggatca ggaaagacct tatcaggaaa 193980
gaccttatca ggaaagacct tatcaggaaa gaccttatca ggaaagacct tatcaggaaa 194040
gaccttatca ggaaagacct tatcaggaaa gaccttatca ggaaagatac caagaaagac 194100
cttatgaaag accttatcag gaaagatacc aagaaagacc ttatgaaaga catcaggaaa 194160
gaccttatca ggaaagatac caagaaagac cttatcagga aagaccttat gaaagatacc 194220
aagaaagacc ttatcaggaa agaccttatc aggaaagacc ttatcaggaa agataccaag 194280
aaagatacca agaaagaccc agacccaaga cagtacacaa caccgtggac atcataatac 194340
ccgaggaact tattttccca agacaaccag agaccagtgt tcctgttaat gacaatgaat 194400
ttgaagaaat agacctgaac cctacacctg atgaaattat tttaaatccg agagatttac 194460
cttcgatgac tcatggtcgg gaaccggtgt atttacctga acaaaccaca tacactgaca 194520
cggtcatgac cgcattaaaa aaattaacaa aatcagaatt gatcaggaca atttcagaaa 194580
ctgtcctaca tagataattc atgaaccaat ctagaccaat cgcttttaca ccaatgtaac 194640
gaatcaaaca taccagaatt gccagttttg ttaaaagcat ctaatccaca tgttattaat 194700
tcatccgatc tttcgtctat gatgtaatta caaaattgta atgctgcctc gtcgtaccct 194760
gctccttttt ttattttcca ggctcctcct acacctcgtc tgatactctc tggtaaatta 194820
cttttaccta atctgacagg tatgtaataa gatcctccgt caaaacattg ccagtttttt 194880
atttcacctc tggtagaaaa aaccacattt gaatttttat ttttctccaa ctcttccatc 194940
tgtattatgt tcgaagtcca attacccatg ttatttctta tgtcgttata tcgttttaca 195000
gtttcaaata tatctacgtt ataaacttga aatgccatga ccgcaagact cagacatatt 195060
aaaaataccc aagaccaagt aaatccgacc caattcttta tcaccgaaat aaacggaata 195120
tcagacaaaa aaacagtctg attcggtcct ttcatttaaa tcacaaaaaa tctttatata 195180
agattttaat attttcatcg ttgtcaatga gacattgttt gatactggaa agtttcagat 195240
aatacataat aataccggtc caccataatt ccacatcatt tcttatgtag tcaccgtttt 195300
ctgtttccac tccaaaataa tacaatggga cgtctatgtt gaaaattctc agtgcaatat 195360
aattccatcc gaccattttg atattaagat gtttttcaga aattgtgtcg gaaaacggaa 195420

-continued atggatctcc gaattttaaa aatgccatga acatatttcc ttcgtatttt agaggggacg 195480
tgtcacatac tatttctctg tctatgattt ttttcttacc gttatgactc atgatgtaaa 195540
cctgtttttc tgtgaatcca tgatccatga ctatcctacc attatatgat aacgcatatt 195600
caatgtttga cttgatgtat tcatactctt tgactatgac atccgaatta agagagaact 195660
cgtgaccatc gtacttgtca aactgatatg attctggtgt gacttctatg tttacttgtt 195720
ctgttgtagg aatgtttctg atcatgtaat tgtcattaat gtttatgatt tctgatgttt 195780
ctttttctct gatgatatta gacgcgtaat ctttataaat gtttgttccg actactgtta 195840
ccacaccaat cacaacgtcc tcctttagta ttttaaacag agattgtaac tccggagtaa 195900
gatgataata ataaaattca aagattgttt caatcattgg tctgtctacc ttgtcaatga 195960
atttgatttt tagtagaaat tcaaagatga tgtccaggca agtattttta aaaagtcttt 196020
ccgtgagact ctggtccgta cctgctttca cgtattctac caattggttt ctgtttgtaa 196080
tgacagacat aaattcatct agattcattg tcccaatgat acccaatgca atcagtacgg 196140
aaatgttggt tgtttttgct ttgtaaaaca actcatcaga ttttgtttcg aacaagttag 196200
cggcaagtct gacaaaaaac aatccttttt gaatctcatt tttatacctt gcctgatact 196260
caattttatg tttgtcaatt tcaatcatct gatccaggac cattttataa atattaccgt 196320
tgtaattcca tcgttttgtt ttgaatatat tatcaaacga catgatgtag tcacttaata 196380
ctctttgacc tttcacgaac tgtgagtaag gctcatttga gaaaatgttg gtgaacacag 196440
ggatcactat ttttccgttg atttttttaa tttcactgaa ttgctcgttg aacatctgga 196500
ggaactctcc acatatgtta cacactgtca tctgatctat ggtatgaata tatttttcag 196560
aaaatttttg aaggttgtcg aactgatccg gagacggttt caagatttct ttcaggagtg 196620
aagtatgttc acacggcatc tgtttcaggg tccgggactg tttccaaatt tttggaaaat 196680
ctatttccac agtaggtgtt ttttctcggt acgtaatttt actgactcct gataatcttg 196740
tctggacatc tttggcaagg aagaatacat aaaagtcatt aaggtgtttt atcatgaacg 196800
caagagacac atacttggta atataagtcg cgtcaaatgt ggaaattaat gcttttgtca 196860
atacatcaaa cgtactgtcg tccaatgcaa atgttgttct gatagggacc acatgacctt 196920
catgacgtag ttccatattt ttacatgcca cgttgtcgtc tatcctgaac ataataagtt 196980
catttgtttt tggattgatg ttgaattcta ccacatgggg gaatttaggt tttgatctgg 197040
tgacgttgac tccgatgttt ctggacccga atttgaactc gataaagttt ttattaaaac 197100
tgtactttgg ataatttact atgagatgag acaagagggt ttcaaaatta ataggtacgg 197160
aaatgatctt ggaagttaat tttccactta atgaactact catttttcca ctgtctggtt 197220
tatgattttt taaaatatga acagtggaat tatgttccat ggaccatatt tgttttggtc 197280
ttgtgataat ttctagacta ttccagaccc aattaaaaaa tggtttcact aaattatttt 197340
cgctatgata caaatcatag ctgagactga tgaccacgtc cttttcaaat atctgacctt 197400
tgttcacaaa cacctctttt agttcagaat cagatgtctc tggattttga tatatggtag 197460
tgaataacaa tctaatgtct gccatgtcca tgtcttgtac tccatataaa ttgttggtaa 197520
ataacacttt ttcttgttca aggaaatcat cgaaattagg taactccagt gatttatgaa 197580
aaaagtttct aatttttttta attattacgt cgatgatatc atccatgatt taaatatgaa 197640
aaagaaccta gtaagtgaaa aaatagaaat tttatatata agtaataaaa cttacttaaa 197700
aactgttaaa tataaaagta aaaatgtctt cttctatcac aactgttttg accgacgagg 197760
aggatattat tctcgctaat aattcttcca acgaggagag tggttctgac actgttaatc 197820
ccacgttcac ctctagtatt tccactctgg ttaataaaaa tgtcaaagtg gtagatcaac 197880
caatggagaa aaaggggga agacgagtga aggtagttgc caagggacaa acatcagatg 197940
aatcatctga caacgaggta gttgttgttc ctaaaaaaac caagaagcct tccaagtcta 198000
ccaagctaat tcccaagtct gagagtgaca ccgatgaaga tttcctcaag acactttcaa 198060
ccaaatcaga cagttctctg agtatgaata atccacttta tgctttggca acacaagatc 198120
ttgggatcgg tgtaatttat gacaagatct gttctcataa tcaaaagatg attcagatca 198180
agaatcttat caaggaaagt tctgcaaagt ttccaactta tgtaaagatg ttcaagtttg 198240
ctgatctcag tgatccatcc aacatagacg tggtcaaaaa gtactgcaac gctctggaaa 198300
aaactgccaa ggcactcaga acatgttgtg gtatcgtaga gaagaaaaca gtaaaaacaa 198360
aaaagccacg agtaaagagt gaggcctttt ctattgacaa ttaaatgtca acatctaata 198420
tttttataaa attaaaaagg atttttgtag acgattctgg taaaatcata gacgaaagtg 198480
atgacttgta taagattttg gaaaatgtaa acattccggg gcatttaaaa aatgttaaat 198540
ttaaattaca atctttttct gaccatgaat ccggtcttat ttttacaggg gaggactcaa 198600
aaggaagagt tcaatattat tacgggaaag atcatgtggc tgccagaaat gaatctagat 198660
tagacctggt cattaacgtt cataagaaca tacacaagat tgaaaatttc ataaaagaac 198720
ataataaaat taccaatcct gtcaccaaag aatatctttt cagtgtcatg ttacaactgg 198780
aaacatcttt gttcatacga ttaggaaaag agaaatatct gaaagccaac ggaaccatag 198840
gattgaacac actgaaacct gaacatgtca tgtcagacca agataacgtg attttaaaat 198900
ttcaaggaaa gaccggggtc atccaagaat ttaatttatc caagaagtcg ttacttggta 198960
aacatgttca gaggttggca aatcttaaaa atgaattttt gttcagtgac acaaataata 199020
acaaattgag tgaaagttac atatacactc agatgaacat gtttgacgta aaaataaaag 199080
atctccgtac gtacggggtc aataagattt ttcttagaga gtgggacaag ttgttgtcag 199140
agaccgatga aattaaaaaa ccaaaaaaaa tgctgaaaca ctgtattgaa atcactgcca 199200
agataatagg tcatgaagcc aacacatgta aatcaaatta tctcataaaa gaaatactgg 199260
aacttgtaga tgataaatgg ttctgtgaca gtacaaaaac acatgacgtg acaggtgtca 199320
tcaaacgatt aatagtgaag tgagttataa taagcaggga catctttttt tgctgctttc 199380
agtgcgttga caatagattc gtactgggtc gaataataat taatcagatt ttggtatttt 199440
gattggagca ttttaatttc agaatctaat tgatcagaat ctatttttga cattataata 199500
gattcttgta aatctttgac gttggtcgtg gtatttttaa tagtggaaaa cacaggattc 199560
gtgtatttta atatactgtt tacaaatttt tgagttttca cttttgaaat ttcttgaaat 199620
ttttttaatc ctatattaat attatcaccg gatttgtatt gagaacctaa ataaatagct 199680
gatataaaaa gaactaataa tataaaaatg aacatttatt aagagtaaaa aaactcaaaa 199740
actaccatga ataataccgg atcggaaatt gttgccgaat atggaaaaat gtatgaaaaa 199800
attagagagt ccaatatgga tttagaaatt acagaattgg aatttacaca gtttgatcct 199860
tccttattgt ccctttcaaa aatgttctcc aatcctaata taaaacccct tactgattct 199920
tatttggaat atatattgaa taaaacttca gatgaaggta acaacattaa aattagaatc 199980
agaatagatt ttgccgtggt aggaggactt gaacttaata acaaacaatt gttggattat 200040
gtagaacatg gatgttggga atcaaaagag accaaggaca tttggttgag tcccgacgag 200100
ttcggtagaa tcacttcagc aacagagaaa caaggtactt atattaataa agtcattcaa 200160
tcaggaaaaa tcaacatgat ttttgtaaat agagccagag ttaaattttc agactttgta 200220
gttgatttta aattaaaaag aaaattaggt aattgtaggc aaggtaatat ttcaaatctg 200280
tataaaagtg tcaacaatgc catgtatcct ccgaatcctt ctcttgaaat tgaacatacc 200340
gggcaattca aaaagccttg gaaagatgtc aaattggaat tcacaaaggt cataagttgg 200400
ataatcggtc acccgataga agagatcttg actaccacga ctccattatt taaaattatt 200460
ccgacaagtg tgatcactcc tgcttatctg atgaattcga tagatccgac ccaacataaa 200520
ttgactccta aaattaacgg ggtcggggtc atgttcaaga ttgataaaaa acatgttctg 200580
gtccagcaaa tgttaggacc aaaggtaata tctatatgga gatacaaaca tcttcttact 200640
gtgacagaag atatttatgg gtctggtgaa tttatttttg attcggatca ttccaaatgt 200700
atttatcctt acatgatctt aggacatgac gtgtccactt acaaatggga agtacaagat 200760
tgtgccaact taccatatga tcatgttctc ataaaatcaa aacaatggac cggtccattc 200820
aatgacatca cagacatgtt gacggctatt tatgaaatga cagtgtcaaa acattcttat 200880
gaaacagacg gtcttatctt gtcatcttcg taccgtcatg gaaagtgtga ttataaaatc 200940
aaggcgacct ctgacattga catcgtagga aaggttagat tcacttacgc aggaaagtca 201000
gatcctagac agatggccac tgacggaatg attcttactg ttgattacat gagtaaaaac 201060
gccactaatg aattggtcaa gatcaacgac aacagaataa aattgtctcc ggaattcgat 201120
tacttgaatg acattttctg tgtgaagacc acacgggtcg atccacaatt ggtcaagtta 201180
tctcatgcag tggtacctat tggattcatt tgtgaatacg atgtcaggac caaagaaatc 201240
atgatacggt tgacaaaatc atccactcat ctatggacaa aatatctggg taataactgg 201300
accactattc agaccatcca acattcggtt cctatcctgg ccgatcttaa attacttagt 201360
aaatggatca agtctccaga agccagagac cacactgttc ttcaagatgt taaaattaac 201420
ggaacaaagt ccatgaacga aatggacgac ggacttgatc ctgatcgact gaatccaaaa 201480
accacatatt tcaaagaaaa cagaatcagg agtcccctgg gatacataag taattttgta 201540
aaatcattac tgatcagttt gtacgcttct aaaatgtttt acagtaattc caagaaggcc 201600
agggtatgtt ccatagattt tggaaatggt gccgacctca caaaatattt ttacgcagga 201660
atacaagaac tgatagcaac tgatcccgac agtgcagcaa ttgacacggc acatgaccga 201720
tacatgaaac ttaacaaaaa cgaaaaaagt aattattaca gatttaatta tttaaaaact 201780
tcgatcagga acgagaactt tgtttctgtc atacggacgg tcactgatca attaaacttt 201840
gatgtcatag actggcaatt tgccgctcac ttcagttgga atcataaaca tattcaaaac 201900
atcatgcact cactttgtga aataacaaaa ccaggtggta gggtcttgat aactaccatg 201960
aacgggaaag gattagaaag tattcttgac aaggatgatt cggtcacttt taaaattcat 202020
cctattgagc cgaccgggta caccacaatc acaaaaacta gtccgacaac attttcggtc 202080
ctgaccccac tcactaccac tacagcaatg accgaataca tcatagaccc cgaccagatg 202140
atcaagacat tttatgatta cggattcgtg ttactcgacc aagggagatt cgacgaggta 202200
ttcaatatca acgttccgtt tttcaaggcc gggtcattac tggaaacacg tccgtccact 202260
gccagtttct ttgctcaaca gagaggtgtg gtccatgaca ttaaaaatac acaattggat 202320
caattactaa agtattatat ttacatggta tttcaacgcg ggacttgagc aggaccgacc 202380
attaataatc ttccgaacta ttatccagga tgtcactgaa ccacgatctc ccgttacatt 202440
ttccaaatcc aatttttgtg atgtctatca attttttata ttccatgatc tttatatcag 202500

-continued agtccatgta tatctcactt cctagatggt tagttttcac atggtcgtcg atcactccat 202560
aacataaata ttccgagtta ctcacccatg aagaaacctt gtatttttct acgttggggt 202620
tgtcattgac atgatgccat ttgtttctca cgttcttgat gtaccgtccg tgtcttccat 202680
gtgggacact gactgaaaaa tgttgtccgt cgaccatgtt atcgtacgaa ggggcgaatg 202740
tgaaaaattc tacaggtacg tcatgatcga atctaatgta tatgacatag aaattagcat 202800
gggtctgact tccgaaagtg acaacagcgt tgtctgttat cacacaaatc tttgcgttca 202860
tcaacccact catgatatcg aacgttttcc aattccaaca accgtcccaa tcggccacgt 202920
ttagtaagtt actttccagg ttgaaatgat gtaaaacatt caaaagtgac cattcgtaca 202980
ctgccttttt aaccatggaa acttcaccga atcctctgag gaaaggacca tttttcttga 203040
agaaagaaat aggatgtccg ttactaccag aagtgtatct tttcatggta tgttccagca 203100
ccagatcttt acatgtccca agaccaggag gaggaaattc tgaagacatg tcatgtcctt 203160
gatccacgaa acccaattca agaaatggca tgttcattct gttgacaaga atagcccact 203220
gatcaccata atgtctacgt agttcatata acttgttatc atatgattct gcgtgaacgt 203280
ctgtttttga ataagccagg aacgcacacg ggtaacaaat tagtttttttc atactgaaag 203340
cctccagtgt tttttcatac tctttggtat gctcatctgt ccacacataa gccagtcgac 203400
gcctgataag atgttgataa atacaggcgt aagtgtaatt catttttttca cgttgatgat 203460
gatgagactc tggaaattct gataaaacag agaaacatac tttgttgacg tcgtacttgt 203520
tcttctcgat cattacgtaa tcatatcctg acatgctatt agaatcagaa agagttgatt 203580
tattatgtag ttcgatgaaa acattactca ttatgtcttt gtatgaaaac tcaggctcgg 203640
cgtctgttgt tttgttggtc acgaacgtgt tgtcagagat cgtgatcaga tctgacctgt 203700
tatggatgat gtctcggaca caccattttg tatgaaacgg aatttcggac atctgataaa 203760
taccgtcatc gacatgatcc acactttcac tcttgtcatt gtaagaaaaa tatctacatc 203820
tgtctaaata actttttcta aaagataaaa ctgtcggttt tccaccgatg ttcctcagtt 203880
tgaaaaagcc gtcctttccg ttgtacaaag ccattttatg gagtacccca ctcatgtcaa 203940
gttctggcca gaaccatgaa aattcttctg gatctaattc tctggtgtca ttatttctgt 204000
aataatattc taatggatca gggcatgatt ttctattgat gaccggatac aaatcaggaa 204060
tgaccgcatg agtaaatggt ctttccacgt ctgctgcata atctatttgc atcaatctca 204120
tgagtcccaa catgtgaaca agagtgtctt ggtcatgaac agaattaacc aagtcatgtt 204180
tacaaaacca ggtgatgaca cctggtttat acttgggata aatttcctcg tacgcatggt 204240
ccatacaatt aagaagtgta ggaacggtca gaacaaattt attaccgtca ggatctatcc 204300
aatatgtttt cttaagaggt acagcattcc agatacatgc ttgttctgcc cagttgataa 204360
gggtgtttat gtaaatataa ctccataact tcattatgga gtctcggacc acagggagta 204420
aattataatt ttttgttttc cagacagtcc atgcttccat tataaatgtg ttttctgcta 204480
tcctcatctg agtgaaataa tgtctgtgta atcttgatac gttcaacgac ttgcgagtcg 204540
ccggatactt gtactcgaac ttgatctttt ctggtacgtc aactaacgga agactattta 204600
tcaaatccac tgatttcttg ataatctgta ggatcttcgg acactgttgt ttttgttcga 204660
cacaactttt ataaagttct ctgtaccaca ttttgcacaa gttcatgagc tccatactgt 204720
tttgtgcacg gtcagaaaaa aaatacaaca gactgacaag gtgttggcgt ttccaagatt 204780
tatcatcttt gatgatattg gctattctac aaattttttt atatttggcg tttgtgtcag 204840
tgtagtaatt atcatacaca catataaatt tatctgtccc aggtagtaaa atttttattc 204900
cagaataaaa tttattattg tgtatgaaat ttatattttg catttaaaaa aactaaaaaa 204960
tagaattgtt aaattttacc aacgaacaat gaaaatcata ttcatgtgaa gacgaatcaa 205020
aatagtcttc aggaatatat gctttattga ctatttgatt attgcctgaa taatcaacta 205080
gttttctacc accactagga tcaatcacca ggtcagtacc tgttaatagc tttcccacta 205140
ttttagcaag tttgagttgt ttttccgaag gattttttct aagtacctcg ttcaaaagga 205200
aagttgaaaa atcgacgttt gagtgtttat ggtccattta atgtataaaa tgtgattgta 205260
aaatgtaaga atcttcacaa tcgttttcgt aatcagagtc gtgatccgat tccatccaca 205320
tatcatcatg caatccaact gaattaacag tattttcata atcatattct ccggtttcgt 205380
actgaactga atcagagtcg taatccaatt catcggattc tatttcttct gatatgaaat 205440
cattatattg tctggaaaaa acagtttcca gtggaataaa tttcacactt tcttctatgg 205500
gcattatatc aggaataaaa tttatatcag gaagcacgat ttgtttgttg gaatatgcct 205560
ctttatcaaa agtcactatg tttacatcca caagaggatt agtattatca tccactaatg 205620
tgtaatcagg aaacaaatat aaatgatttg acatttaaat gagtaaaaaa tctcagccta 205680
aaacaaaagt aatatttatt tttagaaatg atttacgatg gaccaataat ccaactctta 205740
gttttttaga agagctggtt cctaacatgg aattgatacc tcttatgtgt atggcatcgg 205800
aagattttat tccgtctccg tctagaattt taaaaacaaa acttaaactt gattgggctt 205860
ttcagaacaa agtacatgtc gtgtcagaaa tagaaagtct tctgataaaa ttaaaacctg 205920
atctgatagg ttttaacaga tttcctgatc ctggcgattc gtacgataat aaattattga 205980
ttgatttttg taactctcaa aaaatatctt gggtaagttt tcaaacagga tccatttggg 206040
attcaccggc aaatgacaac gtttacattg acaatataac aggaacgtac agggtgtaca 206100
ccggaccaaa aacatttcca acagataatt tatacaaaag tatcaactat ttcgtggaat 206160
atttaaaaga aaaagaaccc gacataaaca tgtacacaag attcaaatct cctaggaaat 206220
acatcaaaga actagacata ggtaatgata tttataattt actcaaaaaa caactgttcg 206280
aactaccaaa ttatactaaa aaaatattgg ggacagtagg cttggacaag ttaacgttga 206340
aacaactacc ttataccaac tcgttcatgt acacaaatca acatgaccct cggaacacag 206400
gaatgtgtga aagttataaa acgatattta atcccgaaac cattcatgac caatacgaca 206460
ccagtgtcat atataaatct attttggatt ttgtaagtga tcccgggatg gaaacagatg 206520
tgtttacgtt caacgtcaca ttaaaaccta atccaggaat agttcaaatc aacctttggt 206580
tatctcttgg atttatcagt catggtgaat tatacaaagc aattctttta caaaaaaatc 206640
ttgacaaaaa gagtctgatg ttgagttggt tgttcacccg agaatacgtt tatcataaaa 206700
attcattgag tgacatcact gattgtaaaa taagtttgtt cacgtacaag cctcgtgttg 206760
atccagataa catgttgatc atgaccagac caagaattaa gagggacagt ccaggtggta 206820
tgaaaatatg taaatcggat ctgtctcaat tacaagaaag tataattgcc aagaaagaag 206880
aacttgaaaa atgtatgatg atatacgatt ctgtcgacac cacagaaaca gggacagtgt 206940
catataaact ccctacagac ataaaccact tgtctcagaa aatcgcatat ttgaaaactc 207000
attctgtggt caacattaat aagataatta atcacaacag aatcatctgt cagaaaagat 207060
tggaaaattt aaaaaaagac gctgatcatg tcaggaacgt aaaagtacaa ttgaaagcct 207120
tgaaattatc agagtctggt atgtctgtcc aaactaataa aatacaagaa aatacatcgg 207180
tggtgttcgg tgtgcacacc actaattttc ctgtcccgtg ggaacatgaa gatgttttga 207240

-continued aaaagttact ttttaaagac agtaggtacg acacaatata tcatcaatgt atcgggatcg 207300
tgaacatttc tgacatggaa aattggtgga gacacaacat atgtgaaatt aatcaaacag 207360
gagtcggaca accgcgtaaa tgtaatcaat attttaagga actaagacat gctttactta 207420
attgtctgat tcaaacagga agtcttaaca gagatggttt gatactgttc gggtcaacat 207480
ggaaccatct taagttttat gcggaattta caaaacttct ggaaacattc atgttggatt 207540
atgacttttt aacatgtaag tacatttatg aaaattcaat cataagtctt cctagtctta 207600
atttgatagg taatgaaatg ggagatttta ttgaaaagtg gttatgaaga taaaaacgta 207660
aaacatagta attaaaaaat aatgtgacaa tgttacatga aggtattcag tccaaactag 207720
ggagagggga accgttcaat attctattac catgggaaca aatacttacg aatcatatgg 207780
attttatgga ggccgcaaag aaatttcctt cagagtacaa acatgtccgg aacatcgtgg 207840
agttggaaga gttattggag aaagataatt cagcagaaag tcatcggaca aacgtgttcc 207900
gtatcaggcc tcttgaaaat atattctatc agacagcgta ctctaacata gattcgtcaa 207960
atgacgtcat ttacgaagaa gaagtatctg tcggaaaaca gccgttcaca caatcattta 208020
attattcagt ggacatggct tcgaggtata ataaaacaat ggaaattaac aagcacatta 208080
acatagaaga aatgttttat gacgaatgga cgattgaaaa atgcatggaa aaatcagacc 208140
tgtctttgtt ttttactcag gtcatacatc aatataataa tcctcaagat tttattttta 208200
ataaaataag aagattgaca aacagtgaat tcatttccat cctgagttgg ttagggaaat 208260
ataatacatt ggccgaggga ttacgagttt taggagatgg tataaaaacc attttttttt 208320
ccatggtaga acctctttgt ctacagacca atgtggtttt cgttcttgtg aaaaaattca 208380
taaaagagac aaacctacta tgttcgttct tctcatgctt cttcgtagac gtttatttcg 208440
tacatttgta cagatacgtt ctaggaggat acgtcagtcc tccgatgttg aagatggtca 208500
aaaaacaaaa atatgatcgg agacatctga tcaagatcgg tgtccaatat ctgaccacca 208560
aagacattaa taatttaatg caaaacataa tcatggttct ccggaacgat tacgacataa 208620
gcacggttcc gatcccggcc ctgattccaa ttctggtaca ttacggagac atcgaacact 208680
ggaaaaaatt attagaatcg gacattgctg attctataag acaacatctt acgaccaatt 208740
gtaatatata tccacatgac gttcaattac ttattattga aaaatttgga ttgacatcgg 208800
agccgaccgt acccgacaat tctgacatag aaaaatatga agaattggat caataccttc 208860
atcatgatgt cattgtcaaa catatagtat ctgatttcgt gaccacagat aaaaaaataa 208920
acatggccat ttttgacaca agtatacaaa cagacgtcct ctgggggttg agtaaattaa 208980
taagaaataa acaacttact tgttgggact ggagtcgctt atccacgacg taacttttca 209040
atgtttttct gatgatattt aagcttggac aatcttatca aattttttat tgttaaaaaa 209100
actggaccta tcaaagccag cacagtagtc acaataataa aaatagtagt taccacaacc 209160
atttatttct tatataaatg aaaacaattc taggaaccga taagatcgca gatcttatat 209220
ttttctttca gaccaatagt gatcaacatg aagcggtcag tatttttgtc agaatcaatg 209280
aaaccagtga ttccgaatgt gctattgtaa tccctcttcc tggagaactg aataatttca 209340
gtagtatcga caccagtgag ggaatcagca aaatgaagga attttacaac aatactaaaa 209400
cattgagaag attcacggga cgtacgacac cgtttgtgtt taccgatgac atgtatcaca 209460
cgttccccat gaagtcagaa ttcagaatgt caaacggtaa cgggatcggt aagtttgatg 209520
ccaaaacatt caatgttcaa cagtgggccg gaagtgtttg tggagacaac gcatggagaa 209580
attctcaatt tctcaacatt tatttcccta aggtagagag gggatttac ggattcaagt 209640

-continued acgtggccaa ggattccatc ggaacccatg agattttcca agcagtggct tctaccacca 209700
caaacacgta tgtcatgacc tatgattatt ctacgtacac acaattgtac tctattctac 209760
cgactcttaa ccagaagggt tttgtccttg ataaggcaac atattcacca gacatgacag 209820
aaacatcagt gtacacactg aagaaggata attgtaatgt gatgtcaatg aacgtggtct 209880
ggcctgtttc tatttacaac atgttggtat tttttggtag tatagacgaa actatttcat 209940
tgcctattta acttttttta aattttcaaa aacataaaaa ataataaata aattacaagt 210000
ccgtaacctg tacaatttaa ctgaagatgt ctgattggtt tgagcaagtt gagaaagact 210060
ctattgataa aatggagaaa ggtttatccg acgaagttga tcggaacttg ttcacttcgg 210120
aaaaggtaac catcggagaa aaggcccagg agctagctaa tagtttggta catggacatc 210180
atgacgacgt caagtggcaa aacattttcg ttcatgattt tttcgcaatg acaaagacag 210240
cgacccagag aacgttttc atggacactt tcacagaaca cctggacaaa ttggcagaag 210300
agcgtggacc cactgtaaag accgtcacca tcaaaaacac aaaatggctg aggaatttca 210360
cgaaggttcc ggaacatcac acgagcatgg atgatgtcat gtacgacatc agaaattctg 210420
tgattttcat cgctcactgt cctgacagaa aaccgttcac agacaagaca gcgaaagatc 210480
tcacaggaga tccattcagc aacagaatag gaagactgag ttcatgtctc tttgagcgat 210540
tcatcgagca gaacatttat actttccaga aggaaagtat gatgaccctg aagtttccta 210600
tcttcaccat tgtgtacaat ttcctgacat atgagattct tgaatacatc gacagggacg 210660
aggactctgt ttgtcttggt atgattgcaa tgtttccacc ccctctcctc gacactatcg 210720
caaagaacaa aacacgattc agtgggaggt tcaccacaca ctgcttcatc atgttcccaa 210780
aaatgttctc cagattgtgt gcaggaattc caagatacga cttctactca agatcggacg 210840
gaccagagcc aaagaggatt gatctgtctg atgtggtctg tctccccgat gaaaaaaaca 210900
agttcatcat ggcactgaca cttggagtct tggagtttat cagattgatc agacattaca 210960
ccctgagtag ttatatcgag agagtcgctg atgtggtcaa cacgtacata ttgccatttg 211020
tcaaacccga acatggctgg aaactcacac cagagatgaa ggacatgatc tacggaaaac 211080
tgttcgagtg ctacccaagg ggggtcgcag agaacgtaga cagagggaca cggaagcagg 211140
aaattcttct caggacactg ttcaattcga gcacaaaggt gcttgagcaa atggaagatc 211200
ctgatttgat agacgcgttc ggacaataca ttgacgacat cagaaaacaa atcaagaagg 211260
ttgacgccga ttacttttag aatgatattg ttgtactcgt tgatttctta gtttactgtt 211320
ttattttttt taatctgttt gaaaatagag aataatatgt ttctgctttc atggttggat 211380
caggagatat aataaatgta tggaccaccc caaatatcaa taaaaatatg aaaaaaaatt 211440
ctacccagaa cgtccccaaa aatttcaata acatttatac acaataagaa tttaaatatg 211500
agttgtgtaa atgctaaaat agtaaagata aatggccatg tataatcatt tgaaaaaaaa 211560
gttagatttg acatttgatc aatgtagtgt acaagacata gaaaaatcta ttcatggtaa 211620
actttttttt taccacgtga ccggagggtc gcaaaatgtg aaaaatctaa aggaatgtat 211680
aaataattta gccataaaca cagccgagtt gtctagcaat ttttggccga acgagttttt 211740
tacaaacaat aaaaaacttc ttcagacccg tgtacctttt tcttgtgtga tatgttatcc 211800
tgacctggtc gatgatcaga ccataataaa tctagaggag attctgactt acctagggtc 211860
taatgataac tttgatacat gcgttattta tcaaggactg tctgacgtga aaacaatgaa 211920
atacgtgaag aggtgtcggg gtatttattt cataacagac aagccttcaa acttcacaac 211980

-continued ttcaaataag cgaatcaatt ataatgtttg tgcaagttac agaaattcaa taagacgatc 212040
ttcttctgtt atggacctca aggatttctc aaagaaagag atacctatca tggattatct 212100
atggaaaaaa acactgtccg aagaatatga agatgatctc acaaaagaca tagctgccac 212160
gttgaaggac attgaaatca aatctacaca gttggaacaa gaggaaaaga gtattaattt 212220
acatcctgtg gtcaagcaca caattccgat aagacacgaa tctgtcataa ttcaagatct 212280
tgaagttcct aaacccatta gacaaaaggt ggcaagtaat tggtttgaaa ccatgacagg 212340
ttttggtaaa ccgaaaaata cagtttgtac gaaaattcac aaatttgatt ctgatctgat 212400
atcgttcacg ttagacaaaa ataaaagtat cagtctgatg aatctgacac cgtattacaa 212460
caacacatta ttcgatcagg aaataaccga agttataaat gtacctattg tccctgtcat 212520
gaagccttcc ccagtaaagg ccactcaggt gaagccttcc ccggtaaagg ccactcaggt 212580
aaaggtcact cctgaaaaac ctgctgtcaa cttcatatca tttctaagtg atctgaagaa 212640
caaagtgacc aaaaaaaata ataagccaaa tccgatcgcc cgtggtaaga agatgaacag 212700
gtctattacc agatcaaaaa aaaacaagag agtaaaggaa gtccctccgc ctcctaagga 212760
agtccctccg cctcctaaaa aattatccaa tgatgaaatt gatgagctga taaagatcac 212820
gtatacggat cagacacatg atctagaaaa atttaccaat agtgaaatac tgctcatgat 212880
cgaagaccgt gatacttctg aaaataaaaa agacggacct gacctggaca atctaaatta 212940
tgtacagaaa gtggaaacca tggatttgga aaaatcagac tgttcagaac tggaattaat 213000
gaattttacc accggagaca actcggctga aaatgctgaa ttagaataca acgagtacgt 213060
ggcaagtgtc atagataaaa ataataaatt aaaaaagaaa aattcttcaa accataattt 213120
taaaaacgca atgaaaaaac ttcgggaaaa tgtcaagctc acgtttgatg attataacaa 213180
tgattacgat taaaaaaatt acagagttaa atggcagatt tgaaaattac agatcgactt 213240
attctatggg tgaacagata ctcaaaatca cttatgattc tttgtcagga catagatact 213300
gaaatttctt tcagtgatta tttggtctgg gtatggagta gtgtctgtca gataaatacc 213360
atattgaccc aggaaaacat tcatagtaca ataacaccag atgtaaacaa tgaatcaata 213420
ggcatgtcag attatcaatt ggtcaatcta ttgttgtatt gtatcatcca gacacaaaaa 213480
tgtatttgta aaaaatataa aaattattgc tgtgtcaatt ggattttaaa caacaaaagt 213540
gtaaagtttc cgaatgtatg ttggaataca aaaaagtacc tggataaaaa ttggacattt 213600
gacagacttt gtttgtctcc tactgtatta aatcattgtc ccaaatcagt ggcacaaaag 213660
gccataaagt cttgtaccat gacgtataat atttttaata taatgatcaa gcaacatcgt 213720
gatgtcctga cagtgtcaaa taaactatat caaatgatgg ttccgtcaat gtccataatg 213780
attccagacc cttattcacc tgtgaatgat aatgtcactg ccatgtctac cacgtgtgat 213840
ctggacatca ttttccaaag tttaaaaact gataaaacaa tcattgaaca aaacaataca 213900
aaagagatca gatcagcatt taatcttata tactctgtcg gtgaggatgc ctaacaagct 213960
catcttgaat attaatactc ttggaatcac gtacctgact ctatcacaaa aacacaatag 214020
acttgctcat gagttggatc tggacccact tgagaatgtc acaccattaa caaaaaacat 214080
ggagcatctg gaaaaaaaat tgatcgcgac caaggagaca ttggtctgtc ttttggaaaa 214140
atgggaaagc tcttcagagg aggacattac accaaactgg aaccttattc cgaatttttg 214200
gaaacagttg aaatgtgatg aatacattaa atcaaatgaa agtccagaca atcaatagat 214260
tcataggtgg taaaaaaacc ataacgtatc atgagttact tacttttta tttcctgatt 214320
ttaacatacc atatttaaca aaagtaatta atttttattc tgaaaaagga atagttgcgt 214380
cttctaatta tccagttgat tactctgcgt gtgatatcat aaaagatagt aaattgtttg 214440
atcaatgtaa atatttaatg tattccaatt ataacgtatt cagtggaggg ctggtttttt 214500
ccacggtcac gaatttgata cgtgaattac ttttttttact ggctgtcaaa ataaaaaacg 214560
aacatggttt tgaaaaatgg tttttacaca ggtcaaataa tttactgttc acaaaacatt 214620
attacataga attagaatta cgtgtacgtg tacctatact tcctatgatc gtcgtgataa 214680
atgcaacact aaaaaatgtc ccgatcaccc ctccaccttta caaaattaat tctgaagcag 214740
caattgatga catgaccacc atagacatat taaattgtct tgaatattac tctgaattgt 214800
tttttatatt ttctctgata aagcaagttc attggcttaa aaaataatat ttaataatca 214860
tatccactat ctgatccgga taatggatca ttcatgaaac cgtcgtcgac atcagaatta 214920
tccagtctgt acaaatcatc gtctgagtga gacatcatcc catcgtaaca catgtgtgtt 214980
cgatgtgaat atctgtcatc ggtcattcct ccaattatta tcagaagttt aaaaatgcta 215040
aagtgctcga actttatctc cggtaagtta tgataggtcc gttgtgcgtt tgtcaaccac 215100
gtacgtattt gtacacggtc caccacgtag atacctatca tgatcacata ggccaagact 215160
tccatgaact tgttatgtat acatgtgtgg tctttgtaca actctgcttc tgtataccat 215220
ttattcttgt caatgtctga caagtcagtg acacaaatac acttgtcagg aacacacgca 215280
catccgaatg atgaattcat gatcgaagat attttaaaat taaacttttt tttcacaaat 215340
tgaaaaaaaa tgtttagttt aacatagtac aggaatctct cgatcaccac acgaaatgga 215400
agcagacctt ctggtaaaga cagaccttct tggatacctc agatcaaaaa ccagaaatga 215460
cattcttctt cttacaaaag aagaaactgt cgtggtctgt tctagtcatg acaaggggga 215520
tattgtaaat gcactcatgg atctgaaact aggactgcct ttgaaaataa acgaacctga 215580
cgtggactcg gaaaagcata ggctctggac taacatagtg gaatacagcc atggactgaa 215640
cacggtattc tgtaaagaag atttagatgt tctgtcatta tcaaaggtca tcaactggtt 215700
cttgttcaag ggtaaaaagt caccggtgct caacatcaag aaaagcgaat ggaactccat 215760
ggacttgttg agtagttact ggtccgagga agcacggtca cacgggcgga atattttcat 215820
gagtcacagc atggccgacc tatggaagga agagctgagg tacctctacg aggtagttct 215880
taaacgtgat gacgtggtct tgtcctcgga acattttaaa aacatcatgt ggtacatcgg 215940
atacgaggtc tccacgttca aaccaacaaa cgcaaagttc atctttgagt tctttcaatc 216000
aaagagggtt ttggatccat acggtggttg gggtgataga atgataggag cagcagcagc 216060
atgtgaggca ggaaaactaa attctacccc agcagtccaa gagtacacat gttgttctcc 216120
caatacactg atgaaggtcc cgttccagaa acttaccgag ttcttgtctg aacgttcaga 216180
cattaaacta gagcacatga taattccatt cagatacgcc aaggtcaaga agaactatta 216240
tgacatggtg ttcttcgaac caccaagaat tgaccgagaa cattttccga cagacattga 216300
acagaccatt ggtccaaacg aaacacaggc ggtgtggttt gcagactttg tgattcctac 216360
ggtggagaaa ctatgggatt gtttggaact gaacggatac ttggtcttca taagcagaag 216420
tggtaagaac gatcctcatg cagaaccatt gactatgtac atagcaggat ggttaggtga 216480
gttcatgggg atgatttaca tgaaccagga agaatcaaag accaggaaga acaaaattca 216540
ctacccgttc cattgcttcc agaagaagaa gaactacagc tgggaagccg gcacaaaata 216600
cagactggca ttcaattatc actacaaggc cattgcacac gaaatccgga aacacactcc 216660
ctaagaaagt accagagtaa atttttatga aaactgaaaa acaattttta aaaagtaatg 216720
tattgacata gcgattgctt tcttctccaa agtacaatcc ttaaaaaagc aatcatgcat 216780
atcacgtatc tttgcgaaaa catcttcaat cttgacaaac aaaagtatgt ccttgctcac 216840
tgtgttgcga ctgatcttgg aatgggagca ggaatagcta aaattttcag agaaaaatac 216900
ggaggggttg attatctgaa aagtcaacat ccgaaagtag gcggattgtg tcatcaggca 216960
gatgaatcct ctctccaact cctggtgtat ctcacaacaa aactcagaag tcgagacgtt 217020
cctacattgt ccaacatcag gtctagtctg gtacagttga aggatctgat ggtcgaacat 217080
aactacacag aactggccat tcctacgatc gcatgtgggc tggaccgaca gtcttgggtg 217140
aacattgaga aaatgcttcg tgatgtgttc aggagcacaa gtatcaatat cactgtctgt 217200
tacctccctg caggaaagga aatcctgaat gggttcgtat aattttttttg taaaaaaatg 217260 attttttatt aatataagga aaaataattg aacatgtctt caaacgtggt acagttattt 217320
tgggacgtct gtggagacgt cgatcagaca tgtgacattg ggaaattgtc tgaagttctg 217380
atatgtacgt tcaagttaca taattggtct cctgtacaaa agacattgta caatagaaat 217440
gcacatttat tgtacaatgg ccggtctgac gaaacaaagg cttacgccaa catggcatgg 217500
gataaacaaa acatcatggt aatttacgtg ttcgatccta tgttgttaga aaaagtaaac 217560
cagttaatga tgatcatcgg atcaaagttg aaagtcacca tgttgtacaa caacagaaat 217620
tatgacaaaa taccgattat gaaatacatt gatgatcatg tgatatatct ggattctgtg 217680
tcttctttga tagtgtttga tcctttaata aaagaaggat acgaccatgt attaaaggat 217740
cttgatagtt ggaaatttcc tgataatata aagaccttgg acatgttcat acatgaaatg 217800
aacatgttaa aaaaacgtct ggaagaaagt acggacggaa catcacaact tgtcggtgct 217860
attcaaacca ccaggaaaat aatggaaacc acaatactaa ataaatccgc cggtctcggt 217920
caaataaaaa catccccgtt cacaagccaa tttgacatgt cgtttatttt cagtccggtc 217980
gataaaaaag caaggtacaa tcccgattac gcgtatcaag aggatagaat aatttcagat 218040
tatcacataa ataaatttat tgataatctg aagaaatgtt tcggaggaga gatatcaaga 218100
gttctgaatt ccacggtgat atttttagat caggaaaatc tcacagcgaa taacattgtc 218160
ctcctgaaag aaaatttaat ttatgccttg tctgactggg ctgatcggtt gatgaacaca 218220
agaacagacg ttaaaatagt cacgtcagag gatcattgga aaaatttcaa aatccctgga 218280
tattaaaaaa tgaatattaa aaaatgaata ttaaaaaatg aatggtatct tacctccctc 218340
tactgacaca ggttaaaaaa tggaaactct tgattctttt ttaaattttt acatcacagg 218400
accacgggag aaatttaccg aaaatttcaa aaatgttcag acagtcatga taggaatgga 218460
caatgaatcc tcgatgactt ttctaaaagg cctctggaca cgacttcata aaaataaaaa 218520
atttcaacat gtcacaggaa atgtcccgac cacatttcca aacattggaa agaagaacaa 218580
agaacttctc ctgatccagg ttccacatgg atatcctcat cataacaaaa tcattttgtt 218640
catggatcat tcactcagta agttggaaac aacattgttt gttcatgaca ccatagattg 218700
gagaacagta ccaaaccata ataacgttgt ggtctctgtc aagtctttgg cagatgccaa 218760
tcttgatcat gacagtgagt ttcacgacca tgtcactgac atgatcagaa acataaacga 218820
ttggaaatta gagaatagaa aagagtacaa taaatattat ggatgtgtac tggaaggagg 218880
accgagaccc gagataaaaa cagaacatga tcttcgagag ttcagcaagg attacaaccc 218940
gtttgaatac cttcagaact ttcaggaaaa gttcagagat ttcagagagg gtaaaaattg 219000
tacacaaatc tgtgctacac tgtacaccct ggcaagtgcc ttgaacgtgt tgtacgtaga 219060
aaaaaaacct ctgacccagg acaacataat gaagtctgcg tatcatgaaa gagtcgtgtt 219120
tggaacgtac aaacctttcc ttgattttgt gaaccaaact ctggagcgag actttttga 219180
gttcatgcct tctggatacg cgtccgagtc cgagttcatg atcatgatca acaacctggt 219240
gacaggtctg ttacatgcag cagaccgttt catgaccaaa ttaattcagg aaaaatttga 219300
tcatgtgttt gtcacaagtg acatggataa ctggaagagt atggtcatcg acggaactcc 219360
tctgatgtca ccacctcatt ctgtgatact tcgacagtct cacagatcca agttgtacga 219420
catagtcgaa gcaggactac ccaggacata cccactgccg tatgaagaga gtctacgaag 219480
agaccgggaa ttatatggtt gtatggaaga ctgaacaaat accggattta attttttat 219540
cataaaaaaa tgaattatca tttataccag tatgataaaa aaagtcacca tgtcgtacaa 219600
gaaaataaaa aagacaaaaa aaattatgac agaattctgt cataaaattc atgctctgaa 219660
tctggagtct ccgggcatac caaaagaagt gatcaagatc ttgataaaaa acatgaacct 219720
ctgttttgat gacatcgacc ggatagagat catgataaat aactctccgg attctgatca 219780
cgtgtcaata gttaattaca tgaacatagt acataagaaa agtcttccga tgatttcaaa 219840
aatttatgat ctgatcatgg aatatgaatt atttttattc ttgaaaaata attcaagaaa 219900
gtatattacc atgggagatt cggaaacaga atattctact gcctcggtaa gatcgagtct 219960
tggttgtccg tctccgacat atcaatataa tgtgacatcg tatgctccgt ggaccgattc 220020
tgataatgat tcagaccaag acaacaaaag atcttggtct gaatcagagt attctgacgg 220080
tccgacacat aacacaatag ggacaatgac agaaccatgg tcggtacatg gtagttcaac 220140
tggttcttca acaactggtt cttcaacaac tggttcttca acaactggtt cttcaacaac 220200
tggttcttca acaactggtt cttcaacaac tggttcttca actggttctt caacaactgg 220260
ttcttcaaca actggttctt caactggttc ttcaacagac tgtttaggta gttcaatttc 220320
ttcgtcatca gacaccttga tagatgtcat gtcgtctggt ttttcttcac caggatctgt 220380
ctgtcctgga tcggatgagg gattaacatt taaaaatgaa aaccagatac ccgagtattt 220440
gataactgaa tcagattacg agatacctat gaagagggca aggtcagatt aattttttt 220500
taaaacatgt tcatggtatt tttttaaaac ataaaaaata catcaaaaaa tatcaagttt 220560
cattatctta aaataatgga aaccatatcc ggatatgtca aatctgactt ggaatacgaa 220620
catgaatctg cttacttgtt gaacggaatg tatacgtaca acggtgaaac tcatcatata 220680
aaaatataca aaagtgaagc cggtaacgaa ctgatcctgg tcacgttaac cggtacgttt 220740
cagatacttg tgaatcaaga cttcacaatt tcactgaata tattttgcac agaaaaaaaa 220800
cagacccgtg aattagaaag aatcagattt gatttgatag atcggaacta ttttatcttt 220860
tacacgtcaa taggaacatt tggatttgaa tattcaaata atcacagtga agaaacgatc 220920
atgattttcg gagaaccaaa cgacaattac atatctaaac gattagtata caattcgtac 220980
aacatcaaat ttaaattatc tttacttgac acggtgtcat ctaatcaata taatatcatg 221040
gatagatcag gtcaggaatt tacaaacgat ggaacagtgg tcgaccactg tcttgacagt 221100
gatcttgaca gtgatcttga cagtgatctt gacagtgacc aggaaagtga tcaagacagt 221160
gaccttgaca gtgaccagga aagtttttta ccaccgtacg tacaaagtca ggaaacctta 221220
ctgaaaaaac tagccgaagt acaagaagaa catgacaacg agacaagtac gttcactcca 221280
gaagaattac tactccgaac ccagggtaag atgaaaaagt taattcataa ccatgtcatg 221340
tacaacatca aaaacatcac agagtacgac tcaaaatatg acactcttgt gttcactgaa 221400
tcgttacatg gtcaactatt ttacaagaca ttcagggtgg ctccttccat ttaccaagaa 221460

-continued

```
aaagaccatc cttctttcgg tacgttgata accaagtttt ctcagggtat caaactcaca 221520
cgaatcaatg tatgaaaatt gctttttat atacacatta tcatattaat cattaaaaat 221580
ggctgctgta caagcatgtt tgaacatttg tggcaatctg aaaaagaaca ctgactttag 221640
tacggtttca accgtgatat tttacaccga acatacctgg gccctggcat ttgtaaatac 221700
cttgagcaag gtaaaaaata aaggttataa acccatcaat tccatgtcta aagggtctag 221760
tcgtgtaata aaaggaatcg gaaaggatga caaagatgtc cttttgataa aatcagttga 221820
cacgattgat tttgattcat ttaatttatt cattgatacc ctttctggtc tacgacaaat 221880
catcatcatg attcattaca ccaaagaaaa tactcttaat attaaatatc cagacatcac 221940
agaaatcatc atccacagaa acacattgaa tgaattcagt acgttgatgc ctggtgaagt 222000
aaaagacact tcagatactt attttcaaaa taaaaatgag tggaatttat tggaacattt 222060
ttcagacaag ccgcaaactt tcatagaaaa cataacggct aatttagcaa agacatgcgt 222120
ggataaatca gatctctgga aagcatgtat gctttacaca ctttccaccg gacttgatct 222180
gatttataac aatgccctga tagaacatga cgcaatacaa ttgggaaatc atacaaagtg 222240
gggaggtttt ttacctaaaa tagaaacaag accacgtaaa gaacccaatt tcacaagtgt 222300
tgtcctggca tcgtgtatag aaatgatcaa caccgtgtat gattccgacc tgacatttga 222360
taatgtattc agttttgatt atcccgtgat cgatgaccgg acaaaaacac tgtctgacaa 222420
aatggttcgt cacatggtga cattgttgat agtggcaatg cgtgacgtaa gtgacaaaat 222480
ggtgacattg ttcttcaaca acaacaccat gttaaatatt aaaatgataa gttcacctga 222540
tcactggaag atactgaaga accttgataa ttatgtttag tcttctgtcc actcgtgatt 222600
gcacggtact tttttattga aaaaaaagat ttaattttac attgtttaac aggtctgatc 222660
cataccacag ctatcatggc aacgttcaaa accaggaggt gtaacatgga ctcgttcagg 222720
aacggagttt ctgataatcc taaaataatg gtggtcacca cagagtatgg tcgagcaata 222780
aaaacatgtg cggtcccacc cccagatgct ttccataata gaatcaccgg tgattctatc 222840
ataacaggaa aactacacag gcttgacatc gatgataaaa catccagaac cctaagagtg 222900
accatcgacg aaccgacgac cttgatgtgt ttcatttgct cagaaactga cacggtacca 222960
ttttcaaaaa cacacaaatg gacagaacaa accgagttcg tttttgaact gacaaaccag 223020
cagacctact ggacattgtt cattgtgaaa agtggaaaga cagacaagcc tcttttgttg 223080
tctgtgttgg aaaaaaacat tccttggaaa acagagtcat gggacatctc tgtgatcgtc 223140
aacgaaaaag aaacactccc ggtgtttcac actacaagga acaaggtcaa agtgatccag 223200
tggcagaatt cattcacagg agaaccgctt atctggatga catcatgcgt ggtcaatgac 223260
gtcccctgta gttctgacaa gttcaggacg ttctcgttgg tgaacgaaac aggaactgac 223320
acacagtgga agtcatttgc cgtgagattc atggatccag aagatcaact tcatatgtac 223380
gtcacaggcg tgtctcctac tccgtggaat cccatggaaa aaaagctagt gaacgttcaa 223440
ctcatgatca aaaaaaatca tctgaagaac aagtgtgatc attgtgagaa gatcggattc 223500
accatccccc agacatgtag cagagacgga aaagaaactc gcgtttgtaa aaagtgcgtt 223560
cacaaaatgg gcaagacatg taagttttgt cagaaggaag tcatggatga tctccctacg 223620
aacaagaaag tcaaattcac aattgacgtg acaaccgacg agtttgatta ttttctgatc 223680
ggctttgtct gtgcctgtgt ccctgtgtat aattaatggg acttgttttt atgtccatac 223740
tatatatata tatttcaaaa gttaaaaata atatcataat ataacccccct gtactaaaca 223800
atctcataat acctgaaaaa tggcctctgt taatggtgat gctgacattg actactccgg 223860
```

actcccacgg tgtagttaca aagaaaggat gtatactgtc acgtcattta aatctttcaa 223920
gggaaaagtc agacgtttct tcggaagatt aagattacct accattaaca tgcacccgat 223980
tgatagagtg atggctgcca taggtaatgt ggacttgtga atttcccccc tggacttttc 224040
ccctggactt ttcccctgga cttttcccct ggacttttcc cctggacttt tcccctggac 224100
ttttcccctg gacttttccc ctggactttt cccctggact tttcccctgg acttttcccc 224160
tggacttttc ccctggactt ttcccctgga cttttcccct ggacttttcc cctggacttt 224220
tcccctggac ttttcccctg gacttttccc ctggactctg acttctgaac tttttttttc 224280
ttacatctga ttcctgtctg gattcttccc ccggatcaca ataaattttt ttagaaaaaa 224340
aaggatttaa taacggcgct ctttatgatc aacgtacact tggaaaataa tggacatccc 224400
aacaattctg agagaagatc cttatgtcac ggggacccgt gacatacctg acgtaaaacc 224460
tgatcaggtc agaccgtatc actgtcaagg tacaactcct ccgggatcta atctgaaaga 224520
atctgaattc gttcagactc ccaaagaaag gtggacagca ggtgaaaact ccatgaccct 224580
gcagcatcct tcggagcagg agtttttggt aattgcctac aaccagcaaa ggatctctag 224640
ttgtcacggg acacgcttac aagataacat tttcaggacc gtgattgaag taggaggaca 224700
tgttagtttt cacacttgtc tggtgaccag acacgacccg gtcatgacca tgataaattg 224760
ccggaatgaa actgtcttgt gtgtgcattt aacaggatgt gaaatgcaaa aattccccgac 224820 gacctgtggt gacatgtatt atcatcacga gcacgttccg tcacagagag agtatgacaa 224880
cgacaatgac atgaaggaag ttgtcctgag gcatgttagg tacgaacaag aaaaacaaga 224940
atggatcaag agtatgacag gatattccga ccttcatgac atcatgttgt acacagaacg 225000
agagccggta catgatcggg ataatacaaa gtgggtcata catgcttcag aaagagaacg 225060
gaagaagatt gtccgaaaca gtctacggac cgcacagaca cgacgtcatt tcgaggacgc 225120
catgttttca cctgatctcg actctgttgt tttcaattgc caaaacacgg cgtacaagag 225180
atgctggaaa ccagagccgt tcatcgaagg aacagtgcat accgacaacg tggttcttcg 225240
atggtctgat ctgtgtgaac caatcacgtg gcatctgaac tcttcctctg gaccatccga 225300
acacctggta catcaattga aagcctcata tgaaatgatg aagaattcaa ttgtcggggt 225360
gttggatgat cttgattttc tgacagtgtt cgaacaccag acatcttttc ttcaaacggt 225420
aaattcaggt gggtttcaaa agaacggagt ggatgacctg agtcagatta aaaatctgcg 225480
aataagttct gtcaggaaaa atcgaccatt tcaaaaacca gaccagacat ggacagaacc 225540
ttggagagaa tcctggagag atcagaagag ggaaccttgg agagatcagc agagagatca 225600
taagagggaa ccttggagaa atcagcagtg gagaaatcag cagagagagc caaggagaaa 225660
tcagcagtgg agagatcaga agagggaacc ttggagagat actaaagcac gagtgtaatt 225720
ttagtctgtt aattttagtc tgttaatttt agtctgttaa ttttagtctg ttaattttag 225780
tctgttaatt ttagtctgtt aattttagtc tgttaatttt agtctgttaa ttttagtctg 225840
tntaatttta gtctgttaat tttagtctgt taattttagt ctgttaattt tagtctgtta 225900
attttagtct gttaatttta gtctgttaat tttagtctgt taattttagt ctgttaattt 225960
tagtctgtta attttagtct gttaatttta gtctgttaat atatttttgt taaaaaaataa 226020 tctataattt ggtatgtcat ggataatcta taatttggat atggtacaac taatcacaca 226080
cgtaagaaat gaaagataag aaataaaagt caataattaa aaagaatgga gtctcatctt 226140
actcttcata atttagtgga tatcataaac ggatctgacc atctagatgt tttacgagtg 226200

-continued accagaactg acgtgaacac aatagtagaa tattcgttac atgattatga ctggcttctc 226260
aggacccaga ttaccttgtt cgaagacatc catgaaaatc ttttcgtcgt gtcaaagaat 226320
ggtactaaca ttccggtgga catggtcgta ctccgtccga cgaatattat tttgataacc 226380
acaaaacagc atcacagatg tgttttgtat tttgacctgt acgaaggtgt catgaaattt 226440
tgtaactgta tcagttctga cccacatgtg tcattacata tgtctggact tcctatgaaa 226500
cacgcacgtt tattttattc atgtgtcagg aatgacctgt gaaaaactgg aaaaacataa 226560
aaaacaccat aagagggaaa ttgcagcacg aagacatggg catgtacata gattccatgt 226620
tcgaaggaaa ggaattcaac caagggactt tcataaattg tacattgatc aaatgtaaat 226680
tgtcaaatgc tcatattgaa aaaagtaagg taaaaagatg tagattgacc aattgtgtta 226740
ttgtaaaaag tgccatcatc aactttaaag ttgatgacag tgagtacgtt tctctgaccg 226800
ataataacgt gattaataaa tctagtatag agacatgtaa tgtgacgttc actgtgttca 226860
aacattgtat gatacataca ggctccagat tactttcgtg tcatatgtac gcctgtgaca 226920
caagtgattc aacaatggtg aattcttact tttcggacaa gacattgatc aatgattgta 226980
aaataaataa cggacatctg acacgttgtg atctcaaaca tgtcatgtcg gataattgca 227040
aatattattc gtgtgtgatc gacgacagtt ttttaaataa atcgtcgatg aacaaatgtg 227100
aattgaccag gacttacctt aataaaagtt catgacaatg ctttttttat ttaaatgaaa 227160
tattaattac atacaattat tcacaacata tcgtttggga aatggacccc cttaaatcac 227220
tcagtaaaac aacgtccaaa tggaatgtac cgtatgacag tcataccagt gacgtagaag 227280
atctttatca agaacatgac actgatcaag agagtgactg ggatccagaa agtgaatgga 227340
acgatgaaaa aagtgacaca gacacagaca cagacacaga cacagaaaaa aatattcttc 227400
cagatgatcc cgaaataaat tgtccgatac tctcagaata cacgttcaca gaatcacgta 227460
taatatctaa tgttcaatta aacttccgta atctgacagg tctcagtata aatcactgtg 227520
aaatcttgaa ctgtgaaata aataattgtg tcataaccaa ttgtaacatg actcaaagtg 227580
tgttaattaa cacacaaagt attaattcag tcgccacgaa gtgctcagga gacaataaca 227640
ctttcaacag atgtatttta caagggtgta catggacaga cgctatttta tactcgaaca 227700
aaatcaacac ctgtaaaata gaaaatagta ccagtagaaa aaacaaatac agacactctc 227760
ttttgaaatc cacacagctc cacaacgact acataaatct gtctgatttt aaaaattgta 227820
tgttggagtt gtgtgtggtc acagacaaaa aaattgccaa acgagtgaaa aatcacatgg 227880
taagtattcc agacgaacct gttgtcccca cttacactta cgtatcagaa gatcaagagg 227940
aatctaaaga atctgacgag tccggggaat ctgaggaatc tgaagaatca gatcaagaaa 228000
catcagaccg tacagaaaaa agtttcttca ttcattgtgt ttttgaccgt tgtacaatta 228060
aaaacagtgt gttaaaaaca tgtacaaaaa gaagttgcac gtcaataaaa tcgtccagtg 228120
aaaagtgcac aattacaaat tgtaatgagt ctgattctga caacatagga tgtacaggta 228180
aagaaaataa atacataaga tgttacatgt acaagagtga catcatcgat tccaagttgt 228240
atggatcaga attatcacag tgtgtcctga ccaattcaga atcatcacgg tcattattca 228300
ggactaccaa aatacaaggt tgtacgatga taaccacaaa acaacaatca tgtgactgtg 228360
atggttctgt ggtcatgtac tgttggatcg acaccagtga ttacataaag tccgacctga 228420
aagaatgtaa gatcagtgat tcgaccatca tgaaatcatt gatgaaaaat tgtgcggtca 228480
caaacacaga gttgacagag aattccgtgt ttctgggaat ctttaaaaaa tgcaacgtgg 228540
tccgttgcaa cgtcacacag gtcaagatac atcggtctgt catagattct actatcatgg 228600
acagagtcac tctgagagac tgtatgtacg taaaagaatt cggttatcag acaacagaaa 228660
aagactgtga taaacaaaaa aaacattcga tcaaattcaa agtccatgat ctgaacaatc 228720
tggagttgac cagaaaaaat cttctactac cagaaaggtc tttgatcaaa tacatgaatt 228780
ctacaaaggt cggatcaaag tacacgacat gatatttttt ttaaaatgaa atttacagta 228840
cttaacgtaa taatttgtat ttttcacaat catggacatg gatatttcca caggcactta 228900
ttctgatctg gaagaagaca ccgtcagttt cactgacctg aacatttcac aattgacgta 228960
caaaatcatg aaaggagtca acactctttt ggtgacgact ccgacatgtg atcacaccat 229020
tgattttttta caaggagctt atcatcataa caaagtgaaa acgtacaaac atgtaattgt 229080
gaacgacaat tttcatatac acaataatat cggatcagga aatggtaatt tgttaatcat 229140
gtacgtcaac accctcacag aagaacatgt caaagacatc attgctttga tattgtatta 229200
cagcgacata ataaaatgta tatatttgat acctacagaa cataatcaac tagtatccat 229260
accaagacat ccagcaagat gtcaggttca tcagttcatc ccttccgaca cagaaccaat 229320
ttttggcagt gaacaagaca taataaataa ggcaatacaa gacacaaagg gcttgatacc 229380
attgatcgac caatgtatga tcacagagat attacaaaaa acagcatggt ttattttaca 229440
aaatatgttg atacacggta aggtttatgg gttggtattt tataaatcat tgtcaaacat 229500
aatattatca aaatacagat acagagagtg tcctacgacc gacgttagaa aaattaattt 229560
ttcaggagat tatctgtctg gtgaattatt tactaactct ccgaaagatc tgttctctac 229620
atgtatcatg gaattgaacg acctggccaa cagagttttt tcaaaatctt ccatgaaaaa 229680
acgaagtcac ctgatagaaa gaaaaaaaaa tcctgtcaag actgacatcc gacgtacaca 229740
cacacgtaca gaaaaagatc tgatggaaaa attaagtagt gtattatatc tggcatctgt 229800
attattagaa gacctggatg tcccgataca tttaaaaaat aaagacatct ggaaactacc 229860
taacgtgtat cgtagattaa aatacactga tccataactg aaataaaaat aaaatttaac 229920
gacttgaatc aatcactacc agattctacc atgtacatgt acacaaagta cggtccttat 229980
ttaaccagga ccagtatata cacagatcca gatggtatat acataacaga agaaaatact 230040
ggtagaatgt gggacatacg gggcagaaa ccaggtgagt atcaaccatg tactttaagc 230100
ttttctcacc tgggtccgtt caaagtagta cttgaaaaca tagaccttgg tataatagac 230160
gacgacgaaa aagtgttttt cgcaaatgat cagagtccgt tattggaagt aaacaaaaag 230220
acaggccata tcataatata tgaaatgtca atagccgtgg agaaatgaaa aaaaataaat 230280
atttcaataa tcatgtctga tgtcaaaagc agaattaaaa atttatttta ttatttcaga 230340
ttcttttata aacttcattc agtgtatgaa ttagacgagt acgaaataga cgaatggata 230400
aaagaaaaaa cgttagataa tcgcacccat ttgattgtgt ccggcatcaa accattttgt 230460
ttgtctgtca tcgcaaagtc ggacacggac ggtatcttct ttggagagta tgaaatatat 230520
ccaggagcat tcagagaata tcctatgacc acggaaacaa acacgtctac ttatatggaa 230580
ctgaacgtaa gaaatcaccc tacattacaa aaggtccgga atcatattct tcctgacgga 230640
tgtacatggg acgattgtta ccaagtcaaa caagacagag aggacaaaag tccacggaag 230700
ccatgtgtta acatgaaatt cataatgaga tggttatgtt acatggatca tgattcggtg 230760
tttcttaatc atcacatgat aaatgatgaa aactacatgt ttagttttcg ccttggtaac 230820
atcacgtata acatattggc cttacgttgt tacggacaac tacagatttc catgacagtc 230880
acattagaag ggcgcgataa tatccagatc aaaaaagtcg ttcctgatga tttatcaaaa 230940
tgcataacac ttaaaaacgg ggctgtcgta ggagtaaatc tctaattttt tatataattc 231000
cattgacatg tgtatgtttt ttatatattt gaaaaaatat ataaaaaaag tatctctcta 231060
cacaatttaa aaagtatctg tgacatactt caacaaaatg ctttccaaga tcagaaaatg 231120 gtttttttgct tgtgtcgagg cccacggact cggtgatcac gaaccgagtg acggggcaga 231180
ttattatggt acagtgtaca ctgtcaaacc ttttacagga attccaggta ctgatgataa 231240
gatcaatgat caagacaaaa gtgtaagtgt gaacactatc atgagaggat attccgatca 231300
agatgatgac tgtatttaca tacgtgaata caaggaggaa gatttcggag aactctaccg 231360
taagatacct ggatgttctc ctcctttgcc gtccattgac gaagcagacg agggaagatg 231420
tcagatcaca ggtggacgtg tcgtaccctt ttctgataac cctgatgtag aacatgagct 231480
aaatctggca gcgtttaatc accgcggatt caaatcaaga ttcactcagg gaaaaccact 231540
taaaagatct atttactcta agaataccac tgacgcctca acagagttcg ttgagattgt 231600
agacattccc gacatagaac ttcctgatca tattccacca ccaccaccca gtagtcctgt 231660
tcaaggtatc tcacgatcag aaagcaaatc tactgatcct ggaaaattcg gagggatcag 231720
ggtcatgttc atggcacctg gagattataa tcaaccttca tataagccca agagaccacc 231780
cagaatgcag gaaatcattt aatgtgtgag aatttatacc ggatcctttg gtcaggactc 231840
tttggtccga atttttatta atttttttat ttactgaaaa ataatcgtat gtattgagag 231900
cgtgatcaca cacactgaca attatattgt ttacttcttg aattgaattc tttactgaaa 231960
aaaaagaata caattgggac agttatcaac atagttgtta ttactcacaa acacttgcaa 232020
taaccaaagc agagaatttc attctacaat ggccggaaga cttaactaca aggacatgtg 232080
ctgtgccgga aacggttggt gcgagtgtca cgaggaaagt acagaacaga cagggagagg 232140
accttctacc aagattgact attccaacga accgcgtgaa cgtttctgga ctcgtacatc 232200
atggaacaat ggcatgccga cctgttttga ggagccggag gatgaggacc tttcacccga 232260
aagtattaag gaccgagtcc aggcttggaa gaaacaggat gagatcgatc acaccaatca 232320
gtctctgcca cttgcttctc cggaagaaat atggcagtgg actgaagatg ctgtcgacct 232380
cctcctggga caacgtccta tgtattctgt gaacagtgaa ccaggagagt gggaagagct 232440
gagcgaagac atcgataacg cagttcaaag caggaccggt gaagtcattg aacttgatgt 232500
agaccgcgag ttggaagaag tcatggggtc tgctggatac aaagcctgga tcaaggattg 232560
ttgtcagaga gcagaggagc cagaacaaga agaagacctg tacgaaaccg gagagagcaa 232620
tgaccaggga gcaggagttt ctcagagaat gttcccgttg acagatgctc agagggcctg 232680
gttcgagaat cggagggggc aatcccagac taggacagag tacgagtttc ctccacccac 232740
tgtgagacca cttaccactg aggaaaccga ctggcttgat caactgaggg atcagagaga 232800
tggcgagcga gtgaggattc ataatctgct ggagagagcg agtgaggacg acagaggaga 232860
gaccccagaa cttgttgaca gatccgagta cgtacttgcg aacgactggc ctatcgatga 232920
cacaatcgtg tcacctgatg acatcgggat catgttcgag agagaggtgt atgacaatga 232980
cctggtggat atcgacgtcg gactgggaca ggctgattca gatgcaagat catctcgtac 233040
ctgggacaac tggttcactg ctctcagaaa tgagtacagg ccccatctgt tcagacaaaa 233100
tgaagacggt gattatgtct gttcaggtga gacctacact ccactgaatg atgaggagga 233160
tgatgatttc ggattcggat tcggcgttgt tccgtacgac atgaccggag attacgacat 233220
catggatgat cctaatcttc tggtcatgcc tgactacgac aacgacaccg acatcaacat 233280
ctaccaggtc gatgctgcta caggaggaga tttggacacc aacttcgggt ctgacaacgg 233340
ctctgacttt ggatccgaat ctgacgacga tccagagtat tactacgagg acggcaacac 233400
catggattac tacaggagga gtatgatcga gatcagacac agactggact atctggatct 233460
tgcagtgagg acacctgacc tgcctggcct tcagagacaa agtagttgtc ttgatcttgt 233520
gtactgggta tgaatgaagt atgaagtatg aagtatgaat gaagtatgaa gtatgaatga 233580
agtatgaagt atgaatgaag tatgaagtat gaatgaagta tgaatgaagt atgaatgaag 233640
tatgaatgaa gtatgaatga agtatgaatg aagtatgaat gtagtatgaa tgtagtatga 233700
atgtagtatg aatgtagtat gaagtatgaa gtatgaagta tgaagtatga atgtagtatg 233760
aatgaagtat gaatgtagta tgaatgtagt atgaagtatg aatgtagcat gtagtatgaa 233820
tgcttttata aaaaaacaaa aaacttcctt gttgtctttt ccctggtccc tggtcccttt 233880
caccaaaaac attttagtag tatgtgataa gatgctttta taaaaaaaca aaaaacttcc 233940
ttgttgtctt ttccctggtc cctggtccct ttcaccaaaa acattttagt agtatgaatg 234000
aagtatgaat gcttttataa aaaaacaaaa aacttccttg ttgtcttttc cctggtccct 234060
ggtccctttc accaaaaaca ttttagtagt atgtgataag atgcttttat aaaaaaacaa 234120
aaaacttcct tgttgtcttt tccctggtcc ctggtccctt tcaccaaaaa cattttagta 234180
gtatgtgata agatgctttt ataaaaaaac aaaaaacttc cttgttgtct tttccctggt 234240
ccctggtccc tttcaccaaa aacattttag tagtatgtga taagatgctt ttataaaaaa 234300
acaaaaaact tccttgttgt cttttccctg gtccctggtc cctttcacca aaaacatttt 234360
agtagtatgt agtatgtagt atgtaataag atgcttttat aaaaaacccc aaattaattt 234420
ttatcataat ataataatcc ccccccaaaa aaccccccatg tctctatttt tttaaaaaaa 234480
ttaaaaaaca atagttctga gtaatgtcat actcttggaa ttattatggg gaccacattg 234540
tatgacatag aaaactattt cccgtacgaa catgatgatt cagacactga ctattatgat 234600
tcagacatag acatagacat agactacgag aatattgtga accgtacccg agaaaggaca 234660
ggactactga gattcttcga cagagagtac ttgtcatttc ctgaagtgac cagtgtgata 234720
ttcacgtcga ccgacagaaa atgcacagat gccttgcttc tgaaattact ttattccaca 234780
gtgcacgaat caataaaatg tgatttctat ccgaactatt cttactccac aaaaattcca 234840
gaaatgtaca acaacatagg gaaaaatcta ggagtacttc ttgtagtgga agtcgactac 234900
ggtattgatt ggcaacatat caagacagta gtggatatat tacctaacgt ggaaaagatc 234960
actgccataa taaacgaatc cgaatactct tactccaaac tatgtccaga actcgtgaac 235020
atacctgatc ttaccattta cataagagta ggaaccttgg gtgatctgaa acatcctgac 235080
gtaatcgacg gaactgctag tctctggttt caagagtggg atctgtcaag gaacacaaca 235140
gtgaaaacca tactatccac attagagaca aaatgcgaag ggaaaagtcc ggaattcatc 235200
ttagggcttt ataatgcaat ggccacaaga cttaccaggt gtaagatcac attctctgac 235260
agattagacg ccggatttga ttatcaagga gggatattgc attttcaaaa cacatgtcct 235320
cataatacac ccacacttaa gagtccggac catatcatgg tagagctttt cggtgaattt 235380
aacataaaca acaccattca gaatgctcgc gatgtttata gattaggaac catgttgtca 235440
gtgttaggaa catacaaagc taaacaagca gacatgacaa gacccttttta catattcaca 235500
agtgattttc taaaaagtaa attatgtctt gacaccttta aatgacacca tagtacgtaa 235560
tagtgtaaat atatattttt tataaaatgt aaaaaaaata cattataatc aactactttt 235620
ttacacaaaa tgatgtcctc taatgtaccc gttaaagcat tcaagagatt aaacctagat 235680

-continued gacataagac gtgacgtctt ggatgccact gcaacaataa tatttacgtc gtataattta 235740
cgtaccagtg aaacagtaat tcattcattg atacacgctg acgtgattcc actgtatgtc 235800
aaatacaatg atcagaaaaa aagaattgac gccatggacc tggtaagtag gcgtatgtta 235860
aatgagataa tcataactcc atgtaaatta gaagtgtaca aatacacagg tatgacaaaa 235920
ggtaacatgt tggtcgtgac aatggaaggg gccgggatgt gggagcacac caaagatctt 235980
gtggatgaac tacctaatct gaagttgatt gccaggatgg tgtcattgcc agactgggtc 236040
aagatcaagg accgtgatca tcccaggccg gacctgacca ggacttatat aagtgtccag 236100
aatctaggtg acatgggttc tcaagatttt ttcattggta tgaccatggt acctcagatt 236160
gacaaagaag acacggtcct ggagatcttg gaaaagctaa ggaaagagtc cgaggggaaa 236220
ggaaaagaca tgatccttgg aatgtacaac ggagccgggg ctcaactagg aatcaagtca 236280
aaacttcttc cttacagttc tgtcgtggac ttttcatacg aacaaggaat ccttgggatg 236340
tcaaactatc aaaaatctcc agatttatac aacagagaca cagaagaaat taccgtgatg 236400
aaacaattca accataccac aggttgttgt ccaggaggac ctggttgtcc aggaggacct 236460
ctgggaggaa aaccctcctg gaagaaaatc atggaacctc aggtcatgtt agaaactgca 236520
gggatgttat cggtcatggg ttctatcagg acagaaagac caggggaacc tacttatgtg 236580
ctcactcctg attactggaa gataaaaaat accctgagag tgttcaaatg acccggagga 236640
atgacccgga ggaatgaccc ggaggaatga cctccaaagg aatatacttt ttttaaaaaa 236700
gaaaaatact tgttaattat taaggttttt accacttaca tacaagaccc gacaagatca 236760
ccactgacaa gacaagatgg ccactgacaa gaccacactg acaagaccac cactgagatc 236820
tcagtacact gtcggagagt tcaccaagaa gtttttccca gaaaatcacc aggaggatca 236880
tggaggtgac tctgggtcat atcttcggga tcttcttgat gatcctgtaa gtaacacaga 236940
gctcctggaa gtcaccacgg tcattttcac ttcggtctac ggttcttaca cgaattccct 237000
ggtcaagtcc atgggataca ccaagaaaac ggctacttct ctgctcaact ttgtgccgag 237060
gcctgtcggt gccagacaac atgacattta caaaggacta ggatacgacg ggaagtctct 237120
gatggtcgtc ggaatcgaca atcctgctaa ctggtacaga cttgacccgt tcattgactt 237180
cctgatcaat ttcaagcagg tcttttgtat gatctcgatg gaacactggg taacatgtgg 237240
ttctcaatgt ccagtttctg tccgaggtca cttcatgaag gtgtttgtgg atgttcacaa 237300
caaccaagag tgtaacaacc ctgactttgt cggaggactc agggactctg atacattctg 237360
ggataaaatc aacccagctg gtccagacgt ctcagcaatg attgacacga caatggagct 237420
cttgaaagat ctggaacatg gtattcagac agacacccag atccgtgatt ccttcgtacc 237480
gggtcaggtc aggagatctc ctgcttacgt gtcaggaatc tacaacggac tggcttcttg 237540
tttcatgaga gggtcgagtc tcagtcgttc ccagggagtg ttccccgatg acatgataca 237600
tccttcctgt agagacacca caggacctcg gtcgttcgga gaagattttg atgactatga 237660
tcatgatcac atgctcctgg attacaccca catgaccatg gaacgattcg gttcttttct 237720
tgggtcactg gattcttaca acaatctcaa agcaggcaaa aacccggtgt ttgtgttcgg 237780
gaccgacttc tggaaactga aatgtgtact gactgtcctg gaaagtcact gccctaccga 237840
cttcatgacc ggtcagtttg atgaggatgg catttatgaa cgggaccgag tgactccaga 237900
gtcagatttc atttgccagt gtcttgattg tatcgggtca gatgattacc aagagcatca 237960
ggataacaat accgaccacg aagatgattc ttcgtatgat tctgaagatt ccggaccttg 238020
tatggccagt cctgaaaact gtgtctgtgg aaaggcccgc caggagacag agaccgaaga 238080

-continued attcaaggac gcttctgatc aatggaccga ctcttctgtg tctgatcagg aaggagccag 238140
aggaagtcct ccttcaaaga agcccgctta cgacaccgca ggacttgaaa agacctggtt 238200
ctgatcatca tttgagaaac cattattctg ataatggaaa ttttattata tttttataaa 238260
agtcatacgt acatacataa ttgtgtcaag gttcttttta cagaaagtaa aaccagccag 238320
taaaaaccag aaagaaaatg ttgtgcaagt acagtaacat tcttgtcagg gacgagccta 238380
ttgacagtcg gccttttcca actgccactg agcacgatct gaccaggtac actgattacc 238440
ctggtctgtt caataacgag gtaaacacaa gagatctgga gagaacaagt actcttgtac 238500
tcagttccaa ataccatacg tacacaagag aatttatcat gtcaatgatt acttcttgtg 238560
tgacagagtc tgccacgtgt atcgtggaat acatcggagt tgatcccaag gaggccaagg 238620
tctacagacg actaggaaag ggaggtggta acatgctggt tgtcggtgtc gagaaggatg 238680
ctgactggac atcacctgct atcaatcggt ttgtcaatga acttccttct gtcaagcacg 238740
ttgtcatgat gatgtcttca gatcattaca agacagtggg tgttccggtc ctggaccgat 238800
cagacattgt tcaggtgtat gtctctgcca cttgtgtgat gcacggtcct gtaaataata 238860
aaagtttcgt cgagggaaca gaagcggcct ggcctattgc tttctcaagt ggcgattcag 238920
tagaccatgt ggtctcgacc acatttgaaa tgttgaatca aaagacccta ggacaagacc 238980
ctatgtttgc tctaggactt tacaacaacc aaggaggtaa tttcaagatg gaagcatacg 239040
atcgtgatca ggtcgggatc gataattact ctcacaacaa cggaatttat gccaataatt 239100
ttgttcagga cagtccattt gagcaaaata acttcttggt ttattacact gtcctgcaag 239160
agtggaaggg aggagtgttg cgtgacagta agatggactt ttgtgacatc ttcgggacaa 239220
tgttgtcgat cagagggtcg tatcttttca gggacggacc tacctgtttt atttttactc 239280
ctgattactg gaggaacagg ttgaccctgg aagagttttt ttaaaaaaga aaaaagatgt 239340
tttttgtaca tgttgaaaaa tgttggtaga acacgttgaa tttcctggtt tgatcaggag 239400
cggactcaac actaatgttt taaacaacac agagatagtg gttttcggac cggtcaaaaa 239460
catttttgtc caaggactga taaagtctgt tctgtatcgt gccaacaaac atgttcatac 239520
cttcatagaa acacacgggg aggtcaacta ttataaaaaa ataaaaatgt tggtcattga 239580
tgtcctgact cataaacagt ggatactgat aaattatctg ataccaaagt taccgaatat 239640
aaaattgatt ttgtcattga tcccgtctgt acaacatagg gggaacctca gtccaagata 239700
taacccggtc aaggtaagaa aagaactctc tagggtattc atcttacatg accggatcac 239760
agaattcaca gacttttctg attttcattt tgggatagtg gactcttgga tcatggacag 239820
acattgtacg gacacccctt gtatgcacag accttgtata catggtccga ccagggagcc 239880
agtaattttg tttgaccggg ccaagaacat tgtaagaacc ggccaaggga tgtacagact 239940
aggattgtac gtcggagtcg gagctcagtt taaactgttc cagaacaaac cagatgtccc 240000
tgttaaatta tcagatttta cttttggtcc cgggatattt cctgaaaaca attcggtcct 240060
ggacaagaac aagtctgttc ctgaggtcaa tgatttcata aaaatggttg acccgggaga 240120
tccagagttc ttggaaaaaa tgggttcttt attttcagtg gtcggatctt acttgtcgta 240180
cgaagataac atgaccgacc tgttcactcc ggatttttgg agatggaagt ttgtactgga 240240
ccgggtcatg acctctgaag tttttaatga aaaataactt tataattaat aattctgttt 240300
atccgaacaa taaaaaatgg acaatagaac ttcattcaga gtctggaccg agaaggtctt 240360
acgagatcgg gttgatgact tacgctcgac cagtacatta atctttacca gtaccaggaa 240420
cgtatggaca gaagacatgg taaataccat gatcacccag aaggtccaga gttccatgtt 240480
tgcatgtatc attcatccgg acatggtcgg ccaagacatg acaatcatga aacatcttgg 240540
agtagggaac ggagacctga caattgtagg aataaaatca tttgtcaatt gggtagaggt 240600
caatgcgttc accaatgcat tggcagagat atgtccggga cttaccaaga tcatttgtat 240660
ggtaagtgtt cttgactgga cccagtgtca caaacctctg atagaagaaa ggaaacacca 240720
gaccaaggtc tgggtcaaca tgcgtggacg taaacacgat gaccttctag gggaacagtt 240780
caacaaagga aagtatgaca cccagggtct ttactccagg atcaagacat ctcagtctgt 240840
cccggacatt attaaacatg tgatgtacac cttggtcagg ggtcatgata cttctgagga 240900
agatcataaa atgtactgcc tgggtgttta cacaggatta cttgatcaga tcaaacacag 240960
acataacgtt cgtacgtttg aagagagggc atgggaatac aaccaggaga acccgatggt 241020
cttgtacgaa aagaaaaaaa agaaccatga caaggcaatg aaaaatctca tcgagaccat 241080
gagagaacga ctccttgatg gtaagactca cacggtcaac aagtacactc acgagtactg 241140
tacacctgag atgttaggta ttgccctttc ggtcattggt tctctttcac tgactgactc 241200
ggtacacgga catgtatttt cttgtgatgt ctggaccgac aagacttaca tcaaagaatt 241260
catctgagag aacttgtcct ctggtccgat gttttttaac acaagatcat ggtcattgga 241320
aaaccaaaaa ccaaaacata ttttttttaac actgaaggtc atgatcattg aaaaaccaaa 241380
acatattttt agcaggggaa ggtcccgacc attgaaaaac taaaatatat atttttttaac 241440 actgaaggtc cgaccattga aaaactaaaa acatattttt taacaccggg aggtcccgac 241500
attgaaaaac taaaatatat atttttaaca ctgaaggtct gaccattgaa aaactaaaaa 241560
cata 241564

<210> SEQ ID NO 2
<211> LENGTH: 5679
<212> TYPE: DNA
<213> ORGANISM: Artificial
<220> FEATURE:
<223> OTHER INFORMATION: nucleotides 1-5679 or 235 885 to 241 564 of
SEQ ID NO 1

<400> SEQUENCE: 2
tatgttttta gtttttcaat ggtcagacct tcagtgttaa aaatatatat tttagttttt 60
caatgtcggg acctcccggt gttaaaaaat atgtttttag tttttcaatg gtcggacctt 120
cagtgttaaa aaatatatat tttagttttt caatggtcgg gaccttcccc tgctaaaaat 180
atgttttggt ttttcaatga tcatgacctt cagtgttaaa aaaatatgtt ttggtttttg 240
gttttccaat gaccatgatc ttgtgttaaa aaacatcgga ccagaggaca agttctctca 300
gatgaattct ttgatgtaag tcttgtcggt ccagacatca caagaaaata catgtccgtg 360
taccgagtca gtcagtgaaa gagaaccaat gaccgaaagg gcaataccta acatctcagg 420
tgtacagtac tcgtgagtgt acttgttgac cgtgtgagtc ttaccatcaa ggagtcgttc 480
tctcatggtc tcgatgagat ttttcattgc cttgtcatgg ttcttttttt tcttttcgta 540
caagaccatc gggttctcct ggttgtattc ccatgccctc tcttcaaacg tacgaacgtt 600
atgtctgtgt ttgatctgat caagtaatcc tgtgtaaaca cccaggcagt acattttatg 660
atcttcctca gaagtatcat gacccctgac caaggtgtac atcacatgtt taataatgtc 720
cgggacagac tgagatgtct tgatcctgga gtaaagaccc tgggtgtcat actttccttt 780
gttgaactgt tcccctagaa ggtcatcgtg tttacgtcca cgcatgttga cccagacctt 840

-continued

```
ggtctggtgt ttcctttctt ctatcagagg tttgtgacac tgggtccagt caagaacact    900

taccatacaa atgatcttgg taagtcccgg acatatctct gccaatgcat tggtgaacgc    960

attgacctct acccaattga caaatgattt tattcctaca attgtcaggt ctccgttccc   1020

tactccaaga tgtttcatga ttgtcatgtc ttggccgacc atgtccggat gaatgataca   1080

tgcaaacatg gaactctgga ccttctgggt gatcatggta tttaccatgt cttctgtcca   1140

tacgttcctg gtactggtaa agattaatgt actggtcgag cgtaagtcat caacccgatc   1200

tcgtaagacc ttctcggtcc agactctgaa tgaagttcta ttgtccattt tttattgttc   1260

ggataaacag aattattaat tataaagtta tttttcatta aaaacttcag aggtcatgac   1320

ccggtccagt acaaacttcc atctccaaaa atccggagtg aacaggtcgg tcatgttatc   1380

ttcgtacgac aagtaagatc cgaccactga aaataaagaa cccatttttt ccaagaactc   1440

tggatctccc gggtcaacca tttttatgaa atcattgacc tcaggaacag acttgttctt   1500

gtccaggacc gaattgtttt caggaaatat cccgggacca aaagtaaaat ctgataattt   1560

aacagggaca tctggtttgt tctggaacag tttaaactga gctccgactc cgacgtacaa   1620

tcctagtctg tacatccctt ggccggttct tacaatgttc ttggcccggt caaacaaaat   1680

tactggctcc ctggtcggac catgtataca aggtctgtgc atacaagggg tgtccgtaca   1740

atgtctgtcc atgatccaag agtccactat cccaaaatga aaatcagaaa agtctgtgaa   1800

ttctgtgatc cggtcatgta agatgaatac cctagagagt tcttttctta ccttgaccgg   1860

gttatatctt ggactgaggt tccccctatg ttgtacagac gggatcaatg acaaaatcaa   1920

ttttatattc ggtaactttg gtatcagata atttatcagt atccactgtt tatgagtcag   1980

gacatcaatg accaacattt ttattttttt ataatagttg acctccccgt gtgtttctat   2040

gaaggtatga acatgtttgt tggcacgata cagaacagac tttatcagtc cttggacaaa   2100

aatgtttttg accggtccga aaaccactat ctctgtgttg tttaaaacat tagtgttgag   2160

tccgctcctg atcaaaccag gaaattcaac gtgttctacc aacatttttc aacatgtaca   2220

aaaaacatct tttttctttt ttaaaaaaac tcttccaggg tcaacctgtt cctccagtaa   2280

tcaggagtaa aaataaaaca ggtaggtccg tccctgaaaa gatacgaccc tctgatcgac   2340

aacattgtcc cgaagatgtc acaaaagtcc atcttactgt cacgcaacac tcctcccttc   2400

cactcttgca ggacagtgta ataaaccaag aagttatttt gctcaaatgg actgtcctga   2460

acaaaattat tggcataaat tccgttgttg tgagagtaat tatcgatccc gacctgatca   2520

cgatcgtatg cttccatctt gaaattacct ccttggttgt tgtaaagtcc tagagcaaac   2580

atagggtctt gtcctagggt cttttgattc aacatttcaa atgtggtcga gaccacatgg   2640

tctactgaat cgccacttga gaaagcaata ggccaggccg cttctgttcc ctcgacgaaa   2700

cttttattat ttacaggacc gtgcatcaca caagtggcag agacatacac ctgaacaatg   2760

tctgatcggt ccaggaccgg aacacccact gtcttgtaat gatctgaaga catcatcatg   2820

acaacgtgct tgacagaagg aagttcattg acaaaccgat tgatagcagg tgatgtccag   2880

tcagcatcct tctcgacacc gacaaccagc atgttaccac ctccctttcc tagtcgtctg   2940

tagaccttgg cctccttggg atcaactccg atgtattcca cgatacacgt ggcagactct   3000

gtcacacaag aagtaatcat tgacatgata aattctcttg tgtacgtatg gtatttggaa   3060

ctgagtacaa gagtacttgt tctctccaga tctcttgtgt ttacctcgtt attgaacaga   3120

ccagggtaat cagtgtacct ggtcagatcg tgctcagtgg cagttggaaa aggccgactg   3180

tcaataggct cgtccctgac aagaatgtta ctgtacttgc acaacatttt ctttctggtt   3240
```

-continued

```
tttactggct ggttttactt tctgtaaaaa gaaccttgac acaattatgt atgtacgtat   3300
gacttttata aaaatataat aaaatttcca ttatcagaat aatggtttct caaatgatga   3360
tcagaaccag gtcttttcaa gtcctgcggt gtcgtaagcg ggcttctttg aaggaggact   3420
tcctctggct ccttcctgat cagacacaga agagtcggtc cattgatcag aagcgtcctt   3480
gaattcttcg gtctctgtct cctggcgggc ctttccacag acacagtttt caggactggc   3540
catacaaggt ccggaatctt cagaatcata cgaagaatca tcttcgtggt cggtattgtt   3600
atcctgatgc tcttggtaat catctgaccc gatacaatca agacactggc aaatgaaatc   3660
tgactctgga gtcactcggt cccgttcata aatgccatcc tcatcaaact gaccggtcat   3720
gaagtcggta gggcagtgac tttccaggac agtcagtaca catttcagtt tccagaagtc   3780
ggtcccgaac acaaacaccg ggtttttgcc tgctttgaga ttgttgtaag aatccagtga   3840
cccaagaaaa gaaccgaatc gttccatggt catgtgggtg taatccagga gcatgtgatc   3900
atgatcatag tcatcaaaat cttctccgaa cgaccgaggt cctgtggtgt ctctacagga   3960
aggatgtatc atgtcatcgg ggaacactcc ctgggaacga ctgagactcg accctctcat   4020
gaaacaagaa gccagtccgt tgtagattcc tgacacgtaa gcaggagatc tcctgacctg   4080
acccggtacg aaggaatcac ggatctgggt gtctgtctga ataccatgtt ccagatcttt   4140
caagagctcc attgtcgtgt caatcattgc tgagacgtct ggaccagctg ggttgatttt   4200
atcccagaat gtatcagagt ccctgagtcc tccgacaaag tcagggttgt tacactcttg   4260
gttgttgtga acatccacaa acaccttcat gaagtgacct cggacagaaa ctggacattg   4320
agaaccacat gttacccagt gttccatcga gatcatacaa aagacctgct tgaaattgat   4380
caggaagtca atgaacgggt caagtctgta ccagttagca ggattgtcga ttccgacgac   4440
catcagagac ttcccgtcgt atcctagtcc tttgtaaatg tcatgttgtc tggcaccgac   4500
aggcctcggc acaaagttga gcagagaagt agccgttttc ttggtgtatc ccatggactt   4560
gaccagggaa ttcgtgtaag aaccgtagac cgaagtgaaa atgaccgtgg tgacttccag   4620
gagctctgtg ttacttacag gatcatcaag aagatcccga agatatgacc cagagtcacc   4680
tccatgatcc tcctggtgat tttctgggaa aaacttcttg gtgaactctc cgacagtgta   4740
ctgagatctc agtggtggtc ttgtcagtgt ggtcttgtca gtggccatct tgtcttgtca   4800
gtggtgatct tgtcgggtct tgtatgtaag tggtaaaaac cttaataatt aacaagtatt   4860
tttctttttt aaaaaaagta tattcctttg gaggtcattc ctccgggtca ttcctccggg   4920
tcattcctcc gggtcatttg aacactctca gggtattttt tatcttccag taatcaggag   4980
tgagcacata agtaggttcc cctggtcttt ctgtcctgat agaacccatg accgataaca   5040
tccctgcagt ttctaacatg acctgaggtt ccatgatttt cttccaggag ggttttcctc   5100
ccagaggtcc tcctggacaa ccaggtcctc ctggacaaca acctgtggta tggttgaatt   5160
gtttcatcac ggtaatttct tctgtgtctc tgttgtataa atctggagat ttttgatagt   5220
ttgacatccc aaggattcct tgttcgtatg aaaagtccac gacagaactg taaggaagaa   5280
gttttgactt gattcctagt tgagccccgg ctccgttgta cattccaagg atcatgtctt   5340
ttcctttccc ctcggactct ttccttagct tttccaagat ctccaggacc gtgtcttctt   5400
tgtcaatctg aggtaccatg gtcataccaa tgaaaaaatc ttgagaaccc atgtcaccta   5460
gattctggac acttatataa gtcctggtca ggtccggcct gggatgatca cggtccttga   5520
tcttgaccca gtctggcaat gacaccatcc tggcaatcaa cttcagatta ggtagttcat   5580
```

-continued ccacaagatc tttggtgtgc tcccacatcc cggccccttc cattgtcacg accaacatgt 5640
taccttttgt catacctgtg tatttgtaca cttctaatt 5679

<210> SEQ ID NO 3
<211> LENGTH: 101
<212> TYPE: DNA
<213> ORGANISM: Artificial
<220> FEATURE:
<223> OTHER INFORMATION: nucleotides 99 129 to 99 230 of SEQ ID NO 1

<400> SEQUENCE: 3
atccaaaata cggaacataa gcaataggat gattactatg caactcagaa acttcaaagg 60
acagaataaa tttattgaaa gcgttgatct ccttgtcgtt g 101

<210> SEQ ID NO 4
<211> LENGTH: 18
<212> TYPE: DNA
<213> ORGANISM: Artificial
<220> FEATURE:
<223> OTHER INFORMATION: fragment of SEQ ID NO 1

<400> SEQUENCE: 4
ctcagaaact tcaaagga 18

<210> SEQ ID NO 5
<211> LENGTH: 22
<212> TYPE: DNA
<213> ORGANISM: Artificial
<220> FEATURE:
<223> OTHER INFORMATION: fragment of SEQ ID NO 1

<400> SEQUENCE: 5
agtgatcttc ttgtcgtaca ta 22

<210> SEQ ID NO 6
<211> LENGTH: 22
<212> TYPE: DNA
<213> ORGANISM: Artificial
<220> FEATURE:
<223> OTHER INFORMATION: fragment of SEQ ID NO 1

<400> SEQUENCE: 6
tacgcgaatg aaccaggcat ct 22

<210> SEQ ID NO 7
<211> LENGTH: 22
<212> TYPE: DNA
<213> ORGANISM: Artificial
<220> FEATURE:
<223> OTHER INFORMATION: fragment of SEQ ID NO 1

<400> SEQUENCE: 7
tgatacttga tcttccgtta ct 22

<210> SEQ ID NO 8
<211> LENGTH: 25
<212> TYPE: DNA
<213> ORGANISM: Artificial
<220> FEATURE:
<223> OTHER INFORMATION: Fragment of SEQ ID NO 1: forward primer

<400> SEQUENCE: 8
atccaaaata cggaacataa gcaat 25

<210> SEQ ID NO 9
<211> LENGTH: 21
<212> TYPE: DNA
<213> ORGANISM: Artificial
<220> FEATURE:
<223> OTHER INFORMATION: Fragment of SEQ ID NO 1: reverse primer

<400> SEQUENCE: 9
caacgacaag gagatcaacg c 21

<210> SEQ ID NO 10
<211> LENGTH: 16
<212> TYPE: PRT
<213> ORGANISM: Artificial
<220> FEATURE:
<223> OTHER INFORMATION: polypeptide fragment of protein L1

<400> SEQUENCE: 10

```
Lys Leu Phe Lys Lys Asn Lys Pro Ala Ile Gly Asp Asn Asn Ser Cys
1               5                   10                  15
```

<210> SEQ ID NO 11
<211> LENGTH: 20
<212> TYPE: PRT
<213> ORGANISM: Artificial
<220> FEATURE:
<223> OTHER INFORMATION: polypeptide fragment of protein L1

<400> SEQUENCE: 11

```
Gly Val Asn Val Asp Val Lys Glu Phe Met Gln Lys Phe Glu Ser Asn
1               5                   10                  15

Leu Ser Asn Cys
            20
```

<210> SEQ ID NO 12
<211> LENGTH: 266
<212> TYPE: PRT
<213> ORGANISM: Piscine poxvirus
<220> FEATURE:
<221> NAME/KEY: MISC_FEATURE
<222> LOCATION: (1)..(266)
<223> OTHER INFORMATION: L1 protein

<400> SEQUENCE: 12

```
Met Gly Val Asn Val Asp Val Lys Glu Phe Met Gln Lys Phe Glu Ser
1               5                   10                  15

Asn Leu Ser Asn Asn Leu Ser Gln Ser Gly Ser Ser Gln Ala Val Ala
            20                  25                  30

Asn Cys Lys Val Asn Ile Gly Ser Ile Ile Phe Gln Ser Asn Val Asn
        35                  40                  45

Cys Ser Val Asn Ile Thr Asn Asn Cys Val Ala Ser Ala Asp Val Ser
    50                  55                  60

Val Ser Ala Val Ile Asn Ala Leu Ser Asp Ala Phe Asn Ser Met Ser
65                  70                  75                  80

Ser Thr Gln Lys Thr Ser Ile Ala Gly Phe Thr Gly Gly Ile Asn Val
                85                  90                  95

Gly Val Ser Ser Thr Ala Gln Thr Phe Ile Gln Asn Met Thr Asn Thr
            100                 105                 110

Ile Asn Gln Ser Cys Ser Ala Ser Ala Val Ala Asn Ser Glu Phe Asn
        115                 120                 125

Leu Gly Thr Leu Ser Phe Gly Ser Cys Lys Asn Tyr Phe Gly Thr Thr
    130                 135                 140
```

-continued

Thr Ile Asn Phe Ile Asn Thr Gly Gln Ala Arg Gly Asn Cys Ala Met
145 150 155 160

Lys Leu Val Ser Asp Leu Gln Leu Gln Ser Asn Asn Ser Asn Thr Gly
165 170 175

Val Gln Asp Ser Val Phe Ser Gly Phe Gly Ser Ile Leu Thr Ala Phe
180 185 190

Gly Asn Leu Leu Gly Gln Tyr Ala Lys Phe Ile Ile Gly Phe Ile Ala
195 200 205

Ile Leu Leu Phe Thr Pro Ile Ile Tyr Leu Ile Val Lys Leu Phe Lys
210 215 220

Lys Asn Lys Pro Ala Ile Gly Asp Asn Asn Ser Ala Val Ile Phe Glu
225 230 235 240

Ser Pro Phe Ile Lys Glu Leu Ala Phe Lys Ser Leu Asn Asn Glu Pro
245 250 255

Leu His Trp Ser Leu Tyr Ser Lys Phe Leu
260 265

<210> SEQ ID NO 13
<211> LENGTH: 21
<212> TYPE: PRT
<213> ORGANISM: Artificial
<220> FEATURE:
<223> OTHER INFORMATION: polypeptide fragment of protein P4

<400> SEQUENCE: 13

Cys His Leu Gln Ala Lys Leu Ser Arg Glu Ser Arg Asp Thr Pro Tyr
1 5 10 15

Glu Lys Ile Val Lys
20

<210> SEQ ID NO 14
<211> LENGTH: 19
<212> TYPE: PRT
<213> ORGANISM: Artificial
<220> FEATURE:
<223> OTHER INFORMATION: polypeptide fragment of protein P4

<400> SEQUENCE: 14

Cys Arg Gln Leu Glu Ala Gln Ser Asp Leu Glu Val Glu Pro Glu Ile
1 5 10 15

Lys Thr Glu

<210> SEQ ID NO 15
<211> LENGTH: 528
<212> TYPE: PRT
<213> ORGANISM: Pseudomonas phage phi6
<220> FEATURE:
<221> NAME/KEY: MISC_FEATURE
<222> LOCATION: (1)..(528)
<223> OTHER INFORMATION: P4 protein

<400> SEQUENCE: 15

Lys Glu Leu Thr Gln Asn Gly Asn Gly Lys Gln Leu Ser Met Phe Trp
1 5 10 15

Ser Gly Ile Ser Ala Glu Glu Trp Thr Val Met Cys Ile Tyr Thr Lys
20 25 30

Gly Ile Ile Ser Lys Leu Ser Leu Val Met Gly Leu Tyr Asp Lys Asp
35 40 45

Val Met Ile Asp Gly Asn Met Arg Ala Ile Thr Phe Cys Gly Pro Leu
50 55 60

-continued

```
Asn Gln Leu Pro Leu Asn Val Asn Leu Lys Arg Val Cys Phe Leu Pro
65                  70                  75                  80

Tyr Met Thr Gly Ser Met Thr Leu Tyr Lys Ser Leu Lys Val Ile Ala
                85                  90                  95

Asp Asp Ile Met Ala Glu Asn Ala Thr Val Asn Asn Leu Ser Ser Ser
            100                 105                 110

Glu Tyr Arg Lys Lys Met Ile Leu Lys Ser Asn Pro Lys Leu Glu Met
        115                 120                 125

Thr Lys Leu Gln Phe Asp Met Phe Met Ser Met Ile Lys Asp Ala Ala
    130                 135                 140

Ser Pro Ile Gln Val Leu Ala Ala Tyr Cys Val Ser Met Lys Glu Gly
145                 150                 155                 160

Gly Thr Gly His Gly Glu Phe Val Lys Phe Ser Asp Leu Thr His Tyr
                165                 170                 175

Ile Gln Thr Ile Trp Leu Ile Leu Thr Lys Leu Gly Tyr Gln Val Ser
            180                 185                 190

Phe Arg Asp Thr Thr Thr Asp Asp Ser Gly His Leu Ile Ile Arg Pro
        195                 200                 205

Ala Ile Thr Pro Val His Leu Gln Ala Lys Leu Ser Arg Glu Ser Arg
    210                 215                 220

Asp Thr Pro Tyr Glu Lys Ile Val Lys Ser Leu Val Leu Gln Ser Lys
225                 230                 235                 240

Glu Leu Leu Glu Phe Leu Ala Tyr Pro Thr Lys Leu Thr Lys Leu Gln
                245                 250                 255

Thr Leu Glu Thr Ala Arg Asp Ala Ala Gly Ser Gly Val Leu Ser Ser
            260                 265                 270

Ile Val Ile Lys Asn Asp Pro Pro Leu Phe His Glu Val Asp Val Val
        275                 280                 285

Gly Phe Ala Glu Cys Gln Ser Ser Ser Asp Leu Lys Asn Val Lys Phe
    290                 295                 300

Leu Gln Pro Glu His Asp Arg Phe Tyr Glu Glu Val Ser Gly Ile Arg
305                 310                 315                 320

Cys Asp Pro Ile Asn Leu Glu Glu Ser Leu His Lys Ile Ser Asn Leu
                325                 330                 335

Ile Pro Thr Ser Ile Arg Ala Gln Met Cys Asn Met Asn Thr Ala Phe
            340                 345                 350

Gly Thr Ser Phe Asp Lys Asp Met Phe Asn Glu Ile Ala Arg Lys Phe
        355                 360                 365

Asp Ala Tyr Gly Gly Ala Tyr Ile Asp Asp Leu Ile Gly Thr Asp Thr
    370                 375                 380

Thr Glu Asp Arg Glu Ala Arg Met Ser Leu Glu Ile Lys Arg Leu Met
385                 390                 395                 400

Ser Leu Val Asp Arg Ser Val Gly Ser Arg Pro Gly Ser Ser Gly Pro
                405                 410                 415

Ser Asn Pro Asn Met Ala Pro Phe Asp Pro Thr His Ser Ser Arg Thr
            420                 425                 430

Lys Phe Leu Gly His Ala Leu His Gly Ala Asp Phe Met Gln Gln Thr
        435                 440                 445

Met Ala Lys Ile Arg Gln Leu Glu Ala Gln Ser Asp Leu Glu Val Glu
    450                 455                 460

Pro Glu Ile Lys Thr Glu Val Met Asn Lys Phe Arg Gln Leu Phe Val
465                 470                 475                 480

Met Asn Arg Asp Leu Tyr Lys Phe Ala Leu Gln Leu Asp Phe Met Ile
```

-continued

```
                485                 490                 495

Lys Leu Val Glu Val Leu Arg Ala Gly Gly His Thr Ile Asp Asp Thr
            500                 505                 510

Ser Leu Ser Ala Asp Leu Phe Thr Asn Ile Tyr Thr Lys Val Arg Pro
        515                 520                 525
```

SALMON GILL POXVIRUS

CROSS REFERENCE TO RELATED APPLICATIONS

The present application is a Section 371 U.S. national stage entry of pending International Patent Application No. PCT/EP2015/080982, international filing date Dec. 22, 2015, which claims priority to SE Patent Application No. SE 1451636-3, filed Dec. 22, 2014, the contents of which are incorporated by reference in their entireties.

TECHNICAL FIELD

The present document is directed to a new virus, herein denoted Piscine poxvirus. The present document is further directed to methods and means for detection and diagnosis of said virus infection as well as the prevention and/or treatment of said virus.

BACKGROUND

Poxviruses differ from other viruses in their size and complexity. They are large, with linear, double stranded DNA encoding for about 200 proteins and is the only known DNA virus that replicates entirely in the cytoplasm[1]. They are reported in both invertebrates (Entomopoxvirinae) and vertebrates (Chordopoxvirinae). Poxvirus infections, in general, are acute, with no strong evidence for latent, persistent, or chronic infections[2]. Variola virus, the causative agent of smallpox, belongs to this group of virus. The vaccinia virus used to prevent smallpox. The narrow host specificity of Variola virus was important in the eradication of smallpox[3].

Hence, some members of the Poxviridae can cause severe, systemic disease, while others, can cause mild, localized disease depending on the virus species, the route of entry, the host species and its immune status[4] The host tropism varies from narrow to broad[5] and the virus is epitheliotrophic, typically causing proliferation of epithelial cells[6].

In general, little is known about poxvirus infections in aquatic animals[7-10].

SUMMARY

The present document is directed to a novel virus herein denoted Piscine poxvirus or alternatively salmon gill poxvirus (SGPV) (both used interchangeably herein), characterized in that it comprises a nucleic acid sequence according to SEQ ID NO:1 or a nucleic acid sequence having at least 85% identity thereto, and/or a nucleic acid sequence complementary thereto. The present document is also directed to the novel Piscine poxvirus, wherein the genome of said Piscine poxvirus consists of a nucleic acid sequence according to SEQ ID NO:1 or a nucleic acid sequence having at least 85% identity thereto, and a nucleic acid sequence complementary thereto.

The present document is also directed to an isolated nucleic acid molecule comprising or consisting of a nucleic acid sequence according to any one of SEQ ID NO:1-9 or a variant thereof having at least 85% identity thereto, or a nucleic acid sequence complementary thereto. Further disclosed herein is a nucleic acid fragment of said isolated nucleic acid molecule, said fragment comprising or consisting of at least 5 contiguous nucleic acid bases of a nucleic acid molecule according to any one of SEQ ID NO:1-9. The nucleic acid fragment may be a nucleic acid primer or nucleic acid probe capable of specifically detecting Piscine poxvirus in a sample, said probe optionally further comprising one or more label(s) for detection of said probe. Such a nucleic acid probe may comprise at least 5, such as about 5-300, 5-100, 10-100, 15-80, 15-50, 18-35, or 15-25 contiguous nucleotides of a nucleic acid sequence according to any one of SEQ ID NO:1-3 or a sequence having at least 85% identity thereto, or a sequence complementary thereto, and optionally one or more label(s) for detection of said probe. The nucleic acid sequence of a nucleic acid probe may be a nucleic acid sequence of any one of SEQ ID NO:4-7. Suitable labels include, but are not limited to, a fluorescent label, such as TAMRA (tetramethylrhodamine), FAM 6-carboxyfluorescein), NED™, VIC®, and/or HEX™. A fluorescent label may be used together with MGBNFQ (Minor Groove Binding Non-Fluorescence Quencher).

The present document is also directed to an isolated nucleic acid fragment as defined herein, wherein said nucleic acid fragment is a primer consisting of at least 5, such as about 5-50, 10-40, 18-30, 12-35 or 15-28 contiguous nucleotides of a nucleic acid sequence according to any one of SEQ ID NO:1-9, such as SEQ ID NO:1-3, or a sequence complementary thereto. A primer may be as defined in any one of SEQ ID NO:8-9.

The present document is also directed to a vector comprising one or more isolated nucleic acid molecule(s) and/or nucleic acid fragment(s) as defined herein. Also disclosed is a host cell comprising one or more nucleic acid molecule(s) and/or nucleic acid fragment(s) or a vector as defined herein.

The present document is further directed to a polypeptide encoded by a consecutive string of at least 12 nucleic acid bases of an isolated nucleic acid molecule or fragment as defined herein, or a nucleic acid sequence reverse complementary thereto. Exemplary polypeptides include, but are not limited to, the peptides according to any one of SEQ ID NO:10-15. Also disclosed herein is an antigen comprising or consisting of a polypeptide as defined herein. Further disclosed is an antibody specifically directed to such an antigen.

The present document is also directed to the use of a nucleic acid fragment as defined herein and/or an antibody as defined herein for detecting the presence (or absence) of a virus, such as specifically detecting the presence or absence of Piscine poxvirus (and/or Piscine poxvirus specific nucleic acids or peptides/proteins) and/or diagnosing a viral infection, such as Piscine poxvirus infection, in a sample. For example, in situ hybridization or polymerase chain reaction may be used for detecting the presence or absence of the Piscine poxvirus and/or diagnosing the Piscine poxvirus viral infection.

The present document is also directed to the use of an isolated nucleic acid molecule or a nucleic acid fragment as defined herein, such as a nucleic acid according to any one of SEQ ID NO:1-9, for preparing a primer and/or probe which specifically detects Piscine poxvirus. Such a primer and/or probe may be used for analysing the presence or absence of Piscine Pox virus in a sample, such as a tissue sample from fish. Such a primer and/or probe is further disclosed elsewhere herein.

The present document is also directed to the use of an isolated nucleic acid molecule or a nucleic acid fragment as defined herein for expressing a peptide, or the use of a polypeptide as defined herein, for preparing an antibody which specifically detects Piscine Pox virus. Such an antibody may be used for analysing the presence or absence of Piscine Pox virus in a sample, such as a tissue sample from fish. Such an antibody is further disclosed elsewhere herein.

The present document is also directed to a method for detecting a virus, such as Piscine poxvirus, said method comprising detecting at least 5 consecutive nucleic acid bases of a nucleic acid sequence according to any one of SEQ ID NO:1-9, or a sequence having at least 85% identity thereto, or a sequence complementary thereto. Such a method may comprise performing a polymerase chain reaction or in situ hybridisation.

The present document is further directed to a method, such as an ex vivo method for detecting the presence of a Piscine poxvirus specific nucleic acid, Piscine poxvirus specific polypeptide or protein, and/or Piscine poxvirus and/or diagnosing a Piscine poxvirus infection in a sample, said method comprising the steps of:

a) contacting the sample with a nucleic acid fragment as defined herein, and/or an antibody as defined herein;
b) detecting the formation of a complex between a Piscine Poxvirus specific nucleic acid or polypeptide, respectively, and said nucleic acid fragment or antibody, respectively.
   wherein the presence of a complex indicates the presence of a Piscine poxvirus specific nucleic acid, Piscine poxvirus specific polypeptide or protein, and or Piscine Poxvirus and/or a Piscine Poxvirus infection in said sample.

The method may be performed ex vivo.

In all aspects of the present document a sample includes, but is not limited to, a tissue sample from fish, such as salmon, rainbow trout, or carpe. The sample may e.g. be a tissue sample from gills, pseudobranc, blood, heart, liver, kidney, spleen, pancreas, pylorus or skeletal musculature, central nervous system, in particular gills.

The present document is also directed to a diagnostic kit for diagnosing a viral infection, such as Piscine poxvirus infection, in a subject, said kit comprising one or more of an isolated nucleic acid molecule as defined herein, a nucleic acid fragment as defined herein, a vector as defined herein, a host cell as defined herein, a polypeptide as defined herein, an antigen as defined herein, and/or an antibody as defined herein and reagents for performing a diagnosis, and optionally instructions for performing such a diagnosis.

The present document is also directed to an isolated nucleic acid molecule as defined herein, a nucleic acid fragment as defined herein, a vector as defined herein, a host cell as defined herein, a polypeptide as defined herein, an antigen as defined herein, an antibody as defined herein and/or an inactivated or attenuated form of a Piscine poxvirus as defined herein for medical use.

The present document is also directed to a pharmaceutical composition comprising one or more of an inactivated or attenuated form of a Piscine poxvirus as defined herein, an isolated nucleic acid molecule as defined herein, a nucleic acid fragment as defined herein, a vector as defined herein, a host cell as defined herein, a polypeptide as defined herein, an antigen as defined herein, and/or an antibody as defined herein. Also disclosed is such a pharmaceutical composition for use as a vaccine.

The present document is also directed to an isolated nucleic acid molecule as defined herein, a nucleic acid fragment as defined herein, a vector as defined herein, a host cell as defined herein, a polypeptide as defined herein, an antigen as defined herein, an antibody as defined herein, an inactivated or attenuated form of a Piscine poxvirus as defined herein and/or a pharmaceutical composition as defined herein for use for the prevention and/or treatment of a Piscine poxvirus infection.

The present document is also directed to an isolated nucleic acid molecule as defined herein, a nucleic acid fragment as defined herein, a vector as defined herein, a host cell as defined herein, a polypeptide as defined herein, an antigen as defined herein, an antibody as defined herein and/or an inactivated or attenuated form of a Piscine poxvirus as defined herein for use in the preparation of a medicament for the prevention and/or treatment a Piscine poxvirus infection.

The present document is also directed to the use of an isolated nucleic acid molecule as defined herein, a nucleic acid fragment as defined herein, a vector as defined herein, a host cell as defined herein, a polypeptide as defined herein, an antigen as defined herein, an antibody as defined herein and/or an inactivated or attenuated form of a Piscine poxvirus as defined herein for the preparation of a medicament for the prevention and/or treatment a Piscine poxvirus infection.

The present document is also directed to a method for preventing and/or treating Piscine poxvirus infection in a subject, such as a fish, such as rainbow trout, carpe or salmon, said method comprising administering a pharmaceutically effective amount of an isolated nucleic acid molecule as defined herein, a nucleic acid fragment as defined herein, a vector as defined herein, a host cell as defined herein, a polypeptide as defined herein, an antigen as defined herein, an antibody as defined herein, an inactivated or attenuated form of a Piscine Poxvirus as defined herein and/or a pharmaceutical composition as defined herein to said subject. The administration of a substance or pharmaceutical composition of the present document may e.g. take place by intraperitoneal injection, dip vaccination, bath vaccination and/or by oral vaccination.

The present document is also directed to the use of a nucleic acid molecule as defined herein as a vector and a vector comprising at least part of an isolated nucleic acid molecule according to any one of SEQ ID NO: 1-9, such as SEQ ID NO 1-3, or a variant thereof.

Other features and advantages of the invention will be apparent from the following detailed description, drawings, examples, and from the claims.

Definitions

As used herein, the term "nucleic acid sequence", "nucleic acid molecule", "nucleic acid" and the like refers to a polynucleotide molecule (DNA—deoxyribonucleic acid, or RNA—ribonucleic acid) comprising a string of nucleic acid bases. These nucleic acid bases are "A" (adenine), "T" (thymidine)/"U" (uracil), "C" (cytidine) and "G" (guanidine). In RNA, "T" is replaced with "U". DNA or RNA may be single-stranded or double-stranded. By an RNA sequence "corresponding to" a nucleic acid sequence expressed as a DNA sequence, the same nucleic acid sequence but wherein "T" is replaced by "U" to get the corresponding RNA sequence is intended. The term "nucleic acid" may comprise both DNA and/or RNA sequences unless one or the other is specifically referred to. Preferably, nucleic acid sequences are DNA sequences in the present document.

cDNA (complementary DNA) can be produced by reverse transcription of RNA.

As used herein in connection with nucleic acid molecules (DNA and RNA molecules) and polypeptides, the term "isolated" means that the molecule or polypeptide has been removed from its original environment. This means that a nucleic acid molecule or polypeptide when present in a living organism is not "isolated" whereas the breaking of chemical bonds and/or by other means separating the sequence from its natural environment (such as by isolating it from the virus particle) means that the nucleic acid molecule or polypeptide is "isolated".

By "identity" is in the context of the present document intended the extent to which two (nucleic or amino acid) sequences have the same residues at the same positions in an alignment, expressed as a percentage. A local algorithm program may be used to determine sequence identity. Local algorithm programs, (such as Smith Waterman) compare a subsequence in one sequence with a subsequence in a second sequence, and find the combination of subsequences and the alignment of those subsequences, which yields the highest overall similarity score. Internal gaps, if allowed, are penalized. Local algorithms work well for comparing two multidomain proteins, which have a single domain or just a binding site in common. Methods to determine identity and similarity are codified in publicly available programs. Preferred computer program methods to determine identity and similarity between two sequences include, but are not limited to, the GCG program package (Devereux, J et al. (1984)) BLASTP, BLASTN, and FASTA[11] (Altschul, S. F. et al. (1990)). The BLASTX program is publicly available from NCBI and other sources [11](BLAST Manual, Altschul, S. F. et al. (1990)). Each sequence analysis program has a default scoring matrix and default gap penalties. In general, a molecular biologist would be expected to use the default settings established by the software program used. By e.g. a sequence having 95% identity it is intended that the amino acid or nucleotide sequence is identical to the reference sequence, except that the amino acid/nucleotide sequence may include up to 5 point mutations per each 100 amino acids or nucleotides of the reference amino acid/nucleotide sequence. In other words, to obtain an amino acid/nucleotide sequence having at least 95% identity to a reference sequence up to 5% of the amino acids/nucleotides in the reference sequence may be deleted or substituted with another amino acid/nucleotide, or a number of amino acids/nucleotides up to 5% of the total number of amino acids/nucleotides in the reference sequence may be inserted into the reference sequence. These mutations of the reference sequence may occur at the terminal positions of the reference amino acid or nucleotide sequence or anywhere between those terminal positions, interspersed either individually among the amino acids or nucleotides in the reference sequence or in one or more contiguous groups within the reference sequence.

By "variant", "variant thereof" or "variants thereof" as used in the present document is intended a nucleic acid or polypeptide sequence(s) having an identity to a specified nucleic acid or polypeptide sequence of at least 85% or at least 90%, such as 85-100%, 86-100%, 87-100%, 89-100%, 90-100%, 91-100%, 92-100%, 93-100%, 94-100%, 95-100%, 96-100%, 97-100%, 98-100%, 99-100% or about 100%. Unless something else is explicitly mentioned herein, whenever a nucleic acid or fragment or part thereof is referred to in this document, also intended is a nucleic acid having at least 85% identity, such as 85-100%, 86-100%, 87-100%, 88-100%, 89-100%, 90-100%, 91-100%, 92-100%, 93-100%, 94-100%, 95-100%, 96-100%, 97-100%, 98-100%, 99-100% or about 100% identity, such as about 85%, 86%, 87% 88%, 89%, 90%, 91%, 92%, 93%, 94%, 95%, 96%, 97%, 98%, 99% or 100% identity thereto. Such a nucleic acid fragment may encode a polypeptide having substantially the same biological activity as the referred to nucleic acid would.

A "probe", such as a DNA probe, refers to an isolated nucleic acid sequence capable of hybridizing to an, at least partially, complementary nucleic acid sequence. A probe often contains a label allowing detection of the complex formed between the probe and the target nucleic acid sequence. Examples of such probes include, but are not limited to radioactive probes, fluorescent agents, chemiluminescent agents, enzyme substrates and enzymes. Further information regarding the use and choice of labels can e.g. be found in [12](Sambrook et al. Molecular Cloning: A laboratory Manual, Cold Spring Harbor Laboratory Press (1989)) and [13](Ausubel et al. Current Protocols in Molecular Biology, Green Publishing Associates and Wiley-Intersciences (1987)).

A double stranded nucleic acid molecule (DNA or RNA molecule) consists of two "complementary" nucleic acid strands. Generally, "A" (adenine) is complementary to "T" (thymidine) in a DNA molecule and "U" (uracil) in an RNA molecule, while "C" (cytidine) is complementary to "G" (guanidine). A thus binds to T and G to C via hydrogen bonds. If in a double-stranded DNA molecule one strand reads "5'-ACGCT-3" its "complementary" strand reads "3'-TGCGA'-5". As used herein, the terms "complement" "complementarity", "complementary" and the like, are thus used to describe single-stranded polynucleotides related by the rules of antiparallel base-pairing. A "reverse complementary" strand and the like expressions refers to a DNA sequence read in the reverse direction on the opposite strand, e.g. the reverse complementary strain to the sequence 5'-ATGC-3' is 5'-GCAT-3'. Complementarity may be "partial" where the base pairing is less than 100%, or it may be "complete" or "total," implying perfect 100% antiparallel complementation between the two polynucleotides. By convention in the art, single-stranded nucleic acid molecules are written with their 5' ends to the left, and their 3' ends to the right.

A "primer" is a nucleic acid strand which serves as a starting point for DNA synthesis. In DNA synthesis, the enzyme (DNA polymerase) used for catalysing DNA synthesis requires an existing nucleic acid strand in order to be able to add new nucleotides to an existing DNA strand. The primer is constructed so that it binds to another DNA strand by antiparallell base paring. In the PCR reaction, the primer is allowed to hybridize to a target DNA molecule whereafter the DNA polymerase synthesises new DNA using the target DNA molecule's sequence as a template.

A "vector" is a DNA or RNA molecule used to carry foreign material to a cell. A vector typically contains sequences for its replication in a host cell and one or more transgene(s). It may also contain one or more promoter sequence for the expression of inserted genes and/or sequence regulating transcription and/or translation. Vectors are typically inserted into their target cells (host cells) by transformation (for bacterial cells, transfection (for eukaryotic cells) or transduction (often used terminology when a viral vector is inserted into a host cell). Viral vectors generally have a modified viral DNA or RNA rendering them non-infectious.

As used herein, a "host cell" includes an individual cell or cell culture which can be or has been a recipient of any vector of this document. Host cells include progeny of a single host cell, and the progeny may not necessarily be completely identical (in morphology or in total DNA complement) to the original parent cell due to natural, accidental, or deliberate mutation and/or change. A host cell includes cells transfected or infected with a vector comprising a nucleic acid of the present document. Host cells may be prokaryotic or eukaryotic cells.

By "polypeptide" is herein intended a string of amino acid bases linked by a covalent peptide (amide) bond between the carboxyl group of one amino acid to an amino group on the adjacent amino acid. Amino acid sequences are usually expressed with their N-terminal to the left and the carboxy-terminal on the right. A polypeptide is generally shorter than a "protein" which latter term is usually used for polypeptides being longer than 50 amino acids. Herein, these two terms may be used interchangeably independently of the length of the amino acid string.

The term "antigen," as used herein, refers to any agent that is recognized by an antibody, while the term "immunogen" refers to any agent that can elicit an immunological response in a subject. The terms "antigen" and "immunogen" both encompass, but are not limited to, polypeptides. In most, but not all cases, antigens are also immunogens.

The term "antibody" is directed to an immunoglobulin molecule and immunologically active parts (fragments) of such immunoglobulin molecules. An antibody is capable of binding an antigen. Natural antibodies are Y-shaped protein molecules containing two each of a heavy chain and a light chain connected with each other by disulfide bonds. Although the overall structure of different antibodies is very similar, the tip of the antibody is highly variable allowing different antibodies to recognize different kinds of antigens. Antibodies are used by the immune system to identify and neutralize foreign objects, such as bacteria and viruses. Antibodies may be coupled to labels, such as fluorescent, chemiluminescent or enzymatic labels, which allow their use for detection of certain antigens in situ and ex situ and diagnosis of disease.

A vaccine or a vaccine composition, as mentioned herein, is intended to refer to a composition resulting in immunological prophylaxis in a subject to which the vaccine is administered. A vaccine composition induces an immune response and thus a long-acting immunity, to a specific antigen. In the present context an antigen is mainly intended to refer to an inactivated form of a virus, or parts or fragments thereof which are still capable of generating an immune response in a subject.

PCR (polymerase chain reaction) is a method for amplification of nucleic acid molecules. The PCR reaction is well-known to the person skilled in the art and involves contacting a sample with a pair of so called oligonucleotide primers (one forward and one reverse primer) under conditions allowing the hybridization between the primers and a target (template) sequence having complementarity to the primers and which target sequence possibly is present in the sample in order to amplify the target sequence.

DETAILED DESCRIPTION

Figure 2:
FIG. 2: IHC Piscine poxvirus (positive area indicated by arrow).

The present document is directed to a novel poxvirus infecting fish, herein denoted Piscine poxvirus or alternatively salmon gill poxvirus (SGPV) (FIG. 2). Both Piscine poxvirus and salmon gill poxvirus may be used herein to denote this virus. The inventors recognize that this is the first poxvirus identified by molecular methods that infects fish. The virus causes severe disease with massive mortalities in farmed Atlantic salmon. The infection has a wide geographical distribution in Norway, affects all age groups of fish and preliminary results suggest no infection of other salmonids. The samples of the virus used for sequencing according to the present document was obtained from salmon from the northern part of Norway. Preliminary results demonstrate that the Piscine poxvirus infects primarily the gills and causes extensive gill pathology with severe respiratory disease. Pathological changes are also seen in kidney and spleen. However, these symptoms may not be directly linked to the virus itself, but may be due to some kind of pathophysiological consequence of the infection.

In 2012, the inventors collected material from an Atlantic salmon fresh water farm experiencing acute high mortality with respiratory disease suspected to be the primary problem. In addition to autopsy and histological examination of several organs, the inventors investigated the gills from two diseased salmons by transmission electron microscopy (TEM). Based on these results, a specimen was selected for high throughput sequencing (for further information see the experimental section). Total RNA was isolated and sequenced. The sequencing yielded 521 710 reads. All reads were translated into protein sequences (all reading frames and both strands) and sequence similarity searches against all available poxvirus sequences available from Gen Bank using tblastx (Altschul et al. (1990) “Basic local alignment search tool.” J. Mol. Biol. 215:403-410) were performed. Two reads with weak similarity to known poxvirus sequences were identified and one of those reads was used to design a real-time PCR assay. Using the assay, a sample with high viral DNA content was selected for Illumina sequencing.

Figure 1:
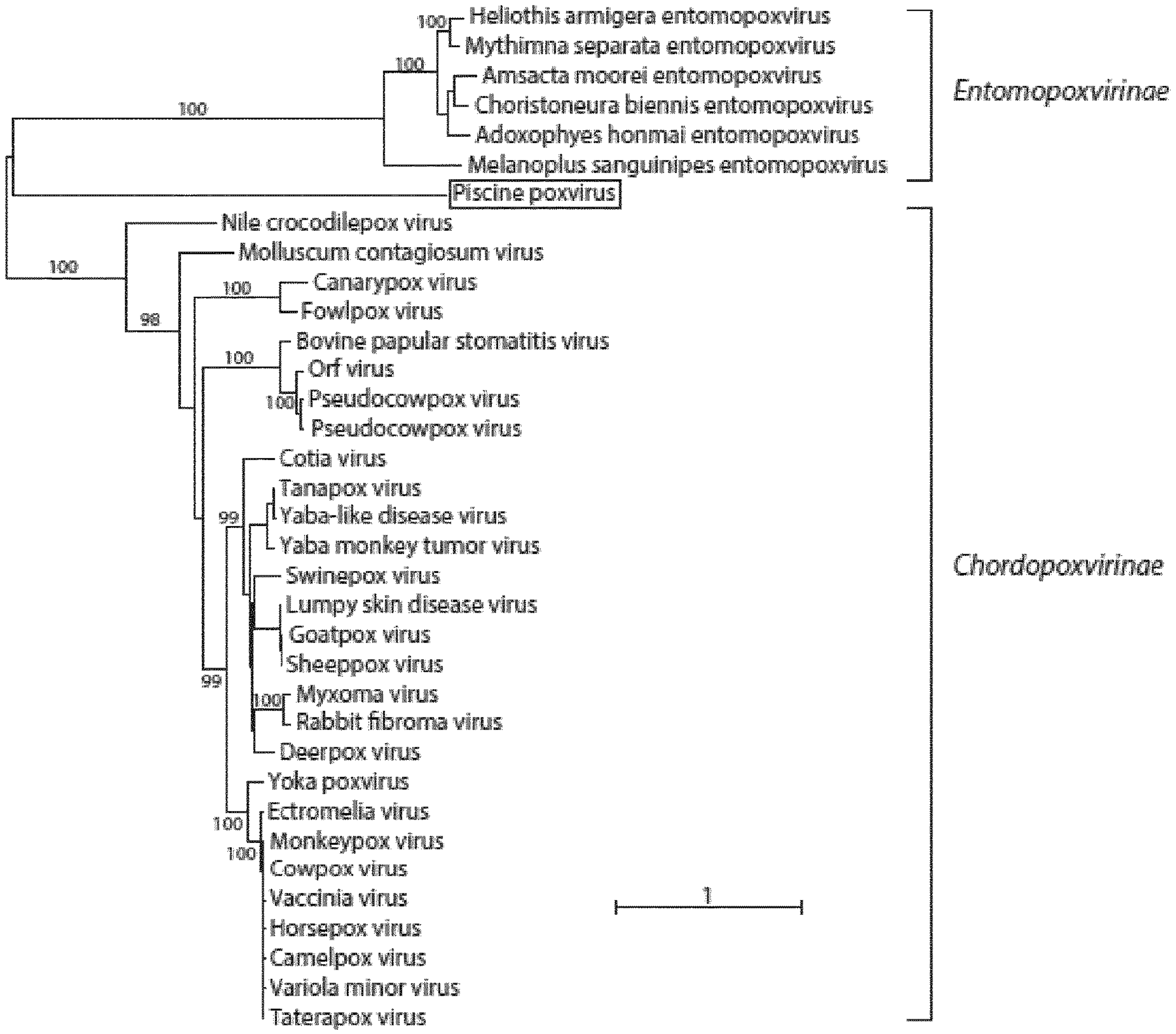
FIG. 1: Phylogenetic analysis of Piscine poxvirus. The analysis was done using maximum likelihood (General Time Reversible substitution model) and rifampicin resistance protein sequences. Bootstrap values above 50% have been indicated.

Based on analyses of the genomic sequence prepared, a large number of potential open reading frames (genes) could be identified. When using the megablast algorithm with default parameters and nucleotide data, surprisingly, no matching sequence regions were found in National Center for Biotechnology Information’s complete collection of viral sequences. Even when looking at potential protein sequences, very few viral matches exceed 4-5 consecutive amino acids. Phylogenetically, the virus appears to belong to a new group of poxviruses (FIG. 1).

Due to the substantial lack of homologous sequences from other Poxviruses, the sequencing of the novel piscine Poxvirus was not straightforward. However, due to this uniqueness, most loci are suitable for the design of both specific probes and primers for e.g. detection/diagnosis of the virus, without risking any substantial cross-reaction to other Poxviruses (or other viruses). Also, due to the genome’s uniqueness most loci are suitable for the development of recombinant vaccines. Also, as the genome is unique, so are the peptides and proteins which can be expressed based on the genome’s sequence. This is relevant for the specificity of detection methods based on detection of proteins/peptides and vaccines based on in vivo or in vitro expressed proteins/peptides.

The Piscine Poxvirus disclosed herein is characterized in that it comprises a nucleic acid sequence according to SEQ ID NO:1 or a variant of said nucleic acid sequence having at least 85% identity thereto, such as 85-100%, 86-100%, 87-100%, 88-100%, 89-100%, 90-100%, 91-100%, 92-100%, 93-100%, 94-100%, 95-100%, 96-100%, 97-100%, 98-100%, 99-100% or about 100% identity thereto, and/or a nucleic acid sequence complementary to said nucleic acid sequence or variant thereof. The present document is also directed to a Piscine poxvirus wherein the genome of said piscine Poxvirus comprises or consists of a nucleic acid sequence according to SEQ ID NO:1 or a variant of said nucleic acid sequence having at least 85% identity thereto, such as 85-100%, 86-100%, 87-100%, 88-100%, 89-100%, 90-100%, 91-100%, 92-100%, 93-100%, 94-100%, 95-100%, 96-100%, 97-100%, 98-100%, 99-100% or about 100% identity thereto, and a nucleic acid sequence complementary to said nucleic acid sequence or variant thereof, i.e. a double stranded DNA genome. SEQ ID NO:1 represents one strand of the genomic DNA of Piscine Poxvirus, which is a linear double-stranded DNA genome.

The present document is also directed to an isolated nucleic acid molecule comprising or consisting of a nucleic acid sequence according to SEQ ID NO:1-9 or a variant thereof having at least 85% identity thereto, such as 85-100%, 86-100%, 87-100%, 88-100%, 89-100%, 90-100%, 91-100%, 92-100%, 93-100%, 94-100%, 95-100%, 96-100%, 97-100%, 98-100%, 99-100% or about 100% identity thereto, or a nucleic acid sequence complementary to said nucleic acid sequence or variant thereof.

The present document is also directed to an isolated nucleic acid molecule, wherein said nucleic acid molecule is a fragment of a nucleic acid sequence according to SEQ ID NO:1-9, such as SEQ ID NO:1-3, wherein said nucleic acid fragment comprises or consists of at least 5 contiguous nucleic acid bases, such as about 5-1000, 5-900, 5-800, 5-700, 5-600, 5-500, 5-400, 5-300, 5-200 or 5-100, 5-90, 5-80, 5-70, 5-60, 5-50, 5-40, 5-30, 5-25, 5-20, 10-100, 10-80, 10-70, 10-60, 10-50, 10-40, 10-30, 15-100, 15-80, 15-70, 15-60, 15-50, 15-40, 15-30, 15-25, 20-100, 20-80, 20-70, 20-60, 20-50, 20-40, 17-50, 18-35, 15-25, 20-30, 18-35 or 15-25 contiguous nucleic acid bases of a nucleic acid sequence according to SEQ ID NO:1-9, or a variant thereof, or a nucleic acid sequence complementary to said nucleic acid sequence according to SEQ ID NO:1-9 or variant thereof.

As mentioned above, the Piscine poxvirus genome turned out to be very unique with little sequence similarity to other poxviruses (or other viruses generally). Most parts of the genome will therefore be unique to the Piscine poxvirus and thus suitable for the development of primers, probes, peptides etc. specific for the Piscine poxvirus. For example, the region of SEQ ID NO:1 spanning from nucleotides 1-5679 (SEQ ID NO:2), the sequence of which is also duplicated between nucleotides 235 885-241 564, is very unique to the Piscine poxvirus. Another region which is very unique to the Piscine poxvirus is the region of SEQ ID NO:1 spanning from nucleotides 99 129 to 99 230 (SEQ ID NO:3). The sequence according to any one of SEQ ID NO:1-9, such as SEQ ID NO:1, 2 and/or 3 may thus be used for preparing a primer and/or probe for specifically detecting Piscine poxvirus (i.e. the primer and/or probe specifically detects Piscine poxvirus) and/or for diagnosing a Piscine poxvirus infection. Such a primer and/or probe may hybridize to a Piscine poxvirus nucleic acid sequence under high stringency conditions.

The sequence according to any one of SEQ ID NO:1-9, such as SEQ ID NO: 1, 2 and/or 3 may also be used for expressing a polypeptide as defined herein for preparing an antibody which specifically detects Piscine poxvirus. The peptides disclosed herein according to SEQ ID NO:10-15 may also be used for preparing an antibody which specifically detects Piscine Poxvirus. Such a primer, probe and/or antibody may be used for analysing the presence or absence of Piscine poxvirus in a sample, such as a tissue sample from fish. Examples of samples to be analysed are disclosed elsewhere herein and include tissue samples form fish and water samples.

A fragment of a nucleic acid as disclosed herein may be a nucleic acid primer or nucleic acid probe capable of detecting or specifically detects Piscine poxvirus in a sample. Such a primer or probe is thus capable of specifically detecting Piscine poxvirus in a sample. By "specifically detecting" or "specifically detects" it is intended that the primer or probe allows the detection of Piscine poxvirus without any cross-reactivity with other known piscine viruses. Preferably, the primer and/or probe does not show any cross-reactivity with other poxviruses either. Cross-reactivity with other poxviruses is not a major concern when working with samples from fish, as Piscine poxvirus is the only poxvirus identified from fish. Most preferably, the primer/probe does not show any cross-reactivity with any other nucleic acid sequences. The primers/probes therefore preferably hybridizes specifically to a Piscine poxvirus nucleic acid sequence as disclosed herein without hybridisation to other nucleic acids. A primer/probe is considered to hybridize specifically when it hybridizes solely to a nucleic acid from Piscine poxvirus. Preferably said hybridization is performed under high stringency conditions.

The expressions "specifically detecting" or "specifically detects" may also be used in the context of immunological (immunohistochemical) detection methods and/or antibodies for detecting Piscine Pox virus. In this context it is intended that the immunological detection method or antibody allows the detection of Piscine poxvirus without any cross-reactivity with other known piscine viruses. Preferably, the antibody does not show any cross-reactivity with other poxviruses either. Most preferably, the antibody does not show any cross-reactivity with any other protein. A possible cross-reactivity with other poxviruses is not a major concern when analysing the presence of Piscine poxvirus in tissue samples from fish, as Piscine poxvirus is the only known poxvirus in fish. The antibody thus specifically binds to a peptide or protein from Piscine poxvirus without showing any cross-reactivity to any other piscine viruses or peptides or proteins generally.

The present document is therefore also directed to a nucleic acid probe comprising at least 5, such as about 5-300, 5-200 or 5-100, 5-90, 5-80, 5-70, 5-60, 5-50, 5-40, 5-30, 5-25, 5-20, 10-100, 10-80, 10-70, 10-60, 10-50, 10-40, 10-30, 15-100, 15-80, 15-70, 15-60, 15-50, 15-40, 15-30, 15-25, 20-100, 20-80, 20-70, 20-60, 20-50, 20-40, 17-50, 18-35, 15-25, 20-30, 18-35 or 15-25 contiguous nucleotides of a nucleic acid sequence according to SEQ ID NO:1-9, such as SEQ ID NO:1-3, or a variant thereof, or a sequence complementary thereto. The nucleic acid part of the probe may consist of a nucleic acid sequence as described above, even if the probe also may include other parts, such as one or more label(s) for detection of said probe or said probe when bound to a target nucleic acid. A probe is generally at least 15 nucleic acid bases long, such as about 15-35, such as 15-35, nucleic acids long, but it may be shorter. The skilled person knows how to select a suitable length for a probe depending on its use. The nucleic acid part of a nucleic acid probe may e.g. comprise or consist of the nucleic acid sequence of SEQ ID NO:4-7.

A primer or a probe in accordance with the present document may be constructed having high specificity, i.e. a large sequence identity, to a target sequence to allow for a specific detection of a target sequence, or it may be constructed with a lower sequence identity to a target sequence to allow for detection of a target sequence having a lower sequence identity to the probe. The specificity of a primer or probe may be affected by the length of the primer or probe. Primer or probe specificity may also be affected by the conditions used for hybridization, such as salt concentration, temperature and pH. A person skilled in the art knows how to elaborate with these so called stringency conditions used for hybridization to affect primer-target or probe-target sequence complex formation. By increasing the pH and/temperature and/or lowering the salt (sodium ion) concentration, the hybridization conditions provide for a higher stringency (i.e. high stringency conditions), i.e. rendering the formation between a primer or a probe and a target sequence more difficult. The person skilled in the art also knows how to elaborate with sequence specificity to a target sequence in order to obtain a primer and/or probe having the desired sequence specificity.

A probe according to the present document generally contains one or more labels which allow the detection of the probe and optionally one or more label(s) for detection of said probe. Examples of such labels include, but are not limited to radioactive labels, fluorescent agents, chemiluminescent agents, enzyme substrates and enzymes. Further information regarding the use and choice of labels can e.g. be found in Sambrook et al. Molecular Cloning: A laboratory Manual, Cold Spring Harbor Laboratory Press (1989) and Ausubel et al. Current Protocols in Molecular Biology, Green Publishing Associates and Wiley-Interspiences (1987). A radioactive label may e.g. be $^{14}C$, $^{32}P$, $^{35}S$, $^{3}H$ or $^{15}O$, which may be detected using suitable radiation detection means. A fluorescent label may e.g. be a fluorescent dye, such as rhodamine, SYBR Green, fluorescein, thiazole orange, FAM, FAM 6-carboxyfluorescein, fluorescein istothiocyanate (FITC), or TAMRA (tetramethylrhodamine), NED™, VIC®, and/or HEX™. Such probes are well known to the person skilled in the art and may be commercially obtained.

MGBNFQ (minor groove binding non-fluorescence quencher) may also be used in combination with a fluorophore to increase the specificity of a shorter probe. MGB itself is not fluorescent. Dihydrocyclopyrroloindole tripeptide minor groove binder (MGB) is a modification of the probe that increases the specificity of probe binding to template DNA. The most commonly used quencher in MGB probes is Non-Fluorescence Quencher, hence the long acronym MGBNFQ. The most commonly used reporter dye is 6-FAM (6-carboxyfluorescein), but a whole array of other fluorophore may be used as dyes/quenchers, including TAMRA (tetramethylrhodamine), NED™, VIC®, and/or HEX™. 6-FAM may for instance be used as a reporter dye in combination with TAMRA as a quencher, or HEX™. may be used as a reporter dye with TAMRA as a quencher.

The label may also be a chemiluminescent agent, an enzyme substrate and/or an enzyme, such as β-galactosidase, horseradish peroxidase, streptavidin, biotin or digoxigenin.

Examples of methods where probes may be used include, but are not limited to, in situ hybridization, analysis of nucleic acid fragments on gels, real time PCR, digital PCR etc.

Methods where probes are used generally involve denaturing double-stranded nucleic acids (i.e. separating the two nucleic acid strands from each other) in a sample, allowing the probe to bind, wash off any unbound probe and detecting the formation of a probe-target sequence complex. However, during real time PCR, the probe instead binds to the target sequence, and is then fragmented by Taq polymerase during the elongation step. Thus, no washing off of the unbound probe is necessary in real time PCR. Methods involving the use of probes include, but are not limited to, polymerase chain reaction (PCR) and in situ hybridisation.

The isolated nucleic acid molecules disclosed herein or variants thereof may also be used for the construction of primers for a PCR reaction. The person skilled in the art is well acquainted with how such primers are to be prepared. The present document is therefore also directed to a nucleic acid fragment, wherein said nucleic acid fragment is a primer consisting of at least 5, such as about 5-50, 10-40, 18-30, 12-35 or 15-28 contiguous nucleotides of a nucleic acid sequence according to SEQ ID NO:1-9, or a variant thereof, or a sequence complementary thereto. A primer having a length of about 18-30 bases is generally considered to ensure an adequate specificity of the primer while the primer is still sufficiently short to easily bind to the template nucleic acid. However, a primer in accordance with the present document may be both shorter and longer. The skilled person knows how to select a suitable length for a primer depending on its use. Exemplary primers are disclosed in SEQ ID NO:8-9. A forward and a reverse primer for use in a real-time PCR reaction for specifically detecting piscine Poxvirus are typically separated by 250 base pairs or less, preferably 200 base pairs or less, although they may be separated by a higher number of base pairs.

For exemplary purposes only, a PCR based detection of Piscine poxvirus may utilize SEQ ID NO:8 as a forward primer, SEQ ID NO:9 as a reverse primer and a probe comprising SEQ ID NO:4 and MGB and a fluorescent probe, such as the ones specified above. Any example of a probe labelled with a reporter dye and a quencher will work. One example is an MGB-modified probe with NFQ quencher ('MGBNFQ') and 6-FAM as reporter dye.

One region of the Piscine poxvirus genome that is suitable for constructing specific primers, probes, polypeptides and/or antibodies is the region spanning from nucleotide 1 to nucleotide 5679 in SEQ ID NO:1, herein denoted SEQ ID NO:2. This is a sequence that is very distinct for the Piscine poxvirus but that is likely to be less variable on a population level. The region is duplicated and also present at nucleotide position 235 885 to 241 564 of SEQ ID NO:1.

PCR (polymerase chain reaction) is a method for amplification of nucleic acid molecules, well-known to the person skilled in the art. In short, PCR involves contacting a sample with a pair of so called oligonucleotide primers (one forward and one reverse primer) under conditions allowing the hybridization between the primers and a target (template) nucleic acid sequence having complementarity to the primers (i.e. the formation of a complex between the respective primers and the target sequence). The target (template) nucleic acid may e.g. be Piscine poxvirus DNA. The primers are constructed to bind on the 3' side of the sense and antisense strands of the target sequence, respectively. Thereafter the primers are extended by using a polymerase, dissociated from the template, re-annealed, extended, dissociated in a number of cycles. The number of cycles may be adjusted depending on the amount of target sequenced present in the sample and the amount of copies needed but is typically 20-40 although it may be both higher and lower. If the target sequence was present in the sample, the PCR reaction will allow for the provision of a number of copies of it (the amplification product).

A PCR reaction may e.g. be used to amplify a nucleic acid sequence e.g. for its subsequent use in a cloning reaction wherein the amplified nucleic acid sequence is inserted into another nucleic acid molecule, such as a vector, or for its sequencing. A PCR reaction may also be used for analyzing a sample for the presence of a specific target sequence, as amplification of the sequence will only occur if the target sequence is present in the sample. The amplification product can be analyzed e.g. by electrophoresis, probe hybridization and/or sequencing.

PCR may also be made quantitative, so that the initial amount of a target nucleic acid in a sample, and consequently e.g. a virus containing this target sequence, can be quantified. PCR can be made quantitative (qPCR) and allow for real time measurement of the amplified product by the use of fluorescent dyes, such as Sybr Green, EvaGreen or fluorophore-containing DNA probes, such as TaqMan.

The present document is also directed to a vector comprising one or more nucleic acid molecule(s) and/or nucleic acid fragment(s) as defined herein.

The Piscine poxvirus, or parts thereof, may also be used as a viral vector for inserting foreign material in a cell. For this purpose, one or more isolated part(s) or the whole of the Piscine poxvirus genome as defined in SEQ ID NO:1, or a DNA sequence complementary thereto, may be used, such as an isolated nucleic acid molecule according to any one of SEQ ID NO:1-9, such as SEQ ID NO:1-3. The present document is thus also directed to a vector comprising one or more isolated part(s) or the whole of the Piscine poxvirus genome as defined in SEQ ID NO:1, or a DNA sequence complementary thereto, such as an isolated nucleic acid molecule according to any one of SEQ ID NO:1-9, such as SEQ ID NO:1-3 or a variant thereof. Also, it is possible to recombinantly assemble different parts of the isolated Piscine poxvirus genome to construct a recombinant vector.

Importantly, such a vector should not contain any infectiously harmful sequence(s). The vector may be used for carrying foreign material into a cell by inserting genetic material of interest into the vector. To accomplish this, the vector is preferably constructed to contain one or more multiple cloning sites allowing for specific opening of the vector to insert the genetic material of interest. The vector may also be constructed to contain sequences for expression of inserted genetic material, such as promoter sequences, ribosome binding sites and/or sequences regulating the translation of the inserted genetic material. Viral vectors generally have a modified viral DNA or RNA rendering them non-infectious.

The present document is also directed to a host cell comprising one or more nucleic acid molecule(s) or fragment(s) thereof, or variant(s) thereof, as disclosed herein or a vector as disclosed herein. The host cell may be a prokaryotic or eukaryotic host cell. A host cell typically allows for the amplification and/or replication of the genetic material inserted (e.g. nucleic acid(s) and/or vector(s)) therein.

The isolated nucleic acid molecules, and fragments and variants thereof may also be used for expressing polypeptides. The present document is therefore also directed to a polypeptide encoded by a consecutive string of at least 12 nucleic acid bases, such as about 12-1000, 12-900, 12-800, 100-500, 100-400, 150-400, 150-300, 12-100, 12-90, 12-80, 12-70, 12-60, 12-50, 12-48, 50-800, 50-700, 50-600, 50-500 nucleic acid bases of a nucleic acid molecule according to SEQ ID NO:1-9 or fragment or variant thereof as defined herein, or a nucleic acid sequence reverse complementary thereto. Such a polypeptide may e.g. be used as an antigen for the preparation of an antibody and/or it may be used to elicit an immune response in an organism. When a variant of a nucleic acid molecule or a fragment of such a nucleic acid molecule as defined herein is used for producing a polypeptide in accordance with the present document, such a polypeptide may have substantially the same biological activity as a polypeptide encoded by a sequence identical to SEQ ID NO:1-9 or a fragment thereof. Exemplary polypeptides constructed based on the Piscine poxvirus genome are shown in SEQ ID NO:10-15.

Also disclosed herein is an antigen comprising a polypeptide as defined herein. Such an antigen may be used for the preparation of an antibody capable of binding specifically to said antigen. Such an antibody may e.g. be used for the detection of a Piscine poxvirus specific peptide in a sample. The antibody may in addition or alternatively also neutralize or reduce the function or activity the antigen (polypeptide). The present document is therefore also directed to an antibody specifically directed to an antigen as defined herein.

The antibody may be e.g. a polyclonal antibody or a monoclonal antibody. The antibody may e.g. be a teleost antibody or a chimeric antibody. An antibody for specifically detecting Piscine poxvirus in a sample, such as a tissue sample from fish, may be directed to a surface protein of said Piscine poxvirus.

An antigen may also be used for the preparation of a vaccine composition used for eliciting an immune response to such an antigen. Such a vaccine composition may be used for the prevention and/or treatment of a Piscine poxvirus infection.

The nucleic acid molecule(s) disclosed in the present document or fragments thereof or variants thereof may be used as primer(s) or probe(s), e.g. for specifically detecting the presence of a Piscine poxvirus specific nucleic acid in a sample and/or for diagnosing a Piscine poxvirus infection in a subject. In particular, in situ hybridization or polymerase chain reaction may be used for such detection and/or diagnosis. Also, an antibody as disclosed herein may be used for specifically detecting the presence of Piscine poxvirus in a sample and/or diagnosing a Piscine poxvirus infection in a subject. Such a detection of an antibody may be effected by labelling the antibody with a label, such as an enzymatic or fluorescent label. Commonly used labels for antibodies include, but are not limited to horseradish peroxidase, alkaline phosphatase and biotin.

Studies of mammalian animal models have demonstrated that protection against disease is associated with antibody responses to both infectious intracellular/mature virion (MV) and extracellular form (EV) of vaccinia virus, which is another poxvirus infecting mammals. The present virus, Piscine poxvirus, has been found to be very distant from other poxviruses in its nucleic acid sequence, i.e. there is a low sequence homology between Piscine poxvirus and other poxviruses. However, even if it is difficult to identify homologues of poxvirus proteins based on e.g. structural similarities, proteins that have been important for the development of vaccines against other poxviruses may be identified. Examples of vaccinia proteins which are expected to have a functional homologue in Piscine poxvirus and which may be of interest as targets for detection of Piscine poxviruses and/or in vaccine development include for example the proteins of Table 1. These proteins have been shown to be targets for neutralizing antibodies for mammal.

TABLE 1

Examples of vaccinia proteins which are expected to have a functional homologue in Piscine poxvirus

| Protein | Location | Role | Neutralize | Ref |
|---|---|---|---|---|
| A27 | MV | Attachment | MV | Ref 14 |
| A28 | MV | Entry/Fusion | MV | Ref 17 |
| D8 | MV | Attachment | MV | Ref 18 |
| H3 | MV | Attachment | MV | Ref 20 |
| L1 | MV | Entry/Fusion | MV | Ref 25 |
| A33 | EV | Spread | — | Ref 22 |
| B5 | EV | Spread | EV | Ref 22 |

The L1 protein is reported to be conserved throughout the poxvirus family and is nearly identical in vaccinia and variolavirus and is an important component in current experimental vaccines[25] (Su 2005). The present inventors have generated antibodies against the corresponding protein in Piscine poxvirus. This was primarily done using amino acid sequence similarity searches, the L1 protein from Piscine poxvirus can for instance be aligned over 66% of the total length and shows 27% sequence identity (vaccinia virus vs. Piscine poxvirus) in the aligned region when using protein BLAST. Antibodies were generated to the sequences L1 amino acids 221-235 (SEQ ID NO:10) and L1 amino acids 2-20 (SEQ ID NO:11). An antibody was also generated to the whole L1 protein (SEQ ID NO:12).

Antibodies have also been generated against protein P4 of Piscine poxvirus (major core protein, SEQ ID NO: 15). Antibodies were generated against P4 amino acids 214-233 (SEQ ID NO:13) and P4 amino acids 453-470 (SEQ ID NO:14). An antibody was also generated to the full P4 protein.

In situ hybridization involves detecting a specific DNA or RNA nucleic acid in a sample, such as a tissue sample. The method generally comprise the steps of fixating the sample, allowing a probe to hybridize to complementary DNA or RNA in the sample, washing off unbound probe and thereafter detecting the formation of a complex between the probe and a target nucleic acid possibly present in the sample. A probe for use in an in situ hybridization reaction is preferably longer than a probe used for detection of a PCR amplified nucleic acid fragment, and is typically about 35 nucleic acid bases long. For exemplary purposes only, in situ hybridization based detection of Piscine poxvirus may involve a probe according to any one of SEQ ID NO:5-7.

The present document is also directed to a method for detecting Piscine poxvirus, said method comprising detecting at least 5, at least 7, at least 10, at least 12, at least 15, such as 5-100, 5-90, 5-80, 5-70, 5-60, 5-50, 5-40, 5-35, 5-30, 5-25, 5-20, 10-80, 10-70, 10-60, 10-50, 10-40, 10-30, 15-100, 15-80, 15-70, 15-60, 15-50, 15-40, 15-30, 20-100, 20-80, 20-70, 20-60, 20-50, 20-40, 20-30, or 20-40, such as 20, 21, 22, 23, 24, 25, 26, 27, 28, 29, 30, 31, 32, 33, 34, or 35 consecutive nucleic acid bases of a nucleic acid sequence according to any one of SEQ ID NO:1-9, or a variant thereof, or a sequence complementary thereto.

Methods suitable for use in such a method include, but are not limited to, polymerase chain reaction (PCR) or in situ hybridisation (both being disclosed in further detail elsewhere herein).

The present document is also directed to a method for detecting the presence of a Piscine poxvirus specific nucleic acid, a Piscine poxvirus specific polypeptide or protein, and/or Piscine poxvirus and/or diagnosing a Piscine poxvirus infection in a sample, said method comprising the steps of:

a) contacting the sample with a nucleic acid fragment as defined herein, a probe as defined herein, and/or an antibody as defined herein;
b) detecting the formation of a complex between a Piscine poxvirus specific nucleic acid or polypeptide, respectively, and said nucleic acid fragment or probe, or antibody, respectively.

wherein the presence of a complex indicates the presence of a Piscine poxvirus specific nucleic acid, a Piscine poxvirus specific polypeptide or protein, and/or Piscine poxvirus and/or a Piscine pox viral infection in said sample. The sample may contain Piscine poxvirus specific nucleic acids, such as DNA, and/or Piscine poxvirus specific polypeptides/proteins.

The method may be performed ex vivo. In an ex vivo method, the biological sample is first isolated from the organism to be tested before the analyzing the presence or absence of Piscine poxvirus. The ex vivo method may be e.g. PCR or in situ hybridization. In situ hybridization may involve the use of nucleic acid based probes binding to Piscine poxvirus specific nucleic acids. The ex vivo method may also be an immunohistochemical method using antibodies binding to Piscine poxvirus specific peptides and/or proteins. The sample to be tested for the presence of Piscine poxvirus may also be a non-biological sample, such as a water sample.

The method for detecting the presence of Piscine poxvirus and/or diagnosing a Piscine poxvirus infection may be followed by administering a pharmaceutical composition, such as a pharmaceutical composition as disclosed herein, in order to treat the Piscine poxvirus infection.

In all aspects of the present document, a sample to be analysed for the presence of Piscine poxvirus or a Piscine poxvirus specific nucleic acid or polypeptide may be a biological sample, such as a tissue sample from fish, such as salmon, carpe or rainbow trout. The tissue sample may be a tissue sample from e.g. gills, pseudobranc, blood, heart, liver, kidney, spleen, pancreas, pylorus or skeletal musculature, or the central nervous system, in particular gills.

The present document is also directed to a diagnostic kit for detecting the presence or absence of Piscine poxvirus in a sample, such as for diagnosing a Piscine poxvirus infection in a subject, said kit comprising one or more of a nucleic acid molecule as defined herein, a nucleic acid fragment as defined herein, a vector as defined herein, a host cell as defined herein, a polypeptide as defined herein, an antigen as defined herein, and/or an antibody as defined herein and reagents for performing a diagnosis, and optionally instructions for performing such a diagnosis.

The present document is also directed to a nucleic acid molecule or variant thereof, a nucleic acid fragment or variant thereof, a vector, a host cell, a polypeptide, an antigen, an antibody and/or an inactivated or attenuated form of a Piscine poxvirus for medical use.

The present document is also directed to a pharmaceutical composition comprising one or more of an inactivated or attenuated Piscine poxvirus, a nucleic acid molecule or variant thereof, a nucleic acid fragment or variant thereof, a vector, a host cell, a polypeptide, an antigen, and/or an antibody as defined herein. Such a pharmaceutical composition may be used as a medicine, such as a vaccine composition, e.g. for the prevention and/or treatment of a Piscine poxvirus infection.

As the Piscine poxvirus genome has a very low identity to other piscine viruses polypeptide sequences obtainable from the genome will represent proteins with unique features when compared with data in publicly available databases. In fact, the virus is so distant from other poxviruses that it is impossible to determine which is the closest relative. The most similar protein when comparing all proteins from Piscine poxvirus with all proteins from the vaccinia virus appears to be the DNA-dependent RNA polymerase subunit rpo132. Here, the blastx algorithm reports <47% identity and the longest conserved sequence motif is ten amino acids.

The general idea of vaccinations is that the patient is exposed to a non virulent version of the pathogen, or parts of the pathogen (proteins) to which a protective response is generated. Alternatively, a synthetic vaccine (recombinant vaccine or DNA vaccine) may be produced instead by using the nucleic acid sequence information of Piscine poxvirus presented herein. By annotation (prediction of the biological function of the genes) of different sequences it is possible to choose the peptide sequences that most will trigger a protective immune response. A recombinant vaccine can for example be made by inserting the gene sequence for the proteins listed in Table 1 above into an expression system (e.g. *E. coli* or insect cells) to generate antigens. To generate a long term immune response the use of an adjuvant is recommended.

A pharmaceutical composition according to the present document may also comprise one or more adjuvant(s) (such as a mineral oil, muramyldipeptides, lipopolysaccharides, glucans and Carbopol®), pharmaceutically acceptable excipients, carrier(s), emulgator(s) etc. Liquid carriers include, but are not limited to water, petroleum, plant and animal oils, such as peanut oil, mineral oil, soybean oil, or sesame oil, and synthetic oils. A liquid composition may also comprise physiological saline solution, saccharide solutions (e.g. dextrose), glycols (e.g. ethylene glycol, propylene glycol, or polyethylene glycol. The active component of a pharmaceutical composition as disclosed herein may constitute about 0.5 to 90% by weight of the pharmaceutical composition. Methods and means for preparing a vaccine composition suitable for storage are well known for the skilled practitioner within this field.

Vaccine components may be in liquid form both as hydrophilic and lipophilic, which phased may often then be mixed in emulsions that need to be stabilized for storage. Examples of vaccine preparations suitable for vaccination of fish may be found in Roar Gudding (Editor) et al. "Fish Vaccinology", Developments in Biological Standardization, 484 pages.

In addition, dry vaccines may also be prepared which are dissolved before use. Such vaccines are particularly useful for dip, bath or oral vaccines that are not using oil adjuvants or the like.

The present document is also directed to a nucleic acid molecule or variant thereof, a nucleic acid fragment or variant thereof, a vector, a host cell, a polypeptide, an antigen, an antibody, an inactivated or attenuated form of a Piscine poxvirus and/or a pharmaceutical composition, as defined herein, for use for the prevention and/or treatment of a Piscine poxvirus infection.

Also disclosed herein is a nucleic acid molecule or variant thereof, a nucleic acid fragment of variant thereof, a vector, a host cell, a polypeptide, an antigen, an antibody and/or an inactivated or attenuated form of a Piscine poxvirus, as defined herein, for use in the preparation of a medicament for the prevention and/or treatment a piscine poxvirus infection.

Also disclosed herein is a method for preventing and/or treating a piscine poxvirus infection in a subject, such as a fish, such as rainbow trout or salmon, said method comprising administering a pharmaceutically effective amount of nucleic acid molecule or variant thereof, a nucleic acid fragment or variant thereof, a vector, a host cell, a polypeptide, an antigen, an antibody, an inactivated or attenuated form of a Piscine poxvirus as defined in claim 1 or 2 and/or a pharmaceutical composition, as defined herein to said subject. The administration may take place by intraperitoneal injection, dip vaccination, bath vaccination and/or by oral vaccination.

When a fragment as disclosed herein is used for medical purposes this typically does not contain any label.

The nucleic acids and polypeptides disclosed herein may be isolated.

The invention will be further described in the following examples, which do not limit the scope of the invention described in the claims.

EXPERIMENTAL SECTION

Example 1: Molecular Identification of the Piscine Poxvirus and Elucidation of the Complete Genomic Sequence In 2012, the inventors collected material from an Atlantic salmon fresh water farm, experiencing acute high mortality with respiratory disease suspected to be the primary problem. In addition to autopsy and histological examination of several organs, the inventors investigated the gills from two diseased salmons by transmission electron microscopy (TEM). Based on histopathological observations, a high quality Atlantic salmon gill specimen that appeared to have a high viral load was identified. The material was of sufficient integrity that both DNA and RNA could be extracted for genetic characterization. The method used for identification of any infectious agent present was based on a strategy referred to as 'computational subtraction', first published by Weber et al. (Nat Genet. 2002 February; 30(2):141-2). Briefly, total RNA was reverse transcribed and amplified using the QuantiTect Whole Transcriptome Kit (QIAGEN). Total RNA was chosen as this would allow us to identify RNA viruses in addition to any DNA-based pathogen (DNA viruses, bacteria etc.). High throughput pyrosequencing was done and 521 710 reads were generated using a GS FLX Titanium sequencing machine (454 Life Sciences). Using the megablast algorithm [27](Zhang et al. 2000. J. Comput. Biol., 7, 203-214) for sequence comparison and the available sequence data from Atlantic salmon as a reference, all reads matching the salmon genome or transcriptome were removed. The remaining reads were assembled into contigs using the software Velvet assembler (Zerbino & Birney 2008. Genome Research 18 (5): 821-829) and a series of sequence comparison tools were used in an attempt to identify any infectious agents. No viruses, bacteria or protists could be found based on the nucleic acid sequence data or the inferred amino acid sequences. The inventors then went back the filtered sequences reads and did sensitive amino acid-based sequence similarity searches against databases of known viral sequences. When translating both the inventors' sequence database and the virus sequence database into all reading frames and including the reverse complement version of both sequence sets, three individual reads were found to have a weak similarity with proteins from known poxviruses. Based on one of these reads, a real-time PCR assays was designed. The primers/probe set (forward primer ATCCAAAATACG-GAACATAAGCAAT (SEQ ID NO:8), reverse primer CAACGACAAGGAGATCAACGC (SEQ ID NO:9), MGB probe CTCAGAAACTTCAAAGGA (SEQ ID NO:4)—all written 5'-3') was used to assess viral load in several series of samples collected from suspected poxvirus outbreaks as well as healthy fish. There was a clear quantitative and qualitative correlation between PCR results and gill pathology. It thus concluded that the sequence did indeed stem from a causally involved virus. Using the real-time PCR assays a specimen was identified that appeared to have a particularly high amount of poxvirus nucleic acids. Poxviruses have DNA genomes, so in order to get more sequence information, total DNA was prepared and sequences using a paired-end strategy and the HiSeq 2500 System (Illumina). Paired-end sequencing will produce pairs of reads that stem from the same sequence regions. The library was designed using DNA fragments that had an average length of 370 basepairs and it was thus assumed that every pair of sequences (101 bases) in the database had this genomic distance between them.

The Illumina sequencing gave a total of 2×169 083 705 reads. All reads were assembled de novo into contigs using the Velvet assembler. A contig containing both original poxvirus reads was identified. This contig had flanking regions that appeared to be repetitive and the length (approximately 20 000 basepairs) indicated that this sequence fragment did not correspond to the complete poxvirus genome. Analyzing the contigs, reads from flanking regions where only one member of the paired reads was mapped could be identified. The rationale was that if one read maps to a particular contig and the corresponding paired read maps unambiguously to another contig, it is likely that these contigs stem from adjacent genomic regions. Primers were designed in order to link the original contig with what appeared to be flanking contigs and PCRs were performed from one contig to the next. This could be done in both directions and through multiple rounds of PCR and sequencing of PCR products, a 241 564 basepair contig could eventually be constructed. This supercontig did not appear to have any flanking contigs and it was concluded that this sequence represented the complete poxvirus genome.

Based on analyses of the genomic sequence, a large number of potential open reading frames (genes) could be identified. When using the megablast algorithm with default parameters and nucleotide data, no matching sequence regions were found in National Center for Biotechnology Information's complete collection of viral sequences. Even when looking at potential protein sequences, very few viral matches exceed 4-5 consecutive amino acids.

Phylogenetically, the virus appears to belong to a new group of poxviruses (FIG. 1). As mentioned above, due to the genome's uniqueness most loci are suitable for the design of both specific probes and primers for e.g. detection/diagnosis of the virus. Also, due to the genome's uniqueness most loci are suitable for the development of recombinant vaccines. Also, as the genome is unique, so are the peptides and proteins which can be expressed based on the genome sequence. This is relevant for the specificity of detection methods based on detection of proteins/peptides and vaccines based on in vivo or in vitro expressed proteins/peptides.

Example 2: Immunological Detection of Piscine Poxvirus

Sections from gills were dewaxed, rehydrated, treated with trypsin 1/100 at 37° C. for 90 min for antigen demasking, washed and the reaction was stopped by incubating the sections in ice cold TBS for 15 min. The sections were incubated for 20 min in Tris-buffered saline (TBS 0.05 m, pH 7.6) with 5% bovine serum albumin (BSA) for prevention of non-specific binding, tilted to remove solution, incubated for at 4° C. overnight with a rabbit antibody (Pacific Immunology) generated against the synthesized peptide of SEQ ID NO:11 that is part of the L1 protein, a transmembrane protein expressed on the surface of the IMV. The antibody was diluted 1/5000 in 2.5% BSA. Visualization was performed using EnVision Kit (Dako) with HRP and AEC as a chromogen or an alkaline phosphatase/fast red visualizing system. The same approach was performed to other antibodies as disclosed herein. Immunohistochemistry with the full protein antibodies will be tested as soon as the antibodies arrive.

Example 3: Isolation of DNA and PCR Protocol

DNA was isolated from heart, kidney, liver, spleen, muscle and gill tissue. Approximately 20 mg of tissue was homogenised in Lysing Matrix D containers (MP Biomedicals GmbH) with 200 μl lysis/binding solution (MagMAX-96 Total RNA Isolation Kit, Ambion) and 1.4 μl β-mercaptoetanol by use of a rotor stator homogenizer. The RNA isolation kit was used according to the manufacturers' recommendations. To perform the magnetic based separation, a KingFisher (Labsystems Oy) was used. After elution, the DNA concentration and purity was measured using a NanoDrop ND-1000 spectrophotometer (Nano—Drop Technologies). All samples had OD260/280 ratios between 1.8 and 2.2. Between 200 and 1000 ng DNA was added to the reaction. The Platinum Quantitative PCR SuperMix-UDG (Life Technologies) was used with primer concentrations of 500 nM, probe concentration 300 nM and the following PCR cycle: 2 min at 50° C. (UDG incubation), 15 min at 95° C. (inactivation of UDG), followed by 50 cycles of 15 seconds at 94° C. (template denaturation), 30 seconds at 55° C. (primer annealing) and 15 seconds primer elongation.

DETAILED DESCRIPTION OF EXPERIMENTS

Materials and Methods

Sample Material.

Samples were collected from three different Norwegian salmon farms in which the fish had suspected SGPV-related disease (gill apoptosis) (Table 2) and at the following clinical stages: premortality (n=20; samples were taken 1 to 3 days before mortality was observed), mortality (n=60; samples were taken from tanks in which mortality occurred and lethargic fish crowded on the bottom), and postmortality (n=10; samples were taken from tanks in which mortality was observed a week prior to sampling). The average weight was 27 g (range, 10 to 40 g).

TABLE 2

Overview of material from Norwegian salmon farms

| | Cases (gill apoptosis) | | | Archival cases 1995-2006 | Controls (no gill apoptosis) | |
|---|---|---|---|---|---|---|
| Diseased fish: | Farm A fish (n) | Farm B fish (n) | Farm C fish (n) | Fish (n)/farms (n) | Diseased fish (n)/farms (n) | Healthy fish (n)/farms (n) |
| Pre-mortality | 20 | — | — | 39/14 | 48/8 | 3/1 |
| Mortality* | 30 | 25 | 5 | | | |
| Post-mortality | 10 | — | — | | | |

*Sampling was performed on 5 dead and 25 moribound fish. Except for the 5 dead fish, all fish used in this study were sampled while still alive.

Archived, formalin-fixed, paraffin-embedded (FFPE) gill tissue was identified from 14 cases with records of gill disease and apoptotic gill epithelial cells. These cases were geographically spread in both fresh- and seawater sites in Norway (Table 2). Included were 12 fish from the first known outbreak of so-called amoebic gill disease in Norway (32). A separate TEM study also demonstrated poxvirus-like particles in those 12 fish. In addition, samples from 48 fish with other gill diseases (without gill epithelial apoptosis) and 3 healthy fish were included as controls (Table 2; see also Table 4).

Tissue Sampling for Histology, TEM, and PCR.

All fish were anesthetized and autopsied, and gill tissues were fixed in neutral phosphate-buffered 10% formalin for histology and in RNAlater (Qiagen Inc., Valencia, Calif., USA) for quantitative PCR (qPCR). Additional organs sampled for histology were heart, liver, intestine, spleen, kidney, muscle, and skin. Additional organs sampled for PCR were spleen, kidney, and skin from five fish in the premortality stage and five dead fish from farm A (Table 2). Formalin-fixed gill tissue from one fish in the premortality stage and one fish in the mortality stage was prepared for TEM as described previously (33).

In Situ Staining Methods.

Paraffin-embedded and hematoxylin and eosin (H&E)-stained sections were made for histology. For a subset of the samples, a terminal deoxynucleotidyltransferase-mediated dUTP-biotin nick end labeling (TUNEL) in situ cell death detection kit AP (Roche, Basel, Switzerland) was used to confirm apoptosis. Prussian blue staining was used to verify hemosiderosis in the spleen and kidney. Staining for osmoregulatory chloride cells and proliferating cell nuclear antigen (PCNA) was performed as described previously (34, 35).

Immunohistochemistry (IHC) for SGPV.

Sections from gills were dewaxed, rehydrated, treated to demask antigen, and blocked with 5% bovine serum albumin in Tris-buffered saline to prevent nonspecific binding. Sections were incubated at 4° C. overnight with a rabbit antibody (Pacific Immunology, Ramona, Calif., USA) generated against the synthesized peptide GVNVDVKEFMQKFESNLSN-Cys (SEQ ID NO:11) which is part of the L1 protein, a transmembrane protein expressed on the surface of the intracellular mature virion). Visualization was performed using an EnVision kit (Dako, Glostrup, Denmark) with horseradish peroxidase and 3-amino-9-ethylcarbazole as the chromogen.

DNA Isolation and qPCR Detection.

DNA was isolated from various tissues using a QIAcube system and a QIAamp DNA minikit according to the manufacturer's recommendations (Qiagen Nordic, Oslo, Norway). For archive material, a QIAamp DNA FFPE tissue kit was used (Qiagen Inc., Valencia, Calif., USA). A qPCR assay based on the SGPV genomic sequence was designed for the molecular detection of virus DNA. The target locus was the homolog of the vaccinia virus (VACV) D13L open reading frame (ORF), which has been suggested to be a unique feature of poxviruses. The assay comprised forward primer ATCCAAAATACGGAACATAAGCAAT (SEQ ID NO:8), reverse primer CAACGACAAGGAGATCAACGC (SEQ ID NO:9), and the minor groove binding (MGB) probe CTCAGAAACTTCAAAGGA (SEQ ID NO:4) labeled with 6-carboxyfluorescein and a minor groove binding nonfluorescence quencher (MGBNFQ). The assay was run using a Platinum quantitative PCR SuperMix-uracil DNA glycosylase (UDG) kit (Life Technologies AS, Oslo, Norway) and the following PCR parameters: 50° C. for 2 min (for UDG incubation), 95° C. for 15 min (for UDG inactivation), and 50 cycles of 94° C. for 15 s, 55° C. for 30 s, and 72° C. for 15 s. Reactions with threshold cycle ($C_T$) values above 40 were repeated for confirmation of the results. All results with $C_T$ values above 45 were considered negative. In this study, there were no $C_T$ values between 35 and 45.

When sections were cut from archival FFPE tissue, healthy fish gill tissue samples were interspersed between the samples from different disease outbreaks to control for carryover contamination. Isolation of DNA from FFPE tissue sections was done with a QIAamp DNA FFPE tissue kit according to the manufacturer's instructions (Qiagen Inc., Valencia, Calif., USA).

RNA and DNA Sequencing.

On the basis of the findings of TEM analyses, an Atlantic salmon gill tissue specimen containing poxvirus-like particles was selected for high-throughput sequencing. Total RNA was isolated from gill tissue fixed in RNAlater (Qiagen Norge, Oslo, Norway) using an RNeasy kit (Qiagen) and treated with Turbo DNA-free DNase (Life Technologies AS, Oslo, Norway) according to the manufacturer's recommendations. After DNase inactivation, 50 ng of total RNA was reverse transcribed and amplified using a QuantiTect whole-transcriptome kit (Qiagen). An initial round of total RNA pyrosequencing was done using a Roche 454 GS-FLX system and Titanium chemistry (454 Life Sciences, a Roche Company, Branford, Conn., USA). All reads (521,710) from all reading frames and both strands were translated into protein sequences, and searches for sequence similarity to all poxvirus sequences available in GenBank were performed using the tblastx program (11). Two reads with weak similarity to known poxvirus sequences were identified, and one of these reads was used to design a qPCR assay (forward primer, ATCCAAAATACGGAACATAAGCAAT (SEQ ID NO:8); reverse primer CAACGACAAGGAGATCAACGC (SEQ ID NO:9); MGB probe, CTCAGAAACTTCAAAGGA (SEQ ID NO:4); all sequences are written 5' to 3'). Using the assay, a gill tissue sample with a high viral DNA content was selected for a subsequent round of sequencing. Total DNA was prepared using a DNeasy kit (Qiagen) and sequenced directly using a paired-end strategy and an Illumina HiSeq 2500 system (Illumina, Inc., San Diego, Calif., USA). Reads were assembled de novo using a Velvet sequence assembler. Primers for PCR-based gap closing were designed using the software Primer Express (version 2.0.0; Applied Bio-systems, Life Technologies Corporation, Carlsbad, Calif., USA), and PCR was performed using a HotStarTaq master mix kit (Qiagen). Amplification products were sequenced directly using Sanger sequencing.

The sequencing with the Illumina system gave a total of 169,083,705 pairs of 101-bp reads. Using the Velvet sequence assembler, a total of 68,968 high-confidence contigs could be generated (coverage, >10 times; length, >100 bp). A contig containing the two reads originally identified as being poxvirus-like was found, and pairs of reads where one partner mapped uniquely to one contig and the other mapped to a different contig were extracted using the poxvirus-like contig as a starting point. Using this information, 24 of the contigs produced by the Velvet sequence assembler could be arranged into a tentative scaffold of the genome. PCR was successful across all gaps, but for a small number of loci, the exact number of low-complexity repeats could not be established using Sanger sequencing due to length and base compositional bias. Instead, the approximate lengths of repeat regions were determined using a 2100 Bioanalyzer and a DNA 1000 kit (Agilent Technologies, Santa Clara, Calif., USA) to analyze the gap PCR products. Only 5 of the original 521,710 reads from the 454 sequencing data set could be mapped back to the final version of the virus genome. The five reads ranged in length from 52 to 528 bases, and the longest read was identical to the one that was used to design the PCR assay.

Genome Annotation.

The SGPV genome was translated by Gene-MarkS software (http://exon.biology.gatech.edu/); long (>80-nucleotide) intergenic regions were checked for the presence of ORFs, and ORFs ranging from 50 to 100 codons were annotated to be predicted protein-coding genes if they showed significant sequence similarity to other proteins or to a conserved domain in the National Center for Biotechnology Information Conserved Domains Database or contained predicted transmembrane helices and/or a signal peptide. Transmembrane helices were predicted using the TMHMM server (http://www.cbs.dtu.dk/services/TMHMM/), and signal peptides were predicted using the SignalP (version 4.1) server (http://www.cbs.dtu.dk/services/SignalP/). Tandem direct repeats were detected using the Tandem Repeats Finder program.

Protein Sequence Analysis and Phylogenetic Trees.

For detection of protein sequence similarity, the nonredundant protein sequence data-base at the National Center for Biotechnology Information (NIH, Bethesda, Md.) was searched using the PSI-BLAST program (37). Predicted proteins of SGPV were assigned to clusters of nucleo-cytoplasmic virus orthologous genes (NCVOGs) using the PSI-COG-NITOR program as previously described (38, 39). For phylogenetic analysis, protein sequences were aligned using the MUSCLE program (40) (http://www.ncbi.nlm.nih.gov/pubmed/15034147), and columns containing a large fraction of gaps (greater than 30%) and columns with low information content were removed from the alignment. The alignment was used to construct an initial maximum likelihood (ML) phylogenetic tree with the FastTree program (http://www.ncbi.nlm.nih.gov/pubmed/20224823) with default parameters. The initial tree and the alignment were fed to the ProtTest program (41) to select the best substitution matrix. For each protein family, the best matrix found by ProtTest was used to construct the final ML tree with the TreeFinder program (42).

For the construction of the phylogenetic tree of poxviruses, multiple-sequence alignments of the sequences of 13 core genes present in all Poxviridae and African swine fever virus (ASFV) were employed. These genes belong to the following NCVOGs: NCVOG0022, major capsid protein; NCVOG0023, a D5-like helicase-primase; NCVOG0031, unclassified DEAD/SNF2-like helicases; NCVOG0038, DNA polymerase elongation subunit family B; NCVOG0076, DNA or RNA helicases of superfamily II; NCVOG0249, packaging ATPase; NCVOG0261, poxvirus early transcription factor (VETF), large subunit; NCVOG0262, poxvirus late transcription factor VLTF-3-like; NCVOG0267, RNA helicase DExH-NPH-II; NCVOG0271, DNA-directed RNA polymerase subunit beta; NCVOG0274, DNA-directed RNA polymerase subunit alpha; NCVOG1117, mRNA capping enzyme; NCVOG1164, A1L late transcription factor VLTF-2.

Reconstruction of Gene Content Evolution.

The tree reconstructed from the concatenated alignment of 13 conserved proteins and the pattern of the presence-absence of SGPV proteins in the current version of the NCVOGs (38) were used to infer the gene loss and gene gain events and to obtain an ML reconstruction of the ancestral gene sets using COUNT software (43), as previously described (39).

Genome Synteny Analysis.

Genome synteny was visualized either with the Artemis genome comparison tool (44) or as dot plots of orthologous gene hits ordered by their positions in the genome (45). The synteny distance between viral genomes was calculated as previously described (45), with minor modifications, and a synteny-based neighbor-joining tree of the Poxviridae was constructed using the Neighbor program in the Phylip package (46).

Nucleotide sequence accession numbers. The complete sequence of the SGPV genome was deposited in GenBank under accession number KT159937.

Results

Evidence for Poxvirus Infection in Farmed Salmon.

The RNA isolated from salmon gill tissue containing poxvirus-like particles included sequences encoding putative proteins with significant similarity to those of poxviruses. A PCR probe was made using one such sequence in order to identify tissue with a high viral DNA content for direct paired-end sequencing. De novo assembly was performed, and gaps were filled in by PCR to generate a unique genome of 241,564 bp, excluding the termini, which were presumed to be covalently closed hairpins, as in other poxviruses. The relationship of the SGPV genome to the genomes of other poxviruses is detailed below.

TABLE 3

Overview of results.

| Clinical stage | No. of fish | Median (range) $C_T$value for poxvirus in gills by qPCR | IHC of gills | Hemophagocytosis |
|---|---|---|---|---|
| Pre-mortality | 220 | 18.1 (15.8-22.4) | 95% | 0% |
| Mortality | 660 | 20.5 (15.7-28.9) | 91.4%* | 66.7% |
| Post-mortality | 110 | 24.7 (18.9-30.7) | 20% | 20% |

*2 dead fish were not suited for IHC because of autolysis.

Figure 3:
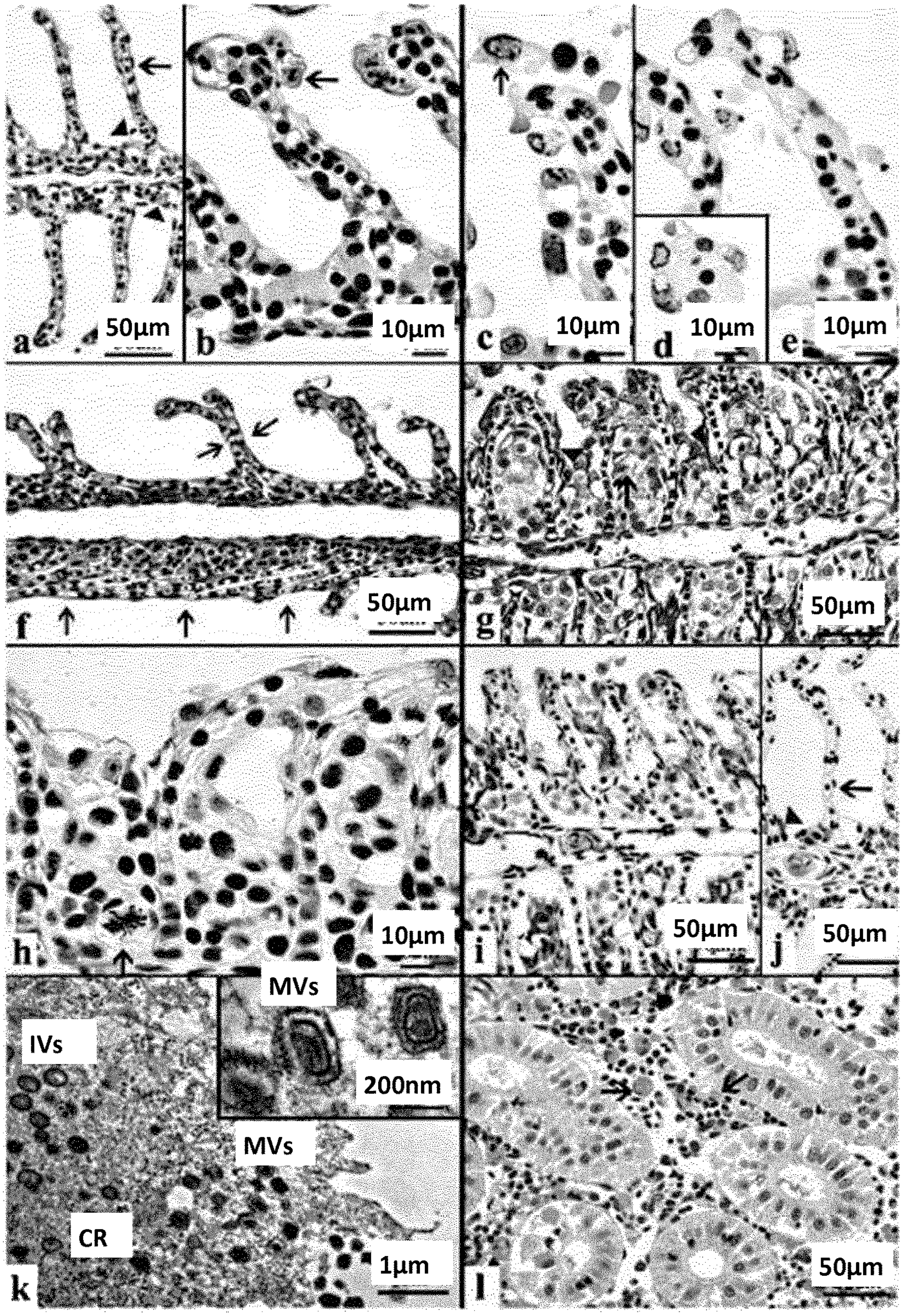
FIG. 3: Normal tissues and pathology in SGPV-infected Atlantic salmon. (a) A normal gill with thin lamellae (arrows) ensures efficient gas exchange. Chloride cells are present in normal numbers and at the normal location (arrowheads). (b and c) Detaching apoptotic cells with central clearing of chromatin (arrows) in the nuclear seen by H&E staining (b) and confirmed by red TUNEL staining (c). (d and e) IHC staining of poxvirus (brown) as cytoplasmic granules (d) and apical budding processes from apoptotic gill epithelial cells (e). (f) H&E staining of collapsed, adherent (arrows) thin lamellae losing apoptotic epithelial cells, creating an atelectasis-like condition hindering gas exchange. (g) H&E staining of proliferating (the arrow indicates metaphase), pale, foamy epithelial cells occluding the normally water-filled interlamellar space for gas exchange. Chloride cells are displaced and degenerated (arrowhead). (h) The lesion in panel g stained by IHC for PCNA showing brown nuclei, including proliferating cells in metaphase (arrow). (i and j) The lesion in panel stained by IHC for chloride cells that are displaced and enlarged (i) compared to the chloride cells in a normal gill (j). (k) TEM showing virus particles consistent with poxvirus in size and shape. Note the presence of crescents (CR), immature virions (IVs), and mature virions (MVs). (l) H&E staining of prominent hemophagocytosis (arrows) in the hematopoietic interrenal tissue. Methods included H&E staining (a, b, f, g, l); IHC staining for TUNEL (c), salmon gill poxvirus (d, e), PCNA (h), and chloride cells (i, j); and TEM (k).

PCR and peptide antibody probes were constructed from SGPV homologs of the highly conserved vaccinia virus D13L gene and L1R virion membrane protein, respectively. Poxvirus DNA was detected by PCR in the gills from all fish sampled from the three outbreak farms, with a trend of increasing $C_T$ values over the disease course being detected (Table 3). In fish removed from tanks 1 to 3 days before death occurred (premortality stage), no lesions were found on autopsy, but most fish had no food in the gut, indicating appetite loss. On histopathology, changes were only found in the gills. Already at this stage, before clinical disease, apoptosis of lamellar epithelial cells were consistently found (FIGS. 1*b* and *c*). Also a general, moderate hypertrophy of this simple squamous epithelium was present, but no major blocking of the respiratory surfaces was found (FIG. 1*b*). A sparse fusion of lamellae due to epithelial proliferation, and a moderate increase in the number of chloride cells were found in a few fish. All gills but one were IHC positive (Table 3). Only apoptotic epithelial cells were stained for poxvirus antigen, either in the cytoplasm or in budding processes stained positive for pox-virus antigen (FIGS. 3*d* and *e*). PCR of spleen and kidney tissue gave no $C_T$ value for four fish, while one fish had a CT value of 33.8 for spleen tissue and a $C_T$ value of 34.4 for kidney tissue. All skin tissue PCRs were positive, with the median $C_T$ value being 29.7 (range, 23.2 to 32.6).

In tanks in which fish were lethargic and there was some mortality (mortality stage), the main autopsy findings were swollen and slightly pale gills. Internal organs were also often pale, some spleens were enlarged, and no feed was found in the gut. Histopathology showed gill apoptosis in all fish at this stage, as described in the premortality stage (FIG. 3*b* to *e*). In addition, more severe gill changes obstructing the respiratory area were present in two different ways. First, in the phase with the severe detachment of apoptotic epithelial cells, the widespread adherence of the thin gill lamellae closed the water-filled space for gas exchange in an atel-ectasis-like manner (FIG. 3*f*). Second, the water-filled space between lamellae was solidified by proliferating epithelial cells (FIG. 3*g*), as demonstrated by PCNA staining (FIG. 3*h*). The proliferation also disrupted the tissue organization of the chloride cells (FIG. 3*i*), and apoptosis of chloride cells was also found. Histopathological lesions were also present in the spleen, kidney, and liver. A pronounced hemophagocytosis by scavenger endothelial cells and macrophages was found in the hematopoietic tissue of the spleen and kidney (FIG. 3*l*). Tissues with hemophagocytosis stained positive for Prussian blue Fe(III), demonstrating hemosiderosis (Table 3). Degenerative liver changes were variable but consistently present in dead fish. On IHC, over 90% of the gills were positive (Table 3), and labeling appeared as it did in the early stages (FIGS. 3*d* and *e*). Furthermore, TEM demonstrated poxvirus-like particles in apoptotic cells (FIG. 3*k*). Crescents, spherical immature virions, and mature virions were seen in the cytoplasm, and these were also present in the extracellular space. Spleen and kidney were PCR negative in 3/5 fish ($C_T$ value range, 32.6 to 35.8). All skin samples were PCR positive, with the median $C_T$ value being 27.1 (range, 22.1 to 31.1).

In tanks in which mortality was observed a week prior to sampling (postmortality stage), most fish had no lesions on autopsy, except one fish had pale gills and four fish had enlarged spleens. Only a minor proliferation of gill epithelial cells, a very few apoptotic cells, and no IHC-positive cells were detected in all except two fish (Table 3). These two fish had pathology similar to that at the premortality stage, showing prevalent apoptosis, IHC-positive cells, and markedly lower $C_T$ values (18.9 and 19.5) than the other fish. We also observed hemophagocytosis in the spleen and kidney at this stage, although to a much lower degree and in fewer fish than in the mortality stage (Table 3). All samples from the control cases with no signs of gill epithelial apoptosis were PCR negative, but a wide range of other gill pathologies as well as evidence for bacterial, fungal, and parasitic infections were present in the unhealthy fish (Table 4).

TABLE 4

Overview of gill lesions in the controls (no gill apoptosis)

| Farm ID | Number of fish | Gill histopathology and visible agents on light microscopy |
|---|---|---|
| D | 9 | Moderate adherences of lamellae and parasitic flagellates (*Ichtyobodo* spp.) |
| E | 4 | Moderate detachment of lamellar epithelial cells |
| F | 4 | Moderately thickened lamellae due to epithelial hypertrophy |
| G | 4 | Severe epithelial proliferation |
| H | 4 | Moderate lifting of epithelial cells and fungal infection |
| I | 3 | Moderate epithelial hypertrophy |
| J | 4 | Severe epithelial proliferation |
| K | 10 | Focal detachment and necrosis of lamellar epithelial cells and bacteria colonizing the apical surface of epithelium |
| L | 6 | Moderate hypertrophy and necrosis of epithelial cells; mucous cell proliferation. |

From each of the 14 archived, formalin-fixed, paraffin-embedded case series, at least one positive gill tissue sample was found by PCR. The 39 diseased fish had a median CT value of 25.9 (range, 20.1 to 36.2). The interspersed control tissues had either high $C_T$ values or no $C_T$ value, indicating low or no cross contamination. All 12 samples from the so-called amoebic gill disease case were positive for poxvirus DNA by qPCR.

Genome Analysis and Evolutionary Relationships of SGPV.

The SGPV genome consists of 241,564 bp (excluding the terminal hairpins) with a 37.5% GC content. The genome contains inverted terminal repeats of 5,679 bp each, similar to other poxviruses. Each of the inverted repeats, in turn, encompasses arrays of direct repeats. However, the tandem direct repeat arrays of SGPV, located at the very ends of the available genomic sequence, consist of only two 89-bp repeat units with 90% identity matches (each of these units consists of two 45-bp repeats with 88% identity). Thus, these direct repeat arrays are much smaller than those detected in other chordopoxviruses, although the possibility that they extend beyond the sequenced portion of the genome cannot be ruled out. Indeed, the highly conserved concatemer resolution sequence that is located between the repeat array and the apex of the terminal hairpin in other poxvirus genomes was not detected at the ends of the available SGPV sequence. The SGPV genome encompasses 206 unique predicted protein-coding genes (4 of these are contained within the terminal repeats and, accordingly, are present in the genome in two copies each; for details on gene prediction, see Materials and Methods). Comparison of the protein sequences encoded by these predicted genes to the sequences in the nonredundant protein sequence database at the National Center for Biotechnology Information (NIH, Bethesda, Md.) using PSI-BLAST identified homologs with significant sequence similarity (E values, <104) for only 60 genes (for several additional predicted proteins, hits with apparently significant E values were identified as originating from regions of low sequence complexity and, accordingly, were dismissed as spurious). In addition to the standard database search, the predicted SGPV protein sequences were compared to the sequences of the NCVOGs (39), clusters of orthologous genes of nucleocytoplasmic large DNA viruses (NCLDVs), using a sequence profile search (see Materials and Methods). This comparison resulted in the assignment of 68 SGPV genes to NCVOGs, including 6 genes that showed no significant similarity to other proteins in BLAST searches. Additionally, a search for conserved domains led to a functional prediction in yet another protein (SGPV102). In total, specific, sequence conservation-based annotations were obtained through these procedures for 71 (34%) SGPV genes (Table 5 and FIG. 3). Among the genes without detectable homologs, 23 contained predicted trans-membrane segments and/or a signal peptide, whereas 111 genes (55%) remained completely uncharacterized. Among the predicted products of these uncharacterized genes, many primarily consisted of low-complexity sequences and/or contained simple amino acid repeats (Table 5). These proteins are likely to be structurally disordered or assume unusual tertiary structures.

Figure 4:
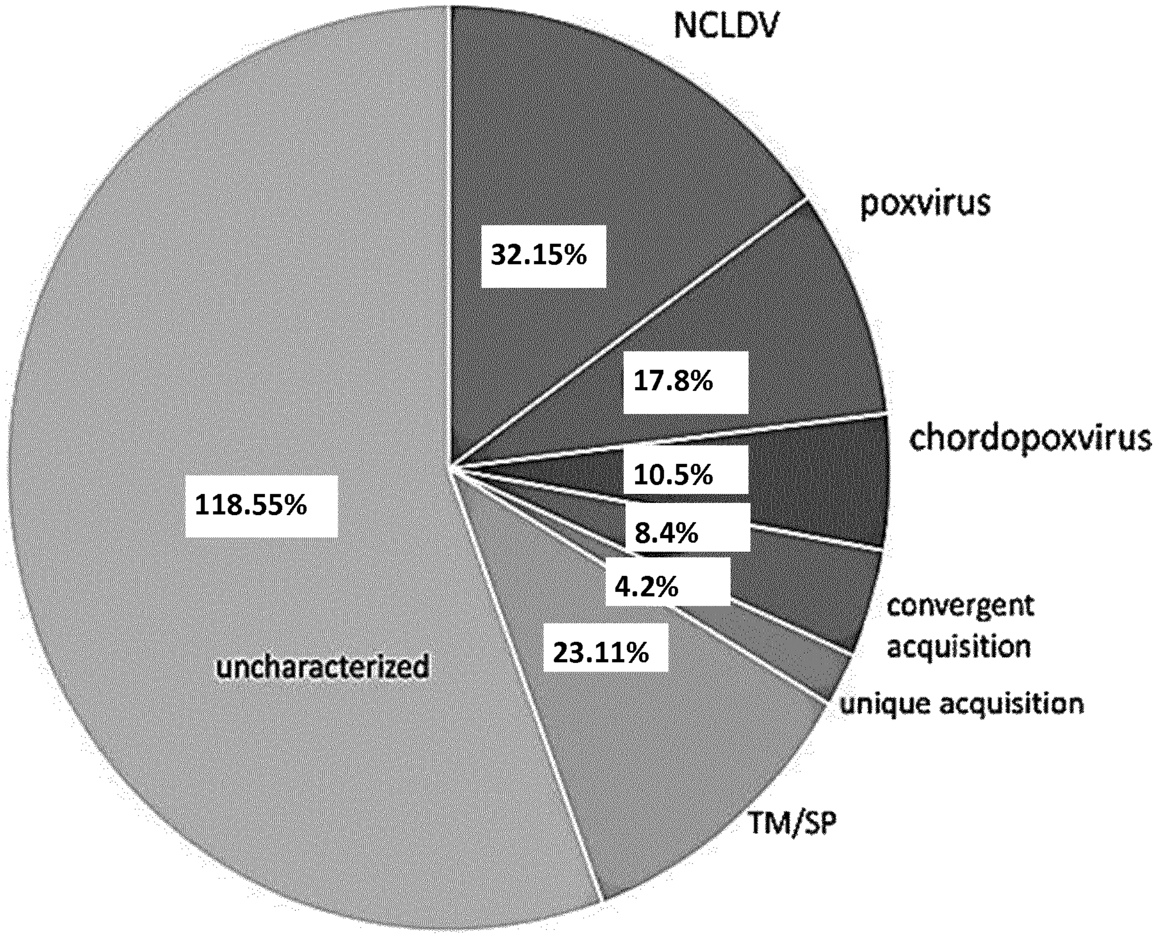
FIG. 4: Distribution of SGPV genes by tiers of inferred origin. The number of genes in each tier and the percentage of the total are indicated. "NCLDV", genes inferred to have been present in the common ancestor of all NCLDV; "poxvirus", genes that originated in the common ancestor of the poxviruses; and "chordopoxvirus", genes that originated in the common ancestor of chordopoxviruses; TM/SP, transmembrane helix/signal peptide.

Among the predicted gene products of SGPV, homologs in other chordopoxviruses were detected for 59 proteins (Table 5 and FIG. 4). Among these conserved chordopoxvirus proteins, 32 belong to the previously inferred ancestral NCLDV gene set (38, 47), 17 are represented in all poxviruses (including entomopoxviruses), and 10 are specific for chordopoxviruses (Table 5 and FIG. 4). Eight genes have homologs in other NCLDVs but most likely were acquired independently (convergently), as suggested by sequence similarity and phylogenetic analysis, and only 4 genes appear to represent unique genes (with respect to the NCLDVs) captured from cellular organisms (Table 5 and FIG. 4; see Discussion below).

Figure 5:
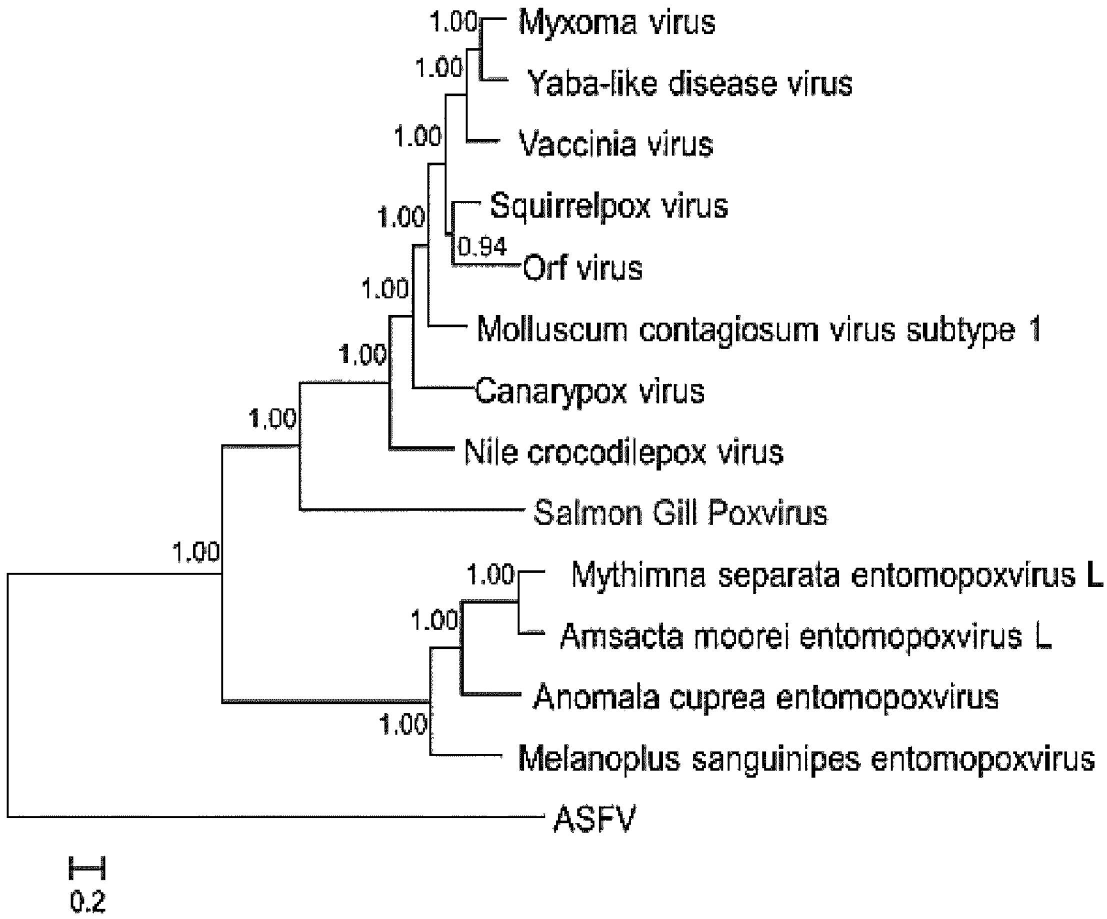
FIG. 5: Phylogenetic tree of poxviruses. The tree was constructed from a multiple-sequence alignment of 13 proteins that are conserved in all poxviruses and ASFV (NCVOG0022, major capsid protein; NCVOG0023, D5-like heli-case-primase; NCVOG0031, unclassified DEAD/SNF2-like helicases; NCVOG0038, DNA polymerase elongation subunit family B; NCVOG0076, DNA or RNA helicases of superfamily II; NCVOG0249, packaging ATPase; NCVOG0261, poxvirus early transcription factor [VETF], large subunit; NCVOG0262, poxvirus late transcription factor VLTF-3-like; NCVOG0267, RNA helicase DExH-NPH-II; NCVOG0271, DNA-directed RNA polymerase subunit beta; NCVOG0274, DNA-directed RNA polymerase subunit alpha; NCVOG1117, mRNA capping enzyme; NCVOG1164, A1L transcription factor VLTF-2). The root position was forced between the two families. Numbers at internal nodes indicate bootstrap support (on a scale of from 0 to 1).

The conserved gene set includes most of the essential genes involved in virus DNA replication and expression as well as the morphogenesis and structure of the virion core and the capsid (see the discussion of some notable exceptions in “Shared and distinct gene functions between SGPV and other chordopoxviruses and unexpected evolutionary patterns among SGPV genes” below). All conserved genes of SGPV showed the highest sequence similarity to the orthologs from chordopoxviruses, with only 3 exceptions, where the highest similarity (albeit by a small margin) was observed with entomopoxvirus orthologs (Table 5). These observations imply that the conserved SGPV genes share an evolutionary history, at least within the poxviruses. Accordingly, we used concatenated multiple-sequence alignments of the sequences of 13 highly conserved genes from this ancestral gene set to construct a maximum likelihood (ML) phylogenetic tree in which the root was placed between ASFV and the poxviruses, given that ASFV and poxviruses are sister groups in the overall NCLDV phylogeny (39). In the resulting tree, SGPV was placed at the root of the chordopoxvirus branch with unequivocal bootstrap support (FIG. 5). Thus, the phylogeny of chordopoxviruses generally follows the phylogeny of their hosts.

Figure 6:
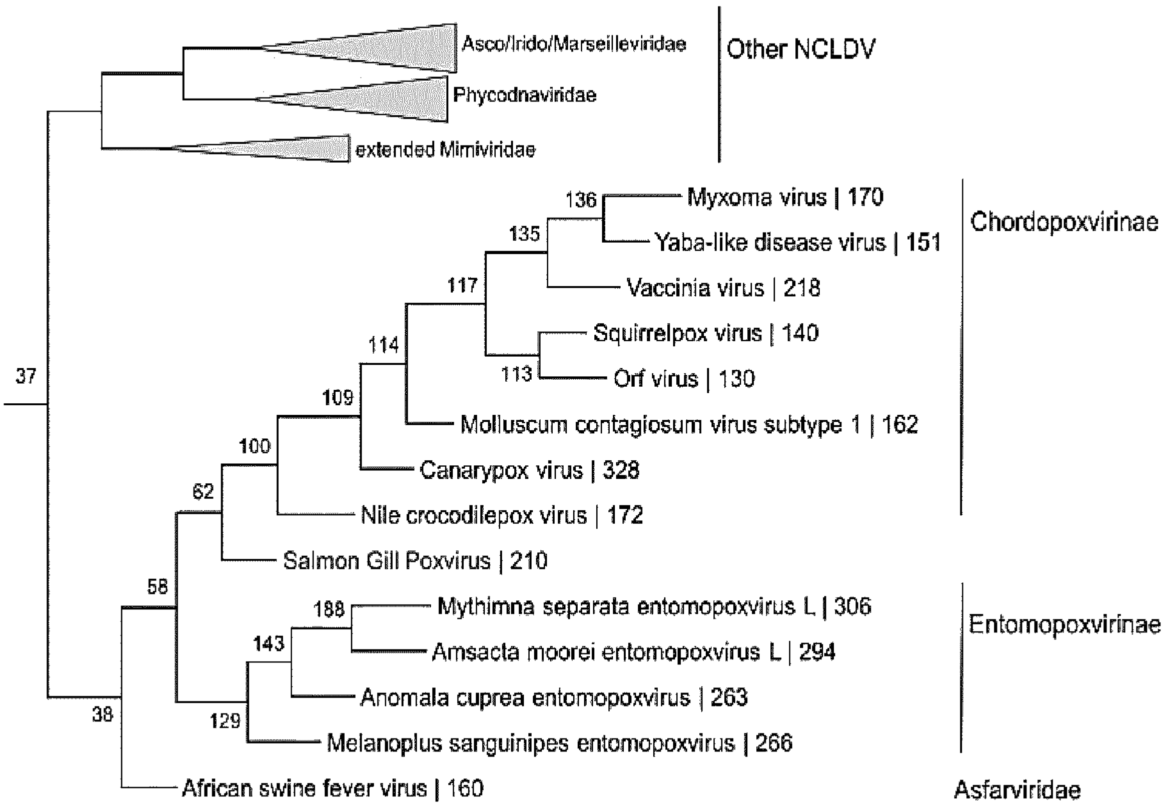
FIG. 6: Reconstruction of the evolution of the gene repertoire of the NCLDVs. The numbers at internal branches (shown only for the ASFV-Poxviridae branch and for the root) indicate the maximum likelihood estimates of the number of genes mapped to the respective ancestral form. The numbers after the virus names indicate the number of annotated genes. The NCLDV families used as outgroups are shown by triangles. The NCLDV tree topology is from reference 39.

In order to gain further insight into the evolution of the gene complement of SGPV, we performed an ML reconstruction of the ancestral gene sets using the poxvirus phylogenetic tree (FIG. 5) as a guide. The inferred ancestral gene sets showed an unexpected pattern (FIG. 6): 58 genes were mapped to the common ancestor of all poxviruses, and 62 genes were mapped to the common ancestor of chordopoxviruses. Thus, taken in their entirety, chordopoxviruses possess almost the same conserved gene set as the entire family Poxviridae, with very few additional conserved genes appearing after the divergence from the common ancestor with entomopoxviruses. In contrast, 38 additional genes were mapped to the common ancestor of the chordopoxviruses infecting tetrapods; i.e., these genes were gained along the tree branch between SGPV and crocodile poxvirus (CrPV). Thus, the reconstruction reveals a dramatic difference in the conserved gene repertoires between the common ancestor of all chordopoxviruses and the tetrapod poxvirus ancestor (FIG. 6). This difference likely reflects a major biological transition, the possible nature of which is discussed in "Shared and distinct gene functions between SGPV and other chordopoxviruses and unexpected evolutionary patterns among SGPV genes" below.

TABLE 5

Predicted genes of SGPV[a]

| SGPV gene | Genome coordinates (protein length[b]) | NCVOG no. | Representation among NCLDVs | VACV gene name | Best hit (GI\|Eval\| % identity\|aln_len\|organism) | Predicted TM and SP | Functional annotation, comments, or inferred origin |
|---|---|---|---|---|---|---|---|
| 001 | 1248-298 (317) | | | | | | Hypothetical protein |
| 002 | 2205-1288 (306) | | | | | | Hypothetical protein |
| 003 | 3227-2241 (329) | | | | | | Hypothetical protein; low sequence complexity |
| 004 | 4788-3361 (476) | | | | | | Hypothetical protein |
| 005 | 5884-4934 (317) | | | | | | Hypothetical protein |
| 006 | 7314-6361 (318) | | | | | | Hypothetical protein |
| 007 | 7770-7438 (111) | | | | | | Hypothetical protein |
| 008 | 8702-7830 (291) | | | | | | Hypothetical protein |
| 009 | 9383-9054 (110) | | | | | 1 TM (C) | Hypothetical type I membrane protein, heptad repeats |
| 010 | 9911-9546 (122) | | | | | | Hypothetical protein; low sequence complexity |
| 011 | 11295-10021 (425) | | | | | | Hypothetical protein; low sequence complexity |
| 012 | 12365-11373 (331) | | | | | | Hypothetical protein |
| 013 | 13629-12421 (403) | | | | | | Hypothetical protein |
| 014 | 15099-13681 (473) | | | | | | Hypothetical protein |
| 015 | 15912-15166 (249) | | | | | | Hypothetical protein |
| 016 | 16318-16007 (104) | | | | | | Hypothetical protein |
| 017 | 17728-16409 (440) | | | | | | Hypothetical protein |
| 018 | 18401-17922 (160) | | | | | | Hypothetical protein |
| 019 | 18870-18373 (166) | | | | | | Hypothetical protein |
| 020 | 19147-18863 (95) | | | | | | Hypothetical protein |
| 021 | 19468-19196 (91) | | | | | | Hypothetical protein |
| 022 | 19721-19533 (63) | | | | | 1 TM (M) | Hypothetical membrane protein |
| 023 | 20272-19751 (174) | | | | | | Hypothetical protein |
| 024 | 21336-20332 (335) | | | | | | Hypothetical protein |
| 025 | 21953-21345 (203) | | | | | | Hypothetical protein |
| 026 | 23067-21967 (367) | | | | | | Hypothetical protein |
| 027 | 24336-23167 (390) | | | | | | Hypothetical protein |
| 028 | 25255-24395 (287) | | | | | | Hypothetical protein |
| 029 | 25986-25294 (231) | | | | | | Hypothetical protein |
| 030 | 26353-26033 (107) | | | | | | Hypothetical protein |
| 031 | 26850-26389 (154) | | | | | 1 TM (C) | Hypothetical type I membrane protein |
| 032 | 27837-26851 (329) | 0017 | Phy, Mimi, Ent | | 401825817\|3.E−11\|28\|180\|*Encephalitozoon hellem* ATCC 50504 | | N-Myristoyl transferase; probable independent acquisition in different viruses; CACQ |
| 033 | 28446-27847 (200) | | | | | | Hypothetical protein |
| 034 | 28512-30752 (747) | 0330 | Most NCLDVs, all families except Asf | | 660515722\|3.E−07\|26\|242\|Armadillidium vulgare iridescent virus | | Divergent RING finger protein, potential E3 subunit of ubiquitin ligase; uncharacterized N-terminal domain upstream of RING |

TABLE 5-continued

Predicted genes of SGPV[a]

| SGPV gene | Genome coordinates (protein length[b]) | NCVOG no. | Representation among NCLDVs | VACV gene name | Best hit (GI\|Eval\| % identity\|aln_len\|organism) | Predicted TM and SP | Functional annotation, comments, or inferred origin |
|---|---|---|---|---|---|---|---|
| | | | | | | | domain; RING proteins in different NCLDVs likely have different origins; this SGPV protein is most similar to homologs from Iri and Phy; CACQ |
| 035 | 31420-30749 (224) | | | | | | Hypothetical protein |
| 036 | 32306-31434 (291) | | | | | | Hypothetical protein |
| 037 | 34172-32325 (616) | | | | | | Hypothetical protein |
| 038 | 34466-34263 (68) | | | | | SP | Hypothetical protein |
| 039 | 34829-34503 (109) | | | | | | Hypothetical protein |
| 040 | 35364-34792 (191) | 0202 | Pox, Iri | | 617520525\|5.E−06\|30\|123\|*Poecilia formosa* | 1 TM (C), SP | Ig domain type I membrane protein; not closely related to Ig domain-containing proteins of other NCLDVs; CACQ |
| 041 | 35957-35583 (125) | | | | | | Hypothetical protein |
| 042 | 36110-36592 (161) | | | | | 1 TM | Hypothetical protein |
| 043 | 36828-37679 (284) | 0284 | Some representatives of most NCLDVs except Asf | | 511086842\|1.E−59\|39\|276\|*Entamoeba histolytica* | | Ser/Thr protein kinase; probable eukaryotic origin; putative ribosomal protein S6K, mTOR pathway component; not closely related to any other NCLDV kinase, likely independent origin; CACQ |
| 044 | 38096-37665 (144) | | | | | 1 TM (M) | Hypothetical membrane protein |
| 045 | 39115-38135 (327) | 1068 | Scattered distribution in all NCLDV families | F2L | 254568556\|8.E−14\|33\|141\|*Komagataella pastoris* GS115 | 1 TM (N) | Trimeric dUTPase highly similar to homologs from Phy but not poxviruses; contains uncharacterized N-terminal domain with a predicted TM; ANC |
| 046 | 39674-39102 (191 | | | | | | Hypothetical protein |
| 047 | 40162-39689 (158) | | | | | | Hypothetical protein |
| 048 | 40352-40882 (177) | | | | | | Hypothetical protein |
| 049 | 41988-40891 (366) | | | | | | Hypothetical protein |
| 050 | 42947-42033 (305) | | | | | | Hypothetical protein |
| 051 | 45667-42950 (906) | | | | 502875360\|8.E−4\|24\|403\|*Planctomyces limnophilus* | | Metalloendopeptidase of the M60-like family; UAQ |
| 052 | 46422-45664 (253) | | | | | 1 TM (C) | Hypothetical type I membrane protein |
| 053 | 46580-46422 (53) | | | | | 1 TM (C) | Hypothetical type I membrane protein |
| 054 | 47190-46636 (185) | | | | | 1 TM (N) | Hypothetical type II membrane protein |
| 055 | 48431-47325 (369) | | | | | | Hypothetical protein |
| 056 | 49116-48292 (275) | | | | | | Hypothetical protein |
| 057 | 50255-49101 (385) | | | | | | Hypothetical protein |

TABLE 5-continued

| Predicted genes of SGPV[a] | | | | | | | |
|---|---|---|---|---|---|---|---|
| SGPV gene | Genome coordinates (protein length[b]) | NCVOG no. | Representation among NCLDVs | VACV gene name | Best hit (GI\|Eval\| % identity\|aln_len\|organism) | Predicted TM and SP | Functional annotation, comments, or inferred origin |
| 058 | 52022-50265 (586) | | | | | | Hypothetical protein |
| 059 | 52040-52516 (159) | 1122 | All Pox, some Iri, Mimi | J5 | | 1 TM | Myristylated membrane protein, entry-fusion complex subunit; ANC; TAAATG |
| 060 | 53257-52439 (273) | | | | | | Hypothetical protein |
| 061 | 53859-53299 (187) | 0258 | All Chor | J4R | 13876678\|1E−08\|31\|186\|lumpy skin disease virus | | DNA-dependent RNA polymerase subunit Rpo22; CPOX |
| 062 | 54821-53886 (312) | 1152 | All Pox, Pith, some Mimi | J3R | 41057489\|3E−42\|36\|276\|bovine papular stomatitis virus | | Poly(A) polymerase small subunit, cap O-methyltransferase; ANC |
| 063 | 55426-54788 (213) | | | | | | Hypothetical protein |
| 064 | 55824-55390 (145) | | | | | 1 TM (M) | Hypothetical membrane protein |
| 065 | 56600-55842 (253) | 1063 | All Pox | L4R | | | DNA-binding virion core protein VP8; POX; TAAATG |
| 066 | 56631-57599 (323) | 1168 | All Pox | L3L | 659488262\|5.E−08\|24\|308\|penguinpox virus | | Virion protein required for early transcription; POX |
| 067 | 59023-57596 (476) | 0295 | Most NCLDV families except Asf and Pan | F10L | 544837\|6.E−26\|28\|396\|variola virus VAR, India-1967, peptide, 439 amino acids | | Protein kinase involved in early stages of virion morphogenesis; ANC |
| 068 | 59043-59897 (285) | 0249 | All NCLDVs | A32L | 12085104\|1.E−17\|28\|264\|Yaba-like disease virus | | DNA packaging ATPase; ANC; TAAATG |
| 069 | 59901-60317 (139) | | | | | | Hypothetical protein |
| 070 | 62029-60323 (569) | 1165 | All Pox | E1L | 9631476\|2.E−14\|23\|381\|*Melanoplus sanguinipes* entomopoxvirus | | Poxvirus poly(A) polymerase catalytic subunit POX |
| 071 | 62691-62071 (207) | 0272 | All Pox, most other NCLDVs | E4L | 38229198\|5.E−18\|29\|174\|Yaba monkey tumor virus | | Transcription factor S-II (TFIIS); ANC; TAAATG |
| 072 | 63448-62681 (256) | | | | | | Hypothetical protein |
| 073 | 64802-63516 (429) | | | | | | Hypothetical protein |
| 074 | 64862-66538 (559) | 1173 | All Pox | E6R | 40556061\|3E−07\|19\|547\|canarypox virus | | Virion protein required for the formation of mature virions; POX; TAAATG |
| 075 | 66539-67645 (369) | | | | | | Hypothetical protein; low sequence complexity |
| 076 | 70831-67634 (1,066) | 0038 | All NCLDVs | E9L | 659488229\|5E−142\|32\|1027\|penguinpox virus | | DNA polymerase ANC |
| 077 | 71147-70848 (100) | 0052 | All NLCDVs | E10R | 40556058\|3E−24\|48\|92\|canarypox virus | 1 TM (false positive) | Disulfide (thiol) oxidoreductase (Erv1/Alr family) involved in disulfide bond formation during virion morphogenesis; ANC; TAAATG |
| 078 | 71159-71788 (210) | | | | | | Hypothetical protein |
| 079 | 72152-71760 (131) | | | | | | Hypothetical protein |
| 080 | 73310-72168 (381) | 1160 | All Chor | I1L | 5830616\|4E−13\|27\|281\|variola minor virus | | DNA-binding virion core protein; CPOX |
| 081 | 74930-73677 (418) | | | | | | Hypothetical protein |
| 082 | 76048-74933 (372) | 1171 | All Chor | I6L | | | Telomere-binding protein involved in viral DNA |

TABLE 5-continued

Predicted genes of SGPV[a]

| SGPV gene | Genome coordinates (protein length[b]) | NCVOG no. | Representation among NCLDVs | VACV gene name | Best hit (GI\|Eval\| % identity\|aln_len\|organism) | Predicted TM and SP | Functional annotation, comments, or inferred origin |
|---|---|---|---|---|---|---|---|
| | | | | | | | encapsidation; CPOX; TAAATG |
| 083 | 77179-76049 (377) | | | | | | Hypothetical protein |
| 084 | 77295-78926 (544) | | | | | | Hypothetical protein |
| 085 | 79246-78857 (130) | | | | | | Hypothetical protein; low sequence complexity |
| 086 | 81234-79657 (526) | | | | | | Hypothetical protein; low sequence complexity |
| 087 | 81913-81221 (231) | | | | | | Hypothetical protein; low sequence complexity |
| 088 | 81912-82319 (136) | | | | | 4 TM | Protein consists of hydrophobic decamer repeats; TM prediction could be spurious |
| 089 | 86171-82275 (1,299) | 0190 | | | | | Hypothetical protein |
| 090 | 88408-86198 (737) | 0031 | Nearly all NCLDVs | D6R | 345107280\|1E−156\|41\|657\|Yoka poxvirus | | SNF2-like helicase involved in early transcription; ANC |
| 091 | 90927-88453 (825) | 0023 | All NCLDVs | D5R | 571798002\|5E−93\|28\|768\|squirrelpox virus | | Primase-helicase; ANC |
| 092 | 91684-90920 (255) | 0211 | All Chor | F9L | 9634782\|8E−06\|33\|123\|fowlpox virus | 1 TM (C) | Myristylated IMV envelope protein; CPOX; TAAATG |
| 093 | 92207-91647 (187) | | | | | | Hypothetical protein |
| 094 | 92262-92876 (205) | 1067 | Mimi | | 494264790\|3E−09\|28\|178\|*Marinobacter algicola* | | Deoxynucleotide monophosphate kinase shared with Mimi, probable bacterial origin; CACQ |
| 095 | 96496-93050 (1,149) | 0037 | Phy, Mimi, Mar, CrPV (multiple paralogs) but not other Pox | | 5121\|2E−53\|25\|933\|*Schizosaccharomyces pombe* | | DNA topoisomerase II; ANC |
| 096 | 96825-96496 (110) | | | | | 1 TM (M) | Hypothetical membrane protein |
| 097 | 97628-96828 (267) | 0211 | Most NCLDVs, all Pox | L1R | 12085043\|2E−29\|31\|225\|Yaba-like disease virus | 1 TM (C) | Myristylated IMV envelope protein; ANC; TAAATG |
| 098 | 99427-97661 (589) | 0022 | All NCLDVs except Pan | D13L | 345107288\|8E−50\|28\|570\|Yoka poxvirus | | Major capsid protein (involved in morphogenesis but not incorporated into virions in poxviruses); ANC |
| 099 | 99845-99456 (130) | 1164 | All NCLDV | A1L | 289183841\|1E−12\|29\|123\|pseudocowpox virus | | Late transcription factor VLTF-2; ANC |
| 100 | 100665-99853 (271) | 0262 | All NCLDVs except Pith | A2L | 571798015\|7E−8\|38\|195\|squirrelpox virus | | Late transcription factor VLTF; ANC |
| 101 | 103192-100967 (742) | 1162 | All Pox, Mimi | A3L | 115531788\|1E−49\|24\|697\|Nile crocodilepox virus | | Poxvirus P4B major core protein; POX |
| 102 | 103950-103237 (238) | | MCV, some Mimi, Phy | | | | J domain-containing protein, putative cochaperonin; distantly related to J domains of other NCLDVs; CACQ |
| 103 | 103956-104498 (181) | 1377 | All Chor | A5R | 40556180\|3E−14\|33\|172\|canarypox virus | | DNA-dependent RNA polymerase subunit Rpo19; CPOX |

TABLE 5-continued

Predicted genes of SGPV[a]

| SGPV gene | Genome coordinates (protein length[b]) | NCVOG no. | Representation among NCLDVs | VACV gene name | Best hit (GI\|Eval\| % identity\|aln_len\|organism) | Predicted TM and SP | Functional annotation, comments, or inferred origin |
|---|---|---|---|---|---|---|---|
| 104 | 105738-104503 (412) | 1179 | All Chor | A6L | | | Virion core protein required for membrane biogenesis and formation of mature virions; CPOX; TAAATG |
| 105 | 107964-105751 (738) | 0261 | All Pox, scattered in other NCLDVs | A7L | 659488305\|2E−104\|32\|734\|penguinpox virus | | VETF, large subunit; ANC |
| 106 | 107945-109252 (436) | 1176 | All Chor | A8R | 40556183\|2E−08\|24\|248\|canarypox virus | | Poxvirus intermediate transcription factor VITF-3 subunit; CPOX; TAAATG |
| 107 | 109518-109261 (86) | | | | | 2 TM | Hypothetical membrane protein |
| 108 | 113053-109535 (1,173) | 0257 | All Pox | A10L | 157939724\|4E−13\|20\|561\|tanapox virus | | Virion core protein P4; POX; TAAATG |
| 109 | 113084-113923 (280) | | | | | | Hypothetical protein |
| 110 | 113964-114296 (111) | | | | | 1 TM (N) | Hypothetical type II membrane protein |
| 111 | 114326-114619 (98) | | | | | | Hypothetical protein; low sequence complexity |
| 112 | 114935-114600 (112) | | | | | | Hypothetical protein containing serine-rich repeats |
| 113 | 115188-115556 (123) | | | | | | Hypothetical protein |
| 114 | 115768-115556 (71) | | | | | 1 TM (N) | Hypothetical type II membrane protein |
| 115 | 117013-115769 (415) | 1045 | Some Iri and Mimi | | 339906034\|2E−07\|30\|145\|Wiseana iridescent virus | | 5'-3' exoribonuclease of the XRN family; NCLDV proteins appear to be monophyletic; ANC |
| 116 | 117383-117045 (113) | | | | | 2 TM | Hypothetical protein |
| 117 | 117721-117401 (107) | | | | | | Hypothetical protein |
| 118 | 118830-117736 (365) | 1122 | All Pox, Mimi, some Iri | A16L | 41057529\|2E−15\|29\|204\|bovine papular stomatitis virus | 1 TM | Myristylated protein, entry-fusion complex subunit; ANC; TAAATG |
| 119 | 119936-118848 (363) | | | | | 2 TM | Hypothetical membrane protein |
| 120 | 119988-121418 (477) | 0076 | All Pox, in many other NCLDVs | A18R | 115531805\|1E−54\|29\|424\|Nile crocodilepox virus | | DNA helicase of superfamily 2, transcript release factor; ANC |
| 121 | 121419-122474 (352) | 2643 | Some Mimi | | 504603808\|3E−15\|30\|151\| *Ornithobacterium rhinotracheale* | | Apurinic-apyrimidinic endonuclease of the exonuclease III family; probable bacterial origin; CACQ |
| 122 | 122812-122465 (116) | 1370 | All Pox | A21L | 506498863\|2E−06\|24\|111\|*Choristoneura rosaceana* entomopoxvirus L. | 1 TM (C) | Type I membrane protein, entry-fusion complex subunit; POX; TAAATG |
| 123 | 122842-125133 (764) | 0035 | CrPV, Ent, some Iri, Mimi | | | | NAD-dependent DNA ligase; poorly conserved sequence but contains intact catalytic residues and shows the closest sequence similarity to NAD-dependent ligases of Ent; ANC |

TABLE 5-continued

<table>
<tr><th colspan="8">Predicted genes of SGPV[a]</th></tr>
<tr><th>SGPV gene</th><th>Genome coordinates (protein length[b])</th><th>NCVOG no.</th><th>Representation among NCLDVs</th><th>VACV gene name</th><th>Best hit (GI|Eval| % identity|aln_len|organism)</th><th>Predicted TM and SP</th><th>Functional annotation, comments, or inferred origin</th></tr>
<tr><td>124</td><td>125105-125602 (166)</td><td>0278</td><td>All Pox, majority of other NCLDVs</td><td>A22R</td><td>659488557|6E−16|32|149|pigeonpox virus</td><td></td><td>RuvC family Holliday junction resolvase; ANC</td></tr>
<tr><td>125</td><td>125599-126816 (406)</td><td>0263</td><td>All Pox</td><td>A23R</td><td>9634858|3E−25|27|395|fowlpox virus</td><td></td><td>Intermediate transcription factor; POX</td></tr>
<tr><td>126</td><td>126817-130305 (1,163)</td><td>0271</td><td>All NCLDVs except some Phy</td><td>A24R</td><td>225194776|0|47|1169|skunkpox virus</td><td></td><td>DNA-directed RNA polymerase subunit beta; TAAATG</td></tr>
<tr><td>127</td><td>130720-130310 (137)</td><td>1418</td><td>All Pox</td><td>A28L</td><td>51317191|3E−17|33|128|Diachasmimorpha longicaudata entomopoxvirus</td><td>1 TM (N)</td><td>Type I membrane protein, entry-fusion complex subunit beta; ANC; TAAATG</td></tr>
<tr><td>128</td><td>131699-130725 (325)</td><td>0260</td><td>All Pox</td><td>A29L</td><td>148912996|9E−08|27|181|goatpox virus Pellor</td><td></td><td>DNA-directed RNA polymerase, 35-kDa subunit; POX</td></tr>
<tr><td>129</td><td>131870-132817 (316)</td><td></td><td></td><td></td><td></td><td></td><td>Hypothetical protein</td></tr>
<tr><td>130</td><td>132821-133525 (235)</td><td></td><td></td><td></td><td></td><td></td><td>Hypothetical protein</td></tr>
<tr><td>131</td><td>133536-135035 (500)</td><td></td><td></td><td></td><td></td><td></td><td>Hypothetical protein</td></tr>
<tr><td>132</td><td>135013-135495 (161)</td><td></td><td></td><td></td><td></td><td></td><td>Hypothetical protein</td></tr>
<tr><td>133</td><td>135919-135470 (150)</td><td></td><td></td><td></td><td></td><td></td><td>Hypothetical protein</td></tr>
<tr><td>134</td><td>136606-135941 (222)</td><td>1115</td><td>All Pox, scattered in other NCLDVs</td><td>D4R</td><td>9634732|1E−15|28|216|fowlpox virus</td><td></td><td>UDG; ANC</td></tr>
<tr><td>135</td><td>136671-138380 (570)</td><td></td><td></td><td></td><td></td><td></td><td>Hypothetical protein; low sequence complexity</td></tr>
<tr><td>136</td><td>138373-139212 (280)</td><td>0259</td><td>All Pox</td><td>D7R</td><td>9629029|4E−17|30|145|molluscum contagiosum virus subtype 1</td><td></td><td>DNA-directed RNA polymerase, 18-kDa subunit; POX</td></tr>
<tr><td>137</td><td>139235-139879 (215)</td><td>0236</td><td>All Pox, most other NCLDVs</td><td>D10R</td><td>9629031|1E−15|29|161|molluscum contagiosum virus subtype 1</td><td></td><td>Nudix hydrolase, decapping enzyme; ANC</td></tr>
<tr><td>138</td><td>141785-139887 (633)</td><td>0027</td><td>All Pox, some Mimi</td><td>D11L</td><td>115531782|2E−174|43|635|Nile crocodilepox virus</td><td></td><td>Superfamily 2 helicase D11; POX; TAAATG</td></tr>
<tr><td>139</td><td>141949-142902 (318)</td><td>0330</td><td>All NCLDVs except Asco and Pith</td><td></td><td>658035022|2E−06|31|75|Malus domestica</td><td></td><td>RING finger-containing E3 ubiquitin ligase; probably independent acquisition in different NCLDV families; CACQ</td></tr>
<tr><td>140</td><td>143889-142951 (313)</td><td>1169</td><td>All Pox</td><td>D12L</td><td>9629033|3E−31|30|289|molluscum contagiosum virus subtype 1</td><td></td><td>Poxvirus mRNA capping enzyme, small subunit; POX; TAAATG</td></tr>
<tr><td>141</td><td>144893-143889 (335)</td><td>1122</td><td>All Pox, some Mimi, Iri</td><td>G9R</td><td>9634797|7E−06|36|78|fowlpox virus</td><td>1 TM</td><td>Myristylated protein, entry-fusion complex subunit; ANC; TAAATG</td></tr>
<tr><td>142</td><td>145769-144894 (292)</td><td>1369</td><td>All Chor</td><td>G8R</td><td>41057481|1E−06|26|171|bovine papular stomatitis virus</td><td></td><td>Protein containing a derived PCNA domain; VLTF-1; CPOX; TAAATG</td></tr>
<tr><td>143</td><td>145819-147291 (491)</td><td></td><td></td><td></td><td></td><td></td><td>Hypothetical protein</td></tr>
<tr><td>144</td><td>147884-147288 (199)</td><td>1182</td><td>All Pox</td><td>G6R</td><td></td><td></td><td>Predicted hydrolase or acyltransferase of the NlpC/P60 superfamily; weak sequence similarity to orthologs in other poxviruses; POX; TAAATG</td></tr>
</table>

TABLE 5-continued

| Predicted genes of SGPV[a] | | | | | | | |
|---|---|---|---|---|---|---|---|
| SGPV gene | Genome coordinates (protein length[b]) | NCVOG no. | Representation among NCLDVs | VACV gene name | Best hit (GI\|Eval\| % identity\|aln_len\|organism) | Predicted TM and SP | Functional annotation, comments, or inferred origin |
| 145 | 148111-147914 (66) | 1368 | All Chor, one Ent, Asf | G5.5R | 289183806\|2E−04\|24\|65\|pseudocowpox virus | | RNA polymerase, subunit 10 (a very small protein, possibly missed during genome annotation of other viruses); POX |
| 146 | 149892-148072 (607) | 1060 | All Pox, scattered in other NCLDVs | G5R | 539191060\|6E−13\|36\|176\|myxoma virus | | Flap endonuclease required for poxvirus genome replication; ANC |
| 147 | 149931-150485 (185) | | | | 505137967\|1E−05\|41\|59\| *Methanomethylovorans hollandica* | | Thioredoxin; no close homologs in other viruses; UAQ |
| 148 | 150507-150884 (126) | | | | | 1 TM (M) | Hypothetical membrane protein |
| 149 | 150881-152773 (631) | 1170 | All Pox | G1L | 115531736\|6E−35\|31\|233\|Nile crocodilepox virus | | Metalloprotease essential for virion morphogenesis; POX; TAAATG |
| 150 | 154796-152760 (679) | 0267 | All Pox, Asf, Mimi | I8R | 41057099\|5E−121\|37\|597\|orf virus | | RNA helicase of superfamily 2 implicated in early transcription termination; ANC; TAAATG |
| 151 | 154823-156076 (418) | 1161 | All Pox, most other NCLDVs | I7L | 115531734\|7E−15\|21\|429\| | | Virion core cysteine protease involved in virion protein maturation; ANC; TAAATG |
| 152 | 156073-156567 (165) | | | | | | Hypothetical protein |
| 153 | 156623-157354 (244) | | | | | 1 TM (C), SP | Hypothetical protein |
| 154 | 157464-164144 (2,227) | 0269 | All Chor; disrupted in some, including VACVs | (B22R VARV) | 422933904\|3E−120\|29\|1049\|cyprinid herpesvirus 2 | 1 TM (C), SP | Giant type I membrane protein with homologs also in cyprinid herpesviruses, suggestive of gene transfer from SGPV to the herpesviruses (see the phylogenetic tree in FIG. 10); implicated in T cell inactivation; paralog of SGPV159 and SGPV162; CPOX |
| 155 | 164257-168030 (1,258) | | | | | 1 TM (C), SP | Hypothetical type I membrane protein |
| 156 | 168031-169008 (326) | | | | | | Hypothetical protein |
| 157 | 168995-169900 (302) | | | | | | Hypothetical protein |
| 158 | 170583-169939 (215) | | | | | | Hypothetical protein |
| 159 | 170638-173652 (1,005) | 0269 | All Chor; disrupted in some, including VACV | 0 | 9634792\|5E−11\|24\|462\|fowlpox virus | 1 TM (C), SP | Giant type I membrane protein with homologs also in cyprinid herpesviruses, suggestive of gene transfer from SGPV to the herpesviruses (see the phylogenetic tree in FIG. 10); implicated in T cell inactivation; paralog of SGPV154 and SGPV162; CPOX |

TABLE 5-continued

| Predicted genes of SGPV[a] | | | | | | | |
|---|---|---|---|---|---|---|---|
| SGPV gene | Genome coordinates (protein length[b]) | NCVOG no. | Representation among NCLDVs | VACV gene name | Best hit (GI\|Eval\| % identity\|aln_len\|organism) | Predicted TM and SP | Functional annotation, comments, or inferred origin |
| 160 | 173910-173665 (82) | | | | | 1 TM (N) | Hypothetical type II membrane protein containing pentapeptide repeats |
| 161 | 173870-181351 (2,494) | | | | | SP | Hypothetical secreted protein |
| 162 | 181528-185433 (1,302) | 0269 | All Chor; disrupted in some, including VACVs | 0 | 9628967\|5E−25\|25\|413\|molluscum contagiosum virus subtype 1 | 1 TM (C), SP | Giant type I membrane protein with homologs also in cyprinid herpesviruses, suggestive of gene transfer from SGPV to the herpesviruses (see the phylogenetic tree in FIG. 10); implicated in T cell inactivation; paralog of SGPV154 and SGPV159; CPOX |
| 163 | 185473-186558 (362) | | | | | | Hypothetical protein |
| 164 | 186693-188648 (652) | | | | | SP | Hypothetical secreted protein |
| 165 | 188749-192687 (1,313) | 0274 | All NCLDVs except for some Phy | J6R | 115531763\|0\|41\|1311\|Nile crocodilepox virus | | DNA-directed RNA polymerase subunit alpha; ANC |
| 166 | 193271-192684 (196) | | | | | 1 TM (C) | Hypothetical type I membrane protein |
| 167 | 193287-194597 (437) | | | | | SP | Hypothetical secreted protein, pentapeptide repeats |
| 168 | 195155-194586 (190) | 0253 | All Pox | H2R | 594019595\|2E−35\|40\|151\|avipoxvirus OKr-2014 | 1 TM (N) | Type II membrane protein, fusion-entry complex subunit; POX; TAAATG |
| 169 | 197626-195161 (822) | 1163 | All Pox | H4L | 6969751\|3E−67\|30\|583\|vaccinia virus Tian Tan | | Pox_Rap94, RNA polymerase-associated transcription specificity factor, Rap94; POX; TAAATG |
| 170 | 197724-198404 (227) | | | | | | Hypothetical protein |
| 171 | 198405-199343 (313) | 0036 | All Pox, Mimi | H6R | 345107272\|5E−60\|40\|310\|Yoka poxvirus | | DNA topoisomerase IB; ANC; TAAATG |
| 172 | 199715-199329 (129) | | | | | SP | Hypothetical secreted protein |
| 173 | 199747-202368 (874) | 1451 | All NCDLVs except Asco and Pan | D1R | 225194732\|4E−110\|33\|867\|volepox virus | | mRNA capping enzyme large subunit; ANC; TAAATG |
| 174 | 204943-202382 (854) | | | | | | Hypothetical protein |
| 175 | 205237-204956 (94) | | | | | | Hypothetical protein |
| 176 | 205654-205238 (139) | | | | | | Hypothetical protein |
| 177 | 205659-207647 (663) | | | | | | Hypothetical protein |
| 178 | 207690-209033 (448) | | | | | | Hypothetical protein |
| 179 | 209178-209951 (258) | | | | | | Hypothetical protein |
| 180 | 210027-211280 (418) | | | | | | Hypothetical protein |
| 181 | 211532-213193 (554) | | | | | | Hypothetical protein |
| 182 | 213211-213954 (248) | | | | | | Hypothetical protein |
| 183 | 213947-214258 (104) | | | | | | Hypothetical protein |
| 184 | 214236-214847 (204) | | | | | | Hypothetical protein |
| 185 | 215300-214851 (150) | | | | | | Hypothetical protein |

TABLE 5-continued

Predicted genes of SGPV[a]

| SGPV gene | Genome coordinates (protein length[b]) | NCVOG no. | Representation among NCLDVs | VACV gene name | Best hit (GI\|Eval\| % identity\|aln_len\|organism) | Predicted TM and SP | Functional annotation, comments, or inferred origin |
|---|---|---|---|---|---|---|---|
| 186 | 215396-216664 (423) | | | | 167525479\|6E−18\|28\|228\|*Monosiga brevicollis* MX1 | | DNA or RNA methyltransferase; UAQ |
| 187 | 216775-217242 (156) | | | | 209734208\|9E−29\|46\|127\|*Salmo salar* | | Macrodomain, most similar to O-acetyl-ADP-ribose deacetylase; UAQ |
| 188 | 217294-218286 (331) | | | | | | Hypothetical protein |
| 189 | 218360-219514 (385) | | | | | | Hypothetical protein |
| 190 | 219572-220492 (307) | | | | | | Hypothetical protein; low sequence complexity; partly consists of tetrapeptide repeats |
| 191 | 220576-221535 (320) | | | | | | Hypothetical protein |
| 192 | 221579-222580 (334) | | | | | | Hypothetical protein |
| 193 | 222676-223716 (347) | | | | | | Hypothetical protein |
| 194 | 224007-224258 (84) | | | | | | Hypothetical protein; hydrophobic; 12-mer repeats |
| 195 | 224390-225718 (443) | | | | | | Hypothetical protein; low sequence complexity |
| 196 | 226126-226542 (139) | | | | | | Hypothetical protein |
| 197 | 226596-227135 (180) | | | | | | Hypothetical protein; cysteine rich; low sequence complexity |
| 198 | 227202-228812 (537) | | | | | | Hypothetical protein; low sequence complexity |
| 199 | 228872-229897 (342) | | | | | | Hypothetical protein |
| 200 | 229951-230268 (106) | | | | | | Hypothetical protein |
| 201 | 230293-230985 (231) | | | | | | Hypothetical protein |
| 202 | 231098-231802 (235) | | | | | | Hypothetical protein |
| 203 | 232049-233533 (495) | | | | | | Hypothetical protein |
| 204 | 233892-233491 (134) | | | | | 4 TM | Hypothetical protein; hydrophobic, consists mostly of hexapeptide repeats; TM prediction might be false positive |
| 205 | 234526-235545 (340) | | | | | | Hypothetical protein |
| 206 | 235633-236631 (333) | | | | | | Hypothetical protein |
| 207 | 236777-238204 (476) | | | | | | Inverted terminal repeat; identical to SGPV001 gene |
| 208 | 238338-239324 (329) | | | | | | Inverted terminal repeat; identical to SGPV002 gene |
| 209 | 239360-240277 (306) | | | | | | Inverted terminal repeat; identical to SGPV003 gene |
| 210 | 240317-241267 (317) | | | | | | Inverted terminal repeat; identical to SGPV004 gene |

[a]In the first column, "SGPV" is omitted from the gene identifiers for brevity; in the last column "SGPV" is included; GI, GenInfo Identifier sequence identification number); aln_len, the length of pairwise protein alignment produced by BLASTP searches; SP, (predicted) signal peptide; TM, (predicted) transmembrane helix (C, M, and N denote the C-terminal, middle, and N-terminal location of the predicted transmembrane helix in the protein, respectively); the percent identity and alignment length are taken directly from BLASTP searches. IMV stands for intracellular mature virions; VARV stands for variola virus. The inferred origin of genes is indicated as follows: ANC, ancestral to NCLDV; POX, ancestral to poxviruses; CPOX, ancestral to chordopoxviruses; CACQ, convergent acquisition (with other NCLDVs); UAQ, unique acquisition. The transcription start element TAAAT is shown for those SGPV genes that have orthologs from other chordopoxviruses (the sequence TAAATG includes the translation start codon of the respective gene). Abbreviations for groups of viruses: Asco, Ascovindae; Asf, Asfarvindae; Chor; Chordopoxvirinae; CrPV, crocodile poxvirus; Ent, Entomopoxvirinae; Iri, Iridoviridae; Mar, Marseilleviridae; MCV, molluscum contagiosum virus; Mimi, Mimiviridae; Pan, Pandoravirus; Phy, Phycodnaviridae; Pith, Pithovirus; Pox, poxviruses.
[b]Protein lengths are in numbers of amino acids.

Figure 7:
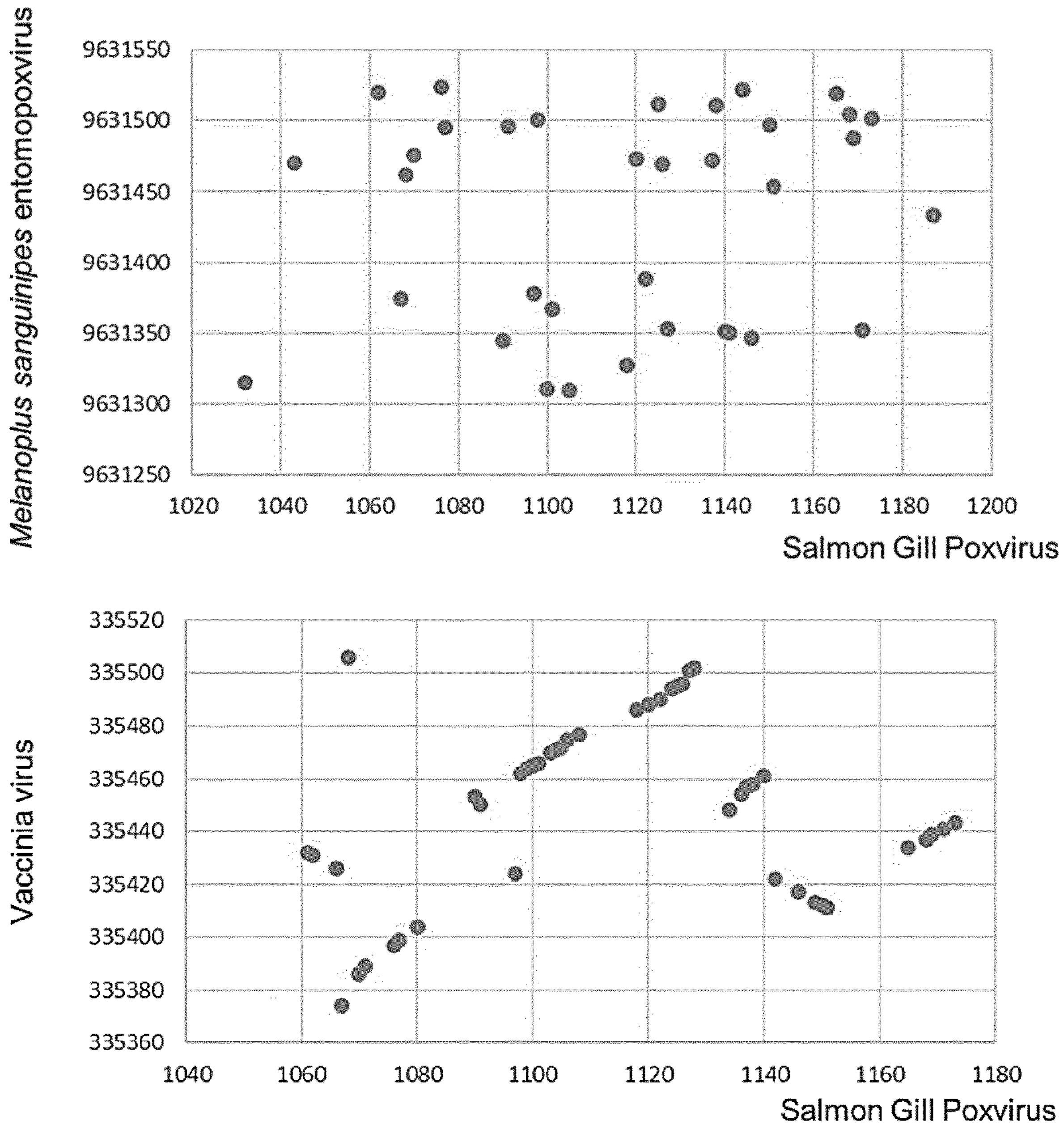
FIG. 7: Dot plot comparison of poxvirus gene orders. Each dot corresponds to a pair of orthologous genes. The horizontal axis shows the SGPV genes, and the vertical axis shows the GenInfo Identifier sequence identification numbers for genes of the respective viruses.
Figure 7:
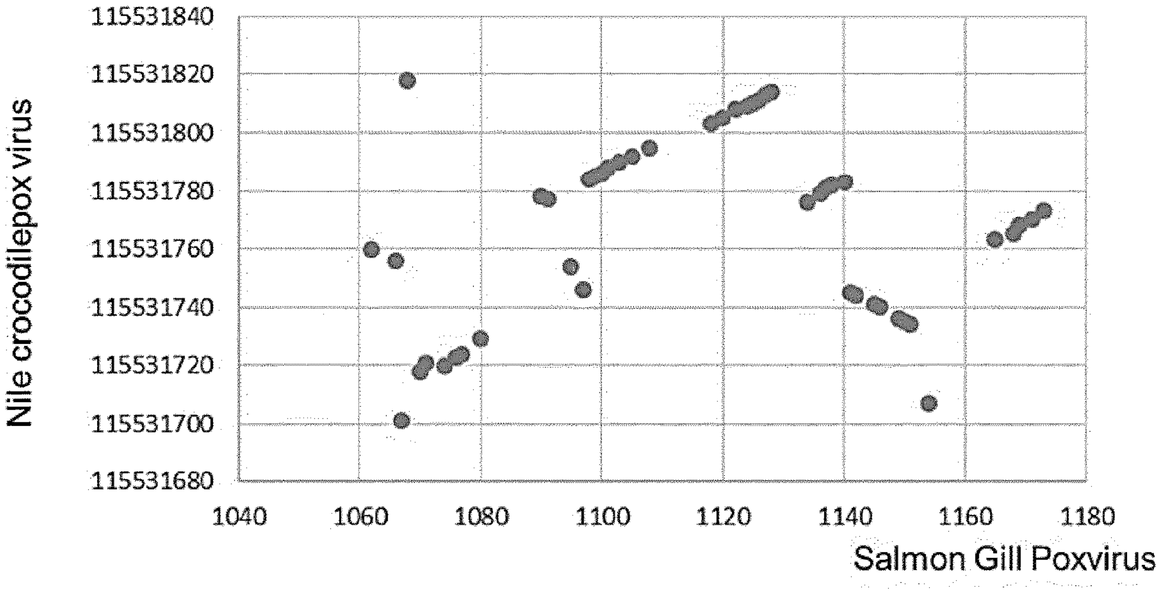
Figure 7:
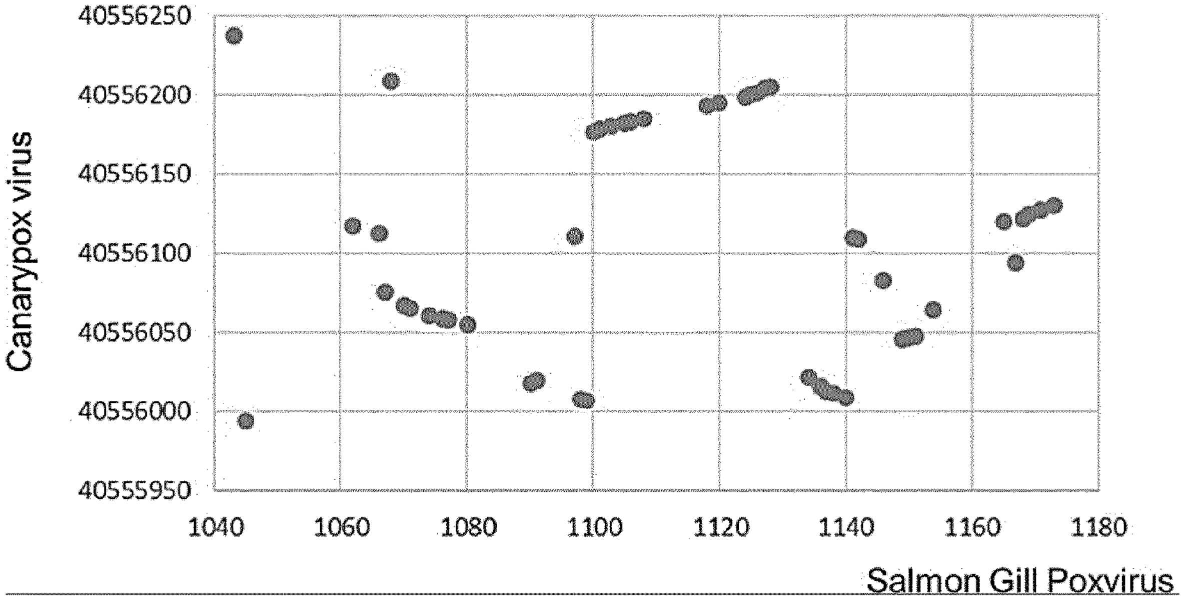
Figure 7:
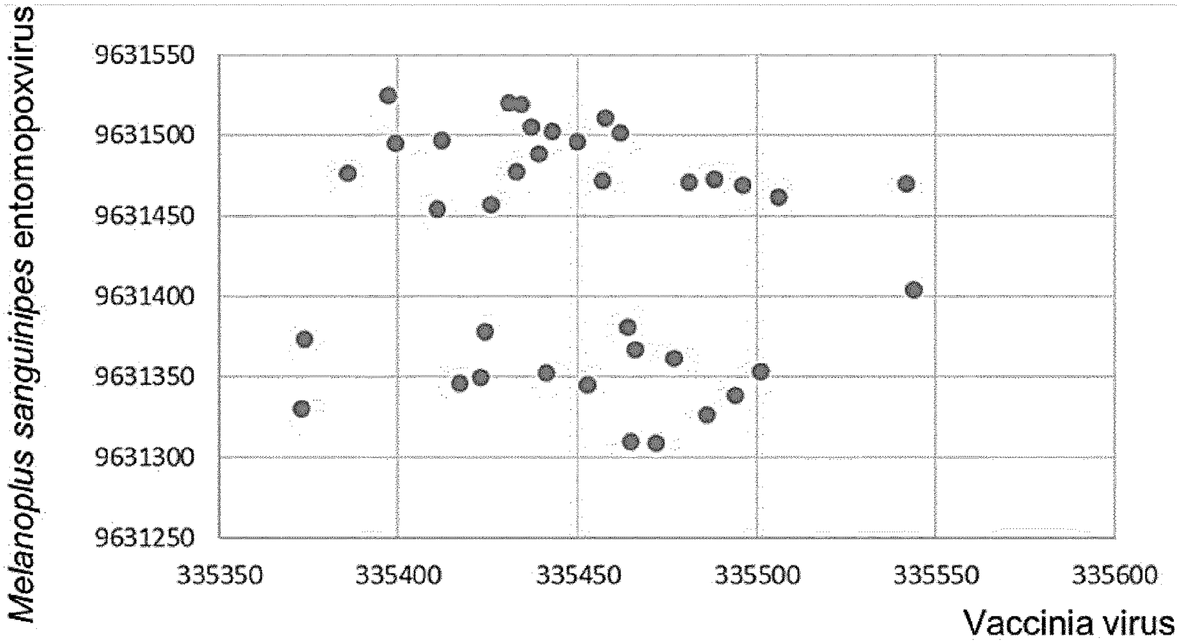
Figure 7:
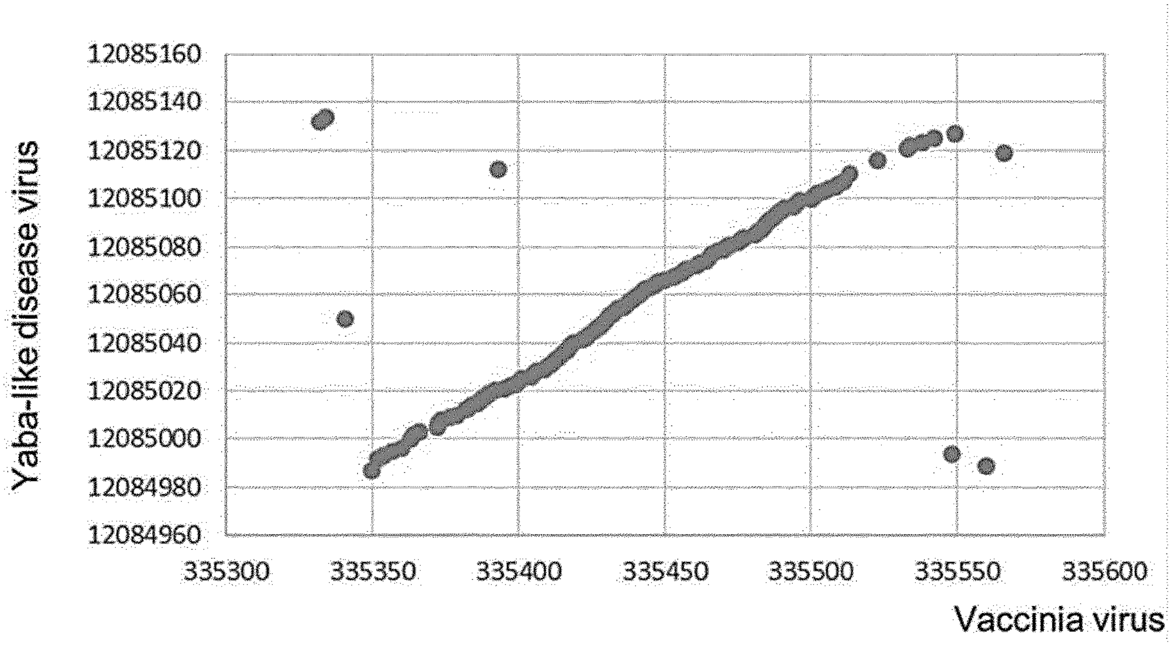
Figure 7:
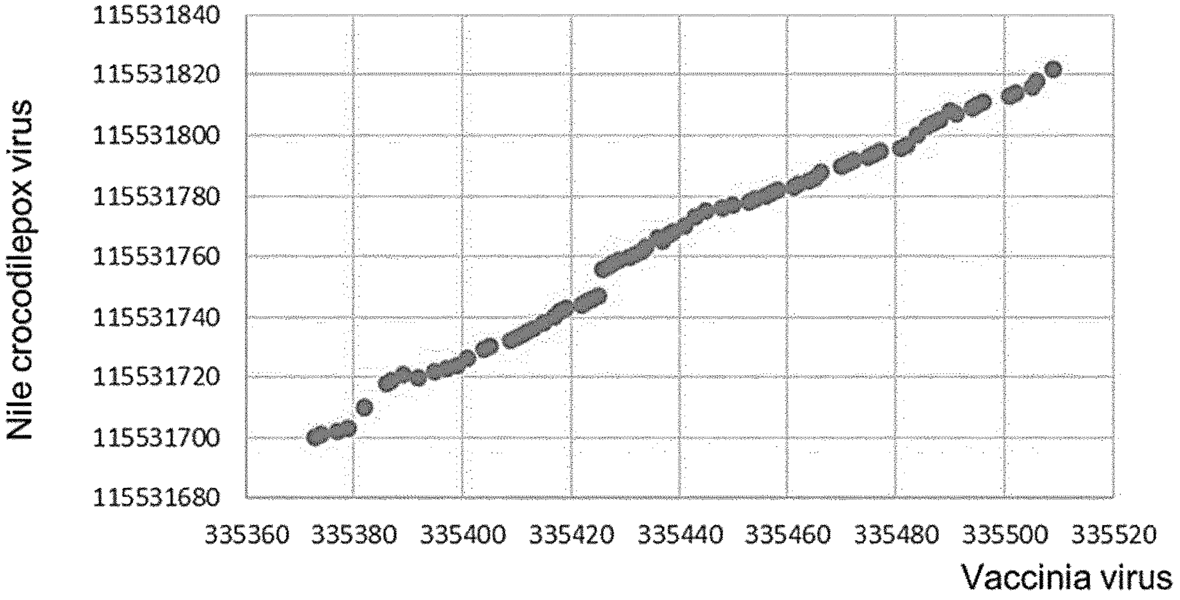
Figure 7:
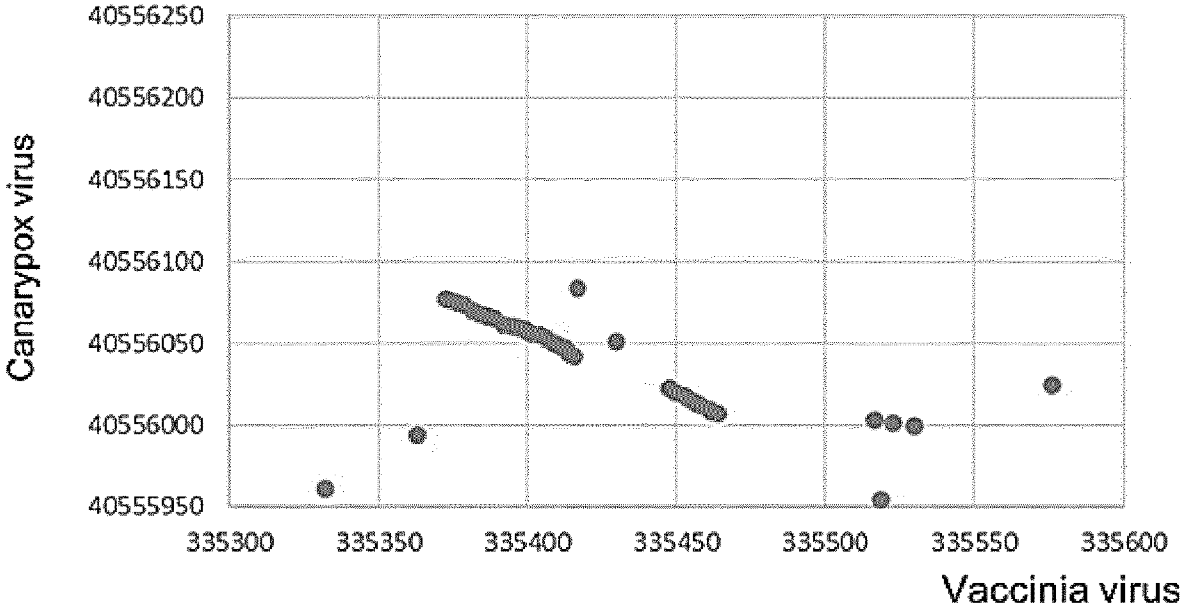
Figure 8:
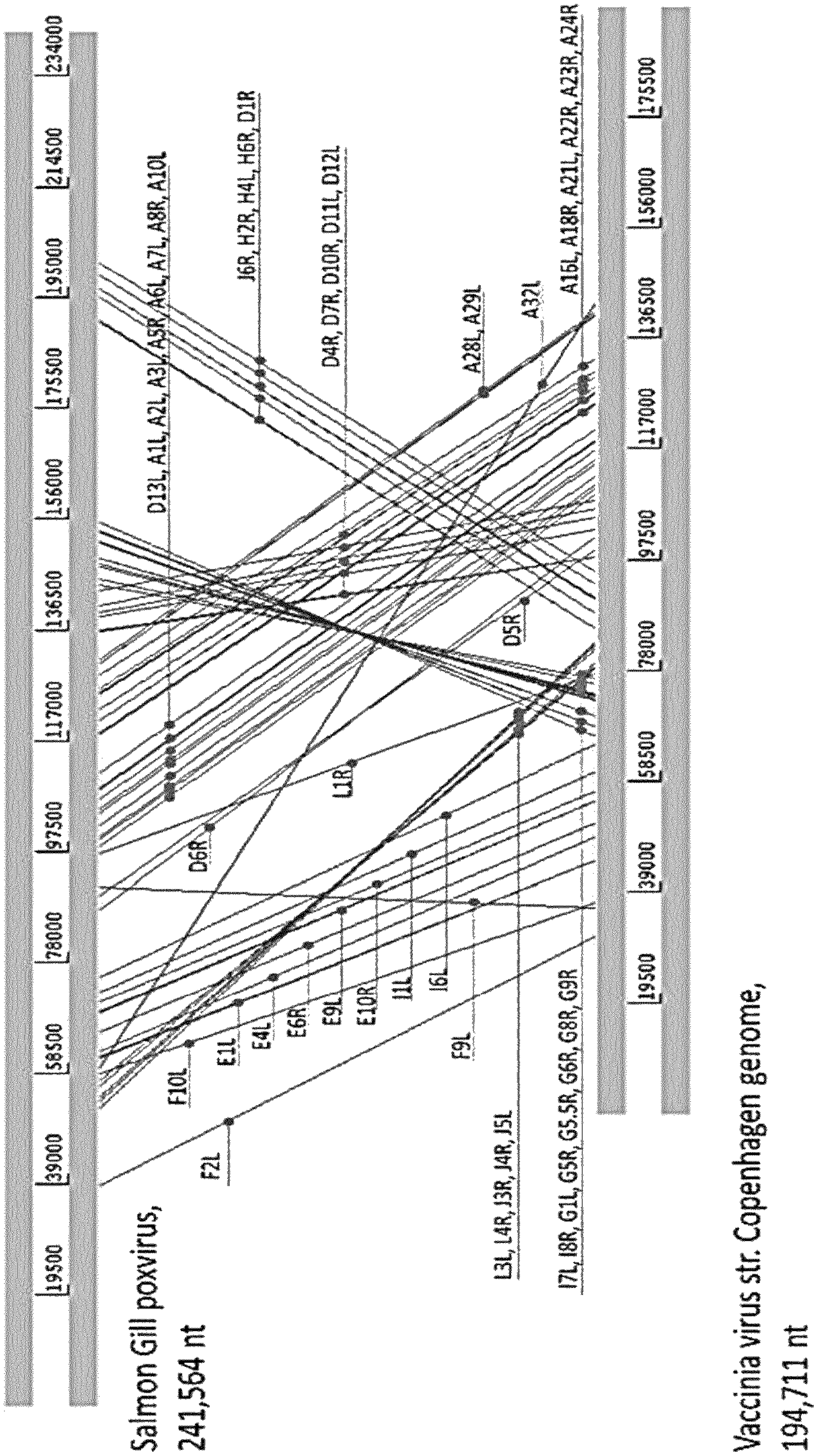
FIG. 8: Alignment of the genome architectures of SGPV and VACV. The alignment was generated using the Artemis tool and the table of gene orthology derived from the NCVOG assignments obtained in this work. The orthologous genes are connected by red lines, and the names of the respective vaccinia virus genes are indicated. nt, nucleotides.
Figure 9:
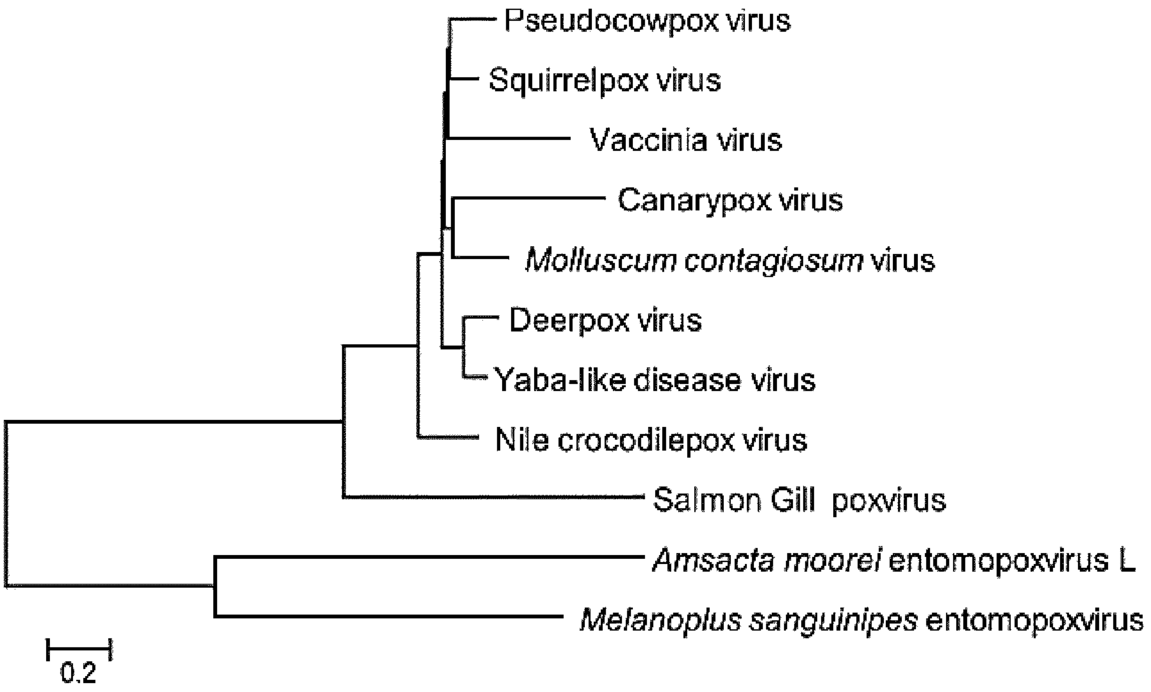
FIG. 9: Synteny-based evolutionary tree of poxviruses. The root between chordopoxviruses and entomopoxviruses was forced. The tree was constructed using the neighbor-joining method, and the distances between the genome architectures of the respective viruses that were estimated as described previously (48) are shown in the table underneath the tree; a unit distance means that the fraction of orthologous gene pairs that belong to synteny blocks is equal to e−1. Amsmo, *Amsacta moorei* entomopoxvirus; Melsa, *Melanoplus sanguinipes* entomopoxvirus; Vacco, vaccinia virus; Deevi, deerpox virus; Psevi, pseudocowpox virus; Canvi, canarypox virus; Crovi, crocodilepox virus; Squvi, squirrelpox virus; Molco, molluscum contagiosum virus; Yabvi, Yaba-like disease virus.

The tetrapod chordopoxviruses, except for avipoxviruses, are characterized by a distinct genome architecture whereby the central portion of the genome shows a nearly perfect conservation of gene synteny and the terminal regions are highly divergent and often contain unique genes, as depicted in the dot plots of FIG. 7. In contrast, genome-wide comparison of the gene orders between SGPV and other chordopoxviruses shows the extensive decay of synteny in SGPV and the complete disappearance of synteny between chordopoxviruses and entomopoxviruses (FIG. 7). Examination of the genomic dot plots (FIG. 7) and a genome architecture alignment (FIG. 8) between SGPV and other chordopoxviruses reveals several conserved gene blocks in the central part of the genome that are separated by strings of nonhomologous genes of variable length, along with at least two inversions of conserved genomic segments. To assess the evolution of the pox-virus genome architecture in more quantitative terms, we calculated the matrix of genome rearrangement distances and used it to construct an evolutionary tree of genome architectures (FIG. 9). This tree shows that the decay of synteny roughly follows the evolution of gene sequences (compare the trees in FIGS. 9 and 5), but the rate of disruption of the ancestral gene order is nonuniform, with the major change mapping to the branch between SGPV and the rest of the chordopoxviruses.

Shared and distinct gene functions between SGPV and other chordopoxviruses and unexpected evolutionary patterns among SGPV genes. Here we discuss the predicted functions and some unusual aspects of evolution of the SGPV genes in the order of the tiers of ancestry, i.e., the point of gene origin for (acquisition by) this virus (FIG. 4). The ancestral NCLDV genes retained by SGPV encode the principal functions required for genome replication and expression, with no genes having been lost since the common ancestor of all poxviruses. However, two genes merit special mention in the context of poxvirus evolution, namely, the genes for DNA topoisomerase II (Topo II; SGPV095) and NAD-dependent DNA ligase (SGPV123). These (putative) ancestral NCLDV genes are uncharacteristic of chordopoxviruses, being present only in CrPV and SGPV, whose genomes encode both Topo II (which has multiple paralogs in CrPV) and Topo IB, which is conserved in the rest of the chordopoxviruses. The evolution of topoisomerases in NCLDVs appears to have been quite complex, involving both differential gene loss and the apparent independent acquisition of homologous genes. Thus, SGPV and CrPV could represent either the ancestral state with two distinct topoisomerase genes or an intermediate state after the Topo IB gene had been acquired but the Topo II gene had not been lost as it was in chordopoxviruses and entomopoxviruses independently.

The NAD-dependent ligase also appears to be an ancestral NCLDV gene but was replaced by the distinct, ATP-dependent ligase in several groups of viruses, including most of the chordo-poxviruses, after the divergence from the common ancestor with CrPV. The finding that SGPV encodes an NAD-dependent ligase but not an ATP-dependent ligase is compatible with this scenario. The predicted NAD-dependent ligase of SGPV shows an unexpectedly low sequence similarity to homologs from other NCLDVs (Table 5), suggestive of some peculiarity in the DNA replication process of this virus.

The next evolutionary tier of the SGPV genes, those that are conserved in all poxviruses (Table 6), includes components of the transcription apparatus, such as several RNA polymerase subunits and the poly(A) polymerase catalytic subunit; several components of the virion core and proteins involved in virion morphogenesis, such as the metalloprotease G1; and six subunits of the fusion-entry complex (homologs of three paralogous subunits of this complex, A16, G9, and J5, are also detectable in mimiviruses and iridoviruses, suggesting that some form of this complex might be ancestral in NCLDVs). Of note is the presence in SGPV of a highly diverged ortholog of the G6 protein, a predicted amidase or acyltransferase that is thought to be important for the virus-host interaction but whose specific function remains obscure.

Figure 10:
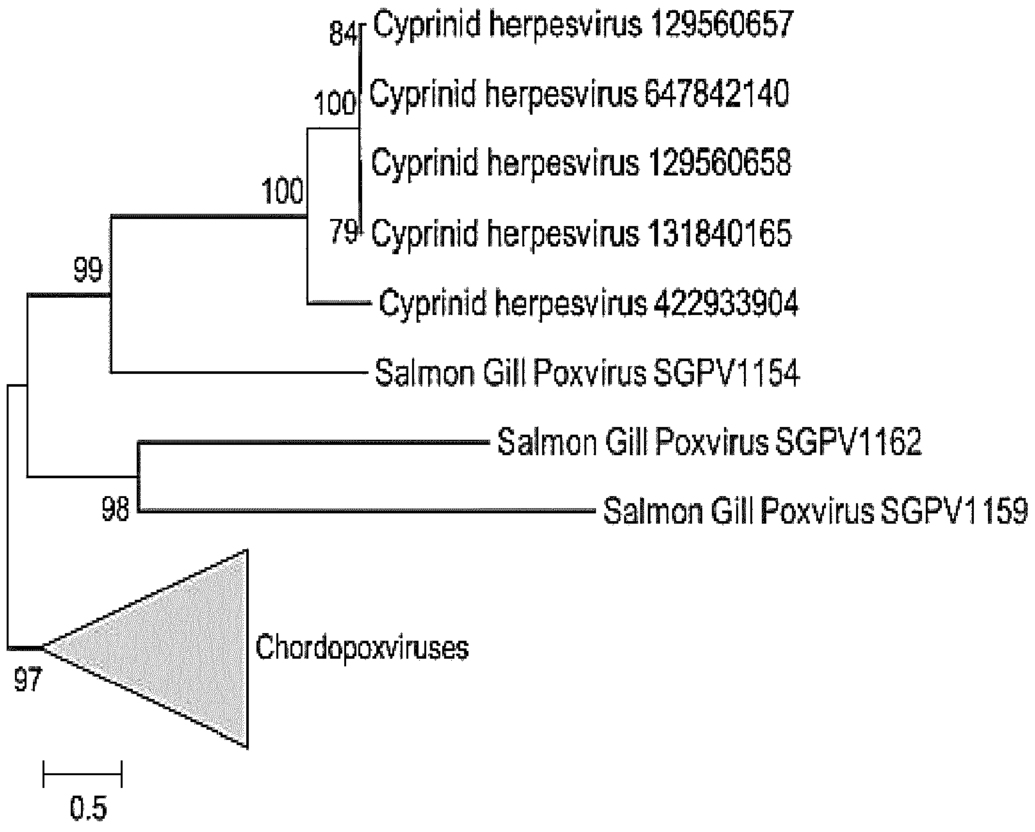
FIG. 10: Phylogenetic tree of the viral B22R-like genes. The numbers on the left show bootstrap values as percentages. The bar shows the scale as the estimated number of amino acid substitutions per site. For the cyprinid herpesviruses, the GI numbers are indicated on the right. The three paralogs from SGPV are shown in red. The chordopoxvirus sequences are collapsed and shown as a triangle.

The genes that are conserved in chordopoxviruses, to the exclusion of entomopoxviruses, follow the same general functional themes, including RNA polymerase subunits, such as A5 and J4; the late-stage transcription factor G8 containing a highly diverged PCNA domain; and proteins involved in core morphogenesis, e.g., the telomere-binding protein 16 and the protein A6 required for virus membrane biogenesis. Particularly notable in this group are three paralogous genes (SGPV154, SGPV159, SGPV162), located near the right end of the genome, that encode homologs of variola virus B22R, a giant type 1 membrane protein implicated in the virus-induced shutdown of the host adaptive immunity, specifically, inhibition of T lymphocytes. Of these three paralogous genes, SGPV154 is similar in length to homologs from other poxviruses, whereas SGPV159 and SGPV162 are considerably shorter and, thus, have apparently been truncated during the evolution of the SGPV lineage. However, the conservation of the predicted signal peptide and the C-terminal transmembrane helix in all three proteins (Table 5) suggests that they remain functional. The proliferation of this gene in SGPV, which parallels its independent triplication in CrPV, implies an important role of this route of counterdefense. Interestingly, homologs of this gene were also detected in cyprinid herpesviruses, suggesting transfer of this gene, involved in virus-host interaction from SGPV (or its relative), to unrelated viruses within the same host (FIG. 10). Moreover, the cluster of SGPV genes that encompasses the three B22R paralogs also contains two other proteins with a similar, very large size (SGPV155 and SGPV161; Table 5) that are predicted to be, respectively, membrane associated and secreted. The sequences of these proteins show no similarity to the B22R sequence, but the proteins might perform roles similar to the role performed by B22R via a distinct mechanism.

TABLE 6

| Conserved chordopoxvirus genes missing in SGPV: | | | | |
|---|---|---|---|---|
| Conserved gene[a] | VACV gene | Known or predicted function | Essential[b] | Comment |
| Genes conserved in chordopoxviruses and entomopoviruses | | | | |
| 1178 | I5R | Membrane protein, fusion-entry complex subunit | Yes | |
| 1181 | A11R | Membrane-associated protein implicated in endoplasmic reticulum recruitment for virion morphogenesis | Yes | |
| 0040 | H1L | Dual-specificity (Ser/Thr and Tyr) protein phosphatase | Yes | Conserved in only two entomopoxviruses |

TABLE 6-continued

| Conserved chordopoxvirus genes missing in SGPV: | | | | |
|---|---|---|---|---|
| Conserved gene[a] | VACV gene | Known or predicted function | Essential[b] | Comment |
| Genes conserved only in chordopoxviruses | | | | |
| 1185 | A20R | DNA polymerase processivity factor | Yes | |
| 1385 | I3L | Single-stranded DNA-binding protein essential for replication | Yes | |
| 1184 | G2R | Late transcription elongation factor | Yes | |
| 1172 | A12L | Virion core protein | Yes | |
| 1177 | F17R | DNA-binding virion core protein | Yes | |
| 1043 | G7L | Virion core protein required for immature virion formation | Yes | |
| 1398 | A19L | Virion core protein | Yes | |
| 0060 | G4L | Glutaredoxin involved in the pathway for cytoplasmic disulfide bond formation | Yes | |
| 1396 | A2.5L | Thioredoxin-like protein involved in the pathway for cytoplasmic disulfide bond formation | Yes | |
| 0012 | A33R | C-type lectin involved in extracellular virion morphogenesis | No | |
| 0268 | A25/A26L | A-type inclusion body-like protein | No | |
| 0255 | O1L | Poorly characterized protein, activator of the extracellular signal-regulated kinase pathway | No | |
| 1167 | F12L | Protein involved in intracellular enveloped virion maturation and cytoskeleton-dependent virion export | No | Inactivated derivative of DNA polymerase, possibly of bacteriophage origin |
| 1367 | G3L | Fusion-entry complex subunit | Yes | |
| 1376 | H7R | Protein involved in MV[c] membrane biogenesis | Yes | |
| 1380 | A14L | Protein involved in MV membrane biogenesis | Yes | |
| 1411 | A17L | Protein involved in MV membrane biogenesis | Yes | |
| 1395 | L2R | Protein involved in MV membrane biogenesis | Yes | |
| 1366 | I5L | MV membrane protein | No | |
| 1383 | I2L | Membrane protein essential for virus entry | Yes | |
| 1391 | J1R | Protein involved in MV formation, assembly complex subunit | Yes | |
| 1416 | D3R | Protein involved in MV formation, assembly complex subunit | Yes | |
| 1412 | A30L | Protein involved in MV formation, assembly complex subunit | Yes | |
| 1392 | A9L | Protein involved in MV morphogenesis | Yes | |
| 0256 | H3L | MV membrane protein involved in cell attachment | No | |
| 1415 | A14.5L | MV membrane protein that enhances virulence | No | |

[a]NCVOG number.
[b]Essentiality was determined for vaccinia virus.
[c]MV, mature virion.

The late-stage genes of chordopoxviruses, as well as most intermediate and some early genes, contain a distinct sequence element within which transcription starts. This element has the sequence TAAAT, where the second T usually corresponds to the second nucleotide of the translation initiation ATG codon of the respective gene. In the process of transcription initiation, the complement of this element serves as the template for the formation of the 5'-terminal poly(A) sequence that is present in many chordopoxvirus transcripts and is produced by RNA polymerase slippage. This TAAAT element is conserved in nearly all SGPV homologs of the respective chordopoxvirus genes (Table 5), suggesting that the main features of transcription initiation are shared by all chordopoxviruses.

Eight genes of SGPV have homologs in other NCLDVs and, thus, are formally assigned to NCVOGs, but as indicated by sequence similarity searches and phylogenetic analysis results (Table 4), they have probably been independently acquired by different viruses, which implies that they play important roles in virus-host interactions. Two of these genes (SGPV034 and SGPV139) encode RING finger proteins that could function as either specialized E3 subunits of ubiquitin ligases or inhibitors of ubiquitin pathways. RING finger-containing E3 proteins are encoded by many NCLDVs, including some of the orthopoxviruses, in which they are essential for pathogenicity. However, viral RING finger domains, including those encoded by the SGPV genome, show limited sequence similarity to each other and have probably been acquired independently. This independent acquisition was likely driven by the selection for virus interaction with the host ubiquitin networks. A similar trend of likely independent acquisition by diverse viruses is apparent for the DnaJ (J) domain, which was detected in the SGPV102 protein sequence. The J domain is present in mimiviruses, some phycodnaviruses, a single chordopoxvirus (molluscum contagiosum virus), as well as polyomaviruses. The polyomavirus J domain has been shown to function as a cochaperonin, enhancing the activity of the Hsc70 chaperone in the infected cells. A similar role in viral protein folding could be played by SGPV102.

Of special interest is the SGPV043 protein, a predicted serine/threonine protein kinase that is highly similar to the eukaryotic ribosomal protein S6 kinase (S6K), with which it shows up to 60% amino acid sequence identity. S6K is a component of the mTOR pathway and, more specifically, of the TORC1 complex, an environmental sensor that promotes anabolic pathways and inhibits catabolic pathways. Thus, this gene, which seems to have been convergently captured by SGPV and several other NCLDVs, could act as a regulator of the global metabolic state of virus-infected cells.

Only four SGPV genes appear to be unique acquisitions from cellular organisms, as they have no homologs in other NCLDVs. These are the metalloendopeptidase SGPV051, the thioredoxin SGPV147, the predicted DNA or RNA methyltransferase SGPV186, and the macrodomain-containing protein SGPV187, a putative O-acetyl-ADP-ribose deacetylase. Each of these proteins showed a high level of divergence from cellular homologs, presumably due to the high rate of evolution upon transfer to the viral genome, precluding a convincing inference of origin by phylogenetic analysis (not shown). The presence of the macrodomain is of special interest. Previously, this domain has been detected in several groups of animal positive-strand RNA viruses and has been shown to inhibit double-strand RNA-dependent phosphorylation of the interferon regulatory factor 3 (IRF-3), a key transcription factor for interferon induction. The macrodomain of SGPV, to our knowledge, is the first domain of this family to be discovered in a DNA virus, and it might play a similar role as an inhibitor of the interferon pathway.

Conserved Poxvirus Genes that are Missing in SGPV: Distinct Pathways of Membrane Biogenesis?

As pointed out above, SGPV lacks numerous genes that are (nearly) fully conserved among the tetrapod-infecting chordopoxviruses, with the implication being that they are lost in SGPV (Table 6). Only three ancestral poxvirus genes appear to have been lost in SGPV; one of these, the gene for the protein phosphatase H1, was, apparently, also independently lost in some entomopoxviruses. The absence in SGPV of the A11, L2, A14, and A17 genes highlights a central functional theme that extends into the longer list of conserved chordopoxvirus genes that are missing in SGPV, namely, membrane biogenesis (Table 6). At least half of the missing genes (14 of 28) encode proteins implicated in this process. Of the seven subunits of a distinct protein complex involved in the association of the viroplasm with membranes, which is required for immature virion formation, only one, the protein kinase F10, an ancestral NCLDV protein that is likely to perform multiple functions, is represented by an ortholog in SGPV (Table 6; two complex subunits, D2 and A15, are not listed because they appear to have been lost in some other chordopoxviruses as well). Taken together, these findings imply that SGPV employs a pathway of membrane biosynthesis that is distinct from that of other chordopoxviruses. Several uncharacterized SGPV proteins contain predicted transmembrane segments (Table 5) but show no detectable sequence similarity to the sequences of proteins of other poxviruses shown to participate in membrane biogenesis; it appears likely that at least some of these SGPV proteins belong to the putative alternative pathway.

Among the other conspicuous gaps in the gene repertoire of SGPV are the single-stranded DNA-binding protein 13 and the DNA polymerase processivity factor A20, two proteins that are essential for VACV DNA replication. Among the predicted SGPV gene products, there are no obvious candidates that could replace these proteins, so the involvement of functionally analogous host proteins seems to be a distinct possibility.

Also missing in SGPV are two components of the thiol-disulfide oxidoreductase pathway, which is essential for the formation of the disulfide bonds in the subunits of the VACV fusion-entry complex, as well as envelope proteins L1 and F9. Orthologs of the L1 protein along with the upstream component of the thiol-disulfide oxidoreductase pathway, the E10 protein, are conserved in nearly all NCLDVs (38), with the implication being that the pathway as such is essential. The two missing subunits, the glutaredoxin G4 and the thioredoxin-like protein A2.5 have no orthologs in other NCLDV families either, indicating that the complete oxidoreductase pathway characterized in VACV evolved only after the divergence of SGPV and the rest of the chordopoxviruses. The predicted SGPV thioredoxin (SGPV147) might be responsible, at least in part, for the missing portion of the pathway.

Discussion

Poxvirus infection in salmon was suspected in the 1990s, as TEM showed apoptotic gill epithelial cells with poxvirus-like particles in samples submitted to the Norwegian Veterinary Institute from acute, high-mortality events in freshwater farms with juvenile fish. Typical poxvirus structures were further characterized in a TEM study of gill disease in Atlantic salmon (9), but no taxonomic assignment was possible in the absence of sequence data. In this study, we confirmed the presence of poxvirus particles and determined the sequence and phylogeny of salmon gill poxvirus, developed qPCR and IHC methods, and analyzed the disease from current as well as archival samples.

As there was no experimental model for SGPV disease, we obtained samples from fish with spontaneous cases of the suspect apoptotic gill disease in two hatcheries without other significant disease problems. As controls we included samples from fish involved in several gill disease outbreaks without apoptosis of gill epithelium as well as healthy fish. We found the SGPV infection by qPCR only in the disease cases and could link the SGPV infection in situ to the apoptotic respiratory epithelium by IHC. We found that the infection was widespread in the gills at least 3 days before the onset of severe clinical disease. Mortality coincided with blocking of the respiratory gill surfaces by two different mechanisms. The SGPV infection seems to induce massive apoptosis and detachment of the epithelium, resulting in the acute adherence of the thin gill lamellae. In other fish, an excessive proliferation of the epithelium blocked the respiratory surfaces. These findings indicate that viral replication precedes the gill pathologies that can be likened to atelectasis and solidification of the lungs, respectively. Hypoxia and osmoregulatory disturbances are the expected pathophysiological consequences from such lesions in fish. This is in keeping with the clinical experience that stopping feeding, raising oxygen levels, and avoiding all stress minimize mortality, which otherwise may approach 100% within hours in a tank of fish. Although the classical Koch's postulates remain to be fulfilled, our findings indicate that SGPV causes a distinct disease primarily affecting the gills in salmon. In fish, localized gill infection seems to be the rule for the suspected poxviruses With regard to systemic pathology and infection, we found that hemophagocytosis was associated with severe disease. In infectious salmon anemia, a severe orthomyxoviral disease of salmon, hemophagocytosis is due to virus attachment to the erythrocyte surfaces. However, only high or no CT values were found in organs of the poxvirus-infected salmon with hemophagocytosis, while low CT values were obtained from the gills in these fish. Hemophagocytosis is possibly a sign of circulatory disturbances aggravating the SGPV disease. It is noteworthy that lethargy, gill pathology, and hemophagocytosis are also reported in koi sleepy disease, associated with a pox virus of gills and seemingly not internal organs (10). Poxviruses are generally epithelio-tropic, and skin tissue samples were positive by PCR both in this study and in the study of koi carp (10). However, we found no skin lesions in the salmon, and at present, we cannot exclude the possibility that skin tissue samples carry just virus shed from the gills. IHC seemed to indicate a very narrow cell tropism, since the simple, squamous lamellar epithelium of the gill was infected, while the adjacent stratified epithelium did not show signs of infection. The high mortality due to respiratory SGPV infection appears to be different from that in poxvirus infections in air-breathing vertebrates, where lung pathology is usually seen as part of a generalized infection. This could be related to the fundamental anatomical differences in the respiratory systems in the two vertebrate groups, where fish have their respiratory surface much more exposed to the exterior.

All salmon sampled a week after mortality had subsided in a tank were still infected, as shown by PCR. However, virus levels were generally lower and hemophagocytosis was much less prominent. These findings suggest that although recurrent, acute outbreaks in a tank are not reported by the farmers, SGPV infection may persist. For how long we do not know, and as the reservoir of infection is also unknown, we cannot rule out the possibility of reinfections. However, our archival samples do show that the infection is found not only in freshwater hatcheries but also in the seawater farms that receive the salmon for additional growth. In the cases of combined amoebic gill disease and SGPV disease that we confirmed here, 82% of the fish died. This is in agreement with the findings of other studies demonstrating that most gill diseases in the seawater rearing phase are complex, with multiple agents being present. Investigation of the role of SGPV in mixed infections will be an important future task, as the gill problems caused by these mixed infections cause considerable losses. To this end, we now have two new diagnostic methods, qPCR and IHC, for the detection of the SGPV in fish tissues, and these are useful for screening and resolving the complex pathology, respectively.

Judging from the archival samples, the SGPV disease emerged in the mid-1990s in Norwegian salmon farms over a wide geographical range. However, SGPV is distinct from other chordo-poxviruses that have been analyzed, and its reservoir is unknown. High mortality, like that caused by SGPV in salmon, can be a sign of a new host-agent system with low compatibility; on the other hand, intensive farming may have changed an old host-agent balance. Further studies are needed to clarify the reservoir and host range of SGPV and other aquatic poxviruses beyond salmon farming. The level of production of farmed food fish grew from 13 million to 66 million tons during the period between 1990 and 2012. Epidemics of orthomyxoviral disease virtually stopped salmon production in Chile and demonstrate the importance of disease control in fish farming. Also, for feral fish populations, introduction of new viruses may have serious consequences, as shown by the mass mortalities associated with rhabdoviral disease in the Great Lakes. We urgently need more knowledge of fish poxviruses, as the global trade and movement of aquaculture animals are growing. Research on the poxviruses of fishes may also bring cures for the aquaculture industry in the form of vaccines and the development of vectors.

Genome analysis of SGPV established the position of this fish-infecting virus at the base of the chordopoxvirus tree, as could be expected under the assumption of virus-host coevolution. However, the differences between the gene complements of SGPV and those of the rest of the chordopoxviruses are extensive, with SGPV lacking 38 genes otherwise conserved in chordopoxviruses. This difference in gene content is spread unevenly across the functional classes of viral genes. Most of the genes involved in genome replication and expression, as well as core and capsid structure and morphogenesis, are shared by SGPV and other chordopoxviruses. In sharp contrast, the majority of the chordopoxviruses genes implicated in viral membrane biogenesis are missing in SGPV. Chordopoxviruses employ a unique pathway of viral membrane derivation from the membranes of the endoplasmic reticulum of the infected cells that requires the participation of multiple viral proteins. The most parsimonious explanation for the absence of most of these proteins in SGPV is that this pathway, at least in its complete form, evolved in viruses infecting tetrapods; however, the alternative scenario, in which the pathway evolved in the ancestral chordopoxvirus but was subsequently lost in SGPV, cannot be ruled out. In addition, the multiprotein complex that in vaccinia virus is involved in viroplasm association with membranes, that is essential for virion maturation, and that so far appears to be conserved in all chordopoxviruses is missing in SGPV. Nevertheless, recognizable poxvirus crescent membranes, immature virions, and mature virions are formed. Thus, SGPV appears to employ a pathway of viral membrane biogenesis similar to that of other chordopoxviruses, despite the absence of key conserved proteins; multiple predicted membrane proteins of SGPV without homologs in other viruses could contribute to this alternative version of membrane biogenesis.

SGPV also lacks the proteins that are involved in the interaction of other chordopoxviruses with host defense systems, such as multiple paralogous genes that encode proteins containing kelch and ankyrin repeats as well as proteins involved in the suppression of host immune mechanisms. The conspicuous exception is the conserved B22R-like giant membrane proteins. However, the SGPV genome encodes numerous uncharacterized genes, many of which encode predicted membrane and secreted proteins as well as predicted nonglobular proteins with low-complexity sequences and simple repeats. Many, if not most, of the protein products of these genes are likely involved in currently unknown interactions with the immunity systems of the fish host. Experimental study of these uncharacterized proteins of SGPV could help the study of the pathogenesis of the gill disease in salmon and, more generally, the mechanisms of the poxvirus-host interaction.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Unless expressly described to the contrary, each of the preferred features described herein can be used in combination with any and all of the other herein described preferred features.

REFERENCES

1 Moss, B. in *Fields Virology 5th Ed* Vol. 2 (eds D. M. Knipe & P. M. Howley) 2905-2946 (Lippincott, Williams & Wilkins, 2007).
2 Buller, R. M. & Palumbo, G. J. Poxvirus pathogenesis. *Microbiological reviews* 55, 80-122 (1991).
3 Fenner, F. *Smallpox and its eradication*. (World Health Organization, 1988).
4 Damon, I. K. in *Fields Virology 5th ed* Vol. 2 (eds D. M. Knipe & J. C. Howard) 2947-2976 (Lippincott Williams & Wilkins, 2007).
5 McFadden, G. Poxvirus tropism. *Nature reviews. Microbiology* 3, 201-213, doi:10.1038/nrmicro1099 (2005).
6 Ginn, P. E., Mansell, J. E. K. L. & Rakich, P. M. in *Pathology of Domestic Animals* Vol. 1 (ed M. G. Maxie) 553-781 (Saunders Elsevier, 2007).
7 Van Bressem, M. F., Van Waerebeek, K., Reyes, J. C., Dekegel, D. & Pastoret, P. P. Evidence of poxvirus in dusky dolphin (*Lagenorhynchus obscurus*) and Burmeister's porpoise (*Phocoena spinipinnis*) from coastal Peru. *Journal of wildlife diseases* 29, 109-113, doi:10.7589/0090-3558-29.1.109 (1993).
8 Osterhaus, A. D., Broeders, H. W., Visser, I. K., Teppema, J. S. & Vedder, E. J. Isolation of an orthopoxvirus from pox-like lesions of a grey seal (*Halichoerus grypus*). *The Veterinary record* 127, 91-92 (1990).
9 Nylund, A. et al. Morphogenesis of salmonid gill poxvirus associated with proliferative gill disease in farmed Atlantic salmon (*Salmo salar*) in Norway. *Archives of virology* 153, 1299-1309, doi:10.1007/s00705-008-0117-7 (2008).
10 Miyazaki, T., lsshiki, T. & Katsuyuki, H. Histopathological and electron microscopy studies on sleepy disease of koi *Cyprinus carpio* koi in Japan. *Dis Aquat Organ* 65, 197-207, doi:10.3354/dao065197 (2005).
11 Altschul, S. F., Gish, W., Miller, W., Myers, E. W. & Lipman, D. J. Basic local alignment search tool. *Journal of molecular biology* 215, 403-410, doi:10.1016/S0022-2836(05)80360-2 (1990).
12 Sambrook et al. Molecular Cloning: *A laboratory Manual*. (Cold Spring Harbor Laboratory Press 1998.
13 Ausubel et al. *Current Protocols in Molecular Biology*. (Publishing Associates and Wiley-Intersciences 1987).
14 Fogg, C. N. et al. Disparity between levels of in vitro neutralization of vaccinia virus by antibody to the A27 protein and protection of mice against intranasal challenge. *J Virol* 82, 8022-8029, doi:10.1128/JVI.00568-08 (2008).
15 Lai, C. F., Gong, S. C. & Esteban, M. The purified 14-kilodalton envelope protein of vaccinia virus produced in *Escherichia coli* induces virus immunity in animals. *J Virol* 65, 5631-5635 (1991).
16 Rodriguez, J. F., Janeczko, R. & Esteban, M. Isolation and characterization of neutralizing monoclonal antibodies to vaccinia virus. *J Virol* 56, 482-488 (1985).
17 Nelson, G. E., Sisler, J. R., Chandran, D. & Moss, B. Vaccinia virus entry/fusion complex subunit A28 is a target of neutralizing and protective antibodies. *Virology* 380, 394-401, doi:10.1016/j.virol.2008.08.009 (2008).
18 Sakhatskyy, P., Wang, S., Chou, T. H. & Lu, S. Immunogenicity and protection efficacy of monovalent and polyvalent poxvirus vaccines that include the D8 antigen. *Virology* 355, 164-174, doi:10.1016/j.virol.2006.07.017 (2006).
19 Hsiao, J. C., Chung, C. S. & Chang, W. Vaccinia virus envelope D8L protein binds to cell surface chondroitin sulfate and mediates the adsorption of intracellular mature virions to cells. *J Virol* 73, 8750-8761 (1999).
20 Davies, D. H. et al. Vaccinia virus H3L envelope protein is a major target of neutralizing antibodies in humans and elicits protection against lethal challenge in mice. *J Virol* 79, 11724-11733, doi:10.1128/JVI.79.18.11724-11733.2005 (2005).
21 Lin, C. L., Chung, C. S., Heine, H. G. & Chang, W. Vaccinia virus envelope H3L protein binds to cell surface heparan sulfate and is important for intracellular mature virion morphogenesis and virus infection in vitro and in vivo. *J Virol* 74, 3353-3365 (2000).
22 Fogg, C. et al. Protective immunity to vaccinia virus induced by vaccination with multiple recombinant outer membrane proteins of intracellular and extracellular virions. *J Virol* 78, 10230-10237, doi:10.1128/JVI.78.19.10230-10237.2004 (2004).
23 Fogg, C. N. et al. Adjuvant-enhanced antibody responses to recombinant proteins correlates with protection of mice and monkeys to orthopoxvirus challenges. *Vaccine* 25, 2787-2799, doi:10.1016/j.vaccine.2006.12.037 (2007).
24 Wolffe, E. J., Vijaya, S. & Moss, B. A myristylated membrane protein encoded by the vaccinia virus L1R open reading frame is the target of potent neutralizing monoclonal antibodies. *Virology* 211, 53-63, doi:10.1006/viro.1995.1378 (1995).
25 Su, H. P. et al. The 1.51-Angstrom structure of the poxvirus L1 protein, a target of potent neutralizing antibodies. *Proc Natl Acad Sci USA* 102, 4240-4245, doi:10.1073/pnas.0501103102 (2005).
26 Galmiche, M. C., Goenaga, J., Wittek, R. & Rindisbacher, L. Neutralizing and protective antibodies directed against vaccinia virus envelope antigens. *Virology* 254, 71-80, doi:10.1006/viro.1998.9516 (1999).
27 Zhang, J. *J. Comput. BioL*, 203-221 (2000).
28 Devereux, J et al. Nucleic Acids Research 12: 387, 1984.
29 Zhang et al. 2000. J. Comput. Biol., 7, 203-214.
30 Zerbino & Birney 2008. Genome Research 18 (5): 821-829).
31 Weber et al. Nat Genet. 2002 February; 30(2):141-2.
32 Steinum T, Kvellestad A, Ronneberg L B, Nilsen H, Asheim A, Fjell K, Nygard S M, Olsen A B, Dale O B. 2008. First cases of amoebic gill disease (AGD) in Norwegian seawater farmed Atlantic salmon, *Salmo salar* L, and phylogeny of the causative amoeba using 18S cDNA sequences. J Fish Dis 31:205-214. http://dx-.doi.org/10.1111/j.1365-2761.2007.00893.x.
33 Gjessing M C, Falk K, Weli S C, Koppang E O, Kvellestad A. 2012. A sequential study of incomplete Freund's adjuvant-induced peritonitis in Atlantic cod. Fish Shellfish Immunol 32:141-150. http://dx.doi.org/10.1016/j.fsi.2011.11.003.
34 Seidelin M, Madsen S S, Blenstrup H, Tipsmark C K. 2000. Time-course changes in the expression of Na, K-ATPase in gills and pyloric caeca of brown trout (*Salmo trutta*) during acclimation to seawater. Physiol Biochem Zool 73:446-453. http://dx.doi.org/10.1086/317737.
35 Haugarvoll E, Bjerkas I, Nowak B F, Hordvik I, Koppang E O. 2008. Identification and characterization of a novel intraepithelial lymphoid tissue in the gills of Atlantic salmon. J Anat 213:202-209. http://dx.doi.org/10.1111/j.1469-7580.2008.00943.x.
36 Benson G. 1999. Tandem Repeats Finder: a program to analyze DNA sequences. Nucleic Acids Res 27:573-580. http://dx.doi.org/10.1093/nar/27.2.573.
37 Altschul S F, Madden T L, Schaffer A A, Zhang J, Zhang Z, Miller W, Lipman D J. 1997. Gapped BLAST and PSI-BLAST: a new generation of protein database search programs. Nucleic Acids Res 25:3389-3402. http://dx-.doi.org/10.1093/nar/25.17.3389.
38 Yutin N, Wolf Y I, Koonin E V. 2014. Origin of giant viruses from smaller DNA viruses not from a fourth domain of cellular life. Virology 466:38-52. http://dx-.doi.org/10.1016/j.virol.2014.06.032.
39 Yutin N, Wolf Y I, Raoult D, Koonin E V. 2009. Eukaryotic large nucleo-cytoplasmic DNA viruses: clusters of orthologous genes and reconstruction of viral genome evolution. Virol J 6:223. http://dx.doi.org/10.1186/1743-422X-6-223.
40 Edgar R C. 2004. MUSCLE: multiple sequence alignment with high accuracy and high throughput. Nucleic Acids Res 32:1792-1797. http://dx.doi.org/10.1093/nar/gkh340.
41 Darriba D, Taboada G L, Doallo R, Posada D. 2011. ProtTest 3: fast selection of best-fit models of protein evolution. Bioinformatics 27:1164-1165. http://dx-.doi.org/10.1093/bioinformatics/btr088.

42 Jobb G, von Haeseler A, Strimmer K. 2004. TREEFINDER: a powerful graphical analysis environment for molecular phylogenetics. BMC Evol Biol 4:18. http://dx.doi.org/10.1186/1471-2148-4-18.

43 Csuros M. 2010. Count: evolutionary analysis of phylogenetic profiles with parsimony and likelihood. Bioinformatics 26:1910-1912. http://dx.doi.org/10.1093/bioinformatics/btq315.

44 Carver T J, Rutherford K M, Berriman M, Rajandream M A, Barrell B G, Parkhill J. 2005. ACT: the Artemis comparison tool. Bioinformatics 21: 3422-3423. http://dx.doi.org/10.1093/bioinformatics/bti553.

45 Novichkov P S, Wolf Y I, Dubchak I, Koonin E V. 2009. Trends in prokaryotic evolution revealed by comparison of closely related bacterial and archaeal genomes. J Bacteriol 191:65-73. http://dx.doi.org/10.1128/JB.01237-08.

46 Felsenstein J. 1996. Inferring phylogenies from protein sequences by parsimony, distance, and likelihood methods. Methods Enzymol 266:418-427. http://dx.doi.org/10.1016/50076-6879(96)66026-1.

47 Koonin E V, Yutin N. 2010. Origin and evolution of eukaryotic large nucleo-cytoplasmic DNA viruses. Intervirology 53:284-292. http://dx.doi.org/10.1159/000312913.

48 Novichkov P S, Wolf Y I, Dubchak I, Koonin E V. 2009. Trends in prokaryotic evolution revealed by comparison of closely related bacterial and archaeal genomes. J Bacteriol 191:65-73. http://dx.doi.org/10.1128/JB.01237-08.

The invention claimed is:

1. An isolated nucleic acid molecule consisting of 18 to 100 contiguous nucleotides of a nucleic acid sequence according to SEQ ID NO:1-9, or a nucleic acid sequence complementary to said nucleic acid sequence, wherein said nucleic acid molecule is a nucleic acid probe comprising a label selected from the group consisting of a radioactive label, a fluorescent label, a chemiluminescent label, an enzyme substrate, and an enzyme molecule.

2. The nucleic acid fragment according to claim 1, wherein said nucleic acid molecule is a nucleic acid probe, the nucleic acid sequence of which probe is as defined in any one of SEQ ID NO:4-7.

3. The nucleic acid molecule according to claim 1, wherein said nucleic acid molecule is a primer, wherein said primer is as defined in any one o SEQ ID NO: 8-9.

4. A method for detecting a Piscine poxvirus in a tissue sample isolated from fish, said method comprising:

a) contacting said sample with a nucleic acid primer and/or probe, wherein said nucleic acid primer and/or probe specifically binds to a nucleic acid consisting of 18 to 100 consecutive nucleic acid bases of a nucleic acid sequence according to any one of SEQ ID NO:1-9, or a sequence complementary thereto, wherein said nucleic acid primer and/or probe comprises a label selected from the group consisting of a radioactive label, a fluorescent label, a chemiluminescent label, an enzyme substrate, and an enzyme molecule; and b) detecting the formation of a complex between said nucleic acid and said probe or primer, wherein the presence of said complex indicates the presence of a Piscine poxvirus specific nucleic acid in said sample.

5. The method of claim 4, wherein said method comprises a polymerase chain reaction method.

6. The method of claim 4, wherein said method comprises in situ hybridization.

7. The method of claim 4, wherein the presence of said Piscine poxvirus specific nucleic acid in said sample is indicative of Piscine poxvirus infection in said sample.

8. The method of claim 4, wherein said label is a fluorophore in combination with a minor groove binding non-fluorescence quencher (MGBNFG).

9. The nucleic acid molecule of claim 1, wherein said label is a fluorophore in combination with a MGBNFG.

10. A composition comprising a first isolated nucleic acid molecule consisting of 18 to 100 contiguous nucleotides of a nucleic acid sequence according to SEQ ID NO:1-9 or a nucleic acid sequence complementary to said nucleic acid sequence, wherein said nucleic acid molecule is a nucleic acid probe comprising a label selected from the group consisting of a radioactive label, a fluorescent label, a chemiluminescent label, an enzyme substrate, and an enzyme molecule; and a second isolated nucleic acid comprising a primer consisting of 18 to 100 contiguous nucleotides of a nucleic acid sequence according to SEQ ID NO:1-9, or a sequence complementary thereto.

11. The method of claim 4, wherein said primer is as defined in any one of SEQ ID NO:8-9.

12. The nucleic acid molecule according to claim 1, wherein said nucleic acid molecule consists of 18 to 100 contiguous nucleotides of a nucleic acid sequence according to SEQ ID NOs:2-3.

13. The method according to claim 4, wherein said nucleic acid primer and/or probe specifically binds to a nucleic acid consisting of 18 to 100 contiguous nucleotides of a nucleic acid sequence according to SEQ ID NOs:2-3.

14. The composition of claim 10, wherein said nucleic acid molecule consists of 18 to 100 contiguous nucleotides of a nucleic acid sequence according to SEQ ID NOs:2-3.

* * * * *